US011208464B2

(12) United States Patent
Armstrong et al.

(10) Patent No.: US 11,208,464 B2
(45) Date of Patent: Dec. 28, 2021

(54) GDF15 FUSION PROTEINS AND USES THEREOF

(71) Applicant: Janssen Biotech, Inc., Horsham, PA (US)

(72) Inventors: Anthony Armstrong, Lawrence Township, NJ (US); Judith Ann Connor, Vsta, CA (US); Jennifer Furman, San Diego, CA (US); Chichi Huang, Malvern, PA (US); Michael J. Hunter, Santee, CA (US); Xiefan Lin-Schmidt, Ambler, PA (US); Serena Nelson, San Diego, CA (US); Shamina M. Rangwala, Furlong, PA (US); Shannon Mullican, Philadelphia, PA (US); Jose Antonio Chavez, Warrington, PA (US)

(73) Assignee: Janssen Sciences Ireland Unlimited Company, Ringaskiddy (IE)

( * ) Notice: Subject to any disclaimer, the term of this patent is extended or adjusted under 35 U.S.C. 154(b) by 222 days.

(21) Appl. No.: 16/412,819

(22) Filed: May 15, 2019

(65) Prior Publication Data

US 2019/0292241 A1 Sep. 26, 2019

Related U.S. Application Data

(62) Division of application No. 15/586,463, filed on May 4, 2017, now Pat. No. 10,336,812.

(60) Provisional application No. 62/333,886, filed on May 10, 2016.

(51) Int. Cl.

| | |
|---|---|
| *A61K 38/19* | (2006.01) |
| *A61K 38/17* | (2006.01) |
| *A61K 38/18* | (2006.01) |
| *A61K 38/16* | (2006.01) |
| *A61K 38/00* | (2006.01) |
| *C07K 14/765* | (2006.01) |
| *C07K 14/51* | (2006.01) |
| *C07K 14/47* | (2006.01) |
| *C07K 14/435* | (2006.01) |
| *C07K 14/46* | (2006.01) |
| *C12N 5/12* | (2006.01) |
| *C12N 15/00* | (2006.01) |
| *C12N 15/11* | (2006.01) |
| *C12N 15/63* | (2006.01) |
| *C12N 15/09* | (2006.01) |
| *C12N 15/62* | (2006.01) |
| *C07K 14/475* | (2006.01) |

(52) U.S. Cl.

CPC ............ *C07K 14/765* (2013.01); *A61K 38/16* (2013.01); *A61K 38/17* (2013.01); *A61K 38/18* (2013.01); *A61K 38/1875* (2013.01); *A61K 38/19* (2013.01); *C07K 14/435* (2013.01); *C07K 14/46* (2013.01); *C07K 14/47* (2013.01); *C07K 14/475* (2013.01); *C07K 14/51* (2013.01); *C12N 5/12* (2013.01); *C12N 15/00* (2013.01); *C12N 15/09* (2013.01); *C12N 15/11* (2013.01); *C12N 15/62* (2013.01); *C12N 15/63* (2013.01); *A61K 38/00* (2013.01); *C07K 2319/31* (2013.01)

(58) Field of Classification Search

None

See application file for complete search history.

(56) References Cited

U.S. PATENT DOCUMENTS

| | | | | |
|---|---|---|---|---|
| 6,420,543 | B1 | 7/2002 | Lee et al. | |
| 7,919,084 | B2 * | 4/2011 | Breit ...................... | C07K 16/22 424/130.1 |
| 10,336,812 | B2 * | 7/2019 | Armstrong ............... | C12N 5/12 |
| 2007/0036806 | A1 | 2/2007 | Glaesner et al. | |
| 2011/0005130 | A1 | 1/2011 | Huang et al. | |
| 2011/0015130 | A1 | 1/2011 | Woei-Jer | |
| 2014/0193427 | A1 * | 7/2014 | Lerner .................. | A61K 45/06 424/158.1 |
| 2014/0213511 | A1 | 7/2014 | Matern | |
| 2015/0023960 | A1 | 1/2015 | Lindhout et al. | |
| 2016/0031960 | A1 | 2/2016 | Lindhout et al. | |
| 2016/0168213 | A1 | 6/2016 | Xiong | |
| 2018/0282403 | A1 * | 10/2018 | Blokzijl ................ | C07K 16/22 |

FOREIGN PATENT DOCUMENTS

| | | | |
|---|---|---|---|
| WO | WO 2010/048670 | A1 * | 5/2010 |
| WO | 2013113008 | A1 | 8/2013 |
| WO | 2013148117 | A1 | 10/2013 |
| WO | 2014120619 | A2 | 8/2014 |
| WO | 2015017710 | A1 | 2/2015 |
| WO | WO 2015/017710 | A1 * | 2/2015 |
| WO | 2015197446 | A1 | 12/2015 |
| WO | 2015198199 | A1 | 12/2015 |
| WO | 2016018931 | A1 | 2/2016 |

(Continued)

OTHER PUBLICATIONS

Breit et al. (2012, Nephrol. Dial. Transplant. 27:70-75).*

(Continued)

*Primary Examiner* — Elizabeth C. Kemmerer

(74) *Attorney, Agent, or Firm* — Seed IP Law Group LLP

(57) ABSTRACT

Fusion proteins containing a half-life extension protein, a linker, and a GDF15 protein are described. Also described are nucleic acids encoding the fusion proteins, recombinant cells thereof, compositions comprising the fusion proteins, and methods of using the fusion proteins for treating or preventing metabolic diseases, disorders or conditions.

20 Claims, 39 Drawing Sheets

Specification includes a Sequence Listing.

(56) References Cited

FOREIGN PATENT DOCUMENTS

WO 2016069925 A1 5/2016

OTHER PUBLICATIONS

Ho et al. (2013, Clin. Chem. 59:1613-1620).*
Abulizi et al. (2017, Sci. Rep. 7(1):1037; pp. 1-10).*
Zimmers et al. (2005, Shock 23(6):543-548).*
Mazagova et al. (2013, Am. J. Physiol. Renal Physiol. 305:F1249-F1264).*
Kempf et al. (2006, Cir. Res. 98:351-350).*
"Albumin-linker-GDF15 fusion protein, SEQ ID 130", Geneseq, (Mar. 26, 2015), Database accession No. BBU47682, URL: EBI, XP002795260, 1 page.
"HSA/MIC-1 fusion protein compound 14", Geneseq, (Feb. 25, 2016), Database accession No. BCK62615, 2 pages.
"HSA/MIC-1 fusion protein compound 16", Geneseq, (Feb. 25, 2016), Database accession No. BCK62627, URL: EBI, XP002795262, 3 pages.
"Human GDF15 protein fragment, SEQ ID 55", Geneseq, (Mar. 26, 2015), Database accession No. BBU47607, URL: EBI, XP002795259, 1 page.
"Human growth differentiation factor 15 (GDF15) mature protein SEQ: 3", Geneseq, (Sep. 25, 2014), Database accession No. BBL23018, URL: EBI, XP002795264, 2 pages.
"Sequence 111 from Patent WO2015017710", EMBL, (Mar. 21, 2015), Database accession No. JD590115, URL: EBI, XP002795261,1 page.
EPO Communication; Application No. 17796596.9; dated Nov. 15, 2019, 12 pages.
Chrysovergis et al., "NAG-1/GDF-15 prevents obesity by increasing thermogenesis, lipolysis and oxidative metabolism.", int. J. Obesity, 2014, pp. 1555-1564, vol. 38.
Collinson, P., "The role of cardiac biomarkers in cardiovascular disease risk assessment.", Curr. Opin. Cardiol., 2014, pp. 366-371, vol. 29(4).
Johnen et al., Tumor-induced anorexia and weight loss are mediated by the TGF-b superfamily cytokine MIC-1.,Nat. Med., 2007, DO. 1333-1340, vol. 13(11).
Kempf et al., "GDF-15 is an inhibitor of leukocyte integrin activation required for survival after myocardial infarction in mice.", Nat. Med., 2011, pp. 581-589, vol. 17(5).
Kempf et al., "Growth differentiation factor 15 predicts future insulin resistance and impaired glucose control in obese nondiabetic individuals: results from the XENDOS trial.", Eur. J Endo., 2012, pp. 671-678, vol. 167.
Macia et al., "Macrophage Inhibitory Cytokine 1 (MIC-1/GDF15) Decreases Food Intake, Body Weight and Improves Glucose Tolerance in Mice on Normal & Obesogenic Diets.", PLoS One, 2012, pp. 1-8, vol. 7(4),e34868.
Mazagova et al., "Genetic deletion of growth differentiation factor 15 augments renal damage in both type 1 and type 2 models of diabetes.", Am. J. Physiol. Renal Physiol., 2013, pp. F1249-F1264, vol. 305.
Mensching et al., "Local substitution of GDF-15 improves axonal and sensory recovery after peripheral nerve injury.", Cell Tissue Res., 2012, pp. 225-238, vol. 350.
Strelau et al., "Progressive Postnatal Motoneuron Loss in Mice Lacking GDF-15.", J. Neurosci., 2009, p. 13640-13648, vol. 29(43).
Tsai et al., "Anorexia/cachexia of chronic diseases: a role for the TGF-β family cytokine MIC-1/GDF15.", J Cachexia Sarcopenia Muscle, 2012, pp. 239-243, vol. 3.
Tsai et al., "Serum Levels of Human MIC-1/GDF15 Vary in a Diurnal Pattern, Do Not Display a Profile Suggestive of a Satiety Factor and Are Related to BML", PLoS One, 2015, pp. 1-15, vol. 10(7):e0133362.
Tsai et al., "TGF-b Superfamily Cytokine MIC-1/GDF15 Is a Physiological Appetite and Body Weight Regulator.", PLoS One. 2013, pp. 1-10, vol. 8(2):e55174.
Wang et al., "hNAG-1 increases lifespan by regulating energy metabolism and insulin/IGF-1/mTOR signaling.", Aging. 2014, pp. 690-700, vol. 6(8).
Xu et al., "GDF15/MIC-1 Functions As a Protective and Antihypertrophic Factor Released From the Myocardium in Association With SMAD Protein Activation.", Circ Res., 2006, pp. 342-350, vol. 98.
Chen et al., "Fusion Protein linkers: Property, Design and Functionality.", Adv. Drug Deliv. Rev., Oct. 15, 2015, pp. 1357-1369, vol. 65(10).
International Search Report relating to corresponding International Patent Application No. PCT/US2017/031197; Date of Mailing of International Search Report: dated Sep. 18, 2017.
Written Opinion relating to corresponding International Patent Application No. PCT/US2017/031197; Date of Mailing of Written Opinion: dated Sep. 18, 2017.
Database Geneseq, "Human mature GDF15 monomer endocing DNA, Seq ID 11", retreved from EBI Accession No. GSN:BAQ98634, Sep. 12, 2013.

* cited by examiner

GDF15

```
              1        2
                       3                                        4       5
  1   ARNGDHCPLG  PGRCCRLHTV  RASLEDLGWA  DWVLSPREVQ  VTMCIGACPS
 51   QFRAANMHAQ  IKTSLHRLKP  DTVPAPCCVP  ASYNPMVLIQ  KTDTGVSLQT
                                   67
101   YDDLLAKDCH  CI
                 8
                 9
```

TGFβ3

```
              1        2 3                                      4      5
  1   ALDTNYCFRN  LEENCCVRPL  YIDFRQDLGW  KWVHEPKGYY  ANFCSGPCPY
 51   LRSADTTHST  VLGLYNTLNP  EASASPCCVP  QDLEPLTILY  YVGRTPKVEQ
                                   67
101   LSNMVVKSCK  CS
                 8
                 9
```

GDF15 FUSION PROTEINS AND USES THEREOF

CROSS REFERENCES TO RELATED APPLICATIONS

The present application is a divisional of U.S. patent application Ser. No. 15/586,463, filed on May 4, 2017, published on Nov. 16, 2017 as US2017/0327560 A1, now U.S. Pat. No. 10,336,812, which claims priority to U.S. Provisional Patent Application No. 62/333,886 filed on May 10, 2016. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "JBI5086USNPDIV_SEQ", creation date of May 7, 2019, and having a size of 404 KB. The sequence listing submitted via EFS-Web is part of the specification and is herein incorporated by reference in its entirety.

FIELD OF THE INVENTION

The invention relates to GDF15 fusion proteins. In particular, the invention relates to a fusion protein comprising a half-life extension protein, a linker and a GDF15 protein, nucleic acids and expression vectors encoding the fusion proteins, recombinant cells thereof, and pharmaceutical compositions comprising the fusion proteins. Methods of producing the fusion proteins and using the fusion proteins to treat metabolic disorders are also provided.

BACKGROUND OF THE INVENTION

GDF15, a member of the TGFβ family, is a secreted protein that circulates in plasma as a 25 kDa homodimer. Plasma levels of GDF15 range between 150 and 1150 pg/ml in most individuals (Tsai et al., *J Cachexia Sarcopenia Muscle.* 2012, 3: 239-243). Plasma levels of GDF15 are increased under conditions of injury, cardiovascular disease and certain types of cancer. This upregulation is thought to be a cytoprotective mechanism. High plasma levels of GDF15 are associated with weight loss due to anorexia and cachexia in cancer, and in renal and heart failure. In a clinical trial, GDF15 levels were an independent predictor of insulin resistance in obese, non-diabetic subjects (Kempf et al., *Eur. J. Endo.* 2012, 167: 671-678). A study in twins showed that the differences in levels of GDF15 within twin pairs correlated to the differences in BMI within that pair, suggesting that GDF15 serves as a long-term regulator of energy homeostasis (Tsai et al., *PLoS One.* 2015, 10(7): e0133362).

While GDF15 has been extensively studied as a biomarker for several cardiovascular and other disease states, a protective role for GDF15 has also been described in myocardial hypertrophy and ischemic injury (Collinson, *Curr. Opin. Cardiol.* 2014, 29: 366-371; Kempf et al., *Nat. Med.* 2011, 17: 581-589; Xu et al., *Circ Res.* 2006, 98:342-50). GDF15 was shown to play an important role in protection from renal tubular and interstitial damage in mouse models of type 1 and type 2 diabetes (Mazagova et al., *Am. J. Physiol. Renal Physiol.* 2013; 305: F1249-F1264). GDF15 is proposed to have a protective effect against age-related sensory and motor neuron loss, and it improves recovery consequent to peripheral nerve damage (Strelau et al., *J. Neurosci.* 2009, 29: 13640-13648; Mensching et al., *Cell Tissue Res.* 2012, 350: 225-238). In fact, GDF15 transgenic mice were shown to have a longer lifespan than their littermate controls, which can indicate that this molecule serves as a long-term survival factor (Wang et al., *Aging.* 2014, 6: 690-700).

Numerous reports have demonstrated the improvement of glucose tolerance and insulin sensitivity in mouse models upon treatment with GDF15 protein. Two independent strains of transgenic mice overexpressing GDF15 have decreased body weight and fat mass, as well as improved glucose tolerance (Johnen et al., *Nat. Med.* 2007, 13:1333-1340; Macia et al., *PLoS One.* 2012, 7:e34868; Chrysovergis et al., *Int. J. Obesity.* 2014, 38: 1555-1564). Increases in whole-body energy expenditure and oxidative metabolism were reported in GDF15 transgenic mice (Chrysovergis et al., 2014, Id.). These were accompanied by an increase in thermogenic gene expression in brown adipose tissue and an increase in lipolytic gene expression in white adipose tissue. Mice lacking the GDF15 gene have increased body weight and fat mass (Tsai et al., *PLoS One.* 2013, 8(2):e55174). An Fc-fusion of GDF15 was shown to decrease body weight and improve glucose tolerance as well as insulin sensitivity in an obese cynomolgus monkey model when administered weekly over a period of six weeks (WO 2013/113008).

The effects of GDF15 on body weight are thought to be mediated via the reduction of food intake and increased energy expenditure. GDF15 may improve glycemic control via body weight-dependent and independent mechanisms.

Together, these observations suggest that increasing levels of GDF15 can be beneficial as a therapy for metabolic diseases. There is a need in the art for GDF15-based compositions that can be used to treat or prevent metabolic diseases, disorders, or conditions.

BRIEF SUMMARY OF THE INVENTION

The invention satisfies this need by providing fusion proteins of GDF15 that demonstrate increased solubility/stability and exhibit features that indicate they can be used to treat or prevent metabolic diseases, disorders, or conditions. Such features include, for example, decreased body weight, increased glucose tolerance, and improved insulin sensitivity of a subject administered with a fusion protein according to an embodiment of the invention.

In one general aspect, the invention relates to a fusion protein comprising: (a) a half-life extension protein, (b) a linker, and (c) a GDF15 protein, wherein the fusion protein is arranged from N-terminus to C-terminus in the order (a)-(b)-(c).

In an embodiment of the invention, the GDF15 protein is a human GDF15 protein or a functional variant thereof. In particular embodiments, the GDF15 protein comprises a mature GDF15 protein or functional variant thereof. In more particular embodiments, the GDF15 protein comprises an amino acid sequence having at least 90% sequence identity to SEQ ID NO: 6-11. In other particular embodiments, the GDF15 protein comprises the amino acid sequence of SEQ ID NO:11, such as an amino acid sequence selected from the group consisting of SEQ ID NOs: 6-11.

In an embodiment of the invention, the half life extension protein is human serum albumin (HSA) or a functional variant thereof. In particular embodiments, the half life extension protein comprises an amino acid sequence having at least 90% identity to SEQ ID NO: 1. In other particular embodiments, the half life extension protein comprises an amino acid sequence selected from the group consisting of SEQ ID NOs: 1-3.

In an embodiment of the invention, the linker is a flexible linker. In particular embodiments, the flexible linker contains the sequence (GGGGS)n wherein n is 2 to 20, preferably 4 to 10 (SEQ ID NO: 129). In another embodiment of the invention, the linker of the fusion protein is a structured linker. In particular embodiments, the structured linker contains the sequence (AP)n (SEQ ID NO: 144) or (EAAAK)n (SEQ ID NO: 130), wherein n is 2 to 20, preferably 4 to 10.

In embodiments of the invention, the fusion protein comprises an amino acid sequence having at least 90% sequence identity to SEQ ID NOs: 5, 25-30, 36-37, 40, 48, 55-60 or 64-75. In particular embodiments of the invention, the fusion protein comprises an amino acid sequence selected from the group consisting of SEQ ID NOs: 5, 25-30, 40, 55-60, and 70. In more particular embodiment of the invention, the fusion protein comprises the amino acid sequence of SEQ ID NO: 60.

In another general aspect, the invention relates to an isolated nucleic acid molecule encoding a fusion protein of the invention.

In another general aspect, the invention relates to an expression vector comprising a nucleic acid molecule encoding a fusion protein of the invention.

In another general aspect, the invention relates to a recombinant host cell comprising a nucleic acid molecule encoding a fusion protein of the invention.

In another general aspect, the invention relates to a method of obtaining a fusion protein of the invention. The method comprises: (1) culturing a host cell comprising a nucleic acid molecule encoding the fusion protein under a condition that the fusion protein is produced, and (2) recovering the fusion protein produced by the host cell.

In another general aspect, the invention relates to a pharmaceutical composition comprising a fusion protein of the invention and a pharmaceutically acceptable carrier.

In another general aspect, the invention relates to a pharmaceutical composition comprising a nucleic acid molecule encoding a fusion protein of the invention and a pharmaceutically acceptable carrier.

In another general aspect, the invention relates to a kit comprising a pharmaceutical composition of the invention.

In another general aspect, the invention relates to a method of treating or preventing a metabolic disease, disorder or condition, the method comprising administering to a subject in need thereof a therapeutically or prophylactically effective amount of a pharmaceutical composition of the invention. In a particular embodiment, the pharmaceutical composition is administered to the subject subcutaneously or intravenously.

According to embodiments of the invention, a method of treating a metabolic disorder selected from the group consisting of type 2 diabetes, elevated glucose levels, elevated insulin levels, obesity, dyslipidemia, diabetic nephropathy, myocardial ischemic injury, congestive heart failure, or rheumatoid arthritis, in a subject in need thereof, comprises administering to the subject a therapeutically effective amount of a pharmaceutical composition comprising a fusion protein comprising an amino acid sequence selected from the group consisting of SEQ ID NOs: 5, 25-30, 40, 55-60, and 70 and a pharmaceutically acceptable carrier. In a particular embodiment, the method comprises administering to the subject a therapeutically effective amount of a pharmaceutical composition comprising a fusion protein comprising the amino acid sequence of SEQ ID NO: 60 and a pharmaceutically acceptable carrier.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1A:
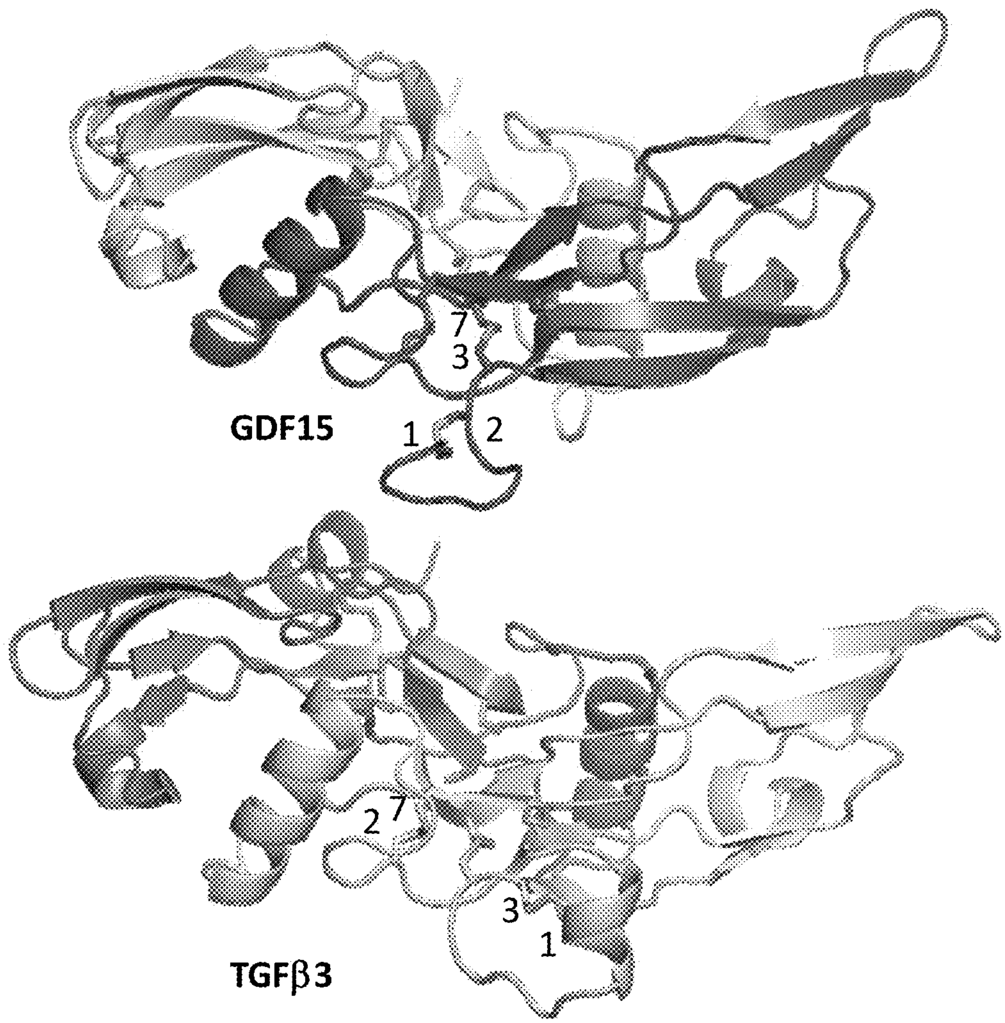
FIGS. 1A and 1B show the crystal structure of GDF15 (SEQ ID NO: 6), where the disulfide pairing of the first and second Cysteine residues (C1-C2) formed a loop at the N terminus of the protein, also shown is the crystal structure of TGFβ3 (SEQ ID NO: 139) for comparison.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

The invention relates to a fusion protein comprising (a) a half life-extension protein, (b) a linker, and (c) a GDF15 protein, wherein the fusion protein is arranged from N-terminus to C-terminus in the order (a)-(b)-(c).

It is found that a fusion protein according to an embodiment of the invention, comprising a half life-extension protein, a linker, and a GDF15 protein, results in an increased half life of the GDF15 protein, and fusion proteins of the invention exhibit metabolic effects that demonstrate their suitability as therapeutics for treating and preventing metabolic diseases, disorders or conditions. Such effects include, but are not limited to, decreasing body weight, increasing glucose tolerance, and improving insulin sensitivity of animals administered with the fusion proteins.

As used herein, the term "fusion protein" refers to a protein having two or more portions covalently linked together, where each of the portions is derived from different proteins.

Fusion proteins according to embodiments of the invention can include any GDF15 protein. As used herein, the term "GDF15 protein" refers to any naturally-occurring wild-type growth differentiation factor 15 protein or a functional variant thereof. The GDF15 protein can be from any mammal, such as a human or another suitable mammal, such as a mouse, rabbit, rat, pig, dog, or a primate. In particular embodiments, the GDF15 protein is a human GDF15 protein or a functional variant thereof. In preferred embodiments, the GDF15 protein is a mature GDF15 protein or a functional variant thereof.

As used herein, the term "mature GDF15 protein" refers to the portion of the pre-pro-protein of GDF15 that is released from the full-length protein following intracellular cleavage at the RXXR furin-like cleavage site. Mature GDF15 proteins are secreted as homodimers linked by disulfide bonds. In one embodiment of the invention, a mature GDF15 protein, shorthand GDF15(197-308) (SEQ ID NO: 6), contains amino acids 197-308 of a full-length human GDF15 protein.

As used herein, "functional variant" refers to a variant of a parent protein having substantial or significant sequence identity to the parent protein and retains at least one of the biological activities of the parent protein. A functional variant of a parent protein can be prepared by means known in the art in view of the present disclosure. A functional variant can include one or more modifications to the amino acid sequence of the parent protein. The modifications can change the physico-chemical properties of the polypeptide, for example, by improving the thermal stability of the polypeptide, altering the substrate specificity, changing the pH optimum, and the like. The modifications can also alter the biological activities of the parent protein, as long as they do not destroy or abolish all of the biological activities of the parent protein.

According to embodiments of the invention, a functional variant of a parent protein comprises a substitution, preferably a conservative amino acid substitution, to the parent protein that does not significantly affect the biological activity of the parent protein. Conservative substitutions include, but are not limited to, amino acid substitutions within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Non-standard or unnatural amino acids (such as 4-hydroxyproline, 6-N-methyl lysine, 2-aminoisobutyric acid, isovaline, and alpha-methyl serine) can also be used to substitute standard amino acid residues in a parent protein.

According to other embodiments of the invention, a functional variant of a parent protein comprises a deletion and/or insertion of one or more amino acids to the parent protein. For example, a functional variant of a mature GDF15 protein can include a deletion and/or insertion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acids to the mature GDF15 protein, preferably, a deletion of 1 to 30 amino acids at the N-terminus of the mature GDF15 protein.

According to yet other embodiments of the invention, a functional variant of a parent protein comprises a substitution, preferably a conservative amino acid substitution, and a deletion and/or insertion, preferably a small deletion and/or insertion of amino acids, to the parent protein.

According to embodiments of the invention, a fusion protein of the invention comprises a GDF15 protein that has an amino acid sequence at least 90% identical to the amino acid sequence of a mature GDF15, such as GDF15(197-308) (SEQ ID NO: 6); or an amino acid sequence at least 90% identical to the amino acid sequence of a mature GDF15 truncated at the N-terminus, such as GDF15(200-308) (SEQ ID NO: 7), GDF15(201-308) (SEQ ID NO: 8), GDF15(202-308) (SEQ ID NO: 9), GDF15(203-308) (SEQ ID NO: 10), or GDF15(211-308) (SEQ ID NO: 11). The GDF15 protein can have at least one of substitutions, insertions and deletions to SEQ ID NO: 6, 7, 8, 9, 10 or 11, as long as it maintains at least one of the biological activities of the GDF15 protein, such as its effects on food intake, blood glucose levels, insulin resistance, and body weight, etc.

In particular embodiments, a fusion protein of the invention comprises a GDF15 protein having the amino acid sequence of SEQ ID NO: 11, including but not limited to, the amino acid sequence of SEQ ID NO: 6, 7, 8, 9, 10 or 11.

Any suitable half life extension protein can be used in fusion proteins according to embodiments of the invention. As used herein, the term "half life extension protein" can be any protein or fragment thereof that is known to extend the half life of proteins to which it is fused. Examples of such half life extension proteins include, but are not limited to, human serum albumin (HSA), the constant fragment domain (Fc) of an immunoglobulin (Ig), or transferrin (Tf). In embodiments of the invention, the half life extension protein comprises HSA or a functional variant thereof. In particular embodiments of the invention, the half life extension protein comprises an amino acid sequence that is at least 90% identity to SEQ ID NO: 1. In preferred embodiments of the invention, the half life extension protein comprises HSA or functional variant thereof wherein the cysteine residue at position 34 of the HSA has been replaced by serine or alanine.

In particular embodiments, a fusion protein of the invention comprises a half life extension protein having an amino acid sequence selected from the group consisting of SEQ ID NOs: 1-3.

Any suitable linker can be used in fusion proteins according to embodiments of the invention. As used herein, the term "linker" refers to a linking moiety comprising a peptide linker. Preferably, the linker helps insure correct folding, minimizes steric hindrance and does not interfere significantly with the structure of each functional component within the fusion protein. In some embodiments of the invention, the peptide linker comprises 2 to 120 amino acids. For example, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 amino acids.

In embodiments of the invention, the linker increases the flexibility of the fusion protein components. In particular embodiments of the invention, the linker can be a flexible linker comprising the sequence (GGGGS)n (SEQ ID NO: 129), including but not limited to, GS-(GGGGS)n SEQ ID NO: 142 or AS-(GGGGS)n-GT SEQ ID NO: 143, wherein n is 2 to 20, such as 2, 3, 4, 5, 6, 7, 8, 9, 10, 11, 12, 13, 14 or 15.

In other embodiments of the invention, the linker is structured. In particular embodiments of the invention, the linker can be a structured linker comprising the sequence (AP)n (SEQ ID NO: 144) or (EAAAK)n (SEQ ID NO: 130), including but not limited to, AS-(AP)n-GT (SEQ ID NO: 145) or AS-(EAAAK)n-GT (SEQ ID NO: 140), wherein n is 2 to 20, such as 2, 3, 4, 5, 6, 7, 8, 9, 10, 11, 12, 13, 14 or 15. In other embodiments of the invention, the linker comprises the sequences (GGGGA)n (SEQ ID NO: 131), (PGGGS)n (SEQ ID NO: 132), (AGGGS)n (SEQ ID NO: 133) or GGS-(EGKSSGSGSESKST)n-GGS (SEQ ID NO: 134) wherein n is 2 to 20.

In embodiments of the invention, the fusion protein comprises an amino acid sequence having at least 90% sequence identity to SEQ ID NOs: 5, 25-30, 36-37, 40, 48, 55-56, 59-60 or 64-75. In particular embodiments of the invention, the fusion protein comprises an amino acid sequence selected from the group consisting of SEQ ID NOs: 5, 25-30, 36-37, 40, 48, 55-56, 59-60 and 64-75. In more particular embodiments of the invention, the fusion protein comprises an amino acid sequence selected from the group consisting of SEQ ID NOs: 5, 25-30, 40, 55-56, 55-56, 59-60, and 70. In further more particular embodiments of the invention, the fusion protein comprises the amino acid sequence of SEQ ID NO: 92, SEQ ID NO: 60 or SEQ ID NO: 26. The fusion protein can also include small extension(s) at the amino- or carboxyl-terminal end of the protein, such as a tag that facilitates purification, such as a poly-histidine tag, an antigenic epitope or a binding domain.

The fusion proteins disclosed herein can be characterized or assessed for GDF15 biological activities including, but not limited to effects on food intake, oral glucose tolerance tests, measurements of blood glucose levels, insulin resistance analysis, changes in body weight, pharmacokinetic analysis, toxicokinetic analysis, immunoassays and mass spec analysis of the level and stability of full-length fusion proteins, and human plasma ex vivo stability analysis.

The invention also provides an isolated nucleic acid molecule encoding a fusion protein of the invention. In embodiments of the invention, the isolated nucleic acid molecule encodes a fusion protein comprising an amino acid sequence having at least 90% sequence identity to SEQ ID NOs: 5, 25-30, 36-37, 40, 48, 55-56, 59-60 or 64-75. In particular embodiments, the isolated nucleic acid molecule encodes a fusion protein comprising an amino acid sequence selected from the group consisting of SEQ ID NOs: 5, 25-31, 36-37, 40, 48, 55-56, 59-60 and 64-75. In more particular embodiments, the isolated nucleic acid molecule encodes a fusion protein comprising an amino acid sequence selected from the group consisting of SEQ ID NOs: 5, 25-30, 40, 55-56, 59-60, and 70. In further more particular embodiments, the isolated nucleic acid molecule comprises the nucleotide sequence of SEQ ID NOs: 76-91.

According to other embodiments of the invention, the nucleic acid molecule encoding the fusion protein can be in an expression vector. Expression vectors include, but are not limited to, vectors for recombinant protein expression and vectors for delivery of nucleic acids into a subject for expression in a tissue of the subject, such as viral vectors. Examples of viral vectors suitable for use with the invention include, but are not limited to adenoviral vectors, adeno-associated virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc. The vector can include any element to establish a conventional function of an expression vector, for example, a promoter, ribosome binding element, terminator, enhancer, selection marker, or an origin of replication.

According to other embodiments of the invention, the nucleic acid molecule encoding the fusion protein can be codon optimized for improved recombinant expression from a desired host cell, such as Human Embryonic Kidney (HEK) or Chinese hamster ovary (CHO) cells, using methods known in the art in view of the present disclosure.

The invention also provides a host cell comprising a nucleic acid molecule encoding a fusion protein of the invention. Host cells include, but are not limited to, host cells for recombinant protein expression and host cells for delivery of the nucleic acid into a subject for expression in a tissue of the subject. Examples of host cells suitable for use with the invention include, but are not limited to HEK or CHO cells.

In another general aspect, the invention relates to a method of obtaining a fusion protein of the invention. In a general aspect, the method comprises: (1) culturing a host cell comprising a nucleic acid molecule encoding a fusion protein under a condition that the fusion protein is produced, and (2) recovering the fusion protein produced by the host cell. The fusion protein can be purified further using methods known in the art.

In some embodiments, the fusion protein is expressed in host cells and purified therefrom using a combination of one or more standard purification techniques, including, but not limited to, affinity chromatography, size exclusion chromatography, ultrafiltration, and dialysis. Preferably, the fusion protein is purified to be free of any proteases.

The invention also provides a pharmaceutical composition comprising a fusion protein of the invention and a pharmaceutically acceptable carrier.

The invention further provides a composition comprising a nucleic acid molecule encoding a fusion protein of the invention and a pharmaceutically acceptable carrier. Compositions comprising a nucleic acid molecule encoding a fusion protein of the invention can comprise a delivery vehicle for introduction of the nucleic acid molecule into a cell for expression of the fusion protein. Examples of nucleic acid delivery vehicles include liposomes, biocompatible polymers, including natural polymers and synthetic polymers, lipoproteins, polypeptides, polysaccharides, lipopolysaccharides, artificial viral envelopes, metal particles, and bacteria, viruses, such as baculoviruses, adenoviruses and retroviruses, bacteriophages, cosmids, plasmids, fungal vectors and other recombination vehicles typically used in the art which have been described for expression in a variety of eukaryotic hosts.

The pharmaceutically acceptable carrier can include one or more of pharmaceutically acceptable excipient, buffer, stabilizer or other materials known to those skilled in the art. Examples of pharmaceutically acceptable carriers include, but are not limited to, one or more of water, saline, buffer, isotonic agents such as sugars, polyalcohols, auxiliary substances such as wetting or emulsifying agents, preservatives, as well as combinations thereof. Such materials should be non-toxic and should not interfere with the efficacy of the active ingredient at the dosages and concentrations employed. The precise nature of the carrier or other material can depend on the route of administration, e.g., intramuscular, subcutaneous, oral, intravenous, cutaneous, intramucosal (e.g., gut), intranasal or intraperitoneal routes. For example, liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included. Compositions for parenteral administration can be stored in lyophilized form or in a solution, and are generally placed into a container having a sterile access port, such as an intravenous solution bag or vial having a stopper pierceable by a hypodermic injection needle.

According to embodiments of the invention, a pharmaceutical composition can comprise one or more additional components, such as another active ingredient.

The invention also relates to kits comprising a pharmaceutical composition of the invention. The kits can contain a first container having a dried fusion protein of the invention and a second container having an aqueous solution to be mixed with the dried fusion protein prior to administration to a subject, or a single container containing a liquid pharmaceutical composition of the invention. The kit can contain a single-dose administration unit or multiple dose administration units of a pharmaceutical composition of the invention. The kit can also include one or more pre-filled syringes (e.g., liquid syringes and lyosyringes). A kit can also comprise instructions for the use thereof. The instructions can describe the use and nature of the materials provided in the kit, and can be tailored to the precise metabolic disorder being treated.

The invention also relates to use of the pharmaceutical compositions described herein to treat or prevent a metabolic disease, disorder or condition, such as type 2 diabetes, elevated glucose levels, elevated insulin levels, obesity, dyslipidemia, diabetic nephropathy, myocardial ischemic injury, congestive heart failure, or rheumatoid arthritis. According to embodiments of the invention, a method of treating or preventing a metabolic disease, disorder or condition in a subject in need of the treatment comprises administering to the subject a therapeutically or prophylactically effective amount of a pharmaceutical composition of the invention. Any of the pharmaceutical compositions described herein can be used in a method of the invention, including pharmaceutical compositions comprising a fusion protein of the invention or pharmaceutical compositions comprising a nucleic acid encoding the fusion protein.

As used herein, "subject" means any animal, particularly a mammal, most particularly a human, who will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more particularly a human.

A "metabolic disease, disorder or condition" refers to any disorder related to abnormal metabolism. Examples of metabolic diseases, disorders or conditions that can be treated according to a method of the invention include, but are not limited to, type 2 diabetes, elevated glucose levels, elevated insulin levels, obesity, dyslipidemia, diabetic nephropathy, myocardial ischemic injury, congestive heart failure, or rheumatoid arthritis.

The terms "treat," "treating," and "treatment" as used herein refer to administering a composition to a subject to achieve a desired therapeutic or clinical outcome in the subject. In one embodiment, the terms "treat," "treating," and "treatment" refer to administering a pharmaceutical composition of the invention to reduce, alleviate or slow the progression or development of a metabolic disorder, such as type 2 diabetes, elevated glucose levels, elevated insulin levels, obesity, dyslipidemia, diabetic nephropathy, myocardial ischemic injury, congestive heart failure, or rheumatoid arthritis.

The term "therapeutically effective amount" means an amount of a therapeutically active compound needed to elicit the desired biological or clinical effect. According to embodiments of the invention, "a therapeutically effective amount" is an amount sufficient to effect beneficial or desired results, including clinical results. A therapeutically effective amount can be administered in one or more administrations. In terms of a disease state, an effective amount is an amount sufficient to ameliorate, stabilize, or delay development of a disease. According to specific embodiments of the invention, a therapeutically effective amount is an amount of a fusion protein needed to treat or prevent a metabolic disease, disorder or condition, such as type 2 diabetes, elevated glucose levels, elevated insulin levels, obesity, dyslipidemia, diabetic nephropathy, myocardial ischemic injury, congestive heart failure, or rheumatoid arthritis.

According to embodiments of the invention, a pharmaceutical composition of the invention can be administered to a subject by any method known to those skilled in the art in view of the present disclosure, such as by intramuscular, subcutaneous, oral, intravenous, cutaneous, intramucosal (e.g., gut), intranasal or intraperitoneal route of administration. In particular embodiments, a pharmaceutical composition of the invention is administered to a subject by intravenous injection or subcutaneous injection.

Parameters such as the dosage amount, frequency of administration, and duration of administration of a pharmaceutical composition to a subject according to an embodiment of the invention are not limited in any particular way. The optimum values of such parameters can depend on a variety of factors, such as the subject to be treated, the particular metabolic disease to be treated, the severity of the disease, the route of administration, etc., and one of ordinary skill in the art will be able to determine the optimum values for such parameters in order to achieve the desired therapeutic or clinical outcome. For example, a pharmaceutical composition can be administered once per day, or more than once per day, such as twice, three times, four times, etc. A typical dosage can range from about 0.1 μg/kg to up to about 100 mg/kg or more of the fusion protein, depending on the factors such as those mentioned above.

EMBODIMENTS

Embodiment 1 is a fusion protein comprising: (a) a half-life extension protein, (b) a linker, and (c) a GDF15 protein; wherein the fusion protein is arranged from N-terminus to C-terminus in the order (a)-(b)-(c).

Embodiment 2 is a fusion protein according to Embodiment 1, wherein the GDF15 protein is a human GDF15 protein or a functional variant thereof.

Embodiment 3 is a fusion protein according to Embodiment 1, wherein the GDF15 protein comprises an amino acid sequence having at least 90% identity to an amino acid sequence selected from the group consisting of SEQ ID NOs: 6-11.

Embodiment 4 is a fusion protein according to Embodiment 1, wherein the GDF15 protein comprises the amino acid sequence of SEQ ID NO: 11.

Embodiment 5 is a fusion protein according to Embodiment 4, wherein the GDF15 protein comprises an amino acid sequence selected from the group consisting of SEQ ID NOs: 6-11.

Embodiment 6 is a fusion protein according to any of Embodiments 1 to 5, wherein the half-life extension protein comprises human serum albumin (HSA) or a functional variant thereof.

Embodiment 7 is a fusion protein according to Embodiment 6, wherein the half-life extension protein comprises an amino acid sequence having at least 90% identity to SEQ ID NO: 1.

Embodiment 8 is a fusion protein according to Embodiment 7, wherein the half-life extension protein comprises an amino acid sequence selected from the group consisting of SEQ ID NOs: 1-3.

Embodiment 9 is a fusion protein according to any of Embodiments 1 to 8, wherein the linker is a flexible linker.

Embodiment 10 is a fusion protein according to Embodiment 9, wherein the linker comprises the sequence (GGGGS)n, wherein n is 2 to 20 (SEQ ID NO: 129), such as GS-(GGGGS)×8 (SEQ ID NO: 12) or AS-(GGGGS)×8GT (SEQ ID NO: 141).

Embodiment 11 is a fusion protein according to any of Embodiments 1 to 9, wherein the linker is a structured linker.

Embodiment 12 is a fusion protein according to Embodiment 11, wherein the linker comprises the sequence (AP)n (SEQ ID NO: 144) or (EAAAK)n (SEQ ID NO: 130), wherein n is 2 to 20, such as AS-(AP)n-GT (SEQ ID NO: 145) or AS-(EAAAK)n-GT (SEQ ID NO: 140).

Embodiment 13 is a fusion protein comprising an amino acid sequence having at least 90% sequence identity to SEQ ID NOs: 5, 25-31, 36-37, 40, 48, 55-60 or 64-75.

Embodiment 14 is a fusion protein according to Embodiment 13, comprising an amino acid sequence selected from the group consisting of SEQ ID NO: 5, 25-31, 36-37, 40, 48, 55-60 and 64-75.

Embodiment 15 is a fusion protein according to Embodiment 14, comprising an amino acid sequence selected from the group consisting of SEQ ID NOs: 5, 25-30, 40, 55-60, and 70.

Embodiment 16 is an isolated nucleic acid molecule encoding the fusion protein of any one of Embodiments 1 to 15.

Embodiment 17 is an isolated nucleic acid molecule comprising the nucleotide sequence of SEQ ID NOs: 76-91.

Embodiment 18 is an expression vector comprising the nucleic acid molecule of Embodiment 16 or 17.

Embodiment 19 is a host cell comprising the nucleic acid molecule of Embodiment 16 or 17.

Embodiment 20 is a method of producing the fusion protein of any one of Embodiments 1 to 15, comprising: (1) culturing a host cell comprising a nucleic acid molecule encoding the fusion protein under a condition that the fusion protein is produced; and (2) recovering the fusion protein produced by the host cell.

Embodiment 21 is a method according to Embodiment 20, wherein the recovering step comprises purifying the fusion protein to remove proteases.

Embodiment 22 is a pharmaceutical composition comprising a therapeutically effective amount of the fusion protein of any one of Embodiments 1 to 15 and a pharmaceutically acceptable carrier.

Embodiment 23 is a pharmaceutical composition comprising a therapeutically effective amount of a nucleic acid molecule encoding the fusion protein of any one of Embodiments 1 to 15 and a pharmaceutically acceptable carrier.

Embodiment 24 is a kit comprising a pharmaceutical composition according to Embodiment 22 or 23.

Embodiment 25 is a method of treating or preventing a metabolic disorder, comprising administering to a subject in need thereof an effective amount of the pharmaceutical composition according to any of Embodiments 22 and 23.

Embodiment 26 is a method according to Embodiment 25, wherein the metabolic disorder is selected from the group consisting of type 2 diabetes, elevated glucose levels, elevated insulin levels, obesity, dyslipidemia, diabetic nephropathy, myocardial ischemic injury, congestive heart failure, or rheumatoid arthritis.

Embodiment 27 is a method according to Embodiment 25 or 26, wherein the pharmaceutical composition is administered to the subject subcutaneously or intravenously.

Embodiment 28 is a method of treating a metabolic disorder selected from the group consisting of type 2 diabetes, elevated glucose levels, elevated insulin levels, obesity, dyslipidemia, diabetic nephropathy, myocardial ischemic injury, congestive heart failure, or rheumatoid arthritis, in a subject in need thereof, the method comprising subcutaneously or intravenously administering to the subject a therapeutically effective amount of a pharmaceutical composition comprising a fusion protein comprising an amino acid sequence selected from the group consisting of SEQ ID NOs: 5, 25-30, 40, 55-60, and 70 and a pharmaceutically acceptable carrier.

Embodiment 29 is a method of treating a metabolic disorder selected from the group consisting of type 2 diabetes, elevated glucose levels, elevated insulin levels, obesity, dyslipidemia, diabetic nephropathy, myocardial ischemic injury, congestive heart failure, or rheumatoid arthritis, in a subject in need thereof, the method comprising administering to the subject a therapeutically effective amount of a pharmaceutical composition comprising a fusion protein comprising the amino acid sequence of SEQ ID NO: 60 and a pharmaceutically acceptable carrier.

Embodiment 30 is a method of any one of Embodiments 25 to 29, wherein the pharmaceutical composition is administered to the subject intravenously or subcutaneously.

Embodiment 31 is a fusion protein of any one of Embodiments 1 to 15 for use in treating or preventing a metabolic disorder selected from the group consisting of type 2 diabetes, elevated glucose levels, elevated insulin levels, obesity, dyslipidemia, diabetic nephropathy, myocardial ischemic injury, congestive heart failure, or rheumatoid arthritis.

EXAMPLES

The following examples of the invention are to further illustrate the nature of the invention. It should be understood that the following examples do not limit the invention and that the scope of the invention is to be determined by the appended claims.

Example 1: Design of Fusion Molecules Comprising GDF15—Effect of GDF15 Truncations Like other TGFβ family members, GDF15 is synthesized as a pre-pro-protein that forms a dimer in the endoplasmic reticulum and undergoes furin cleavage to produce secreted mature GDF15 (amino acids 197-308). The secreted mature GDF15 homodimer is about 25 k Daltons, and each monomer has the potential to form up to 4 intramolecular disulfide bonds with a single intermolecular disulfide linking the homodimer components.

Figure 1B:
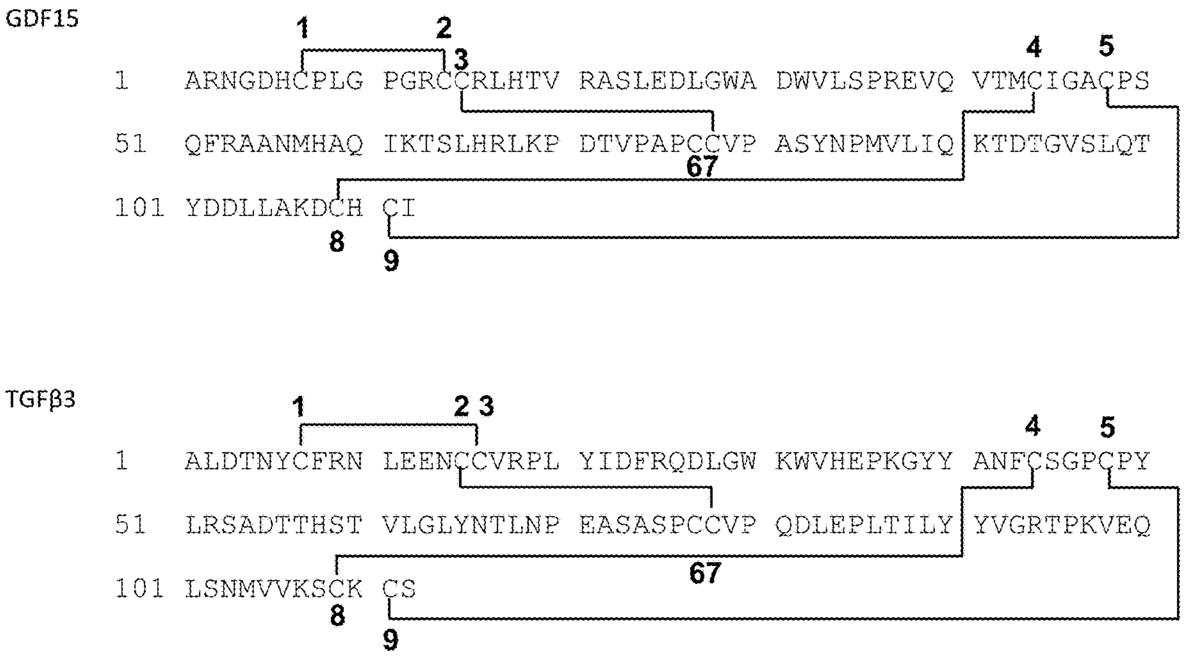

The crystal structure of GDF15 was determined in the invention and is depicted in FIGS. 1A and 1B. The crystal structure shows that the C-terminus of the mature GDF15 is buried in the dimer interface, while the N-terminus is exposed. This exposed terminus allows for the linkage of fusion proteins, such as half life extension proteins, to the N-terminus of GDF15.

The crystal structure also depicts the novel disulfide paring pattern of GDF15 cysteine residues. While TGFβ1 has C1-C3 and C2-C7 pairing (i.e., pairing between its first and third cysteine residues as well as between its second and seventh cysteine residues), GDF15 has C1-C2 and C3-C7 pairing (see FIGS. 1A and 1B). This unique disulfide pairing results in a loop formed by the C1-C2 pairing that is located at the N-terminus of the protein and away from the cysteine knot that contains other disulfide bonds. The structure predicts that the N-terminus of GDF15 may not be critical for dimer formation or overall protein folding, and that GDF15 and N-terminal fusion molecules thereof may be tolerable to N-terminal deletions that delete C1 and C2, residues within the C1-C2 loop, or even residues C-terminal to C2.

Example 2: Design of Fusion Molecules Comprising GDF15—Effect of the Linker

Different linkers between the HSA molecule and the GDF15 molecule were evaluated. Both flexible linkers, containing the sequence (GGGGS)n (SEQ ID NO: 129), and structured linkers, containing the sequence (AP)n (SEQ ID NO: 144) or (EAAAK)n (SEQ ID NO: 130), wherein n is 2 to 20, were evaluated.

Fusion proteins comprising the different linkers were compared for their biophysical properties, their effect on the efficacy of food intake in lean mice, their mouse pharmacokinetic (PK) values, and their ex vivo stability in human blood. The results of tested linker variants are shown in Table 1. The molecule comprising SEQ ID NO: 31, which contained the $(EAAAK)_8$ (SEQ ID NO: 138) linker, showed aggregation by HPLC. The remaining seven linker variants in Table 1 demonstrated no aggregation.

TABLE 1

Summary of linker variant analysis

| SEQ ID NO* | Linker of | Aggregation | Good Mouse PK (WT) | Ex vivo stability in human blood |
|---|---|---|---|---|
| 25 | AS$(GGGGS)_2$GT | No | Yes | Yes |
| 5 | GS$(GGGGS)_4$ | No | Yes | Yes |
| 26 | AS$(GGGGS)_8$GT | No | Yes | Yes |
| 27 | AS$(AP)_5$GT | No | Yes | Yes |
| 28 | AS$(AP)_{10}$GT | No | Yes | Yes |
| 29 | AS$(AP)_{20}$GT | No | Yes | Yes |
| 30 | AS$(EAAAK)_4$GT | No | Yes | Yes |
| 31 | AS$(EAAAK)_8$GT | YES | Not tested | Not tested |

*-6xHis tag was attached at the N-terminus for purification purpose

Linker stability was also evaluated for these variants by in vivo studies in mice and by ex vivo stability studies in human whole blood and plasma samples. Two forms of detection were used to analyze the results from these studies. An immunoassay with anti-GDF15 capture and anti-HSA detection antibody pairs was used to evaluate how intact the linker was by measuring the presence of both molecules on either side of the linker. A broader picture of the whole-molecule integrity was analyzed by liquid chromatography-mass spectrometry (LC-MS) analysis using different surrogate peptide sequences from both HSA and GDF15. The immunoassay demonstrated a stable PK profile for all of the linker variants and no loss of spiked plasma sample concentration for any of the linker variants observed over 48 hours. The LC-MS results were consistent with the immunoassay showing that the surrogate peptides from different parts of the HSA and GDF15 molecules were intact. The PK profile of the linker variants analyzed by LC-MS using surrogate peptides showed a similar trend for different linker variants, where they all had detectable levels at day 7. All the variants in Table 1 except for SEQ ID 31 had desirable biophysical properties and PK values.

The linker variants were evaluated for their in vivo activity by carrying out food intake studies in lean mice. Table 2 shows the influence of the linker variants on the efficacy of the fusion protein in decreasing food intake. There was a clear influence of the linker on the efficacy. With regard to the flexible (GGGGS)n (SEQ ID NO: 129) linkers, an increase in the linker length from 2 to 4 to 8 dramatically increased the fusion protein efficacy. For the more rigid (AP)n (SEQ ID NO: 144) linkers, the trend was less obvious, suggesting that the degree of freedom of the GDF15 molecule within the fusion protein plays a critical role in its efficacy.

TABLE 2

Effect of the linker on the in vivo efficacy of HSA-GDF15 fusion proteins in lean mice

| SEQ ID NO* | Linker | % Decrease in food intake (mean) |
|---|---|---|
| 25 | AS(GGGGS)$_2$GT | 28.8 |
| 5 | GS(GGGGS)$_4$ | 40.5 |
| 26 | AS(GGGGS)$_8$GT | 60.7 |
| 27 | AS(AP)$_5$GT | 48.2 |
| 28 | AS(AP)$_{10}$GT | 66.2 |
| 29 | AS(AP)$_{20}$GT | 55.1 |
| 30 | AS(EAAAK)$_4$GT | 51.9 |

*-6xHis tag was attached at the N-terminus for purification purpose

Example 3: Design of Fusion Molecules Comprising GDF15—Effect of HSA Mutations Recombinant proteins with the half life extension protein human serum albumin fused to the N-terminus of GDF15 through a linker were designed. This design should allow for the GDF15 dimerization interface to remain unperturbed and allow for the formation of the native inter-chain disulfide linkages, resulting in a GDF15 homodimer with HSA fusion extended from each GDF15 arm. With this approach, only a single gene is required to generate the HSA-GDF15 homodimer.

Native human serum albumin protein contains 35 cysteine (Cys, C) residues that form 17 disulfide bonds, with the Cys-34 residue being the only free cysteine in the molecule. This free Cys-34 has been shown to function as a free radical scavenger, by trapping multiple reactive oxygen species (ROS) and reactive nitrogen species (RNS). This free Cys was thus mutated to minimize the risk of heterogeneity due to oxidation.

The free cysteine at position 34 of HSA was mutated to either serine or alanine, and the GDF15 fusion molecules with either a HSA(C34S) or a HSA(C34A) mutation were analyzed. Both of the molecules were purified using a three-step purification method: (i) ion-exchange chromatography, (ii) hydrophobic interaction chromatography, and (iii) size-exclusion chromatography. When they were first generated, HPLC analysis showed that both molecules were pure and aggregation-free (Table 3).

However, two weeks after its generation, the fusion protein containing the HSA(C34A) mutation (comprising SEQ ID NO: 48) showed aggregation by HPLC, while the fusion protein containing the HSA(C34S) mutation (SEQ ID NO: 40) remained aggregation-free after four weeks.

TABLE 3

The influence of mutating HSA C34 on fusion protein aggregation

| SEQ ID NO | HSA mutation | % aggregation when purified | % aggregation 2 weeks post purification |
|---|---|---|---|
| 40 | C34S | 0 | 0 |
| 48 | C34A | 0 | 33.29 |

Example 4: Protease Cleavage Propensity on GDF15

It was observed by the inventors that the arginine residue at amino acid position 198 of GDF15 (R198) is susceptible to protease degradation within the HSA-GDF15 fusion molecules. Such degradation results in a heterogeneous population and is undesirable for therapeutic compositions. The cleavage can be prevented by a protease inhibitor cocktail. Purification methods were investigated for the removal of the protease. Table 4 lists the two types of HSA affinity columns that were tested for purification of HSA-GDF15 fusion proteins, as measured by HPLC. At the time of purification, the HSA-GDF15 fusion proteins purified by both methods were 100% pure and intact. At low concentrations (2-5 mg/ml), proteins purified by both methods remained intact for the entire test period of 4 weeks. However, at high concentrations (40-50 mg/ml), only the antibody-based HSA resin (CaptureSelect) produced protease-free proteins that remain intact for the entire 4 week test period. The HSA-ligand-based resin (Albupure) generated proteins that were intact initially but demonstrated degradation over time when stored at high concentrations. Adding a protease inhibitor cocktail (PI) and EDTA completely arrested the degradation of the high concentration HSA-GDF15 fusion protein batch purified using the Albupure resin. Thus, the purification method plays a critical role in generating a stable therapeutic composition. Corresponding degradation was not observed in vivo or ex vivo, suggesting that once the therapeutic composition has been made protease-free, degradation of the fusion proteins is not an issue in vivo. Therefore, purification methods that can effectively remove potential proteases during production, such as those using the CaptureSelect resin, are key to successfully manufacturing GDF15 therapeutics that are homogenous, intact and stable.

TABLE 4

Protease cleavage of the HSA-GDF15 fusion proteins can be eliminated by sample purification methods

| Concentration | Resin | +PI/ EDTA | % degraded population of HSA-GDF15 (SEQ ID 60) | | | | |
|---|---|---|---|---|---|---|---|
| | | | WEEK 0 | WEEK 1 | WEEK 2 | WEEK 3 | WEEK 4 |
| Low | Capture Select | No | 0 | 0 | 0 | 0 | 0 |
| Low | Albupure | No | 0 | 0 | 0 | 0 | 0 |
| High | Capture Select | No | 0 | 0 | 0 | 0 | 0 |
| High | Albupure | No | 0 | 3.04 | 9.47 | 11.57 | 13.89 |
| High | Capture Select | Yes | 0 | 0 | 0 | 0 | 0 |
| High | Albupure | Yes | 0 | 0 | 0 | 0 | 0 |

Example 5: N-Terminal Deletion Variants of GDF15

The GDF15 crystal structure depicted in FIGS. 1A and 1B predicts that the N-terminus of GDF15 involved in the deletion variants is not critical for dimer formation and overall protein folding. It also predicts that such N-terminal deletions should not affect any potential receptor interaction. HSA-GDF15 fusion proteins comprising various deletions of the N terminal of GDF15 were tested for in vivo activity.

Figure 17:
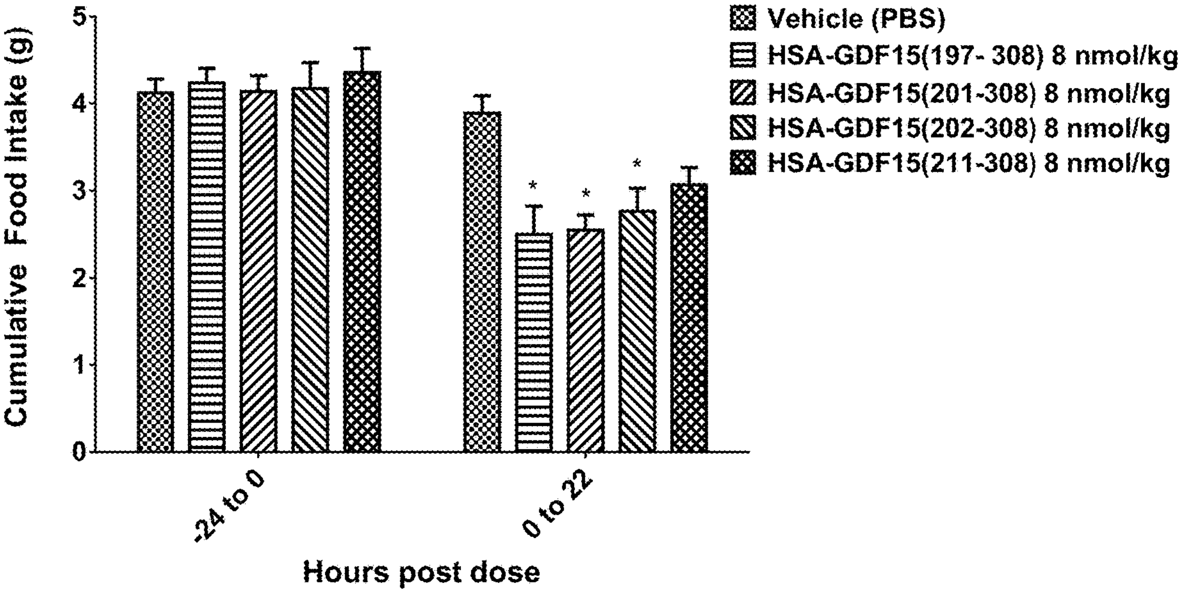
FIG. 17 shows acute food intake in lean C57BL6N male mice before and after the administration of various N-terminal deletion variants of GDF15. (SEQ ID NOs: 92, 111, and 112, compared to wild type fusion with no deletion (SEQ ID 26 with a 6×His tag attached at the N-terminus). N=8 animals per group; *–p<0.05, as compared to vehicle; p values were calculated using Two-way RM ANOVA and Tukey's test for multiple comparisons.
Figure 18:
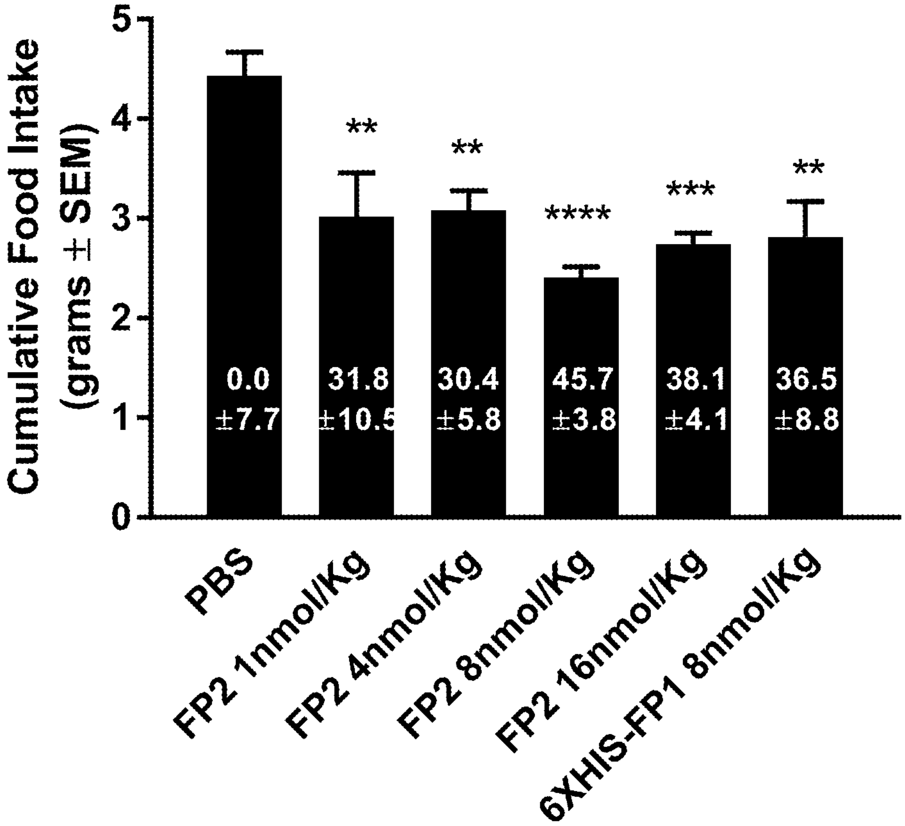
FIG. 18 shows the effect of a single dose of FP2 on food intake in C57BL/6 mice; specifically, cumulative food intake at 24 hours post administration is shown. Values shown within the bars are % reduction compared to PBS group (mean±SEM); N=8 animals per group for all groups, except N=6 in 6×His-FP1. –p<0.01, *–p<0.001, ****–p<0.0001; p values were calculated using Two-way ANOVA and Dunnetts's test for multiple comparisons.

GDF15 N-terminal deletion variants were designed that removed the protease cleavage site at GDF15 (R198). Immediately following the R198 residue, there is a potential deamidation site at residues N199-G200, and substrate deamidation is also not favored in therapeutic compositions. GDF15 N-terminal deletions can remove both the proteolytic cleavage site and the deamidation sites simultaneously. The resulting GDF15 deletion variants that were incorporated into fusion proteins with HSA included GDF15 (201-308; SEQ ID NO: 8), GDF15 (202-308; SEQ ID NO: 9), and GDF15 (211-308; SEQ ID NO: 11). In vivo studies in mice showed that the N-terminal deletion variants of GDF15 are still active in reducing food intake (FIG. 17). The experimental results confirmed that such GDF15 N-terminal deletion variants express properly, form appropriate dimers, and are active in vivo.

Example 6: Inactive Mutants of GDF15

Table 5 lists twelve mutants of GDF15 that were made to eliminate GDF15 in vivo activity and identify the functional epitope of GDF15. The mutants include five single mutants, two double mutants, and five triple mutants. HSA-GDF15 fusion proteins comprising these mutations were characterized for their biophysical properties and activities (Table 5). Out of the 12 mutants, one did not express and four formed aggregates over time, indicating that the mutations interrupt protein folding and biophysical properties. Of the remaining seven mutants, four of them contained a single mutation of GDF15, and these mutants were tested in mice for food intake reduction compared to wild type. Three of the single mutants (I89R, I89W and W32A) lost in vivo activity, while the remaining mutant (Q60W) is as active as the wild type. These results indicated that the I89R, I89W or W32A mutation interrupts the interaction of the receptor/co-receptor with GDF15, suggesting that the functional epitopes of GDF15 are around residues 189 and W32. The numbering of the mutation is based on the mature GDF15 present in fusion protein, e.g., "1" refers to the 1$^{st}$ amino acid of the mature GDF15 (SEQ ID NO: 6) and "89" refers to the 89$^{th}$ amino acid of the mature GDF15 protein.

TABLE 5

Summary of the biophysical properties and activities of fusion proteins comprising GDF15 mutants

| SEQ ID NO | Mutations in GDF15 | Biophysical properties | Activities |
|---|---|---|---|
| 5 | Wild type | Expresses well, stable | Wild type activity |
| 64 | I89R | Expresses well, stable | Complete loss of activity |
| 65 | I89W | Expresses well, stable | Complete loss of activity |
| 66 | L34A, S35A, R37A | Expresses well, stable | |
| 67 | V87A, I89A, L98A | Expresses well, unstable | |
| 68 | L34A, S35A, I89A | Expresses well, stable | |
| 69 | V87A, I89A | Expresses well, stable | |
| 70 | Q60W | Expresses well, stable | As active as wild type |
| 71 | W32A | Expresses well, stable | Complete loss of activity |
| 72 | W29A | Expresses well, unstable | |
| 73 | Q60A, S64A, R67A | Expresses well, unstable | |
| 74 | W29A, Q60A, I61A | Does not express | |
| 75 | W29A, W32A | Expresses well, unstable | |

*- 6xHis tag was attached at the N-terminus for purification purpose

Example 7: Expression and Purification Methods

Expression

For expression of 20 ml and greater, the expression was done using HEK Expi293™ cells grown in Expi293™ Expression media. The cells were grown at 37° C. while shaking at 125 RPM with 8% $CO_2$. The cells were transfected at $2.5 \times 10^6$ cells per ml using the Expi293™ Expression Kit. For each liter of cells transfected, 1 mg of total DNA was diluted in 25 ml of Opti-MEM, and 2.6 ml of Expi293™ reagent was diluted in 25 ml of Opti-MEM and incubated for 5 minutes at room temperature. The diluted DNA and diluted Expi293 reagent were combined and incubated for 20 minutes at room temperature. The DNA complex was then added to the cells. The cells were placed in the shaking incubator overnight. The day after transfection, 5 ml of Enhancer 1 from the kit was diluted into 50 ml of Enhancer 2 from the kit, and the total volume of the two Enhancers was added to the cells. The transfected cells were placed back into the incubator for 4 days until they were harvested. The cells were concentrated by centrifugation at 6,000 g for 30 minutes and then filtered with a 0.2 μm filter before the purification step.

The expression was also done in CHO cells. The plasmid was purified and characterized. Prior to transfection, 1 aliquot of 200 μg of plasmid DNA containing the coding region of HSA-GDF15 was linearized by restriction enzyme digestion with Acl I. The digestion with this restriction endonuclease ensures the removal of the ampicillin resistance gene. Two linearized 15 μg DNA aliquots were transfected into two $1\times10^7$ CHO cells (designated transfection pool A and B) using the BTX ECM 830 Electro Cell Manipulator (Harvard Apparatus, Holliston, Mass.). Cells were electroporated 3 times at 250 volts with 15 millisecond pulse lengths and 5 second pulse intervals in a 4 mm gap cuvette. Transfected cells were transferred to MACH-1+L-glutamine in a shake flask and incubated for 1 day. Transfection pool A and transfection pool B were centrifuged, resuspended in MACH-1+MSX, and transferred to shake flasks to incubate for 6 days. Transfected HSA-protein fusion-producing cells from transfection pool A and transfection pool B were pooled and plated in methylcellulose on day 8 post-electroporation.

Purification

Two-step purification using CaptureSelect resin and size exclusion chromatography was used. Cell supernatants from transiently transfected Expi293™ cells were loaded onto a pre-equilibrated (PBS, pH 7.2) HSA CaptureSelect column (CaptureSelect Human Albumin Affinity Matrix from ThermoFisher Scientific) at an approximate capacity of 10 mg protein per ml of resin. After loading, unbound proteins were removed by washing the column with 10 column volumes (CV) of PBS pH7.2. The HSA-GDF15 that was bound to the column was eluted with 10 CV of 2M $MgCl_2$ in 20 mM Tris, pH 7.0. Peak fractions were pooled, filtered (0.2μ), and dialyzed against PBS pH 7.2 at 4° C. After dialysis, the protein was filtered (0.20 again and concentrated to an appropriate volume before loading onto a 26/60 superdex 200 column (GE Healthcare). Protein fractions that eluted from the size exclusion chromatography (SEC) column with high purity (determined by SDS-PAGE) were pooled. The concentration of protein was determined by the absorbance at 280 nm on a BioTek Synergy HT™ spectrophotometer. The quality of the purified proteins was assessed by SDS-PAGE and analytical size exclusion HPLC (SE-HPLC, Dionex HPLC system). Endotoxin levels were measured using a LAL assay (Pyrotell®-T, Associates of Cape Cod).

Two-step purification using Albupure resin and SEC was also used. HSA-GDF15 fusion proteins were purified at room temperature using AlbuPure resin (ProMetic BioSciences Ltd) which utilizes an immobilized synthetic triazine ligand to selectively bind HSA. The expression supernatants were applied to the AlbuPure resin. The resin was then washed, first with 4 CV PBS pH 7.2 followed by 4 CV of 50 mM Tris pH 8.0, 150 mM NaCl buffer. The HSA-GDF15 that was bound to the column was eluted with 4 CV of PBS pH 7.2 buffer containing 100 mM Na Octanoate. The protein-containing fractions were concentrated to a 10 mL volume using a 30,000 kDa molecular weight cutoff spin concentrator (Amicon) and then applied to a 26/60 Superdex S200 pg column (GE) that was equilibrated in PBS pH 7.2 buffer. SEC fractions containing HSA-GDF15 homodimer were identified via SDS-PAGE and pooled for analysis. The protein purities were assessed by SDS-PAGE and SE-HPLC.

The Examples 8-14, and 19 involve characterization of an exemplary fusion protein of the invention, which has the amino acid sequence of SEQ ID NO: 60. This fusion protein is a fully recombinant protein that exists as a homodimer of a fusion of HSA with the mature human GDF15 through a 42-amino acid linker consisting of glycine and serine residues, GS-$(GGGGS)_8$ (SEQ ID NO: 12). The predicted molecular weight of this fusion protein is 162,696 Daltons, and the single native free cysteine at position 34 of HSA has been mutated to serine. This particular HSA-GDF15 fusion protein will be referred to simply as "FP1" in the following examples, for simplicity. A 6×His-tagged variant of FP1 (6×His-FP1, SEQ ID NO: 26), containing an AS-(GGGGS)×8-GT (SEQ ID NO: 141) linker, was used for comparison in some of the following examples.

Example 8: Effects of FP1 on the Food Intake of C57Bl/6 Mice

The purpose of this experiment was to demonstrate the dose-responsive effect of FP1 on the inhibition of food intake in C57Bl/6 mice.

Male C57Bl/6 mice were acclimated for a minimum of 72 hours in BioDAQ cages. Mice were then grouped based on food intake in the previous 24 hours into six groups of eight. Between 4:00 and 5:00 pm, animals were weighed and dosed with vehicle or a composition comprising FP1 via subcutaneous injection. The change in food weight for each cage was recorded continuously by the BioDAQ system for a period of 48 hours after the injections. 6×His-FP1 was used for comparison in this study.

Figure 2:
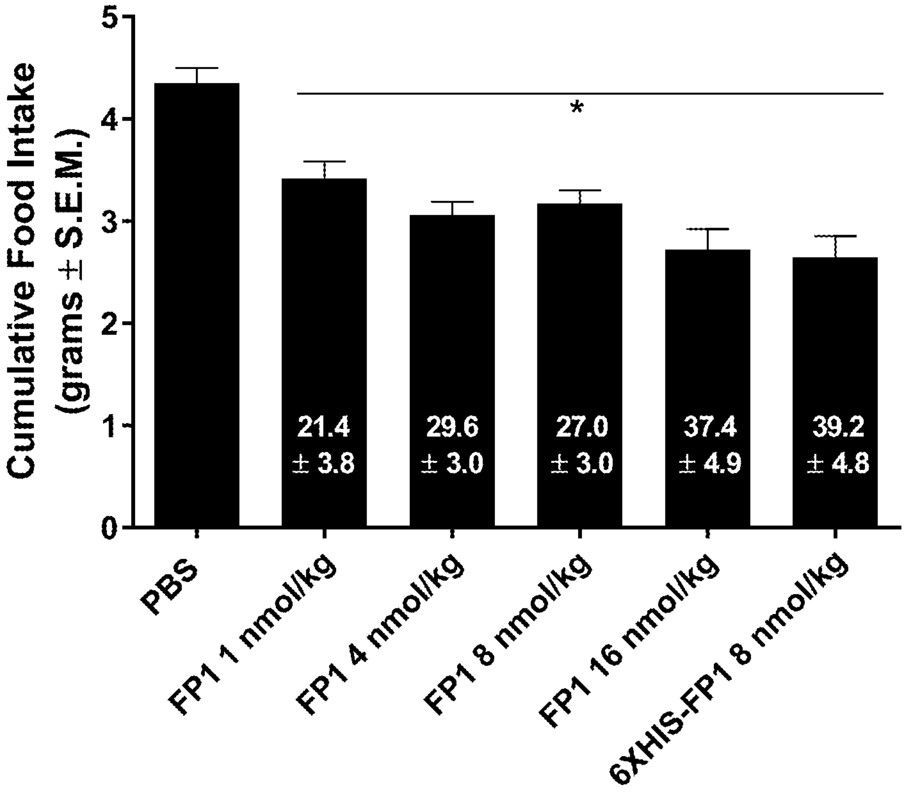
FIG. 2 shows the effects of subcutaneous administration of fusion proteins according to embodiments of the invention, e.g., fusion proteins FP1 (SEQ ID NO: 60) and 6×His-FP1 (SEQ ID NO: 26 with a 6×His tag attached at the N-terminus), on food intake in C57BL/6 mice, the cumulative food intake at 24 hours post-administration is depicted. Values shown within the bars are % reduction compared to vehicle (PBS) group ±SEM; N=8 animals per group for all groups, except N=9 in FP1 16 nmol/kg group. *–$p<0.05$, as compared to vehicle; p values were calculated using One-way ANOVA and Tukey's test for multiple comparisons.

The results (FIG. 2 and Table 6) were expressed as an average of cumulative food intake for a given time interval. The results indicated that subcutaneous administration of FP1 to C57BL/6 mice significantly inhibited food intake relative to vehicle-treated animals at all doses and time points tested. 6×His-FP1 reduced food intake at the 8 nmol/kg dose.

TABLE 6

Effects of subcutaneous administration of FP1 on food intake in C57BL/6 mice; Cumulative food intake at 12, 24 and 48 hours post administration is shown

| | Cumulative Food Intake (g) | | |
|---|---|---|---|
| Treatment | 12 hours | 24 hours | 48 hours |
| PBS | 3.7 ± 0.2 | 4.3 ± 0.1 | 8.4 ± 0.3 |
| FP1, 1 nmol/kg | 2.9 ± 0.1* | 3.4 ± 0.2** | 7.0 ± 0.3** |
| FP1, 4 nmol/kg | 2.3 ± 0.2**** | 3.1 ± 0.1**** | 6.6 ± 0.3*** |
| FP1, 8 nmol/kg | 2.1 ± 0.2**** | 3.2 ± 0.1*** | 6.4 ± 0.2**** |
| FP1, 16 nmol/kg | 1.7 ± 0.2**** | 2.7 ± 0.2**** | 6.2 ± 0.3**** |
| 6xHis-FP1, 8 nmol/kg | 1.8 ± 0.2**** | 2.6 ± 0.2**** | 6.0 ± 0.2**** |

Data are expressed as Mean ± SEM.
*p ≤ 0.05, versus PBS;
**p ≤ 0.01, versus PBS;
***p ≤ 0.001, versus PBS;
****p ≤ 0.0001, versus PBS
One-Way ANOVA-Tukey's multiple comparisons test;
n = 8/group

Example 9: Effects of FP1 on Food Intake in Sprague Dawley Rats

The purpose of this experiment was to demonstrate the dose-responsive effect of FP1 on the inhibition of food intake in Sprague Dawley rats.

Male Sprague-Dawley rats were acclimated for a minimum of 72 hours in the BioDAQ cages. Rats were then grouped based on food intake in the previous 24 hours into six groups of eight. Between 4:00 and 5:00 pm, animals were weighed and dosed with vehicle or a composition comprising the fusion protein via subcutaneous injection. The change in food weight for each cage was recorded continuously by the BioDAQ system, for a period of 48 hours after the injections. 6xHis-FP1 was used for comparison in this study.

Figure 3:
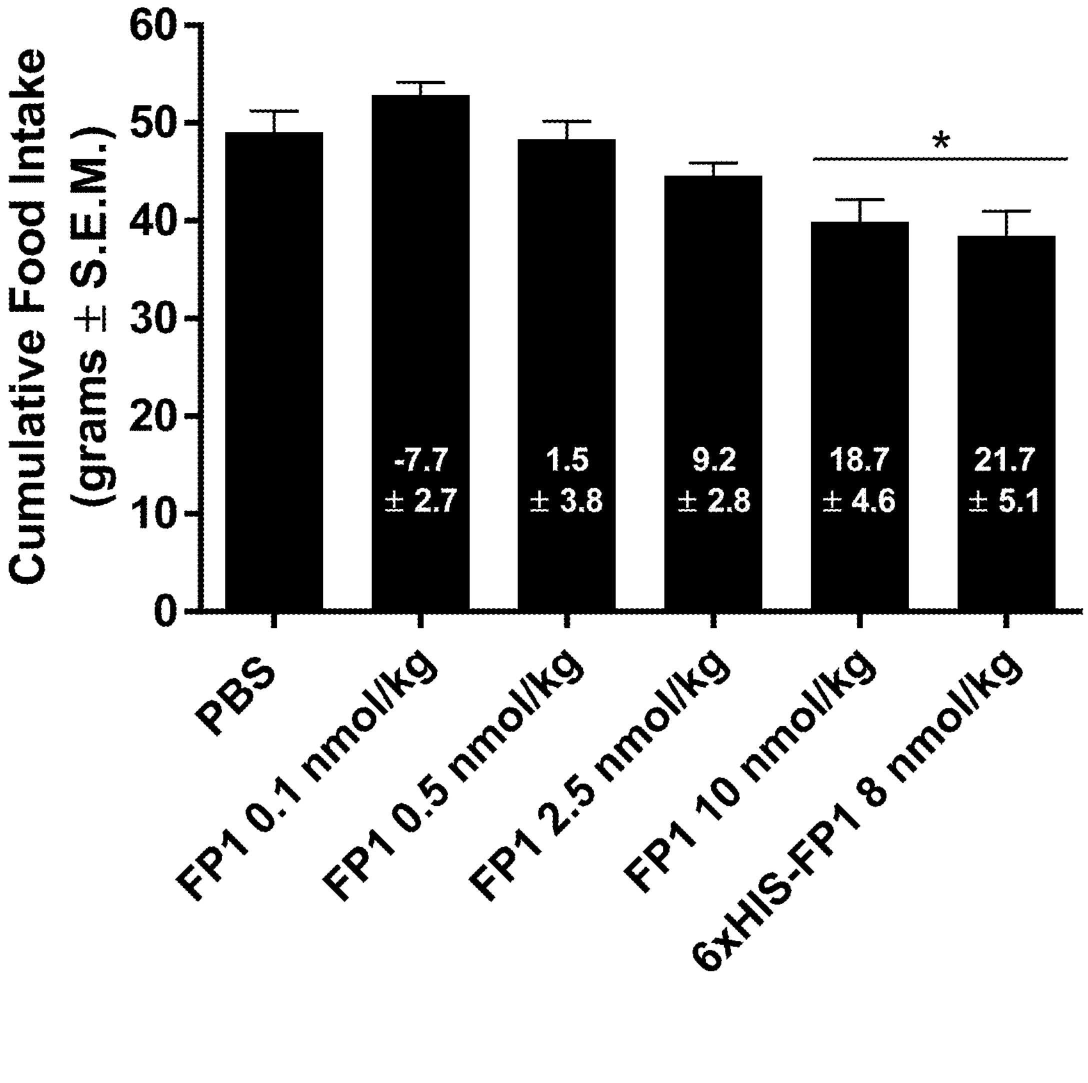
FIG. 3 shows the effects of subcutaneous administration of FP1 and 6×His-FP1 (SEQ ID NO: 26 with a 6×His tag attached at the N-terminus) on food intake in Sprague-Dawley rats, the cumulative food intake at 48 hours post-administration is depicted. Values shown within the bars are % reduction compared to vehicle (PBS) group ±SEM; N=8 animals per group. *–$p<0.05$, as compared to vehicle; p values were calculated using One-way ANOVA and Tukey's test for multiple comparisons.

The results are shown in FIG. 3 and Table 7. Subcutaneous administration of FP1 inhibited food intake at doses of 2.5 nmol/kg and 10 nmol/kg compared to vehicle-treated animals. The inhibition reached statistical significance only with the highest dose tested (10 nmol/kg) at 24 and 48 hours post-administration. 6xHis-FP1 reduced food intake at the 8 nmol/kg dose, and the effect was significant at 24 and 48 hours.

TABLE 7

Effects of subcutaneous administration of FP1 on food intake in Sprague-Dawley rats; cumulative food intake at 12, 24 and 48 hours post administration is shown

| | Cumulative Food Intake (g) | | |
|---|---|---|---|
| Treatment | 12 hours | 24 hours | 48 hours |
| PBS | 20.6 ± 1.3 | 25.3 ± 1.3 | 49.1 ± 2.1 |
| FP1, 0.1 nmol/kg | 23.3 ± 1.4 | 26.9 ± 0.8 | 52.8 ± 1.3 |
| FP1, 0.5 nmol/kg | 22.6 ± 1.7 | 25.1 ± 1.0 | 48.3 ± 1.8 |
| FP1, 2.5 nmol/kg | 20.0 ± 1.4 | 22.0 ± 1.0 | 44.6 ± 1.4 |
| FP1, 10 nmol/kg | 18.7 ± 0.9 | 19.9 ± 1.0* | 39.9 ± 2.3* |
| 6xHis-FP1, 8 nmol/kg | 17.0 ± 1.5 | 18.8 ± 1.4** | 38.4 ± 2.5** |

Data are expressed as Mean ± SEM.
*p ≤ 0.05, versus PBS;
**p ≤ 0.01, versus PBS
One-Way ANOVA-Tukey's multiple comparisons test;
n = 8/group

Example 10: Effects of FP1 on Glucose Homeostasis and Body Weight in Diet-Induced Obese (DIO) Mice The purpose of this experiment was to evaluate the effects of FP1 on food intake, body weight, and glucose homeostasis throughout two weeks of treatment in DIO C57Bl/6 mice.

Male DIO mice were weighed, and FP1 was dosed subcutaneously at 2 mL/kg every three days (q3d) at Day 0, 3, 6, 9, and 12. The vehicle and rosiglitazone treatment groups were dosed with PBS on a similar regimen. The control rosiglitazone was provided in the diet at 0.015% ad libitum. Mouse and food weights were recorded daily. Glucose was measured using a glucometer (One Touch®Ultra®, Lifescan, Milpitas, Calif.). Fat and lean mass was quantitated in conscious mice by time-domain NMR (TD-NMR) using the Bruker Mini-Spec LF110. For an oral glucose tolerance test (OGTT), mice were fasted for 4 hours. Blood glucose was measured via tail snip at 0, 30, 60, 90, and 120 minutes post oral gavage administration of 2 g/kg glucose at 10 mL/kg. Insulin was measured at 0, 30, and 90 minutes post glucose administration.

At the end of the study, the mice were euthanized via $CO_2$ inhalation, and a terminal blood sample was collected. Serum was placed into a 96 well plate on wet ice and then stored at −80° C. The liver was removed, and the fat content relative to the total mass of liver sections was assessed using TD-NMR with the Bruker MiniSpec mq60 according to the manufacturer's instructions.

The fasted homeostatic model assessment of insulin resistance (HOMA-IR) was calculated based on the product of fasted glucose (in mg/dL) and insulin (in mU/L) divided by a factor of 405.

Treatment of DIO mice with FP1 q3d at 1 nmol/kg and 10 nmol/kg reduced body weight (Table 8) and food intake (Table 9). The reductions reached statistical significance only at certain time points, as described below.

Figure 4:
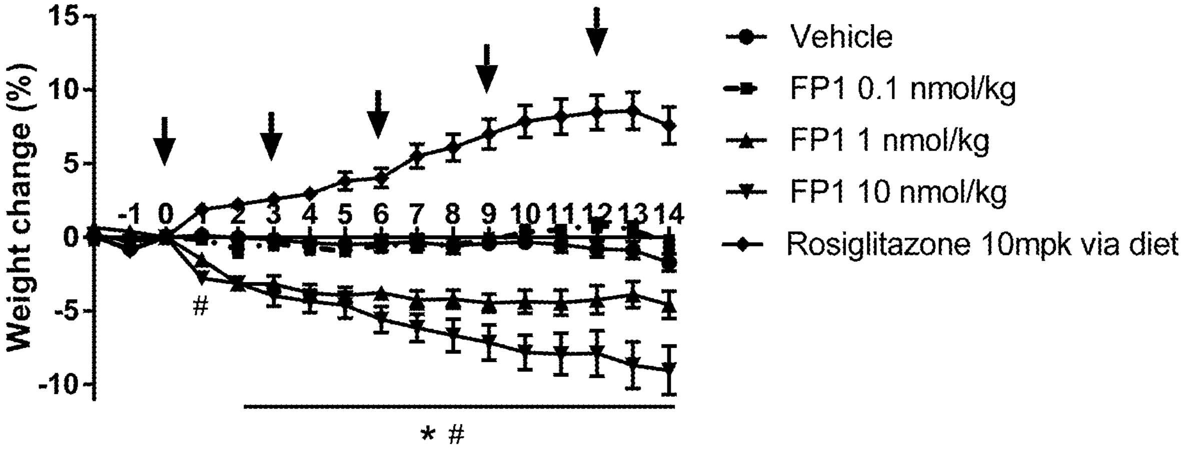
FIG. 4 shows the change in body weight of diet induced obese (DIO) mice during treatment with FP1. Arrows indicate time (days) of subcutaneous administration post initial dose (Day 0); N=8 animals per group. *–$p<0.05$, for FP1 1 nmol/kg group as compared to vehicle; #–$p<0.05$, for FP1 10 nmol/kg group as compared to vehicle; p values were calculated using Two-way RM ANOVA and Tukey's test for multiple comparisons.

Fp1 decreased body weight at doses of 1 (from day 2 to 14) and 10 nmol/kg (from day 1 to 14) in DIO mice (Table 8 and FIG. 4). A significant reduction in food intake was seen at days 1 and 2 of the study at the dose of 1 nmol/kg and at days 1, 8 and 9 at the 10 nmol/kg dose (Table 9).

TABLE 8

Body weight change (% of starting) during treatment with FP1 in DIO mice

| Treatment | Vehicle | FP1 (nmol/kg) | | | Rosiglitazone |
|---|---|---|---|---|---|
| Day | n/a | 0.1 | 1 | 10 | 10 mpk/day |
| −2 | 0.1 ± 0.2 | −0.1 ± 0.4 | 0.6 ± 0.4 | 0.2 ± 0.3 | 0.1 ± 0.2 |
| −1 | −0.8 ± 0.3 | −0.2 ± 0.3 | 0.4 ± 0.3 | −0.3 ± 0.4 | −0.9 ± 0.2 |
| 0 | 0.0 ± 0.0 | 0.0 ± 0.0 | 0.0 ± 0.0 | 0.0 ± 0.0 | 0.0 ± 0.0 |
| 1 | 0.1 ± 0.2 | −0.1 ± 0.4 | −1.5 ± 0.5 | −2.8 ± 0.4* | 1.9 ± 0.2 |
| 2 | 0.0 ± 0.3 | −0.8 ± 0.5 | −3.2 ± 0.4* | −3.1 ± 0.5* | 2.2 ± 0.5 |
| 3 | −0.2 ± 0.4 | −0.4 ± 0.4 | −3.2 ± 0.6* | −4.0 ± 0.7* | 2.6 ± 0.5 |
| 4 | −0.4 ± 0.5 | −0.7 ± 0.5 | −3.8 ± 0.6* | −4.4 ± 0.8* | 3.0 ± 0.5* |
| 5 | −0.5 ± 0.4 | −1.0 ± 0.3 | −4.0 ± 0.5* | −4.6 ± 0.9* | 3.8 ± 0.6* |
| 6 | −0.4 ± 0.6 | −0.5 ± 0.5 | −3.8 ± 0.4* | −5.6 ± 0.9* | 4.0 ± 0.7* |
| 7 | −0.3 ± 0.5 | −0.5 ± 0.5 | −4.3 ± 0.6* | −6.1 ± 0.9* | 5.5 ± 0.8* |
| 8 | −0.6 ± 0.5 | −0.5 ± 0.5 | −4.2 ± 0.6* | −6.7 ± 1.1* | 6.1 ± 0.9* |
| 9 | −0.4 ± 0.5 | −0.2 ± 0.5 | −4.5 ± 0.6* | −7.2 ± 1.2* | 7.0 ± 1.0* |
| 10 | −0.3 ± 0.5 | 0.3 ± 0.5 | −4.4 ± 0.8* | −7.8 ± 1.2* | 7.8 ± 1.1* |
| 11 | −0.5 ± 0.5 | 0.5 ± 0.4 | −4.4 ± 0.8* | −7.9 ± 1.4* | 8.2 ± 1.2* |
| 12 | −0.8 ± 0.6 | 0.8 ± 0.5 | −4.3 ± 1.0* | −7.9 ± 1.5* | 8.5 ± 1.2* |
| 13 | −0.8 ± 0.6 | 0.5 ± 0.5 | −3.9 ± 0.9* | −8.7 ± 1.6* | 8.6 ± 1.3* |
| 14 | −1.7 ± 0.6 | −0.4 ± 0.5 | −4.6 ± 1.0* | −9.0 ± 1.7* | 7.6 ± 1.3* |

Data are expressed as Mean ± SEM.
n = 8 per group.
*= p < 0.05, compared to that of the vehicle treated group.

TABLE 9

Daily food intake (gm) during treatment with FP1 in DIO mice

| Treatment | Vehicle | FP1 (nmol/kg) | | | Rosiglitazone |
|---|---|---|---|---|---|
| Day | n/a | 0.1 | 1 | 10 | 10 mpk/day |
| −2 | 2.9 ± 0.1 | 3.0 ± 0.2 | 2.9 ± 0.1 | 2.8 ± 0.1 | 2.8 ± 0.1 |
| 0 | 3.0 ± 0.1 | 3.0 ± 0.1 | 2.8 ± 0.1 | 2.8 ± 0.1 | 3.0 ± 0.1 |
| 1 | 2.9 ± 0.1 | 3.1 ± 0.1 | 2.1 ± 0.2* | 1.5 ± 0.1* | 3.6 ± 0.1* |
| 2 | 3.0 ± 0.1 | 3.0 ± 0.1 | 2.3 ± 0.1* | 2.6 ± 0.2 | 3.9 ± 0.2* |
| 3 | 2.8 ± 0.1 | 3.0 ± 0.1 | 2.6 ± 0.1 | 2.4 ± 0.2 | 3.5 ± 0.1* |
| 4 | 2.3 ± 0.1 | 2.6 ± 0.1 | 2.2 ± 0.1 | 2.3 ± 0.1 | 3.3 ± 0.1* |
| 5 | 2.8 ± 0.1 | 3.0 ± 0.1 | 2.8 ± 0.1 | 2.6 ± 0.1 | 3.7 ± 0.2* |
| 6 | 2.8 ± 0.1 | 3.1 ± 0.1 | 2.9 ± 0.1 | 2.4 ± 0.2 | 3.7 ± 0.2* |
| 7 | 2.7 ± 0.1 | 2.9 ± 0.1 | 2.6 ± 0.1 | 2.4 ± 0.1 | 3.8 ± 0.2* |
| 8 | 2.7 ± 0.1 | 2.9 ± 0.1 | 2.6 ± 0.1 | 2.1 ± 0.1* | 3.5 ± 0.2* |
| 9 | 3.0 ± 0.1 | 3.3 ± 0.1 | 2.8 ± 0.1 | 2.5 ± 0.2* | 4.3 ± 0.2* |
| 10 | 2.6 ± 0.1 | 3.0 ± 0.1 | 2.6 ± 0.1 | 2.2 ± 0.1 | 3.6 ± 0.1* |
| 11 | 2.9 ± 0.1 | 3.1 ± 0.1 | 2.7 ± 0.2 | 2.6 ± 0.2 | 3.4 ± 0.1* |
| 12 | 2.7 ± 0.1 | 3.1 ± 0.1 | 3.0 ± 0.1 | 3.0 ± 0.2 | 3.6 ± 0.2* |
| 13 | 2.6 ± 0.1 | 2.8 ± 0.1 | 2.8 ± 0.1 | 2.2 ± 0.2 | 3.2 ± 0.1* |

Data are expressed as Mean ± SEM.
n = 8 per group.
*= $p < 0.05$, compared to that of the vehicle treated group.

Figure 5A:
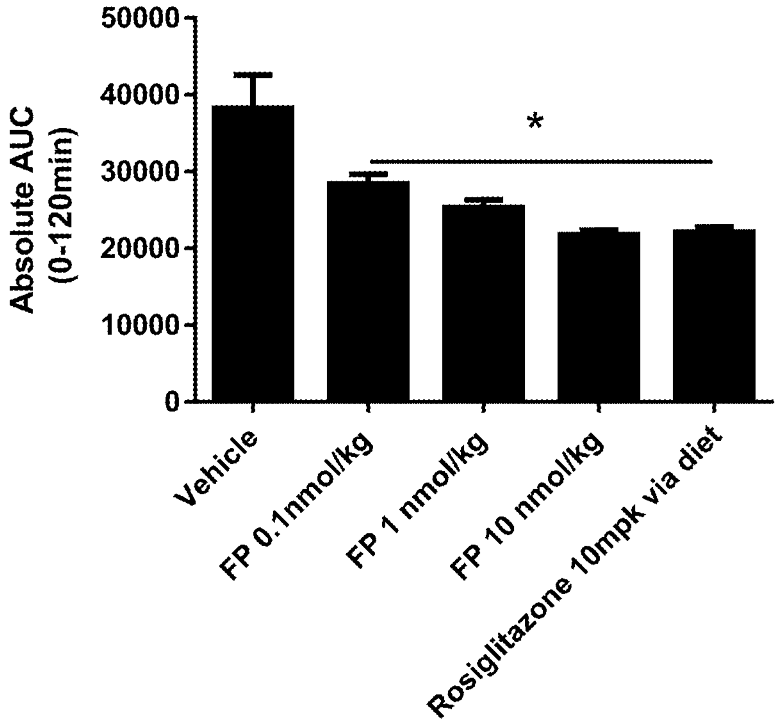
FIGS. 5A and 5B show the blood glucose levels in DIO mice during an oral glucose tolerance test (OGTT) after 14 days of dosing of FP1 every 3 days (q3d), the levels are expressed as the area under the curve. N=8 animals per group. *–$p<0.05$, for FP1 1 nmol/kg group as compared to vehicle; p values were calculated using One-way ANOVA and Tukey's test for multiple comparisons.
Figure 5B:
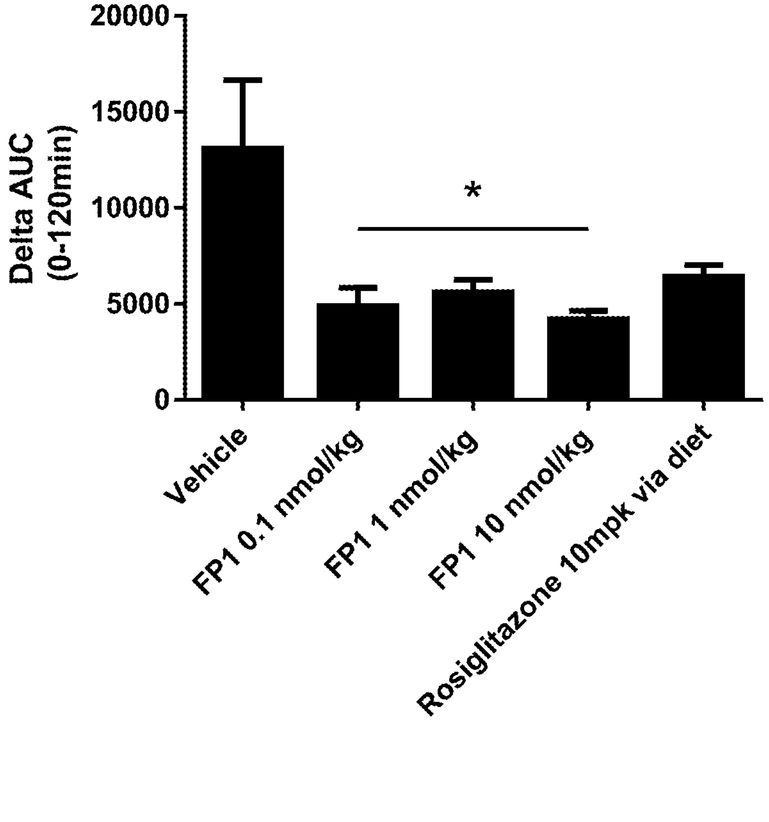

In an OGTT performed on day 14 of the study, FP1 significantly lowered glucose levels compared to vehicle-treated animals at all time points after time 0 at all three doses tested (Table 10). This was further quantitated as total area under the curve (AUC) and delta AUC, which were significantly lower compared to vehicle for all three doses tested (Table 10 and FIGS. 5A and 5B).

TABLE 10

Blood glucose (mg/dL) levels during an OGTT after fourteen days of q3d dosing of FP1 in DIO mice

| Treatment | Dose (nmol/kg) | Time after Glucose Challenge (min) 0 | 30 | 60 | 90 | 120 | Total AUC (mg/dL/120 min) | Delta AUC (mg/dL/120 min) |
|---|---|---|---|---|---|---|---|---|
| Vehicle | NA | 209.6 ± 16.5 | 399.4 ± 46.4 | 338.5 ± 46.3 | 297.5 ± 38.0 | 269.3 ± 36.6 | 38244.4 ± 4308.2 | 13089.4 ± 3573.0 |
| FP1 | 0.1 | 196.6 ± 7.6 | 319.0 ± 21.5* | 241.6 ± 14.4* | 196.0 ± 12.8* | 184.0 ± 6.3* | 28408.1 ± 1236.1* | 4885.5 ± 955.1* |
| | 1 | 164.0 ± 7.2 | 251.4 ± 13.0* | 227.6 ± 12.6* | 191.9 ± 9.4* | 180.6 ± 13.1* | 25295.6 ± 1026.7* | 5615.6 ± 647.6* |
| | 10 | 146.6 ± 5.9 | 195.6 ± 14.5* | 197.1 ± 6.9* | 172.1 ± 6.3* | 174.9 ± 13.8* | 21768.8 ± 603.0* | 4211.4 ± 425.8* |
| Rosi-glitazone | 10 mpk/day | 130.8 ± 6.0 | 199.1 ± 12.9* | 204.4 ± 8.5* | 184.1 ± 10.9* | 169.1 ± 5.7* | 22115.6 ± 671.9* | 6425.6 ± 599.6 |

Data are expressed as Mean ± SEM. n = 8 per group.
*= $p < 0.05$, compared to that of the vehicle treated group.

Figure 6:
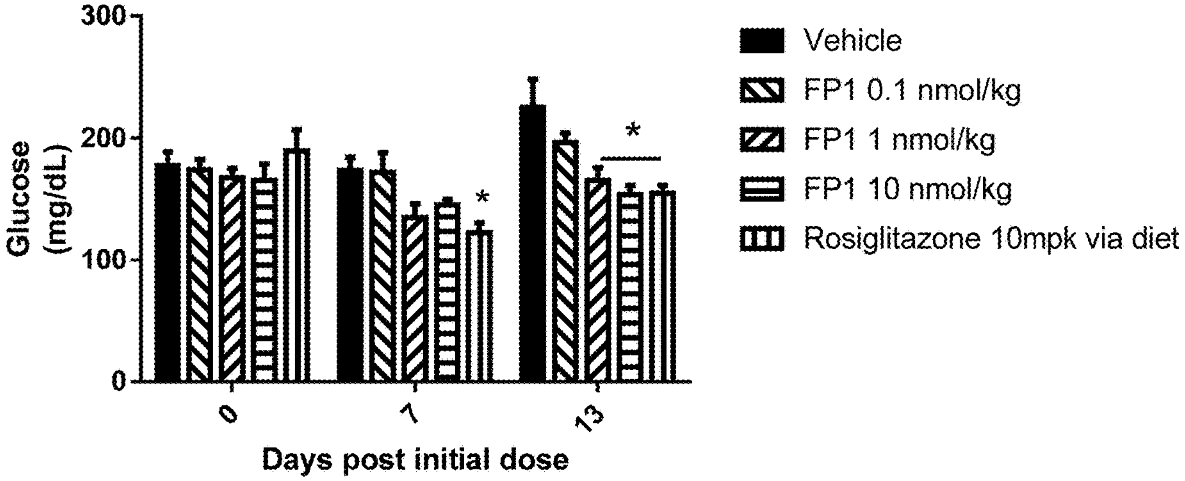
FIG. 6 shows the fed blood glucose levels in DIO mice during treatment with FP1. N=8 animals per group. *–$p<0.05$, as compared to vehicle; p values were calculated using Two-way RM ANOVA and Tukey's test for multiple comparisons.

Fed blood glucose levels were measured at the start (day 0), at day 7 and at day 13 of the study (Table 11 and FIG. 6). FP1 decreased blood glucose in a statistically significant manner at doses of 1 nmol/kg and 10 nmol/kg on day 13 of the study.

TABLE 11

Fed blood glucose during treatment of DIO mice with q3d treatment of FP1

| Treatment | Dose (nmol/kg) | Time after start of treatment (days) 0 | 7 | 13 |
|---|---|---|---|---|
| Vehicle | NA | 177.6 ± 10.9 | 173.6 ± 10.6 | 225.3 ± 23.0 |
| FP1 | 0.1 | 174.1 ± 8.5 | 171.8 ± 16.3 | 196.4 ± 8.1 |
| | 1 | 167.5 ± 7.8 | 135.1 ± 11.2 | 165.3 ± 10.3* |
| | 10 | 165.3 ± 13.7 | 145.3 ± 4.9 | 153.8 ± 7.5* |
| Rosiglitazone | 10 mpk/day | 189.6 ± 17.3 | 122.6 ± 8.1* | 154.8 ± 6.5* |

Data are expressed as Mean ± SEM.
n = 8 per group.
*= $p < 0.05$, compared to that of the vehicle treated group.

Figure 7:
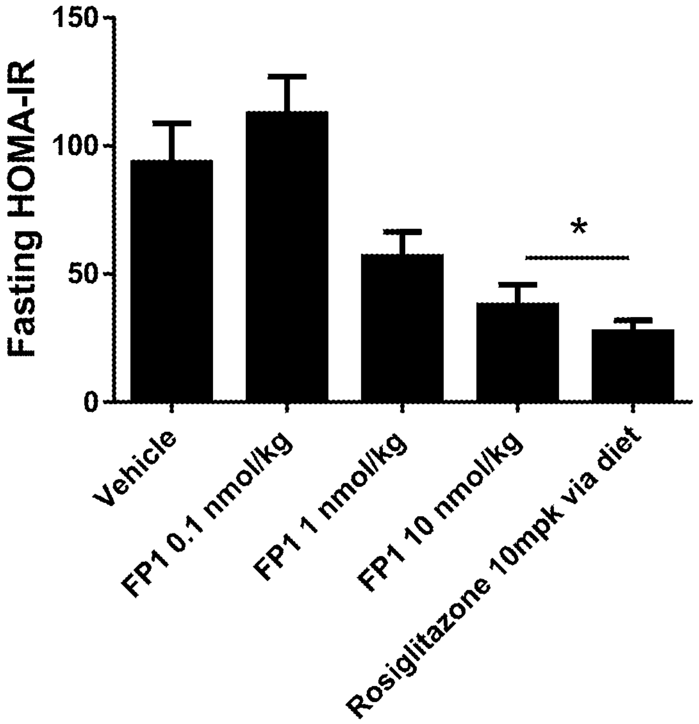
FIG. 7 shows the 4 hour fasting homeostatic model assessment of insulin resistance (HOMA-IR) in DIO mice after 14 days of treatment with FP1. N=8 animals per group. *–$p<0.05$, as compared to vehicle; p values were calculated using One-way ANOVA and Tukey's test for multiple comparisons.

Plasma insulin levels during the OGTT were significantly higher for FP1 than for the corresponding vehicle group for a 0.1 nmol/kg dose at 30 minutes, and lower at the 1 and 10 nmol/kg doses at the same time point (Table 12). The insulin excursion during the OGTT, as measured by total AUC, was higher than the vehicle group for the 0.1 nmol/kg dose of FP1 (Table 12), and lower at the 1 and 10 nmol/kg dose. In both cases, statistical significance was reached only at the lowest dose. At the 90 minute time point, mice treated with 1 and 10 nmol/kg of FP1 had lower insulin levels; however, this effect did not achieve statistical significance. HOMA-IR, used as a measure of insulin sensitivity, was measured on day 14 of the study. At this time point, FP1 decreased HOMA-IR, or improved insulin sensitivity, at 10 nmol/kg (Table 13 and FIG. 7).

TABLE 12

Plasma insulin (pg/mL) levels during an OGTT after fourteen days of q3d dosing of FP1 in DIO mice

| Treatment | Dose (nmol/kg) | Time after Glucose Challenge (min) 0 | 30 | 90 | Total AUC (pg/mL/90 min) |
|---|---|---|---|---|---|
| Vehicle | NA | 6096.0 ± 774.3 | 14660.0 ± 3031.2 | 5034.4 ± 405.1 | 902151.9 ± 143123.2 |
| FP1 | 0.1 | 7861.0 ± 779.5 | 33825.8 ± 7902.0* | 6494.4 ± 797.0 | 1834808.8 ± 381276.1* |
| | 1 | 4808.1 ± 795.8 | 13061.8 ± 2226.3 | 3443.5 ± 342.5 | 763218.1 ± 119766.8 |
| | 10 | 3478.3 ± 634.6 | 7147.0 ± 823.8 | 2958.0 ± 414.0 | 462528.8 ± 44653.1 |
| Rosiglitazone | 10 mpk/day | 2965.6 ± 524.2 | 2203.1 ± 193.5* | 1180.0 ± 57.1 | 179025.0 ± 9970.7 |

Data are expressed as Mean ± SEM.
n = 8 per group.
*= $p < 0.05$, compared to that of the vehicle treated group.

TABLE 13

Fasted HOMA-IR in DIO mice after fourteen days of q3d treatment of FP1

| Treatment | Dose (nmol/kg) | HOMA-IR |
|---|---|---|
| Vehicle | NA | 93.5 ± 15.3 |
| FP1 | 0.1 | 112.4 ± 14.6 |
| | 1 | 56.7 ± 9.7 |
| | 10 | 37.7 ± 8.2* |
| Rosiglitazone | 10 mpk/day | 27.3 ± 4.7* |

Data are expressed as Mean ± SEM.
n = 8 per group.
*= $p < 0.05$, compared to that of the vehicle treated group.

The magnitude of weight loss achieved by day 13 did not result in measurable changes in absolute fat mass or percent fat mass at any dose (Table 14). At the 10 nmol/kg dose, there was a significant decrease in absolute lean mass. This decrease was not observed when expressed as percent lean mass. Liver weights were measured during terminal necropsy on day 15 of the study (Table 15). FP1 decreased absolute liver weight and liver weight as a percentage of body weight at the 10 nmol/kg dose. A decrease was observed at the 1 nmol/kg dose, but this did not reach statistical significance for either parameter. Liver fat was measured on a biopsy by NMR (Table 16). FP1 fusion protein decreased hepatic fat content, expressed as a percentage of liver biopsy weight, at 1 and 10 nmol/kg doses. The reduction was significant at the higher dose.

TABLE 14

Body composition after thirteen days of treatment with FP1 q3d in DIO mice

| Treatment | Dose (nmol/kg) | Fat Mass (g) | Lean Mass (g) | Fat Mass (% of body) | Lean Mass (% of body) |
|---|---|---|---|---|---|
| Vehicle | NA | 11.6 ± 0.5 | 29.6 ± 0.4 | 23.4 ± 0.8 | 59.6 ± 0.9 |
| FP1 | 0.1 | 12.2 ± 0.4 | 29.7 ± 0.4 | 24.1 ± 0.6 | 58.5 ± 0.6 |
| | 1 | 12.1 ± 0.3 | 28.0 ± 0.4 | 25.1 ± 0.3 | 58.3 ± 0.6 |
| | 10 | 10.6 ± 0.3 | 27.7 ± 0.4* | 23.1 ± 0.3 | 60.6 ± 0.6 |
| Rosiglitazone | 10 mpk/day | 14.9 ± 0.6* | 30.0 ± 0.5 | 27.2 ± 0.4* | 55.0 ± 0.6* |

Data are expressed as Mean ± SEM.
n = 8 per group.
*= $p < 0.05$, compared to that of the vehicle treated group.

TABLE 15

Liver weight after fifteen days of treatment with FP1 q3d in DIO mice

| Treatment | Dose (nmol/kg) | Liver weight (g) | Liver Weight (% of body) |
|---|---|---|---|
| Vehicle | NA | 2.6 ± 0.1 | 5.4 ± 0.2 |
| FP1 | 0.1 | 2.9 ± 0.2 | 5.8 ± 0.2 |
| | 1 | 2.2 ± 0.1 | 4.6 ± 0.2 |
| | 10 | 1.9 ± 0.1* | 4.2 ± 0.1* |
| Rosiglitazone | 10 mpk/day | 2.5 ± 0.2 | 4.6 ± 0.2 |

Data are expressed as Mean ± SEM.
n = 8 per group.
*= $p < 0.05$, compared to that of the vehicle treated group.

TABLE 16

Liver fat content measured after fifteen days of treatment with FP1 q3d in DIO mice

| Treatment | Dose (nmol/kg) | Fat (%) |
|---|---|---|
| Vehicle | NA | 27.3 ± 2.1 |
| FP1 | 0.1 | 26.0 ± 1.4 |
| | 1 | 22.5 ± 1.4 |
| | 10 | 17.8 ± 1.6* |
| Rosiglitazone | 10 mpk/day | 25.9 ± 0.8 |

Data are expressed as Mean ± SEM.
n = 8 per group.
*= $p < 0.05$, compared to that of the vehicle treated group.

Example 11: Effects of FP1 on Blood Glucose Levels and Body Weight in Ob/Ob Mice The purpose of this experiment was to evaluate the effects of FP1 on body weight and blood glucose levels over eight days of treatment in obese, hyperglycemic, leptin-deficient ob/ob mice.

Male ob/ob mice were weighed and FP1 was administered subcutaneously at 2 mL/kg every three days (q3d) at Day 0, 3 and 6. Mouse and food weights were recorded daily. Glucose was measured daily using a glucometer. At the end of the study, mice were euthanized, and a terminal blood sample was collected.

Figure 8:
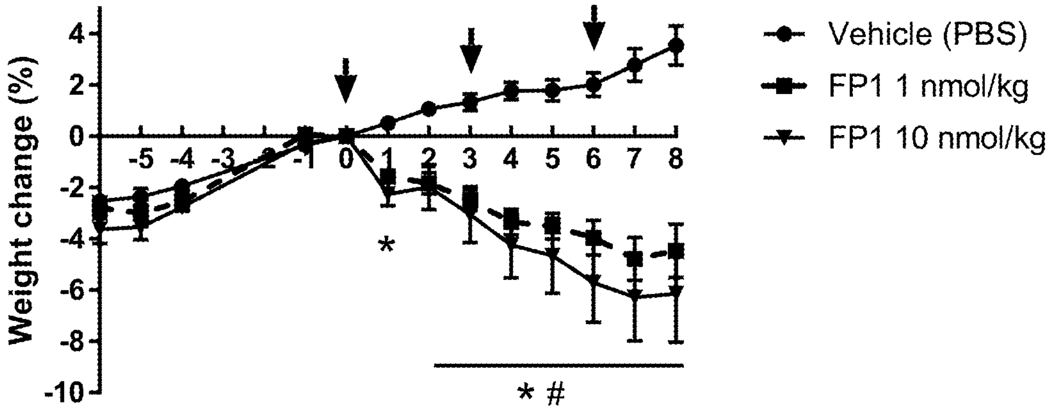
FIG. 8 shows the change in body weight in ob/ob mice during treatment with FP1 every 3 days (qd3). Arrows indicate time (days) of subcutaneous administration post initial dose (Day 0); N=9 animals per group. *–p<0.05, for FP1 10 nmol/kg group as compared to vehicle; #–p<0.05, for FP1 1 nmol/kg group as compared to vehicle; p values were calculated using Two-way RM ANOVA and Tukey's test for multiple comparisons.

FP1, at the 1 nmol/kg dose, significantly decreased body weight (expressed as a percentage of starting body weight) in ob/ob mice starting at day 2 until day 8, relative to vehicle-treated mice. FP1, at the 10 nmol/kg dose, decreased body weight (expressed as a percentage of starting body weight) in ob/ob mice starting at day 1 until day 8 relative to vehicle-treated mice (Table 17 and FIG. 8).

TABLE 17

Body weight change (% of starting) during treatment with FP1 q3d in ob/ob mice

| Treatment | Vehicle | FP1 | |
|---|---|---|---|
| Day | n/a | 1 nmol/kg | 10 nmol/kg |
| −6 | −2.5 ± 0.3 | −2.8 ± 0.4 | −3.6 ± 0.5 |
| −5 | −2.4 ± 0.3 | −3.0 ± 0.5 | −3.5 ± 0.5 |
| −4 | −1.9 ± 0.2 | −2.5 ± 0.4 | −2.8 ± 0.3 |
| −1 | −0.3 ± 0.3 | 0.1 ± 0.2 | −0.3 ± 0.2 |
| 0 | 0.0 ± 0.0 | 0.0 ± 0.0 | 0.0 ± 0.0 |
| 1 | 0.5 ± 0.2 | −1.6 ± 0.2 | −2.3 ± 0.5* |
| 2 | 1.1 ± 0.2 | −1.8 ± 0.4* | −2.0 ± 0.9* |
| 3 | 1.3 ± 0.3 | −2.5 ± 0.4* | −3.1 ± 1.1* |
| 4 | 1.8 ± 0.3 | −3.3 ± 0.5* | −4.2 ± 1.3* |
| 5 | 1.8 ± 0.4 | −3.5 ± 0.5* | −4.7 ± 1.5* |
| 6 | 2.0 ± 0.5 | −4.0 ± 0.7* | −5.7 ± 1.6* |
| 7 | 2.8 ± 0.6 | −4.8 ± 0.8* | −6.3 ± 1.7* |
| 8 | 3.5 ± 0.8 | −4.5 ± 1.0* | −6.1 ± 1.9* |

Data are expressed as Mean ± SEM.
n = 8 per group.
*= $p < 0.05$, compared to that of the vehicle treated group.

Figure 9:
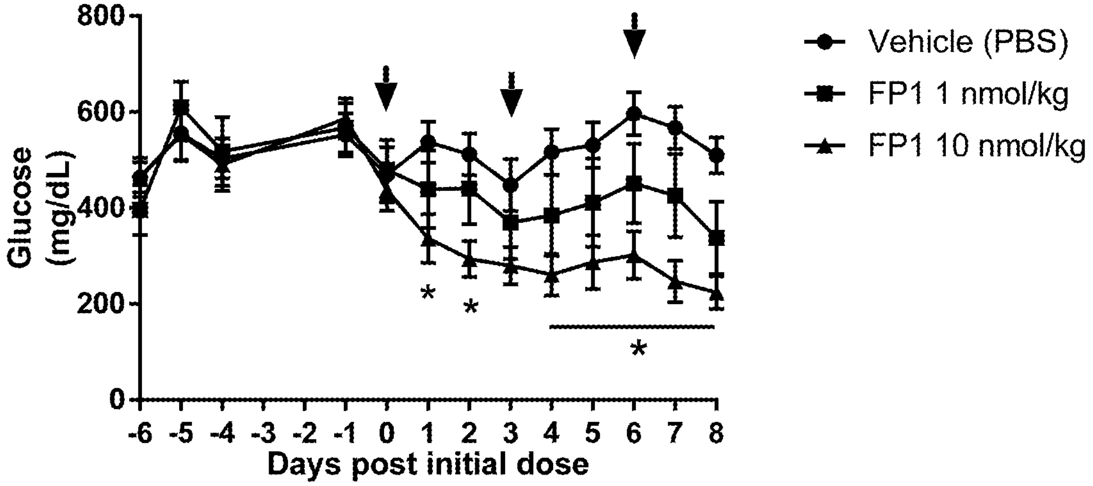
FIG. 9 shows the blood glucose levels in ob/ob mice during treatment with FP1. Arrows indicate time (days) of subcutaneous administration post initial dose (Day 0); N=9 animals per group. *–p<0.05, for FP1 10 nmol/kg group as compared to vehicle; #–p<0.05, for FP1 1 nmol/kg group as compared to vehicle; p values were calculated using Two-way RM ANOVA and Tukey's test for multiple comparisons.

FP1, at the 10 nmol/kg dose, decreased fed blood glucose values in ob/ob mice on study day 1 and 2 and from day 4 until day 8 relative to vehicle-treated mice. A reduction in in blood glucose was observed at 1 nmol/kg; however, this effect did not reach statistical significance (Table 18 and FIG. 9).

TABLE 18

Fed blood glucose during treatment of ob/ob mice with FP1 q3d

| Treatment | Vehicle | FP1 | |
|---|---|---|---|
| Day | n/a | 1 nmol/kg | 10 nmol/kg |
| −6 | 463.6 ± 31.2 | 395.7 ± 52.0 | 463.6 ± 41.0 |
| −5 | 554.9 ± 57.5 | 609.6 ± 53.6 | 552.9 ± 53.0 |
| −4 | 502.9 ± 41.6 | 517.9 ± 71.6 | 490.3 ± 54.4 |
| −1 | 552.1 ± 45.1 | 567.2 ± 51.2 | 586.0 ± 42.6 |
| 0 | 468.8 ± 57.3 | 479.7 ± 61.8 | 437.0 ± 42.7 |
| 1 | 537.0 ± 42.8 | 439.0 ± 80.4 | 336.2 ± 51.0* |
| 2 | 511.7 ± 43.5 | 440.0 ± 74.3 | 293.7 ± 37.6* |
| 3 | 447.8 ± 54.2 | 369.6 ± 75.9 | 279.4 ± 38.8 |
| 4 | 516.3 ± 47.0 | 384.6 ± 84.0 | 261.2 ± 43.7* |
| 5 | 531.0 ± 47.1 | 410.9 ± 92.2 | 286.9 ± 55.8* |
| 6 | 596.1 ± 45.1 | 451.1 ± 82.6 | 301.9 ± 49.3* |
| 7 | 566.7 ± 44.3 | 425.3 ± 86.9 | 246.7 ± 43.5* |
| 8 | 509.9 ± 37.6 | 337.8 ± 75.1 | 223.4 ± 34.1* |

Data are expressed as Mean ± SEM.
n = 8 per group.

Example 12: Multispecies Pharmacokinetics

Mouse Pharmacokinetics

Figure 10:
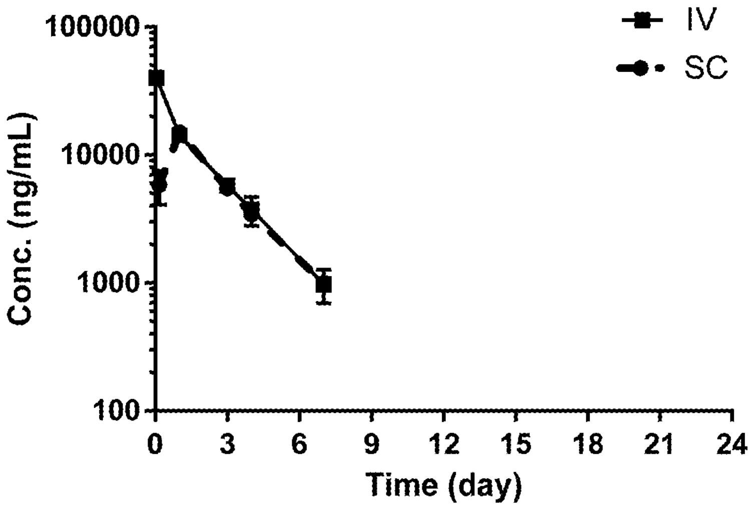
FIG. 10 shows the mean (±standard deviation, SD) of the serum drug concentration-time profile of FP1 following 2 mg/kg intravenous (IV) and subcutaneous (SC) administration in C57Bl/6 mice.

FP1 was administered to female C57Bl/6 mice at a dose of 2 mg/kg IV and SC in PBS, pH 7. Blood samples were collected, serum was processed and drug concentrations were measured up to 7 days following both routes of administration. The concentration of FP1 was determined using an immunoassay method. The serum drug concentration-time profile is summarized in Tables 19 and 20 and illustrated in FIG. 10.

TABLE 19

Serum concentration (nM) of FP1 over time following a single SC administration in C57Bl/6 female mice

| | FP1 - SC Dose | | | | | | |
|---|---|---|---|---|---|---|---|
| Timepoint | Animal 56 Result (nM) | Animal 57 Result (nM) | Animal 58 Result (nM) | Animal 60 Result (nM) | Animal 63 Result (nM) | Average Result (nM) | Std Dev |
| 4 hr | 32.299 | 50.735 | 42.766 | 32.407 | 23.018 | 36.245 | 10.698 |
| 24 hr | 88.822 | 106.418 | 88.648 | 103.841 | 80.346 | 93.615 | 11.093 |
| 72 hr | 33.563 | 38.473 | 32.473 | 33.625 | 32.769 | 34.181 | 2.451 |
| 96 hr | 20.639 | 24.988 | 21.247 | 19.356 | 20.771 | 21.400 | 2.124 |
| Day 7 | 5.399 | 6.919 | 7.234 | 5.994 | 5.637 | 6.237 | 0.803 |

TABLE 20

Serum concentration (nM) of FP1 over time following a single IV administration in C57Bl/6 female mice

| | FP1 - IV Dose | | | | | | |
|---|---|---|---|---|---|---|---|
| Timepoint | Animal 52 Result (nM) | Animal 53 Result (nM) | Animal 65 Result (nM) | Animal 66 Result (nM) | Animal 70 Result (nM) | Average Result (nM) | Std Dev |
| 1 hr | 240.419 | 233.318 | 232.484 | 276.913 | 272.727 | 251.172 | 21.857 |
| 24 hr | 86.823 | 95.774 | 80.201 | 93.153 | 88.853 | 88.961 | 6.027 |

TABLE 20-continued

Serum concentration (nM) of FP1 over time following a single IV administration in C57Bl/6 female mice

| Timepoint | FP1 - IV Dose Animal 52 Result (nM) | Animal 53 Result (nM) | Animal 65 Result (nM) | Animal 66 Result (nM) | Animal 70 Result (nM) | Average Result (nM) | Std Dev |
|---|---|---|---|---|---|---|---|
| 72 hr | 33.634 | 37.447 | 33.108 | 41.680 | 34.034 | 35.981 | 3.612 |
| 96 hr | 22.666 | 20.588 | 19.458 | 33.718 | 20.361 | 23.358 | 5.909 |
| Day 7 | 7.401 | 5.606 | 4.896 | 8.556 | 4.205 | 6.133 | 1.803 |

Pharmacokinetic analysis revealed a terminal half-life of 1.67 and 1.57 days for FP1 in C57Bl/6 mice following SC and IV administration, respectively (Table 21). FP1 demonstrated a mean bioavailability of ~71% following SC administration.

TABLE 21

Mean (±SD) pharmacokinetic parameters of FP1 following 2 mg/kg IV and SC administration in female C57Bl/6 mice

| Route | | $t_{1/2}$ (day) | CL or CL/F (ml/day/kg) | Vss (ml/kg) | $C_{max}$ (ng/ml) | $T_{max}$* (day) | $AUC_{0-last}$ (day*ng/ml) | $AUC_{0-inf}$ (day*ng/ml) |
|---|---|---|---|---|---|---|---|---|
| SC | Mean | 1.67 | 49.48 | | 14994 | 1 | 38315 | 40734 |
| | (SD) | (0.14) | (4.791) | | (1776) | | (3851) | (4072) |
| IV | Mean | 1.57 | 35.00 | 69.03 | 40231 | 0.04 | 55263 | 57531 |
| | (SD) | (0.19) | (3.13) | (5.8) | (3500) | | (4853) | (5416) |

Note:
*Tmax (median)

Rat Pharmacokinetics

Figure 11:
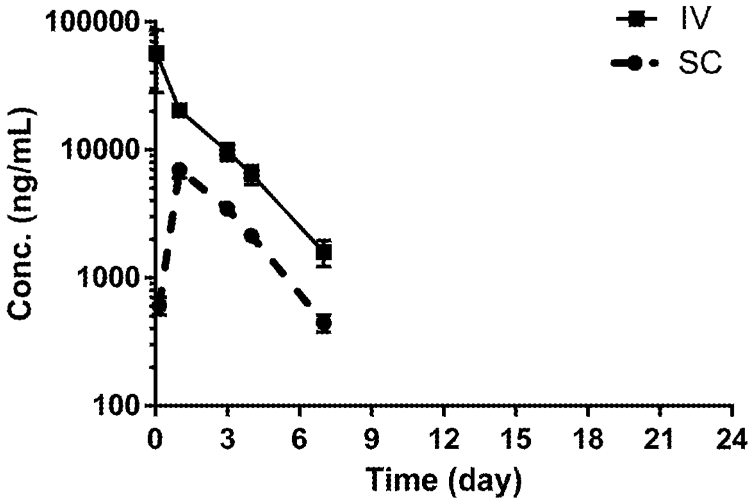
FIG. 11 shows the mean (±SD) of the serum drug concentration-time profile of FP1 following 2 mg/kg IV and SC administration in Sprague-Dawley rats.

FP1 was administered to female Sprague Dawley rats at a dose of 2 mg/kg IV and SC in PBS, pH 7. Blood samples were collected, serum was processed and drug concentrations were measured up to 7 days following both routes of administration. The concentration of FP1 was determined using an immunoassay method. The serum drug concentration-time profile is summarized in Tables 22 and 23 and illustrated in FIG. 11.

TABLE 22

Serum concentration (nM) of FP1 over time following a single SC administration in female Sprague Dawley rats.

| Timepoint | FP1 - Group 3 (SC Dose) Animal 53 Result (nM) | Animal 55 Result (nM) | Animal 67 Result (nM) | Animal 68 Result (nM) | Animal 69 Result (nM) | Average Result (nM) | Std Dev |
|---|---|---|---|---|---|---|---|
| 4 hr | 4.766 | 3.500 | 3.932 | 3.546 | 3.250 | 3.799 | 0.593 |
| 24 hr | 45.118 | 53.192 | 39.196 | 39.823 | 40.804 | 43.627 | 5.826 |
| 72 hr | 18.900 | 24.102 | 23.124 | 23.718 | 18.933 | 21.755 | 2.615 |
| 96 hr | 12.193 | 14.333 | 14.185 | 14.669 | 11.256 | 13.327 | 1.511 |
| Day 7 | 2.805 | 2.821 | 2.447 | 3.438 | 2.358 | 2.774 | 0.426 |

TABLE 23

Serum concentration (nM) of FP1 over time following a single IV administration in female Sprague Dawley rats

| | FP1 - Group 4 (IV Dose) | | | | | | |
|---|---|---|---|---|---|---|---|
| Timepoint | Animal 51 Result (nM) | Animal 52 Result (nM) | Animal 57 Result (nM) | Animal 64 Result (nM) | Animal 66 Result (nM) | Average Result (nM) | Std Dev |
| 1 hr | 43.620* | 382.676 | 403.255 | 443.080 | 510.105 | 356.547 | 181.560 |
| 24 hr | 102.665* | 142.661 | 139.066 | 124.528 | 126.425 | 127.069 | 15.728 |
| 72 hr | 46.720 | 60.105 | 67.090 | 59.257 | 70.423 | 60.719 | 9.127 |
| 96 hr | 29.409 | 39.897 | 41.225 | 42.258 | 48.074 | 40.173 | 6.779 |
| Day 7 | 6.976 | 11.251 | 8.913 | 9.540 | 13.006 | 9.937 | 2.298 |

*Repeat analysis confirmed results

Pharmacokinetic analysis revealed a terminal half-life of 1.34 and 1.51 days for FP1 in Sprague Dawley rats following SC and IV administration, respectively (Table 24). FP1 demonstrated a mean bioavailability of ~23% following SC administration.

TABLE 24

Mean (±SD) pharmacokinetic parameters of FP1 following 2 mg/kg IV and SC administration in Sprague Dawley rats

| Route | | $t_{1/2}$ (day) | CL or CL/F (ml/day/kg) | Vss (ml/kg) | $C_{max}$ (ng/ml) | $T_{max}$* (day) | $AUC_{0\text{-}last}$ (day*ng/ml) | $AUC_{0\text{-}inf}$ (day*ng/ml) |
|---|---|---|---|---|---|---|---|---|
| SC | Mean | 1.34 | 100.09 | | 6987 | 1 | 19250 | 20112 |
| | (SD) | (0.04) | (3.97) | | (417) | | (794) | (820) |
| IV | Mean | 1.51 | 24.75 | 53.41 | 59000 | 0.04 | 83028 | 86525 |
| | (SD) | (0.12) | (8.53) | (17.15) | (25031) | | (20126) | (20881) |

Note:
*Tmax (median)

Monkey Pharmacokinetics

Figure 12:
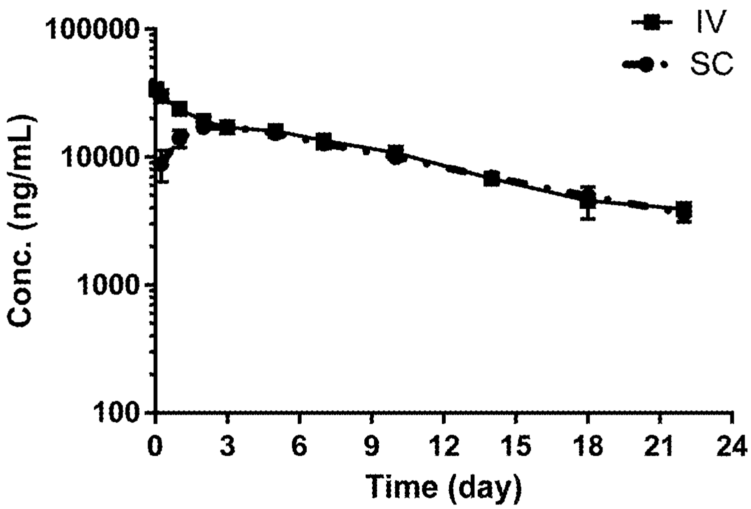
FIG. 12 shows the mean (±SD) of the serum drug concentration-time profile of FP1 following 1 mg/kg IV and SC administration in cynomolgus monkeys, as determined by immunoassays.

FP1 was administered to naïve male cynomolgus monkeys (*Macaca fascicularis*) at a dose of 1 mg/kg IV and SC in PBS, pH 7. Blood samples were collected, serum was processed and drug concentrations were measured up to 21 days following both routes of administration, using immunoassay bioanalysis. The serum drug concentration-time profile is summarized in Tables 25 and 26 and illustrated in FIG. 12.

TABLE 25

Serum concentration (nM) of FP1 over time following a single SC administration in cynomolgus monkeys as determined by immunoassay

| | FP1 (SC Dose) | | | | |
|---|---|---|---|---|---|
| Timepoint | Animal 110 (nm) | Animal 111 (nM) | Animal 112 (nM) | Average Result (nM) | Std Dev |
| Predose | <LLOQ | <LLOQ | <LLOQ | <LLOQ | N/A |
| 6 hr | 49.304 | 43.784 | 72.110 | 55.066 | 15.017 |
| 24 hr | 93.368 | 71.958 | 96.863 | 87.396 | 13.483 |
| 48 hr | 107.689 | 97.509 | 115.144 | 106.781 | 8.853 |
| 72 hr | 113.601 | 104.190 | 104.449 | 107.414 | 5.360 |
| 120 hr | 101.490 | 95.049 | 91.717 | 96.085 | 4.968 |
| 168 hr | 82.167 | 75.435 | 81.569 | 79.724 | 3.726 |
| 240 hr | 71.033 | 56.732 | 59.266 | 62.344 | 7.631 |
| 336 hr | 44.380 | 42.758 | 42.571 | 43.236 | 0.995 |
| 432 hr | 30.911 | 29.445 | 32.839 | 31.065 | 1.702 |
| 528 hr | 21.277 | 20.404 | 26.427 | 22.703 | 3.255 |

TABLE 26

Serum concentration (nM) of FP1 over time following a single IV administration in cynomolgus monkeys as determined by immunoassay

| | FP1 (IV Dose) | | | | |
|---|---|---|---|---|---|
| Timepoint | Animal 104 (nM) | Animal 105 (nM) | Animal 106 (nM) | Average Result (nM) | Std Dev |
| Predose | <LLOQ | <LLOQ | <LLOQ | <LLOQ | N/A |
| 1 hr | 212.661 | 235.168 | 189.000 | 212.276 | 23.087 |
| 6 hr | 190.315 | 185.331 | 183.575 | 186.407 | 3.497 |
| 24 hr | 141.743 | 155.943 | 146.487 | 148.058 | 7.229 |
| 48 hr | 111.765 | 126.105 | 120.744 | 119.538 | 7.246 |
| 72 hr | 105.076 | 106.955 | 106.441 | 106.157 | 0.971 |
| 120 hr | 92.591 | 103.882 | 103.757 | 100.077 | 6.483 |
| 168 hr | 71.368 | 93.055 | 87.706 | 84.043 | 11.298 |
| 240 hr | 71.554 | 65.093 | 65.685 | 67.444 | 3.572 |
| 336 hr | 46.184 | 38.961 | 41.696 | 42.280 | 3.647 |
| 432 hr | 34.589 | 31.266 | 19.492 | 28.449 | 7.933 |
| 528 hr | 26.885 | 24.154 | 22.422 | 24.487 | 2.250 |

Pharmacokinetic analysis revealed a terminal half-life between 8.5 and 9.2 days for FP1 in cynomolgus monkeys following SC and IV administration, respectively with a mean bioavailability of ~88% following SC administration (Table 27).

TABLE 27

Mean (±SD) pharmacokinetic parameters of FP1 following 1 mg/kg IV and SC administration in cynomolgus monkeys.

| Route | | $t_{1/2}$ (day) | CL or CL/F (ml/day/kg) | Vss (ml/kg) | $C_{max}$ (ng/ml) | $T_{max}$* (day) | $AUC_{0\text{-}last}$ (day*ng/ml) | $AUC_{0\text{-}inf}$ (day*ng/ml) |
|---|---|---|---|---|---|---|---|---|
| SC | Mean | 8.5 | 3.9 | | 17776 | 3 | 211030 | 256202 |
| | (SD) | (1.5) | (0.3) | | (950) | | (11332) | (20192) |
| IV | Mean | 9.2 | 3.4 | 45.6 | 34001 | 0.04 | 239758 | 292206 |
| | (SD) | (0.5) | (0.1) | (1.6) | (3698) | | (6095) | (11516) |

Note:
*Tmax (median)

Figure 13:
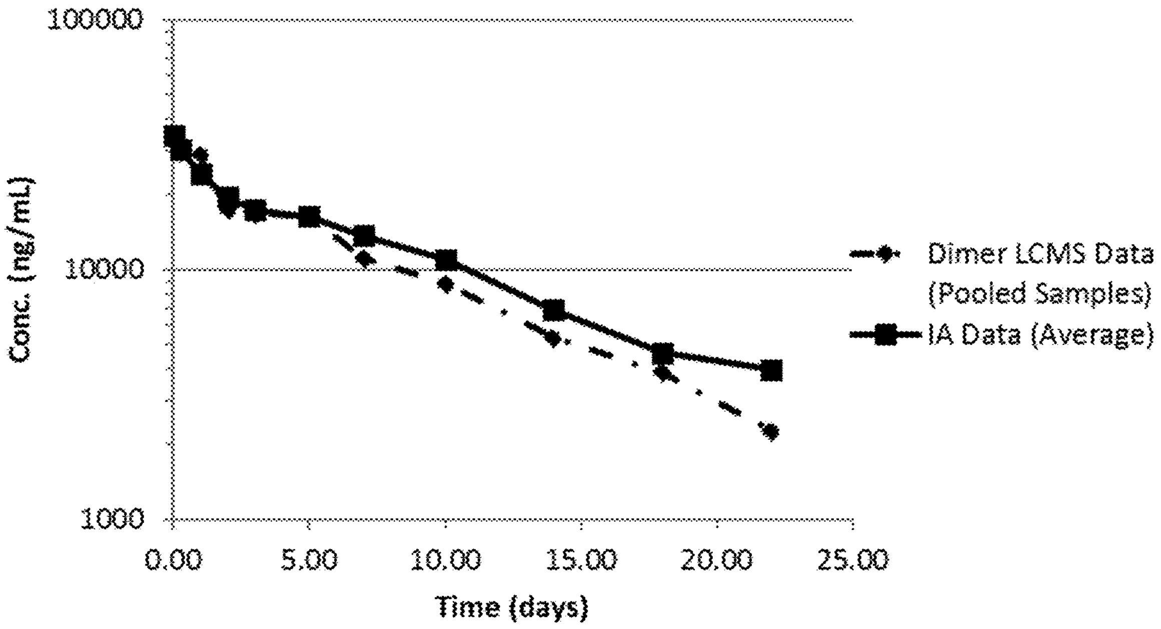
FIG. 13 shows the serum concentration (ng/mL) of FP1 as an intact dimer over time following a single IV administration in cynomolgus monkeys, as determined by immuno-affinity (IA) capture-LCMS analysis.
Figure 14:
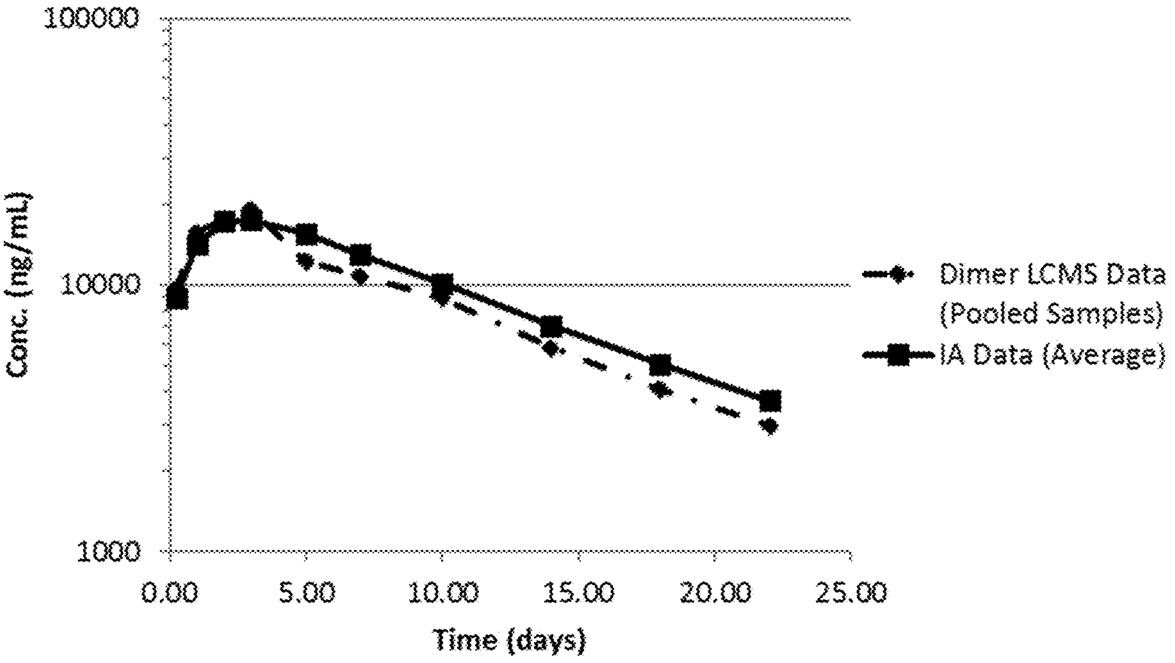
FIG. 14 shows the serum concentration (ng/mL) of FP1 as an intact dimer over time following a single SC administration in cynomolgus monkeys, as determined by immuno-affinity capture-LCMS analysis.

Immuno-affinity capture-LCMS analysis was used to quantitate the concentration of intact dimer present in the serum of cynomolgus monkeys after IV and SC administration (Tables 28 and 29 and FIGS. 13 and 14). Concentrations determined by this method were similar to concentrations determined by the immunoassay (IA), demonstrating that FP1 circulates as an intact dimer, with no detectable metabolic liability in cynomolgus monkeys.

TABLE 28

Serum concentration (ng/mL) of FP1 as an intact dimer over time following a single IV administration in cynomolgus monkeys as determined by immuno-affinity capture-LCMS analysis.

| Day | Dimer Intact MS Data (Pooled Samples) | IA Data (Average) |
|---|---|---|
| 0.00 | 0 | 0 |
| 0.04 | 33347 | 34537 |
| 0.25 | 29686 | 30328 |
| 1.00 | 28787 | 24089 |
| 2.00 | 17249 | 19449 |
| 3.00 | 16827 | 17272 |
| 5.00 | 16159 | 16282 |
| 7.00 | 11124 | 13674 |
| 10.00 | 8746 | 10973 |
| 14.00 | 5328 | 6879 |
| 18.00 | 3857 | 4629 |
| 22.00 | 2252 | 3984 |

TABLE 29

Serum concentration (ng/mL) of FP1 as an intact dimer over time following a single SC administration in cynomolgus monkeys as determined by immuno-affinity capture-LCMS analysis.

| Day | Dimer Intact MS Data (Pooled Samples) | IA Data (Average) |
|---|---|---|
| 0.00 | 0 | 0 |
| 0.25 | 9625 | 8959 |
| 1.00 | 15799 | 14219 |
| 2.00 | 17671 | 17373 |
| 3.00 | 19130 | 17476 |
| 5.00 | 12284 | 15633 |
| 7.00 | 10808 | 12971 |
| 10.00 | 8910 | 10143 |
| 14.00 | 5814 | 7034 |
| 18.00 | 4074 | 5054 |
| 22.00 | 2967 | 3694 |

The concentration of analytes in cynomolgus monkey serum after IV and SC administration was also measured by immuno-affinity capture-trypsin digestion-LC-MS/MS analysis (Tables 30 and 31). Selected tryptic peptides, namely, ALV (ALVLIAFAQYLQQSPFEDHVK) (SEQ ID NO: 135), ASL (ASLEDLGWADWVLSPR) (SEQ ID NO: 136), and TDT (TDTGVSLQTYDDLLAK) (SEQ ID NO: 137), which are located within FP1 near the N-terminus of the HSA region, the N-terminus of GDF15, and the C-terminal of GDF15, respectively. The peptides were monitored as surrogate peptides of FP1. The concentrations of all of the surrogate peptides were similar to each other and the concentrations measured by immunoassay, demonstrating that the GDF15 sequence in FP1 remains intact and linked to the full HSA sequence in vivo.

TABLE 30

Serum concentration (ng/mL) of surrogate peptides representing various regions of FP1 over time following a single IV administration in cynomolgus monkeys as determined by immuno-affinity capture-trypsin digestion-LC-MS/MS analysis.

| Time point | | FP1 Average (ng/mL) | | | Std Dev | | | IA Data |
|---|---|---|---|---|---|---|---|---|
| Day | hour | ALV | TDT | ASL | ALV | TDT | ASL | (ng/mL) |
| 0.00 | 0 | <LLOQ | <LLOQ | <LLOQ | N/A | N/A | N/A | 0.0 |
| 0.04 | 1 | 32400.0 | 39766.7 | 33333.3 | 2623.0 | 3162.8 | 2722.7 | 34536.9 |
| 0.25 | 6 | 29100.0 | 27166.7 | 30600.0 | 3439.5 | 1006.6 | 2095.2 | 30328.1 |
| 1.00 | 24 | 24366.7 | 23300.0 | 23800.0 | 4215.8 | 3996.2 | 4100.0 | 24088.7 |
| 2.00 | 48 | 19433.3 | 17733.3 | 18700.0 | 1457.2 | 1193.0 | 854.4 | 19448.6 |
| 3.00 | 72 | 18100.0 | 17200.0 | 17166.7 | 360.6 | 871.8 | 1001.7 | 17271.6 |
| 5.00 | 120 | 15966.7 | 14033.3 | 14233.3 | 1001.7 | 642.9 | 1011.6 | 16282.3 |
| 7.00 | 168 | 13733.3 | 11800.0 | 12100.0 | 1115.0 | 600.0 | 300.0 | 13673.6 |
| 10.00 | 240 | 9303.3 | 8570.0 | 8570.0 | 2290.1 | 1682.2 | 1685.9 | 10973.0 |
| 14.00 | 336 | 5860.0 | 5890.0 | 6056.7 | 415.8 | 312.2 | 388.0 | 6878.9 |
| 18.00 | 432 | 4143.3 | 4400.0 | 4226.7 | 374.3 | 52.9 | 571.2 | 4628.6 |
| 22.00 | 528 | 2830.0 | 3256.7 | 2753.3 | 355.4 | 420.0 | 319.0 | 3984.0 |

TABLE 31

Serum concentration (ng/mL) of surrogate peptides representing various regions of FP1 over time following a single SC administration in cynomolgus monkeys as determined by immuno-affinity capture-trypsin digestion-LC-MS/MS analysis.

| Time point | | FP1 Average (ng/mL) | | | Std Dev | | | IA Data |
|---|---|---|---|---|---|---|---|---|
| Day | hour | ALV | TDT | ASL | ALV | TDT | ASL | (ng/mL) |
| 0.00 | 0 | <LLOQ | <LLOQ | <LLOQ | N/A | N/A | N/A | 0.0 |
| 0.25 | 6 | 9323.3 | 7430.0 | 8123.3 | 1900.3 | 2471.6 | 1954.1 | 8959.1 |
| 1.00 | 24 | 15233.3 | 13390.0 | 14533.3 | 2926.3 | 3222.0 | 2683.9 | 14219.2 |
| 2.00 | 48 | 15366.7 | 14000.0 | 14166.7 | 2579.4 | 1646.2 | 2311.6 | 17373.0 |
| 3.00 | 72 | 17300.0 | 16033.3 | 15333.3 | 1571.6 | 1001.7 | 986.6 | 17476.0 |
| 5.00 | 120 | 15333.3 | 13366.7 | 13666.7 | 1222.0 | 1692.1 | 1501.1 | 15632.9 |
| 7.00 | 168 | 13333.3 | 11633.3 | 11700.0 | 709.5 | 472.6 | 781.0 | 12970.9 |
| 10.00 | 240 | 8496.7 | 7376.7 | 8343.3 | 1475.5 | 189.0 | 1039.1 | 10143.2 |
| 14.00 | 336 | 6046.7 | 6116.7 | 6253.3 | 90.2 | 118.5 | 110.6 | 7034.5 |
| 18.00 | 432 | 4593.3 | 5250.0 | 4636.7 | 802.6 | 1157.5 | 621.7 | 5054.2 |
| 22.00 | 528 | 3056.7 | 3490.0 | 3116.7 | 424.5 | 687.7 | 220.5 | 3693.7 |

Human Plasma Stability Assay

Figure 15:
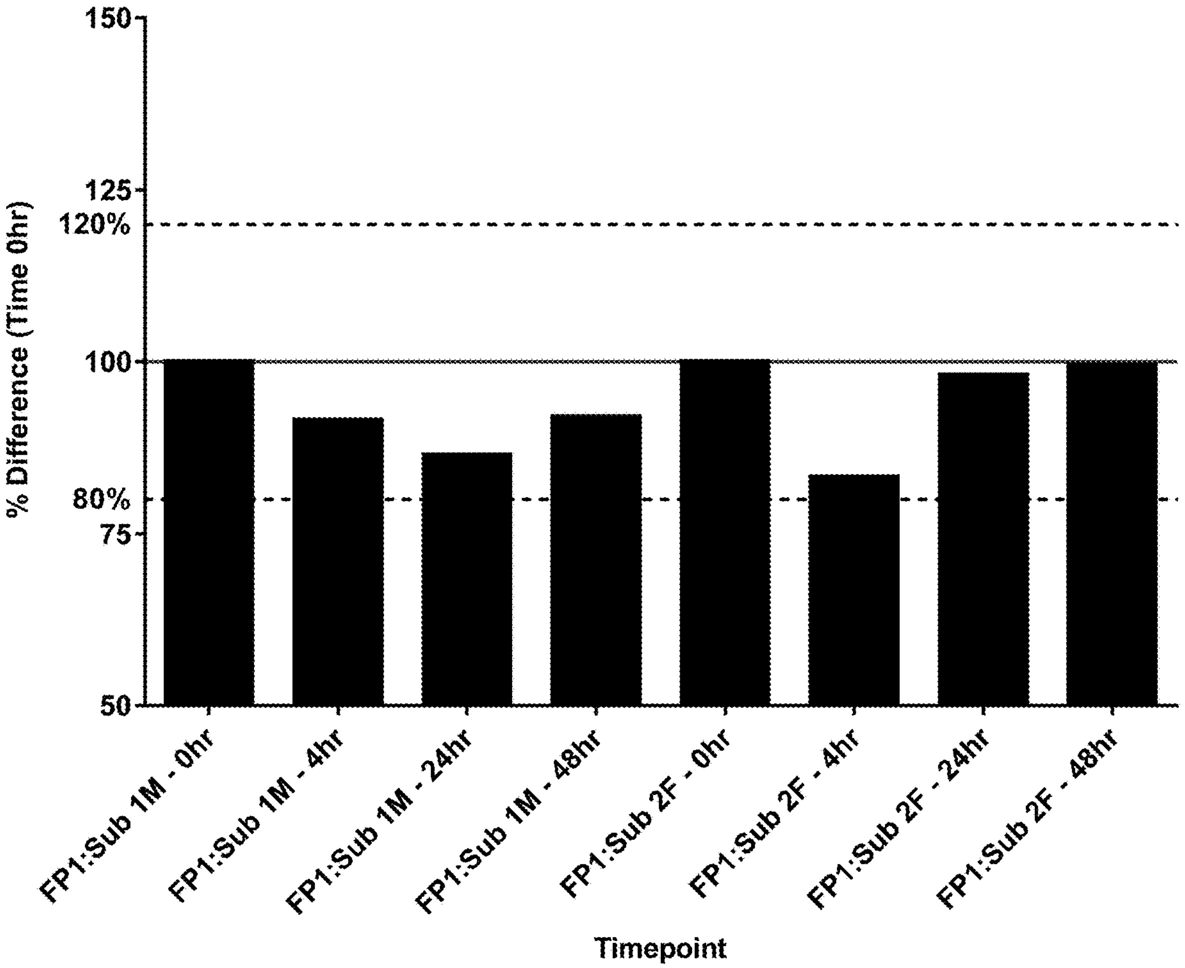
FIG. 15 shows the concentration of FP1, represented as a % of the starting concentration, after 0, 4, 24 and 48 hours of ex vivo incubation in plasma obtained from two human subjects (Sub), as determined by immunoassay.

The purpose of this study was to analyze the ex vivo stability of FP1 in human plasma. Fresh, non-frozen human plasma was generated from heparinized blood from two subjects (one male and one female) by centrifugation. FP1 was incubated in this matrix at 37° C. with gentle mixing, for 0, 4, 24 and 48 hours. The concentration of FP1 was determined using an immunoassay method. The average percent difference from the starting concentration (0 hours) ranged from −4.1 to −12.9 and did not increase over time, demonstrating that FP1 is stable in human plasma for up to 48 hours ex vivo (Table 32 and FIG. 15).

TABLE 32

FP1 concentration (μg/mL) after 0, 4, 24, and 48 hours (hr) of ex vivo incubation in plasma obtained from two human subjects (Sub) as determined by immunoassay

| Ex Vivo Sample | Sub 1 Male Conc. (ug/mL) | % Diff T0 | Sub 2 Female Conc. (ug/mL) | % Diff T0 | Average Conc. (ug/mL) | % Diff T0 |
|---|---|---|---|---|---|---|
| Plasma - T0 hr_FP1 | 11.503 | N/A | 12.649 | N/A | 12.076 | N/A |
| Plasma - T4 hr_FP1 | 10.524 | −8.5 | 10.521 | −16.8 | 10.523 | −12.9 |
| Plasma - T24 hr_FP1 | 9.934 | −13.6 | 12.402 | −2.0 | 11.168 | −7.5 |
| Plasma - T48 hr_FP1 | 10.582 | −8.0 | 12.575 | −0.6 | 11.578 | −4.1 |

Figure 16:
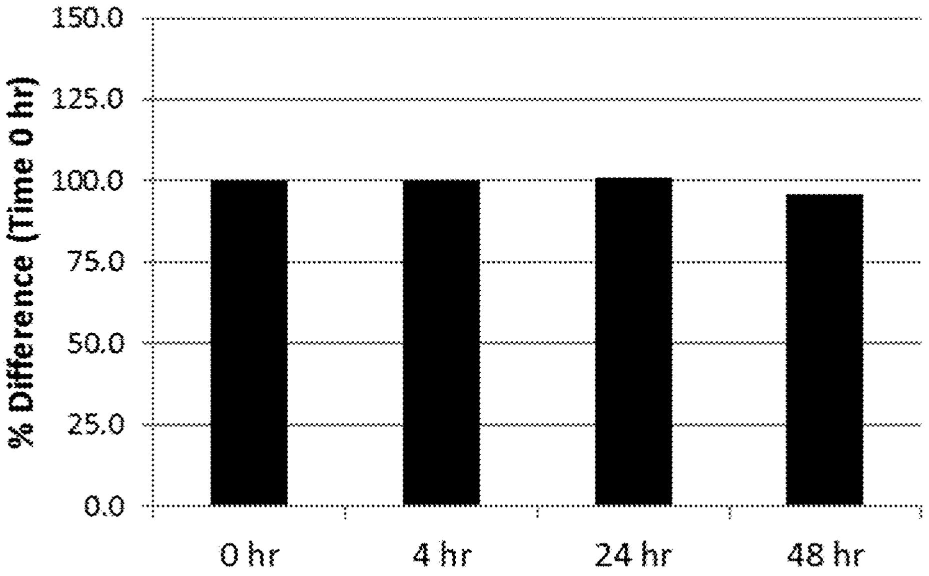
FIG. 16 shows the average concentration of FP1, represented as a % of time 0, as an intact dimer after 0, 4, 24 and 48 hours of ex vivo incubation in plasma obtained from two human subjects (Sub), as determined by intact mass immuno-affinity capture-LCMS analysis.

Immuno-affinity capture-LCMS was used to quantitate the concentration of intact dimer present after incubation in human plasma. Concentrations determined by this method were stable over time (0, 4, 24, and 48 hours), demonstrating that FP1 remains an intact dimer in human plasma ex vivo up to 48 hours (Table 33 and FIG. 16).

TABLE 33

Average FP1 concentration (μg/mL) and % difference from starting concentration as an intact dimer after 0, 4, 24, and 48 hours (hr) of ex vivo incubation in plasma obtained from two human subjects as determined by immuno-affinity capture-LCMS analysis

| | Dimer Conc. (ug/mL) | % Difference |
|---|---|---|
| 0 hr | 15.8 | 100.0 |
| 4 hr | 15.8 | 100.1 |
| 24 hr | 15.9 | 100.9 |
| 48 hr | 15.2 | 96.0 |

Example 13: IR Strategy

Immune response (IR) assays will be developed for anti-drug antibody (ADA) detection in animals and clinical samples. The IR assay will identify ADA-positive samples for comparison of ADA status with pharmacokinetic/toxicokinetic (PK/TK) results, enabling assessment of FP1 exposure and pharmacokinetics. The clinical IR assay will be used to screen serum samples, confirm specificity of ADA-positive samples, and determine the ADA titer for confirmed positive samples. Neutralizing antibody (NAb) assay development will follow for use in confirmed positive samples from ADA-positive subjects in Phase 1 of the program. Additionally, determination of ADA cross-reactivity to endogenous GDF15 will follow for use in Phase 2 of the program. An immunogenicity risk assessment will be conducted prior to the first in human (FIH) study, and additional immune response characterization assays can be implemented if they are warranted.

Example 14: Toxicology Plan

Since the endogenous target receptor for GDF15 has not been identified, there is a lack of in vitro binding and functional data for FP1. However, single and multiple dose pharmacology and efficacy studies in rats, mice and cynomolgus monkeys have demonstrated activity of FP1 in these species, showing its effect of reducing food intake, decreasing body weight and modulating oral glucose tolerance. The rat and monkey will be the rodent and non-rodent toxicology testing species, respectively, based on the efficacy results, with the understanding that the intrinsic potency of FP1 on the receptor in these species (versus that of humans) has not been fully characterized.

The Examples 15-19 involve characterization of another exemplary fusion protein of the invention, described in Example 5, which has the amino acid sequence of SEQ ID NO: 92 (encoded by nucleotide sequences SEQ ID NOs: 95 (codon optimization 1) or 110 (codon optimization 2)). This fusion protein is a fully recombinant protein that exists as a homodimer of a fusion of HSA (C34S) with the deletion variant of the mature human GDF15 (201-308; SEQ ID NO: 8) through a 42-amino acid linker consisting of glycine and serine residues, GS-$(GGGGS)_8$ (SEQ ID NO: 12). The single native free cysteine at position 34 of HSA has been mutated to serine. This particular HSA-GDF15 fusion protein will be referred to as "FP2" in the following examples, for simplicity.

Example 15: Effects of FP2 on the Food Intake of C57Bl/6 Mice

FP2 was evaluated for its ability to reduce food intake in male C57Bl/6 mice after a single dose. Male C57Bl/6N mice (age 10-12 weeks) obtained from Taconic Biosciences (Hudson, N.Y.) were used in the study. Mice were singly housed in a temperature-controlled room with 12-hour light/dark cycle (6 am/6 pm) and allowed ad libitum access to water and chow. Male C57Bl/6 mice were acclimated for a minimum of 72 hours in the BioDAQ cages; mice were then grouped based on food intake in the last 24 hours into six groups of eight each. Between 4:00-5:00 pm, animals were weighed and dosed with vehicle or compounds via subcutaneous injection. Change in food weight for each cage was recorded continuously by the BioDAQ system, for a period of 48 hours after compound administration. 6×His-FP1 was used as a comparator in this study.

FP2 had significant effects on reducing food intake at 12, 24 and 48 hours after administration at all dose levels tested (Table 34). There was a reduction in percent change in food intake relative to PBS at all time points and all dose levels (Table 35) in mice.

TABLE 34

Effect of a Single Dose of FP2 on Food Intake over 48 hours in C57Bl/6 Mice
Cumulative Food Intake (g)

| Treatment | 12 hours | 24 hours | 48 hours |
|---|---|---|---|
| PBS | 3.7 ± 0.2 | 4.4 ± 0.2 | 8.8 ± 0.4 |
| FP2, 1 nmol/kg | 2.8 ± 0.4* | 3.0 ± 0.4** | 6.9 ± 0.7* |
| FP2, 4 nmol/kg | 2.4 ± 0.2*** | 3.1 ± 0.2** | 7.0 ± 0.3* |
| FP2, 8 nmol/kg | 1.9 ± 0.2**** | 2.4 ± 0.1**** | 6.2 ± 0.2*** |
| FP2, 16 nmol/kg | 1.8 ± 0.1**** | 2.7 ± 0.1*** | 6.3 ± 0.4** |
| 6xHis-FP1, 8 nmol/kg | 2.3 ± 0.3*** | 2.8 ± 0.4** | 6.6 ± 0.7** |

Data are expressed as Mean ± SEM.
*p ≤ 0.05, versus PBS
**p ≤ 0.01, versus PBS
***p ≤ 0.001, versus PBS
****p ≤ 0.0001, versus PBS, respectively
Statistical analyses used: ANOVA and Dunnett's multiple comparisons test.
n = 8/group, except for 6xHis-FP1 8 nmol/kg (n = 6).

TABLE 35

Effect of a Single Dose of FP2 on Percent Reduction in Food Intake (Relative to Vehicle) over 48 hours in C57Bl/6 Mice
Percentage of inhibition relative to PBS

| Treatment | 12 hours | 24 hours | 48 hours |
|---|---|---|---|
| PBS | 0.0 ± 7.9 | 0.0 ± 7.7 | 0.0 ± 5.9 |
| FP2, 1 nmol/kg | 22.4 ± 12.5* | 31.8 ± 10.5** | 21.8 ± 8.1* |
| FP2, 4 nmol/kg | 36.6 ± 7.2*** | 30.4 ± 5.8** | 20.2 ± 4.7* |
| FP2, 8 nmol/kg | 47.0 ± 6.2**** | 45.7 ± 3.8**** | 29.7 ± 3.9*** |
| FP2, 16 nmol/kg | 49.2 ± 4.1**** | 38.1 ± 4.1*** | 27.8 ± 5.1** |
| 6xHis-FP1, 8 nmol/kg | 36.9 ± 9.9*** | 36.5 ± 8.8** | 24.6 ± 8.2** |

The anorectic effect of FP2 is expressed as the relative reduction in food intake compared with the respective PBS controls.
Data are expressed as Mean ± SEM.
*p ≤ 0.05, versus PBS
**p ≤ 0.01, versus PBS
***p ≤ 0.001, versus PBS
****p ≤ 0.0001, versus PBS, respectively
Statistical analyses used: ANOVA and Dunnett's multiple comparisons test.
n = 8/group, except for 6xHis-FP1 8 nmol/kg (n = 6).

Example 16: Effects of FP2 on Food Intake in Sprague Dawley Rats

FP2 was evaluated for its ability to reduce food intake and body weight gain in male Sprague-Dawley rats after a single dose. The animals were obtained from Charles River Labs (Wilmington, Mass.) at 200-225 g body weight and used within one week of delivery. They were housed one per cage on alpha dry bedding and a plastic tube for enrichment in a temperature-controlled room with 12-hour light/dark cycle. They were allowed ad libitum access to water and were fed laboratory rodent diet; Irradiated Certified PicoLab® Rodent Diet 20, 5K75* (supplied from Purina Mills, St. Louis, Mo. via ASAP Quakertown, Pa.). Animal weights were taken and recorded for each rat prior to dosing.

Animals were acclimated for a minimum of 72 hours in the BioDAQ cages; rats were then grouped based on food intake in the last 24 hours into six groups of eight each. Between 4:00-5:00 pm, animals were weighed and dosed with vehicle or compounds via subcutaneous injection. Change in food weight for each cage was recorded continuously by the BioDAQ system, for a period of 48 hours after compound administration. 6×His-FP1 was used as a comparator in this study.

Figure 19:
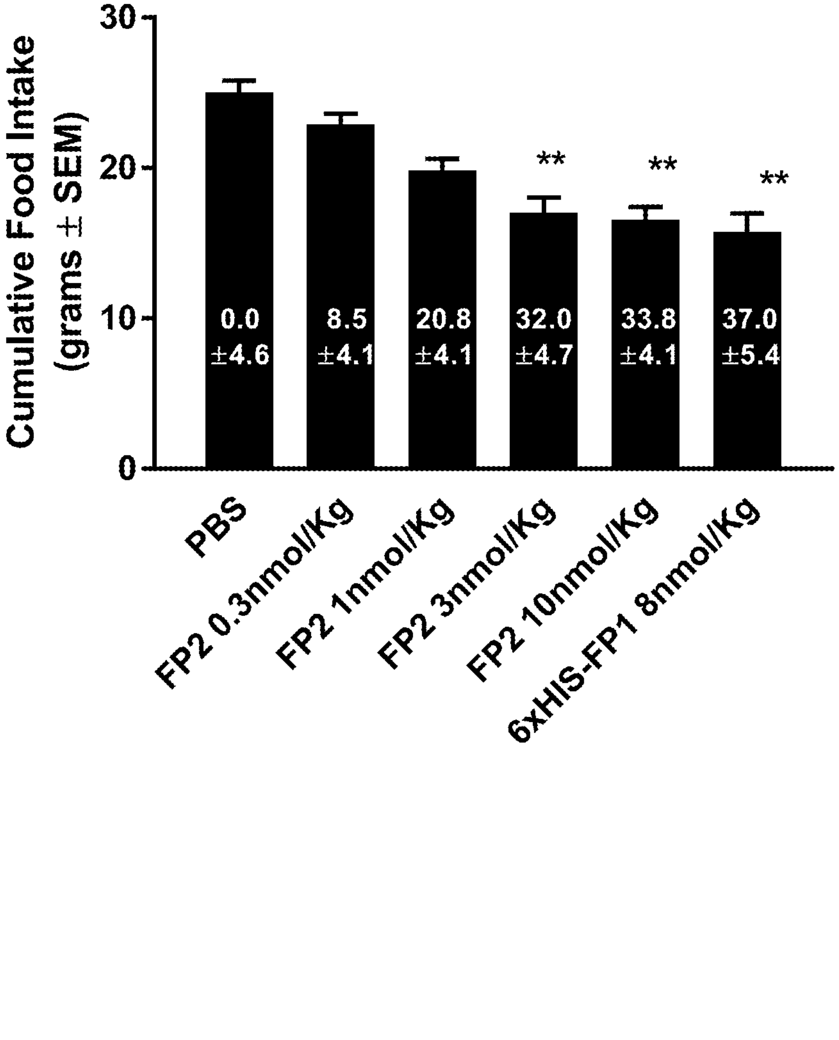
FIG. 19 shows cumulative food intake measured in Sprague-Dawley rats at 24 hours post administration of a single dose of FP2. Values shown within the bars are % reduction compared to PBS group (mean±SEM); N=8 animals per group. **–p<0.01, p values were calculated using Two-way ANOVA and Tukey's test for multiple comparisons.

Dose-dependent reductions of food intake were tested after a single dose of FP2. No significant differences in food intake were observed at the dose of 0.3 nmol/kg. Significant effects in reduction of food intake were observed 12 hours but not 24 or 48 hours at 1 nmol/kg. Significant reductions in food intake were observed at all time points for the 3 and 10 nmol/kg dose levels (Table 36, FIG. 19). There was a reduction in percent change in food intake relative to PBS at all time points and all dose levels (Table 37).

TABLE 36

Effect of a single dose of FP2 on food intake over 48 hours in Sprague Dawley rats.
Cumulative Food Intake (g)

| Treatment | 12 hours | 24 hours | 48 hours |
|---|---|---|---|
| PBS | 21.7 ± 0.6 | 25.0 ± 0.8 | 53.1 ± 1.6 |
| FP2, 0.3 nmol/Kg | 19.5 ± 0.9 | 22.9 ± 0.7 | 48.4 ± 1.5 |
| FP2, 1 nmol/Kg | 17.5 ± 0.9* | 19.8 ± 0.8 | 47.0 ± 2.6 |
| FP2, 3 nmol/Kg | 16.1 ± 1.2** | 17.0 ± 1.0** | 39.2 ± 3.2** |
| FP2, 10 nmol/Kg | 15.8 ± 0.9*** | 16.5 ± 0.9** | 36.5 ± 3.2** |
| 6XHis-FP1 8 nmol/Kg | 15.0 ± 1.4*** | 15.7 ± 1.2** | 37.2 ± 4.5** |

Data are expressed as Mean ± SEM.
*p ≤ 0.05, versus PBS
**p ≤ 0.01, versus PBS
***p ≤ 0.001, versus PBS, respectively
Statistical analyses used: ANOVA and Dunnett's multiple comparisons test.
n = 8/group

TABLE 37

Effect of a single dose of FP2 on percent reduction in food intake (relative to vehicle) over 48 hours in Sprague Dawley rats.
Percentage of inhibition relative to PBS

| Treatment | 12 hours | 24 hours | 48 hours |
|---|---|---|---|
| PBS | 0.0 ± 4.0 | 0.0 ± 4.6 | 0.0 ± 4.3 |
| FP2 0.3 nmol/kg | 10.0 ± 4.7 | 8.5 ± 4.1 | 8.8 ± 3.9 |
| FP2 1 nmol/kg | 19.3 ± 4.7* | 20.8 ± 4.1 | 11.5 ± 5.5 |
| FP2 3 nmol/kg | 25.9 ± 6.1** | 32.0 ± 4.7** | 26.2 ± 6.5** |

TABLE 37-continued

Effect of a single dose of FP2 on percent reduction in food intake (relative to vehicle) over 48 hours in Sprague Dawley rats.
Percentage of inhibition relative to PBS

| Treatment | 12 hours | 24 hours | 48 hours |
|---|---|---|---|
| FP2 10 nmol/kg | 27.4 ± 4.8*** | 33.8 ± 4.1** | 31.2 ± 6.4** |
| 6XHis-FP1 8 nmol/kg | 30.8 ± 6.6*** | 37.0 ± 5.4** | 29.9 ± 8.8** |

The anorectic effect of FP2 is expressed as the relative reduction in food intake compared with the respective PBS controls.
Data are expressed as Mean ± SEM.
*p ≤ 0.05, versus PBS
**p ≤ 0.01, versus PBS
***p ≤ 0.001, versus PBS, versus PBS, respectively
Statistical analyses used: ANOVA and Dunnett's multiple comparisons test.
n = 8/group

Example 17: Effects of FP2 on Food Intake, Body Weight and Glucose Homeostasis in Diet-Induced Obese (DIO) C57Bl/6 Mice FP2 was evaluated for its ability to reduce food intake and body weight and improve glucose homeostasis on repeat dosing in male DIO C57Bl/6 mice over a period of 8 days. Male DIO C57Bl/6 mice (age 21 weeks, high fat-fed for 15 weeks) obtained from Taconic Biosciences (Hudson, N.Y.) were used in the study. Mice were singly housed in a temperature-controlled room with 12-hour light/dark cycle (6 am/6 pm) and allowed ad libitum access to water and fed with Research Diet D12492 (Research Diets, New Brunswick, N.J.). Mice were acclimated >1 week in the mouse housing room prior to the experiment. The endpoints of the study were measurements of food intake, body weight, body composition and glycemic endpoints (OGTT, blood glucose). One day prior to dosing, animals were weighed and grouped by body weight (BW). Mice were dosed by subcutaneous injection. Animals dosed with FP2 received this compound on Day 0, Day 3, and Day 6, Day 9 and Day 12. The vehicle group and rosiglitazone group received sterile PBS s.c. on these days as well. Rosliglitazone was provided in the diet at 0.015% w/w ad libitum. BW and food intake were recorded daily, over a period of fifteen days. Blood glucose was measured on Days 0, 7 and 13. An oral glucose tolerance test (OGTT) was performed on Day 14. Insulin levels were measured at selected time points during the OGTT. Mice were euthanized with $CO_2$ and terminal blood samples were collected for exposure via cardiac puncture on day 15. A separate PK arm was run with three mice per dose group with a total of 15 mice.

Exposure-Response (E-R) Analysis for FP2 in DIO Mouse

Most animals in the pharmacodynamics (PD) (efficacy) arms had undetectable drug concentrations on the last study day when the pharmacokinetics (PK) samples were obtained, potentially due to immunogenicity. Therefore, the mean PK profiles from the PK arms, instead of individual PK from the PD arms, were used to conduct exposure-response (from day 3, 6 and 9, respectively) for the % weight change from baseline in the PD arms at the corresponding dose level. This method assumes that the PK arms behave similarly to the PD arms in terms of drug exposure.

The $E_{max}$ model (GraphPad Prism 6, log(agonist) vs. response) was used to correlate exposure with response data (log transformed drug concentrations). Hill Slope was set to be 1. Note that the model fitted $EC_{10}$ to $EC_{50}$ values were within two fold amongst day 3, 6 and 9, despite that the $E_{max}$ estimates were different ($E_{max}$=−4.26%, −8.18% and −9.85%, respectively). Some animals on day 9 also showed the loss of drug exposure, due to potential ADA formation and therefore, the E-R parameter estimates based on day 9 data should be interpreted with caution.

The effects of two weeks of exposure of FP2 on food intake, body weight, glucose homeostasis, and liver fat content was assessed in diet induced obese male C57Bl/6 mice. Trough exposure between 1.7 and 3.3 nM FP2 for the 0.3 nmol/kg treatment group, between 7.1 and 14 nM for the 1.0 nmol/kg treatment group, between 20.8 and 41.6 nM for the 3.0 nmol/kg treatment group, and between 28.5 and 112.9 nM FP2 for the 10 nmol/kg treatment group was maintained until day 9 in the PK arm of the study (n=2 or 3, Table 49). After day 9, a decrease in circulating levels was observed in the majority of animals despite continued q3d dosing (Table 49). Consistent with this accelerated clearance, the majority of animals in the PD arm of the study had undetectable circulating levels of FP2 on day 15 (Table 50).

Figure 20:
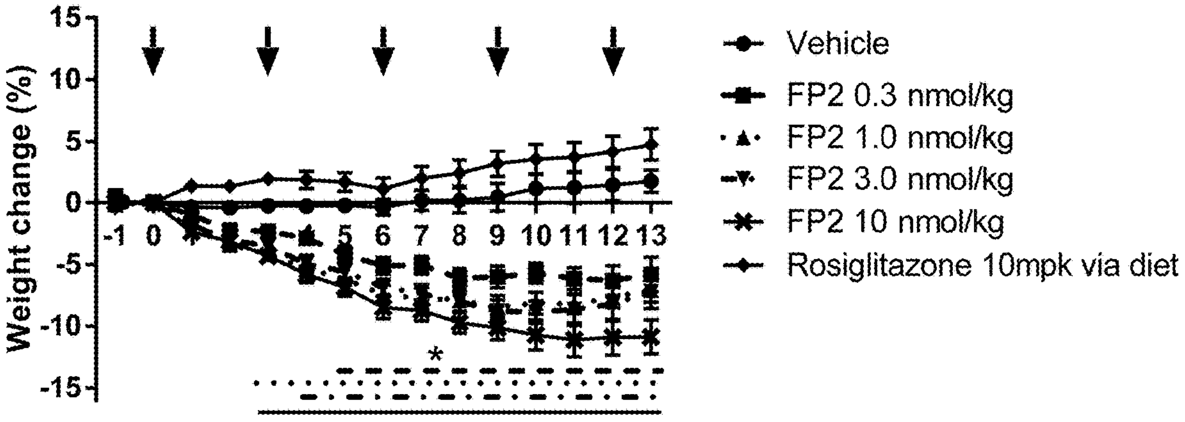
FIG. 20 shows the percent change in body weight during treatment with FP2 q3d in DIO mice. Arrows indicate the time of subcutaneous injections of FP2; N=6 animals per group; *–p, 0.05, as compared with the vehicle, using Two Way ANOVA and Tukey's test for multiple comparisons.
Figure 23:
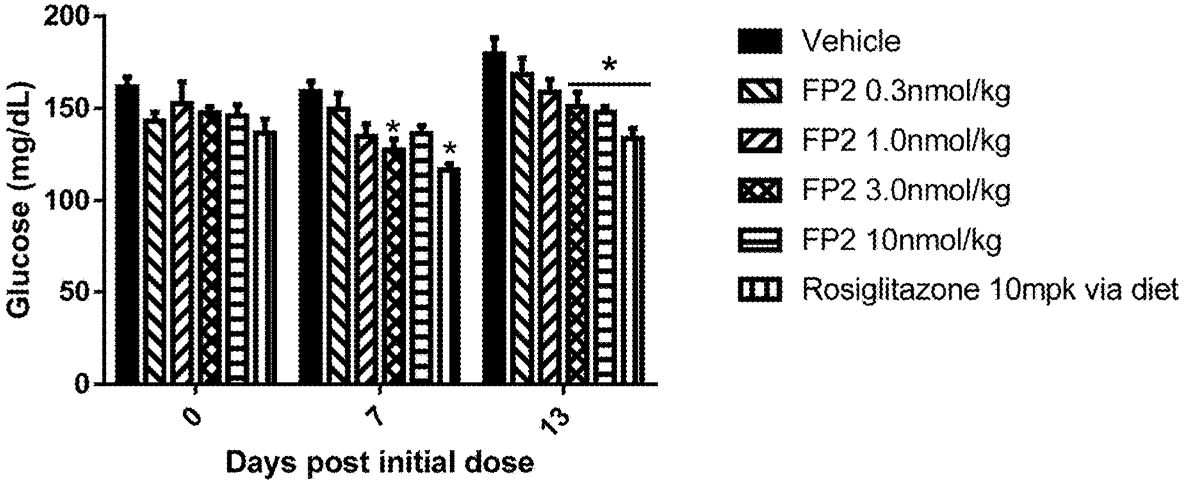
FIG. 23 shows the fed blood glucose levels after 8 days of q3d dosing of FP2 in DIO mice. *–p<0.05, as compared to Vehicle, using Two Way RM ANOVA and Tukey's multiple comparisons test, n=8 animals per group.

Treatment of DIO mice with FP2 q3d reduced food intake (Table 38), body weight (Table 39, 40 and FIG. 20) and fed blood glucose compared to vehicle treatment (Table 43 and FIG. 23). A significant reduction in food intake was seen on day 2, day 5, and day 8 for 0.3 nmol/kg, from day 1 through day 7 for 1.0 nmol/kg, on day 1, day 2, day 4 through day 6, and day 8 for 3.0 nmol/kg, and on day 1, day 3 through day 6, day 8 and day 9 for 10.0 nmol/kg. Percent body weight changes were significant from day 5 through day 13 for 0.3 nmol/kg, from day 3 through day 13 for 1.0 nmol/kg and 10.0 nmol/kg, and from day 4 through day 13 for 3.0 nmol/kg. Changes in grams of body weight were significant from day 8 for 0.3 nmol/kg, from day 6 for 1.0 nmol/kg, from day 7 for 3.0 nmol/kg and from day 5 for 10.0 nmol/kg. Decreases in fed blood glucose levels were significant on day 7 for the animals in the 3.0 nmol/kg dose level and were significant on day 13 for the animals in the 3.0 and 10.0 nmol/kg dose levels.

Figure 21A:
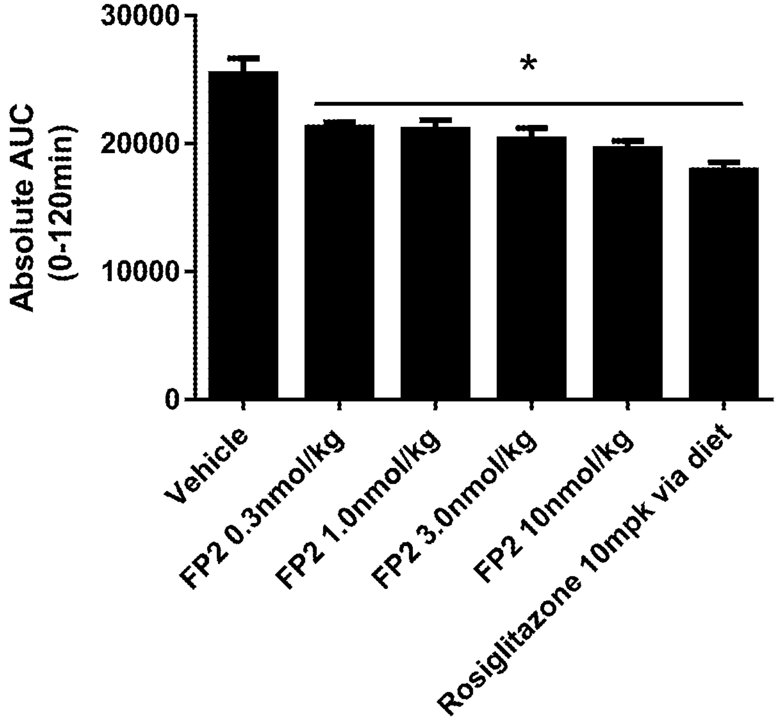
FIGS. 21A and 21B show the area under the curve (AUC) for the blood glucose concentration levels during an OGTT test after 14 days of q3d dosing of FP2 in DIO mice. *–p<0.05, using One Way ANOVA and Tukey's multiple comparisons test, using n=8 animals per group.
Figure 21B:
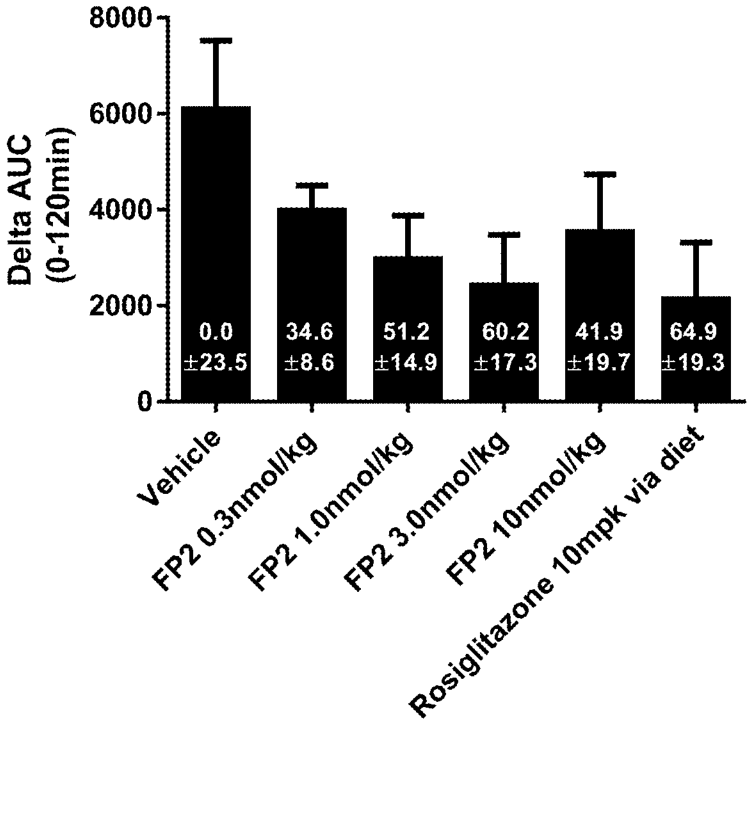
Figure 22A:
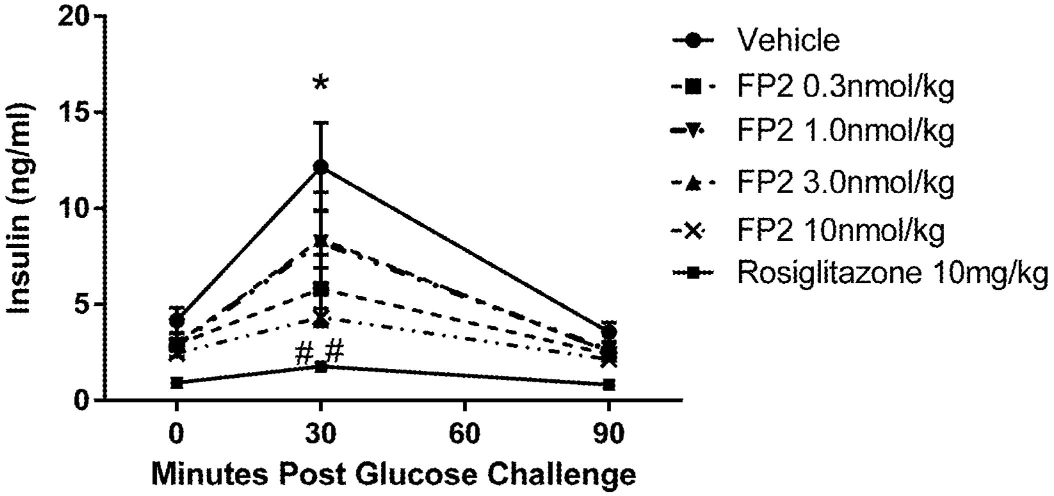
FIG. 22A shows the plasma insulin levels during an OGTT after 8 days of q3d dosing of FP2 in DIO mice. *–p<0.05, Vehicle vs. FP2 (0.3 nmol/kg); FP2 (10 nmol/kg); and Rosiglitazone. #–p<0.05, as compared to Rosiglitazone (10 mg/kg), using Two Way RM ANOVA and Tukey's multiple comparisons test.
Figure 22B:
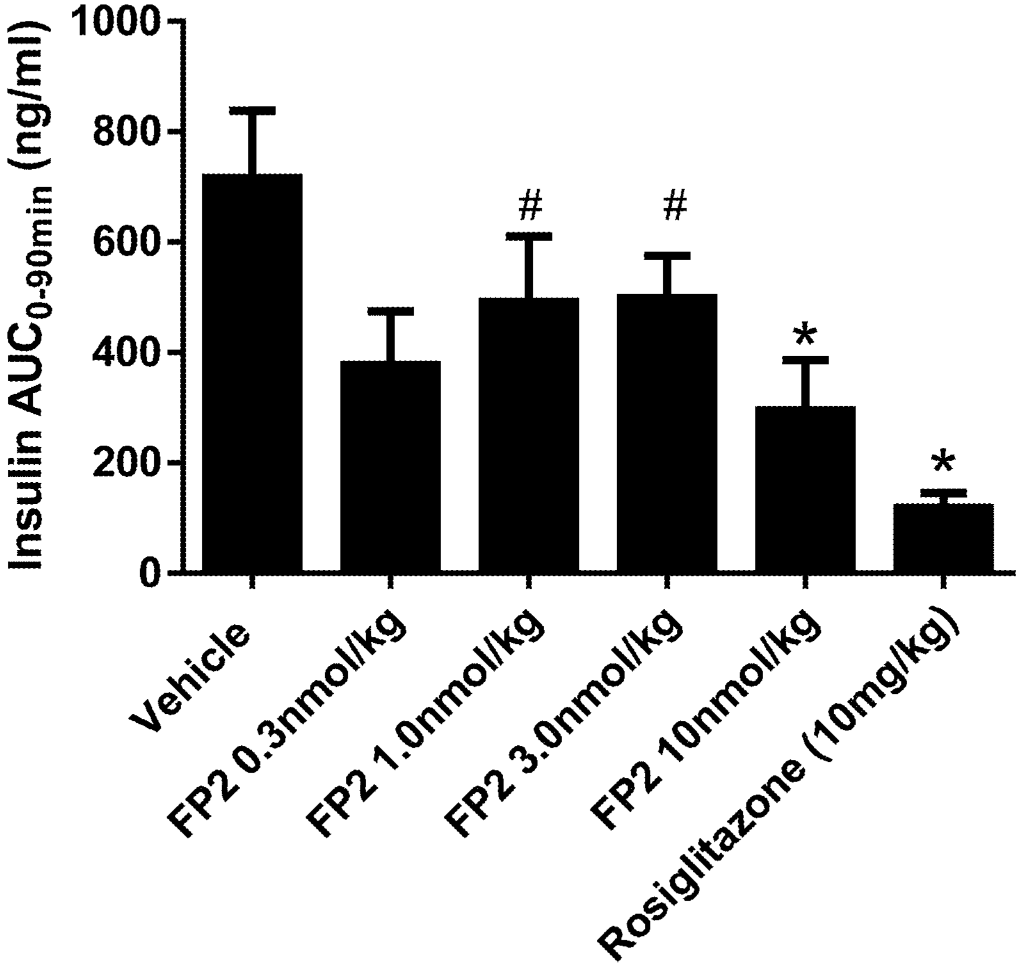
FIG. 22B shows the AUC for the plasma insulin levels during an OGTT after 8 days of q3d dosing of FP2 in DIO mice. *–p<0.05, as compared to Vehicle; #–p<0.05, as compared to Rosiglitazone.
Figure 24:
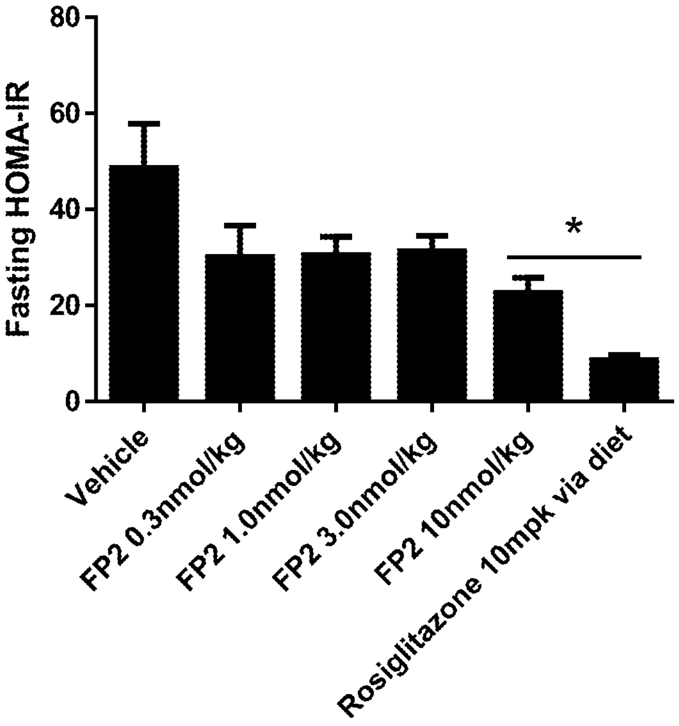
FIG. 24 shows fasting HOMA-IR after 14 days of treatment with FP2 q3d, followed by 5-hour fast on Day 14, in DIO mice. *–p<0.05, as compared to Vehicle, using One Way ANOVA and Tukey's multiple comparisons test, for n=8 animals per group.

DIO mice treated with FP2 q3d had improved glucose tolerance on day 14 compared to vehicle treatment during an oral glucose challenge (Table 41; FIGS. 21A and 21B). Glucose was significantly lower at 30 minutes for the 0.3 nmol/kg group, at 60 minutes and 120 minutes for the 1.0 nmol/kg group, at 120 minutes for the 3.0 nmol/kg group, and at 30, 90, and 120 minutes for the 10.0 nmol/kg group. Total area under the curve was significant for all dose groups. Insulin levels during the glucose challenge were significantly lower for 0.3 and 10.0 nmol/kg groups at 30 minutes (Table 42; FIGS. 22A and 22B). In addition, compared to vehicle treated animals, there was a significant reduction in the calculated fasted HOMA-IR in DIO mice after 14 days of treatment with FP2 q3d at 10.0 nmol/kg indicative of improved insulin sensitivity (Table 44 and FIG. 24).

Body composition was measured by MRI on day −1 before the start of the study and on day 13 (Table 47 and Table 48). DIO mice treated with FP2 at 1.0 nmol/kg and 10.0 nmol/kg had significant reductions in fat mass on day 13; whereas there were no changes in lean mass for any treatment groups. On day 13, the 10.0 nmol/kg treatment group had a significant increase in percent lean mass and a significant reduction in percent fat mass compared to the vehicle treated group. Changes from day −1 to day 13 were significant for lean mass in the 0.3 nmol/kg, 1.0 nmol/kg, and 10.0 nmol/kg treatment groups and were significant for percent lean mass in the 1.0, 3.0, and 10.0 nmol/kg treatment groups. Changes from day −1 to day 13 were significant for fat mass and percent lean mass in all treatment groups compared to vehicle.

There was no significant difference in endogenous mouse GDF15 serum levels between vehicle treated animals and mice treated with FP2 q3d for 15 days (Table 46).

Conclusion: the results suggest that the higher drug exposure is generally associated with greater % weight change from baseline on a population level across the studied dose groups on day 3, 6 and 9.

Exposure to FP2 over two weeks led to reduced food intake, decreased body weight, decreased blood glucose, improved glucose tolerance and insulin sensitivity in DIO mice. Significant decreases in food intake over multiple days were achieved at 1.0, 3.0, and 10.0 nmol/kg q3d. Body weight was decreased significantly starting three to five days after the initiation of the study. Fed blood glucose on day 13 was significantly decreased after q3d administration of FP2 at 3.0 and 10.0 nmol/kg. Insulin sensitivity represented by significantly decreased fasting HOMA-IR was achieved 14 days after 10.0 nmol/kg FP2 administered q3d. On day 13, a significant increase in percent lean mass and a significant reduction in percent fat mass was observed in DIO mice treated q3d with 10.0 nmol/kg FP2.

TABLE 38

Effect of FP2 on daily food intake (g) over 13 days of treatment.

| Treatment | Vehicle | FP2 (nmol/kg) | | | | Rosiglitazone |
|---|---|---|---|---|---|---|
| Day | N/A | 0.3 | 1.0 | 3.0 | 10.0 | 10 mpk/day |
| 0 | 2.0 ± 0.1 | 1.9 ± 0.1 | 2.2 ± 0.2 | 1.9 ± 0.2 | 1.9 ± 0.2 | 2.2 ± 0.1 |
| 1 | 2.4 ± 0.2 | 2.1 ± 0.1 | 1.6 ± 0.1* | 1.5 ± 0.1* | 1.3 ± 0.1* | 2.7 ± 0.1 |
| 2 | 2.5 ± 0.1 | 1.8 ± 0.1* | 1.7 ± 0.2* | 1.9 ± 0.1* | 2.0 ± 0.1 | 3.0 ± 0.2 |
| 3 | 2.5 ± 0.1 | 2.1 ± 0.1 | 1.7 ± 0.1* | 1.9 ± 0.1 | 1.8 ± 0.1* | 2.8 ± 0.2 |
| 4 | 2.6 ± 0.1 | 2.0 ± 0.1 | 1.8 ± 0.1* | 1.9 ± 0.1* | 1.9 ± 0.1* | 2.9 ± 0.2 |
| 5 | 2.8 ± 0.1 | 2.1 ± 0.2* | 2.2 ± 0.1* | 2.2 ± 0.0* | 1.9 ± 0.1* | 2.7 ± 0.2 |
| 6 | 2.8 ± 0.1 | 2.3 ± 0.2 | 2.1 ± 0.1* | 2.2 ± 0.1* | 2.0 ± 0.1* | 2.8 ± 0.2 |
| 7 | 2.6 ± 0.2 | 2.3 ± 0.1 | 2.0 ± 0.1* | 2.0 ± 0.2 | 2.1 ± 0.1 | 2.9 ± 0.2 |
| 8 | 2.7 ± 0.2 | 2.1 ± 0.1* | 2.2 ± 0.1 | 2.0 ± 0.1* | 2.0 ± 0.1* | 3.1 ± 0.2 |
| 9 | 2.8 ± 0.1 | 2.3 ± 0.1 | 2.3 ± 0.2 | 2.3 ± 0.2^ | 2.1 ± 0.2* | 3.2 ± 0.1 |
| 10 | 2.6 ± 0.1 | 2.5 ± 0.1 | 2.4 ± 0.2 | 2.3 ± 0.2^ | 2.1 ± 0.2 | 3.0 ± 0.2 |
| 11 | 2.9 ± 0.1 | 2.5 ± 0.1 | 2.8 ± 0.2 | 2.6 ± 0.4 | 2.6 ± 0.1 | 3.3 ± 0.1 |
| 12 | 2.8 ± 0.1 | 2.7 ± 0.2 | 2.8 ± 0.1 | 2.8 ± 0.2 | 2.9 ± 0.1 | 3.1 ± 0.2 |
| 13 | 2.7 ± 0.1 | 2.5 ± 0.2 | 2.6 ± 0.1 | 2.6 ± 0.1 | 2.2 ± 0.1 | 3.1 ± 0.2 |

Values represent mean ± SEM for data from 8 animals per time per group, except n = 7 when noted by ^
*$p < 0.05$, versus vehicle
Statistical analyses used: Two-Way ANOVA RM, Tukey's multiple comparison test

TABLE 39

Effect of FP2 on Percent Body Weight Change Over 13 days of Treatment

| Treatment | Vehicle | FP2 (nmol/kg) | | | | Rosiglitazone |
|---|---|---|---|---|---|---|
| Day | N/A | 0.3 | 1.0 | 3.0 | 10.0 | 10 mpk/day |
| −1 | −0.1 ± 0.4 | 0.5 ± 0.2 | −0.1 ± 0.1 | −0.4 ± 0.2 | 0.0 ± 0.6 | 0.1 ± 0.2 |
| 0 | 0.0 ± 0.0 | 0.0 ± 0.0 | 0.0 ± 0.0 | 0.0 ± 0.0 | 0.0 ± 0.0 | 0.0 ± 0.0 |
| 1 | −0.4 ± 0.5 | −1.0 ± 0.3 | −2.2 ± 0.4 | −1.8 ± 0.6 | −2.4 ± 0.5 | 1.3 ± 0.4 |
| 2 | −0.4 ± 0.3 | −2.2 ± 0.4 | −3.4 ± 0.6 | −3.0 ± 0.6 | −3.1 ± 0.4 | 1.3 ± 0.5 |
| 3 | −0.3 ± 0.4 | −2.3 ± 0.4 | −4.2 ± 0.6* | −3.5 ± 0.6 | −4.3 ± 0.5* | 1.9 ± 0.5 |
| 4 | −0.3 ± 0.5 | −2.9 ± 0.5 | −5.3 ± 0.6* | −4.9 ± 0.7* | −5.8 ± 0.7* | 1.8 ± 0.7 |
| 5 | −0.2 ± 0.4 | −4.2 ± 0.7* | −6.2 ± 0.6* | −5.6 ± 0.7* | −6.8 ± 0.7* | 1.7 ± 0.8 |
| 6 | −0.4 ± 0.6 | −5.1 ± 0.7* | −7.4 ± 0.8* | −6.9 ± 0.7* | −8.5 ± 0.9* | 1.1 ± 0.9 |
| 7 | 0.2 ± 0.8 | −5.1 ± 0.7* | −7.7 ± 0.9* | −7.4 ± 0.7* | −8.7 ± 0.9* | 2.0 ± 1.0 |
| 8 | 0.2 ± 1.0 | −6.1 ± 0.8* | −7.9 ± 0.9* | −8.0 ± 0.8* | −9.7 ± 0.8* | 2.4 ± 1.1 |
| 9 | 0.5 ± 1.1 | −6.0 ± 0.9* | −8.4 ± 0.9* | −8.8 ± 0.9* | −10.1 ± 1.0* | 3.1 ± 1.0 |
| 10 | 1.1 ± 1.2 | −5.7 ± 0.8* | −8.1 ± 0.9* | −8.9 ± 0.9* | −10.7 ± 1.2* | 3.5 ± 1.2 |
| 11 | 1.2 ± 1.3 | −6.1 ± 0.9* | −8.2 ± 0.8* | −8.6 ± 1.3* | −11.1 ± 1.4* | 3.7 ± 1.2 |
| 12 | 1.4 ± 1.3 | −6.3 ± 1.2* | −7.7 ± 0.8* | −8.2 ± 1.4* | −10.9 ± 1.4* | 4.1 ± 1.3 |
| 13 | 1.7 ± 0.9 | −5.8 ± 1.4* | −7.1 ± 1.0* | −7.2 ± 1.4* | −10.9 ± 1.4* | 4.7 ± 1.3 |

Values represent mean ± SEM for data from 8 animals per time per group
*$p < 0.05$, versus Vehicle
Statistical analyses used: Two-Way ANOVA RM, Tukey's multiple comparison test

TABLE 40

| Effect of FP2 on body weight change (g) over 13 days of treatment | | | | | | |
|---|---|---|---|---|---|---|
| Treatment | Vehicle | FP2 (nmol/kg) | | | | Rosiglitazone |
| Day | N/A | 0.3 | 1.0 | 3.0 | 10.0 | 10 mpk/day |
| −1 | 44.6 ± 0.6 | 44.5 ± 0.6 | 44.5 ± 0.6 | 44.5 ± 0.6 | 44.5 ± 0.6 | 44.5 ± 0.6 |
| 0 | 44.6 ± 0.6 | 44.3 ± 0.6 | 44.6 ± 0.6 | 44.7 ± 0.6 | 44.6 ± 0.7 | 44.4 ± 0.6 |
| 1 | 44.5 ± 0.7 | 43.8 ± 0.6 | 43.6 ± 0.6 | 43.9 ± 0.7 | 43.5 ± 0.7 | 45.0 ± 0.7 |
| 2 | 44.5 ± 0.7 | 43.3 ± 0.7 | 43.1 ± 0.6 | 43.3 ± 0.7 | 43.2 ± 0.7 | 45.0 ± 0.7 |
| 3 | 44.5 ± 0.7 | 43.2 ± 0.7 | 42.7 ± 0.6 | 43.1 ± 0.7 | 42.6 ± 0.6 | 45.3 ± 0.7 |
| 4 | 44.5 ± 0.7 | 43.0 ± 0.7 | 42.2 ± 0.6 | 42.5 ± 0.7 | 42.0 ± 0.7 | 45.2 ± 0.7 |
| 5 | 44.5 ± 0.7 | 42.4 ± 0.7 | 41.8 ± 0.5 | 42.2 ± 0.7 | 41.5 ± 0.6* | 45.2 ± 0.7 |
| 6 | 44.5 ± 0.7 | 42.0 ± 0.7 | 41.3 ± 0.6* | 41.6 ± 0.7 | 40.7 ± 0.5* | 44.9 ± 0.8 |
| 7 | 44.7 ± 0.7 | 42.0 ± 0.7 | 41.1 ± 0.6* | 41.4 ± 0.7* | 40.6 ± 0.5* | 45.3 ± 0.8 |
| 8 | 44.7 ± 0.7 | 41.6 ± 0.7* | 41.1 ± 0.7* | 41.1 ± 0.7* | 40.2 ± 0.6* | 45.5 ± 0.8 |
| 9 | 44.8 ± 0.7 | 41.6 ± 0.8* | 40.8 ± 0.7* | 40.8 ± 0.8* | 40.0 ± 0.8* | 45.8 ± 0.7 |
| 10 | 45.1 ± 0.7 | 41.8 ± 0.8* | 41.0 ± 0.8* | 40.8 ± 0.8* | 39.8 ± 0.8* | 46.0 ± 0.8 |
| 11 | 45.2 ± 0.8 | 41.6 ± 0.8* | 40.9 ± 0.7* | 40.8 ± 0.9* | 39.6 ± 0.9* | 46.1 ± 0.8 |
| 12 | 45.3 ± 0.7 | 41.5 ± 0.9* | 41.2 ± 0.7* | 41.0 ± 0.9* | 39.7 ± 0.9* | 46.3 ± 0.9 |
| 13 | 45.4 ± 0.7 | 41.7 ± 0.9* | 41.4 ± 0.8* | 41.5 ± 0.9* | 39.7 ± 0.9* | 46.5 ± 0.9 |

Values represent mean ± SEM for data from 8 animals per time per group
*p < 0.05, versus Vehicle
Statistical analyses: Two-Way ANOVA RM, Tukey's multiple comparison test

TABLE 41

| Effect of FP2 on blood glucose (mg/dL) levels during an OGTT after 14 days of treatment | | | | | | | | |
|---|---|---|---|---|---|---|---|---|
| | Dose | Time after Glucose Challenge (min) | | | | | Total AUC (mg/dL/ | Δ AUC (mg/dL/ |
| Treatment | (nmol/kg) | 0 | 30 | 60 | 90 | 120 | 120 min) | 120 min) |
| Vehicle | NA | 161 ± 10 | 225 ± 17 | 228 ± 14 | 208 ± 18 | 213 ± 19 | 25429 ± 1228 | 6094 ± 1430 |
| FP2 | 0.3 | 144 ± 4 | 163 ± 14* | 209 ± 11 | 180 ± 12 | 171 ± 7 | 21270 ± 399* | 3985 ± 521 |
| | 1.0 | 151 ± 9 | 179 ± 18 | 188 ± 7 | 179 ± 13 | 163 ± 8* | 21096 ± 754* | 2972 ± 907 |
| | 3.0 | 149 ± 8 | 180 ± 18 | 179 ± 11* | 164 ± 6 | 163 ± 9* | 20338 ± 876* | 2426 ± 1058 |
| | 10.0 | 134 ± 6 | 163 ± 7* | 190 ± 13 | 152 ± 7* | 163 ± 8* | 19599 ± 614* | 3539 ± 1198 |
| Rosiglitazone | 10 mpk/ day | 132 ± 9 | 152 ± 10* | 162 ± 13* | 138 ± 9* | 159 ± 9* | 17904 ± 632* | 2139 ± 1179 |

Values represent mean ± SEM for data from 8 animals per time per group
*p < 0.05, versus Vehicle
Statistical analyses: Two-Way ANOVA RM, Tukey's multiple comparison test for Glucose Values;
One-Way ANOVA, Tukey's multiple comparison test for AUC

TABLE 42

| Effect of FP2 on insulin (ng/mL) levels during an OGTT after 14 days of treatment | | | | | |
|---|---|---|---|---|---|
| | Dose | Time after Glucose Challenge (min) | | | Total AUC |
| Treatment | (nmol/kg) | 0 | 30 | 90 | (ng/mL/90 min) |
| Vehicle | NA | 4.2 ± 0.7 | 12.2 ± 2.3 | 3.6 ± 0.5 | 716.1 ± 122.0 |
| FP2 | 0.3 | 2.9 ± 0.6 | 5.8 ± 1.8* | 2.4 ± 0.4 | 377.1 ± 97.3 |
| | 1.0 | 2.9 ± 0.4 | 8.2 ± 2.6 | 2.6 ± 0.4 | 491.8 ± 118.2 |
| | 3.0 | 3.0 ± 0.3 | 8.4 ± 1.5 | 2.5 ± 0.3 | 498.6 ± 77.0 |
| | 10.0 | 2.4 ± 0.4 | 4.3 ± 0.5* | 2.1 ± 0.4 | 295.5 ± 32.0* |
| Rosiglitazone | 10 mpk/day | 0.9 ± 0.1 | 1.8 ± 0.2* | 0.8 ± 0.1 | 118.5 ± 9.6* |

Values represent mean ± SEM for data from 8 animals per time per group
*p < 0.05, versus Vehicle
Statistical analyses: Two-Way ANOVA RM, Tukey's multiple comparison test for insulin Values;
One-Way ANOVA, Tukey's multiple comparison test for AUC

TABLE 43

Effect of FP2 on fed blood glucose (mg/dL) levels

| Treatment | Dose (nmol/kg) | Time after start of treatment (days) 0 | 7 | 13 |
|---|---|---|---|---|
| Vehicle | NA | 162 ± 5 | 159 ± 6 | 180 ± 9 |
| FP2 | 0.3 | 143 ± 5 | 150 ± 9 | 168 ± 9 |
| | 1.0 | 153 ± 12 | 135 ± 7 | 159 ± 7 |
| | 3.0 | 148 ± 3 | 127 ± 6* | 151 ± 8* |
| | 10.0 | 146 ± 6 | 136 ± 4 | 148 ± 3* |
| Rosiglitazone | 10 mpk/day | 137 ± 7 | 117 ± 4* | 134 ± 6* |

Values represent mean ± SEM for data from 8 animals per time per group
*p < 0.05, versus Vehicle
Statistical analyses: Two-Way ANOVA RM, Tukey's multiple comparison test

TABLE 44

Fasted HOMA-IR in DIO mice after 14 days of q3d treatement with FP2

| Treatment | Dose (nmol/kg) | HOMA-IR |
|---|---|---|
| Vehicle | NA | 48.7 ± 9.2 |
| FP2 | 0.1 | 30.1 ± 6.6 |
| | 1.0 | 30.5 ± 3.8 |
| | 3.0 | 31.3 ± 3.2 |
| | 10.0 | 22.7 ± 3.1* |
| Rosiglitazone | 10 mpk/day | 8.7 ± 1.0* |

Values represent mean ± SEM for data from 8 animals per time per group
*p < 0.05, versus Vehicle
Statistical analyses: One-Way ANOVA, Tukey's multiple comparison test

TABLE 45

Liver weight after 15 days of treatment with FP2 q3d in DIO mice

| Treatment | Dose (nmol/kg) | Liver Weight, (g) | Liver Weight (% of body) |
|---|---|---|---|
| Vehicle | NA | 1.9 ± 0.1 | 4.3 ± 0.3 |
| FP2 | 0.1 | 1.7 ± 0.1 | 4.0 ± 0.1 |
| | 1.0 | 1.7 ± 0.0 | 4.2 ± 0.1 |
| | 3.0 | 1.8 ± 0.1 | 4.2 ± 0.1 |
| | 10.0 | 1.7 ± 0.1 | 4.2 ± 0.1 |
| Rosiglitazone | 10 mpk/day | 1.9 ± 0.1 | 4.1 ± 0.2 |

Values represent mean ± SEM for data from 8 animals per time per group
*p < 0.05, versus Vehicle
Statistical analyses: One-Way ANOVA, Tukey's multiple comparison test

TABLE 46

Serum mouse GDF15 (pg/mL) levels after 15 days of treatement with FP2 q3d in DIO mice

| Treatment | Dose (nmol/kg) | mGDF15 |
|---|---|---|
| Vehicle | NA | 258.3 ± 21.4 |
| FP2 | 0.1 | 214.1 ± 10.3 |
| | 1.0 | 191.6 ± 12.7 |
| | 3.0 | 254.5 ± 28.6 |
| | 10.0 | 202.0 ± 10.0 |
| Rosiglitazone | 10 mpk/day | 509.6 ± 26.2* |

Values represent mean ± SEM for data from 8 animals per time per group
*p < 0.05, versus Vehicle
Statistical analyses: One-Way ANOVA, Tukey's multiple comparison test

TABLE 47

Effect of JNJ-64739090 q3d in DIO mice on body composition (g) measured by MRI

| Treatment | Dose (nmol/kg) | Fat (g) Day −1 | Fat (g) Day 13 | Δ Fat (g) | Lean (g) Day −1 | Lean (g) Day 13 | Δ Lean (g) |
|---|---|---|---|---|---|---|---|
| Vehicle | NA | 17.4 ± 0.6 | 18.2 ± 0.6 | 0.9 ± 0.3 | 25.4 ± 0.3 | 25.1 ± 0.3 | −0.4 ± 0.2 |
| FP2 | 0.3 | 17.0 ± 0.6 | 15.2 ± 0.8 | −1.9 ± 0.6* | 25.8 ± 0.7 | 24.5 ± 0.5 | −1.2 ± 0.2* |
| | 1.0 | 17.0 ± 0.6 | 14.9 ± 0.6* | −2.1 ± 0.4* | 25.8 ± 0.5 | 24.6 ± 0.4 | −1.2 ± 0.2* |
| | 3.0 | 17.4 ± 0.7 | 15.1 ± 1.1 | −2.3 ± 0.5* | 25.3 ± 0.4 | 24.2 ± 0.4 | −1.1 ± 0.1 |
| | 10.0 | 16.7 ± 0.6 | 13.2 ± 0.8* | −3.6 ± 0.5* | 26.1 ± 0.6 | 24.5 ± 0.6 | −1.7 ± 0.2* |
| Rosiglitazone | 10 mpk/day | 17.2 ± 0.6 | 19.1 ± 0.5 | 1.9 ± 0.6 | 25.5 ± 0.7 | 25.1 ± 0.6 | −0.4 ± 0.2 |

Values represent mean ± SEM for data from 8 animals per time per group
*p < 0.05, versus Vehicle
Statistical analyses: One-Way ANOVA, Tukey's multiple comparison test

TABLE 48

Effect of FP2 q3d in DIO mice on body composition (%) measured by MRI

| Treatment | Dose (nmol/kg) | Fat (%) Day −1 | Fat (%) Day 13 | Δ Fat (%) | Lean (%) Day −1 | Lean (%) Day 13 | Δ Lean (%) |
|---|---|---|---|---|---|---|---|
| Vehicle | NA | 38.1 ± 1.0 | 40.1 ± 1.0 | 2.1 ± 0.3 | 55.9 ± 0.9 | 55.3 ± 0.9 | −0.6 ± 0.3 |
| FP2 | 0.3 | 37.6 ± 1.2 | 36.3 ± 1.3 | −1.3 ± 0.9* | 56.8 ± 1.3 | 59.0 ± 1.4 | 2.2 ± 0.8 |
| | 1.0 | 37.2 ± 1.1 | 35.8 ± 0.9 | −1.4 ± 0.5* | 56.7 ± 1.1 | 59.5 ± 1.0 | 2.8 ± 0.6* |
| | 3.0 | 38.3 ± 1.4 | 36.1 ± 2.0 | −2.3 ± 0.7* | 55.9 ± 1.2 | 58.7 ± 2.0 | 2.8 ± 0.8* |
| | 10.0 | 36.9 ± 1.1 | 33.1 ± 1.5* | −3.8 ± 0.8* | 57.5 ± 1.0 | 61.7 ± 1.4* | 4.2 ± 0.7* |
| Rosiglitazone | 10 mpk/day | 38.0 ± 1.2 | 41.1 ± 0.9 | 3.1 ± 0.9 | 56.2 ± 1.2 | 53.9 ± 0.8 | −2.3 ± 0.8 |

Values represent mean ± SEM for data from 8 animals per time per group
*p < 0.05, versus Vehicle
Statistical analyses: One-Way ANOVA, Tukey's multiple comparison test

TABLE 49

| FP2 serum exposures (nM) of the PK arm during q3d treatment in DIO mice | | | | | | | | |
|---|---|---|---|---|---|---|---|---|
| | | Time Post Initial Dose (Time post last dose) | | | | | | |
| Treatment Group | Subject ID | Day 3 | Day 6 | Day 9 | Day 12 | Day 14 (48 hr) | Day 15 (72 hr) | Day 17 (120 hr) |
| 0.1 | 9 | 1.930 | 2.993 | <LOQ | <LOQ | <LOQ | <LOQ | <LOQ |
| nmol/kg | 10 | 1.853 | 3.369 | 2.817 | <LOQ | <LOQ | <LOQ | <LOQ |
| | 11 | 1.715 | 2.637 | 2.568 | 2.709 | 3.441 | 1.313 | <LOQ |
| 1.0 | 9 | 8.198 | 9.660 | 9.645 | <LOQ | <LOQ | <LOQ | <LOQ |
| nmol/kg | 10 | 7.073 | 10.595 | 8.966 | <LOQ | <LOQ | <LOQ | <LOQ |
| | 11 | 6.689 | 13.967 | 10.802 | <LOQ | <LOQ | <LOQ | <LOQ |
| 3.0 | 9 | 20.802 | 26.329 | 27.863 | <LOQ | <LOQ | <LOQ | <LOQ |
| nmol/kg | 10 | 23.563 | 32.020 | 41.576 | 1.168 | <LOQ | <LOQ | <LOQ |
| | 11 | 21.704 | 30.101 | <LOQ | <LOQ | <LOQ | <LOQ | <LOQ |
| 10.0 | 9 | 28.495 | 33.050 | <LOQ | <LOQ | <LOQ | <LOQ | <LOQ |
| nmol/kg | 10 | 70.779 | 112.898 | <LOQ | <LOQ | <LOQ | <LOQ | <LOQ |
| | 11 | 70.404 | 111.767 | 55.117 | <LOQ | <LOQ | <LOQ | <LOQ |

Data are expressed as concentration for each animal.
<LOQ = below limit of quantitation; LOQ is 0.494 nM
** Values at Day 3, 6, 9 and 12 are immediately prior to next dose

TABLE 50

| Terminal serum exposures (nM) of FP2 after 15 days of q3d treatment in DIO mice | | | | |
|---|---|---|---|---|
| Animal | Treatment Group (nmol/kg) | | | |
| ID | 0.1 | 1.0 | 3.0 | 10.0 |
| 1 | 2.567 | <LOQ | <LOQ | <LOQ |
| 2 | <LOQ | <LOQ | <LOQ | 44.149 |
| 3 | <LOQ | <LOQ | <LOQ | <LOQ |
| 4 | 1.144 | 0.678 | <LOQ | <LOQ |
| 5 | <LOQ | <LOQ | <LOQ | <LOQ |
| 6 | 3.440 | <LOQ | <LOQ | <LOQ |
| 7 | 2.727 | <LOQ | <LOQ | <LOQ |
| 8 | <LOQ | <LOQ | <LOQ | <LOQ |

Data are expressed as concentration for each animal.
<LOQ = below limit of quantitation; LOQ is 0.494 nM

Example 18: FP2 Multispecies Pharmacokinetics and Immune Response

Mouse Pharmacokinetics

Figure 25:
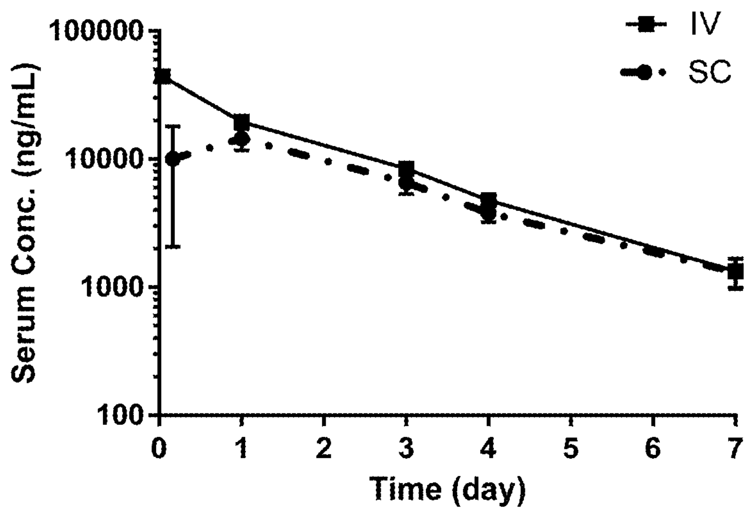
FIG. 25 shows serum concentrations of FP2 following 2 mg/kg intravenous (IV) and 2 mg/kg subcutaneous (SC) administration in C57Bl/6 mice. Values represent mean±SD (n=5 samples per timepoint).

The pharmacokinetic properties of FP2 were evaluated when administered subcutaneously to female C57Bl/6 mice. FP2 was administered subcutaneously (n=5 samples per time point) and intravenously (n=5 samples per time point) to female C57Bl/6 mice (Sage Laboratories, St Louis, Mo.) at a dose level of 2.0 mg/kg in PBS, (pH 7.3-7.5). The collection of sample at the last time point was via a terminal bleed. Blood samples were collected, serum processed and drug concentrations were measured up to 168 hours. The levels of FP2 were measured using an immunoassay method. The drug concentration profiles in plasma are summarized in Table 51 and 52 and illustrated in FIG. 25.

Pharmacokinetic analysis of FP2 in C57Bl/6 mice demonstrated a terminal half-life of ~1.51 and ~1.76 days following IV and SC dosing respectively, with a mean bioavailability of ~61% following SC administration.

TABLE 51

| Serum concentration (ng/mL) of FP2 following a single subcutaneous (SC) dose in C57Bl/6 mice | | | | | | | |
|---|---|---|---|---|---|---|---|
| | FP2 - SC Dose | | | | | | |
| Timepoint | Animal 31 Result (ng/mL) | Animal 32 Result (ng/mL) | Animal 33 Result (ng/mL) | Animal 35 Result (ng/mL) | Animal 36 Result (ng/mL) | Average Result (ng/mL) | Std Dev (ng/mL) |
| 4 hr | 11310.11 | 6323.44 | 23489.21 | 4357.74 | 4835.54 | 10063.21 | 7995.0 |
| 24 hr | 12378.58 | 10896.80 | 17769.03 | 15928.14 | 15404.08 | 14475.33 | 2785.0 |
| 72 hr | 5127.95 | 5569.27 | 6727.37 | 7909.66 | 7550.32 | 6576.91 | 1210.5 |
| 96 hr | 3059.83 | 3350.25 | 4042.04 | 4095.15 | 4431.94 | 3795.84 | 569.0 |
| 168 hr | 784.61 | 1202.66 | 1364.68 | 1557.60 | 1678.02 | 1317.51 | 348.9 |

TABLE 52

Serum concentration (ng/mL) of FP2 following a single intravenous (IV) dose in C57Bl/6 mice

| | FP2 - IV Dose | | | | | | |
|---|---|---|---|---|---|---|---|
| Timepoint | Animal 37 Result (ng/mL) | Animal 40 Result (ng/mL) | Animal 41 Result (ng/mL) | Animal 45 Result (ng/mL) | Animal 48 Result (ng/mL) | Average Result (ng/mL) | Std Dev (ng/mL) |
| 1 hr | 49573.59 | 42382.59 | 40001.18 | 43085.75 | 46443.59 | 44297.34 | 3742.9 |
| 24 hr | 22173.85 | 19120.39 | 19393.78 | 19798.29 | 17459.96 | 19589.25 | 1696.7 |
| 72 hr | 8334.33 | 7989.10 | 8573.44 | 9086.37 | 8186.68 | 8433.98 | 422.5 |
| 96 hr | 4478.83 | 4699.80 | 4749.93 | 5331.39 | 4579.08 | 4767.81 | 332.3 |
| 168 hr | 1044.24 | 1419.64 | 1393.44 | 1835.63 | 979.49 | 1334.49 | 343.6 |

TABLE 53

Pharmacokinetic parameters of FP2 following 2 mg/kg IV and 2 mg/kg SC administration in C57Bl/6 mice.

| Route | | $t_{1/2}$ (day) | CL or CL/F (ml/day/kg) | Vz or Vz/F (ml/kg) | $C_{max}$ (ng/ml) | $T_{max}$* (day) | $AUC_{0-last}$ (day* ng/ml) | $AUC_{0-inf}$ (day* ng/ml) |
|---|---|---|---|---|---|---|---|---|
| SC | Mean | 1.76 | 43 | 108 | 15619 | 1 | 44972 | 48379 |
| | SD | 0.16 | 8 | 20 | 4870 | | 8563 | 9147 |
| IV | Mean | 1.51 | 25 | 55 | 44297 | 0.042 | 76269 | 79253 |
| | SD | 0.18 | 1 | 6 | 3743 | | 3788 | 4051 |

Rat Pharmacokinetics

Figure 26:
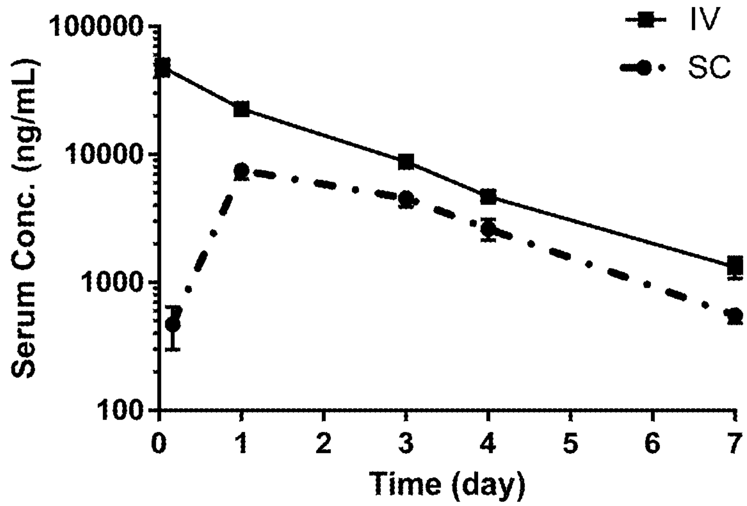
FIG. 26 shows serum concentrations of FP2 following 2 mg/kg intravenous (IV) and 2 mg/kg subcutaneous (SC) administration in Sprague Dawley rats. N=5 samples per time point.

FP2 was administered subcutaneously (n=5 samples per time point) and intravenously (n=5 samples per time point) to female Sprague-Dawley rats (Sage Laboratories, St. Louis, Mo.) at a dose level of 2.0 mg/kg in PBS, (pH 7.3-7.5). The collection of sample at the last time point was via a terminal bleed. Blood samples were collected, serum processed and drug concentrations were measured up to 168 hours. The levels of FP2 were measured using an immuno-assay method. The drug concentration profiles in plasma are summarized in Table 54 and 55, and illustrated in FIG. 26. Pharmacokinetic parameters calculated from these data are summarized in Table 56.

Pharmacokinetic analysis of FP2 in Sprague Dawley rats demonstrated a terminal half-life of ~1.46 and ~1.37 days following IV and SC dosing respectively, with a mean bioavailability of ~28% following SC administration.

TABLE 54

Serum concentration (ng/mL) of FP2 following a single subcutaneous (SC) dose in Sprague-Dawley rats.

| | FP2 - SC Dose | | | | | | |
|---|---|---|---|---|---|---|---|
| Timepoint | Animal 01 Result (ng/ml) | Animal 02 Result (ng/ml) | Animal 03 Result (ng/ml) | Animal 04 Result (ng/ml) | Animal 05 Result (ng/ml) | Average Result (ng/ml) | Std Dev (ng/ml) |
| 4 hr | 730.95 | 257.94 | 469.95 | 496.34 | 400.65 | 471.16 | 172.2 |
| 24 hr | 9236.27 | 6658.79 | 7728.92 | 7449.56 | 6502.60 | 7515.23 | 1092.1 |
| 72 hr | 4559.04 | 4464.72 | 5619.82 | 4287.25 | 3844.15 | 4555.00 | 655.6 |
| 96 hr | 2791.97 | 2452.35 | 3387.55 | 2316.06 | 2176.00 | 2624.79 | 483.8 |
| 168 hr | 622.32 | 606.36 | <80.00 | 514.19 | 476.49 | 554.84 | 70.7 |

TABLE 55

Serum concentration (ng/mL) of FP2 following a single intravenous (IV) dose in Sprague-Dawley rats.

| | FP2 - IV Dose | | | | | | |
|---|---|---|---|---|---|---|---|
| Timepoint | Animal 06 Result (ng/ml) | Animal 07 Result (ng/ml) | Animal 08 Result (ng/ml) | Animal 09 Result (ng/ml) | Animal 10 Result (ng/ml) | Average Result (ng/ml) | Std Dev (ng/ml) |
| 1 hr | 60785.80 | 47392.80 | 43046.54 | 46014.25 | 44547.65 | 48357.41 | 7134.5 |
| 24 hr | 25470.36 | 24729.88 | 21157.29 | 20497.32 | 21459.71 | 22662.91 | 2267.1 |

TABLE 55-continued

Serum concentration (ng/mL) of FP2 following a single intravenous (IV) dose in Sprague-Dawley rats.

| | FP2 - IV Dose | | | | | | |
|---|---|---|---|---|---|---|---|
| Timepoint | Animal 06 Result (ng/ml) | Animal 07 Result (ng/ml) | Animal 08 Result (ng/ml) | Animal 09 Result (ng/ml) | Animal 10 Result (ng/ml) | Average Result (ng/ml) | Std Dev (ng/ml) |
| 72 hr | 8208.46 | 9262.13 | 8866.76 | 8635.93 | 8843.83 | 8763.42 | 384.1 |
| 96 hr | 4433.18 | 4833.22 | 4995.63 | 4630.60 | 4604.13 | 4699.35 | 218.1 |
| 168 hr | 1083.14 | 1469.35 | 1614.61 | 1394.17 | 1053.89 | 1323.03 | 245.7 |

TABLE 56

Pharmacokinetic parameters of FP2 following 2 mg/kg IV and 2 mg/kg SC administration in Sprague-Dawley Rats.

| Route | | $t_{1/2}$ (day) | CL or CL/F (ml/day/kg) | Vz or Vz/F (ml/kg) | $C_{max}$ (ng/ml) | $T_{max}$* (day) | $AUC_{0\text{-}last}$ (day* ng/ml) | $AUC_{0\text{-}inf}$ (day* ng/ml) |
|---|---|---|---|---|---|---|---|---|
| SC | Mean | 1.37 | 84 | 165 | 7515 | 1 | 22614 | 24036 |
| | SD | 0.04 | 10 | 17 | 1092 | | 2509 | 2893 |
| IV | Mean | 1.46 | 23 | 49 | 48357 | 0.042 | 83271 | 86089 |
| | SD | 0.12 | 2 | 6 | 7135 | | 6081 | 5820 |

Monkey Pharmacokinetics

FP2 was administered subcutaneously at 1 mg/kg and intravenously at 1 mg/kg to three male cynomolgus monkeys each in PBS, (pH 7.0-7.6). Blood samples were collected, plasma processed and drug concentrations were measured up to 21 days.

Figure 27:
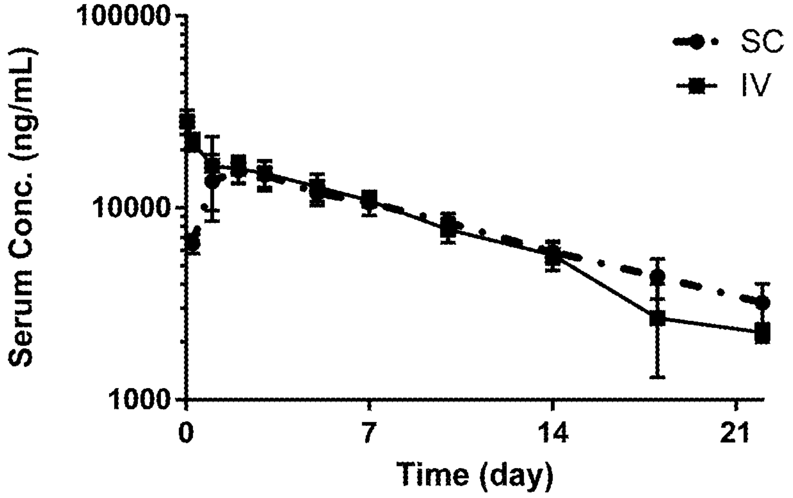
FIG. 27 shows plasma concentrations of FP2 in cynomolgus monkeys analyzed by immunoassay. Values represent mean±SD of n=3, except n=2 for IV at day 22 (528 hr). IV—intravenous, SC—subcutaneous.
Figure 28:
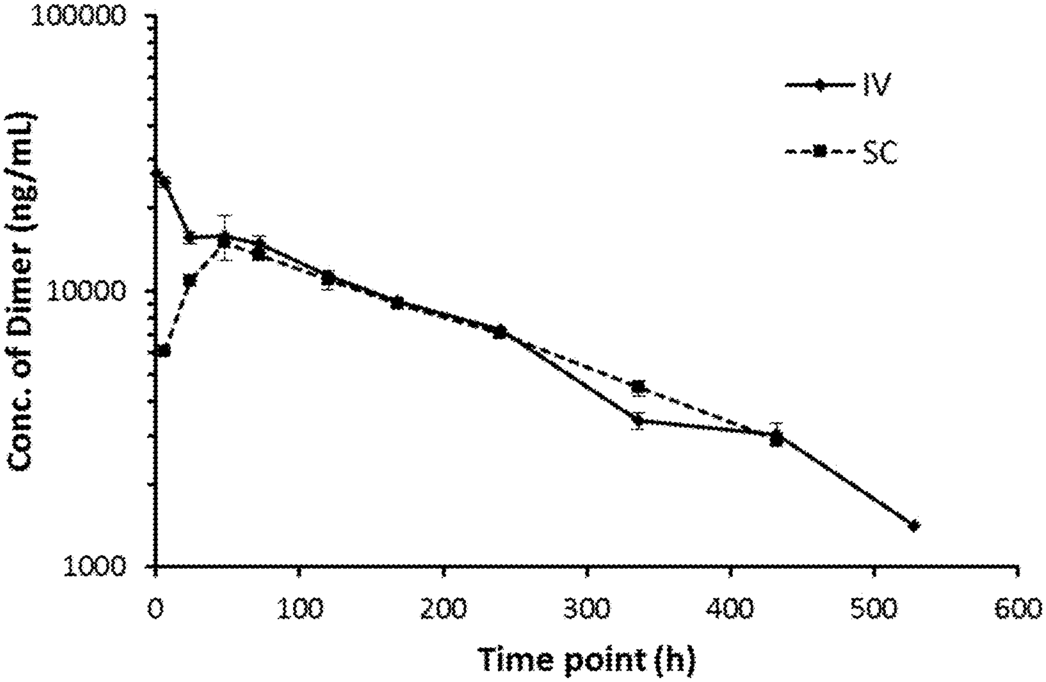
FIG. 28 shows plasma concentrations of FP2 as intact dimer in cynomolgus monkeys analyzed by LCMS. Values represent mean±SEM of n=3, except n=2 for subcutaneous (SC) at 168 hours, n=1 for SC at 120 hours and 432 hours, and n=1 for IV—intravenous at 168 hours and 432 hours.

The pharmacokinetics (PK) of FP2 was characterized following administration of a single dose IV (1.0 mg/kg) and SC (1.0 mg/kg) in cynomolgus monkeys. The plasma drug concentration-time profile after SC administration is summarized in Tables 57 and 58 for immunoassay and LCMS analyses respectively and after IV administration in Tables 59 and 60 for immunoassay and LCMS analyses respectively. The immunoassay data is graphed in FIG. 27, and the LCMS data is represented in FIG. 28.

Using results from the immunoassay analysis, the mean NCA-based terminal half-life (t½) for FP2 was ~7.05 and ~8.51 days following IV and SC dosing, respectively. The mean PK parameters following IV and SC administration are summarized in Table 61. Using results from the immunoassay bioanalysis, the mean non-compartment model estimated terminal half-life (t½) for FP2 was 7.05 and 8.51 days following IV and SC dosing, respectively. The mean bioavailability (F %) of FP2 was estimated to be ~98.5% based on $AUC_{0\text{-}last}$ and estimated to be ~109.2% based on $AUC_{0\text{-}inf}$ in cynomolgus monkeys following SC administration.

TABLE 57

Plasma concentration (ng/mL) of FP2 measured by immunoassay following a single SC dose in cynomolgus monkeys.

| | Immunoassay | | | | |
|---|---|---|---|---|---|
| Time (hr) | Animal 704 | Animal 705 | Animal 706 | SC Ave | Std Dev |
| 0 | <80.0 | <80.0 | <80.0 | <80.0 | N/A |
| 6 | 7365.3 | 6128.5 | 6056.9 | 6516.9 | 735.6 |
| 24 | 19716.8 | 10903.8 | 10554.7 | 13725.1 | 5191.9 |
| 48 | 18191.7 | 14353.7 | 14464.7 | 15670.0 | 2184.5 |

TABLE 57-continued

Plasma concentration (ng/mL) of FP2 measured by immunoassay following a single SC dose in cynomolgus monkeys.

| | Immunoassay | | | | |
|---|---|---|---|---|---|
| Time (hr) | Animal 704 | Animal 705 | Animal 706 | SC Ave | Std Dev |
| 72 | 17813.9 | 14207.5 | 12684.0 | 14901.8 | 2634.5 |
| 120 | 13823.9 | 11445.8 | 10590.8 | 11953.5 | 1675.3 |
| 168 | 12359.6 | 10103.8 | 9467.8 | 10643.8 | 1519.7 |
| 240 | 9457.9 | 7642.6 | 8109.1 | 8403.2 | 942.7 |
| 336 | 6796.8 | 5679.8 | 5235.7 | 5904.1 | 804.3 |
| 432 | 5581.3 | 3830.6 | 3746.5 | 4386.1 | 1035.9 |
| 528 | 4126.2 | 2613.4 | 2879.3 | 3206.3 | 807.7 |

N/A = not applicable

TABLE 58

Plasma concentration (ng/mL) of FP2 measured by LCMS following a single SC dose in cynomolgus monkeys.

| | LC/MS | | | | |
|---|---|---|---|---|---|
| Time (hr) | Animal 704 | Animal 705 | Animal 706 | SC Ave | SEM |
| 0 | <1000 | <1000 | <1000 | <1000 | N/A |
| 6 | 6110.0 | 5910 | 6200.0 | 6073.3 | 85.7 |
| 24 | # | 10420.0 | 11300.0 | 10860.0 | 359.3 |
| 48 | 16560.0 | 13510.0 | 14960.0 | 15010.0 | 880.8 |
| 72 | 13690.0 | 13450.0 | 13380.0 | 13506.7 | 93.9 |
| 120 | 11040.0 | # | # | 11040.0 | N/A |
| 168 | # | 8680.0 | 9400.0 | 9040.0 | 293.9 |
| 240 | 6940.0 | 7070.0 | 7140.0 | 7050.0 | 58.6 |
| 336 | 4400.0 | 4580.0 | 4430.0 | 4470.0 | 55.7 |
| 432 | — | 2910.0 | — | 2910.0 | N/A |
| 528 | <1000 | <1000 | <1000 | <1000 | N/A |

— = initial run failed, not enough sample for repeat analysis
# = mislabeled tube, sample excluded from the analysis
N/A = not applicable

TABLE 59

Plasma concentration (ng/mL) of FP2 measured by immunoassay following a single IV dose in cynomolgus monkeys.

| | Immunoassay | | | | |
|---|---|---|---|---|---|
| Time (hr) | Animal 701 | Animal 702 | Animal 703 | IV Ave | Std Dev |
| 0 | <80.0 | <80.0 | <80.0 | <80.0 | N/A |
| 1 | 29938.3 | 31139.0 | 23545.3 | 28207.6 | 4082.0 |
| 6 | 24711.9 | 21173.0 | 20434.4 | 22106.4 | 2286.5 |
| 24 | 19648.4 | 21420.9 | 8662.7 | 16577.3 | 6911.3 |
| 48 | 17790.1 | 17107.0 | 12983.1 | 15960.0 | 2600.7 |
| 72 | 17889.4 | 13871.1 | 13692.4 | 15151.0 | 2373.3 |
| 120 | 15298.6 | 11982.5 | 11361.5 | 12880.9 | 2116.7 |
| 168 | 11752.0 | 10982.8 | 9933.8 | 10889.5 | 912.7 |
| 240 | 8921.1 | 7465.0 | 6733.4 | 7706.5 | 1113.6 |
| 336 | 6572.8 | 5750.5 | 4687.6 | 5670.3 | 945.1 |
| 432 | 1099.6 | 3425.0 | 3458.0 | 2660.9 | 1352.2 |
| 528 | <80.0 | 2069.0 | 2416.2 | 2242.6 | N/A |

N/A = not applicable

TABLE 60

Plasma concentration (ng/mL) of FP2 measured by LCMS following a single IV dose in cynomolgus monkeys

| | LC/MS | | | | |
|---|---|---|---|---|---|
| Time (hr) | Animal 701 | Animal 702 | Animal 703 | IV Ave | SEM |
| 0 | <1000 | <1000 | <1000 | <1000 | N/A |
| 1 | 25340.0 | 28820 | 26220.0 | 26793.3 | 1044.7 |
| 6 | 24610.0 | 26340.0 | 23810.0 | 24920.0 | 746.6 |
| 24 | 18410.0 | 18680.0 | 9810.0 | 15633.3 | 2912.7 |
| 48 | 16290.0 | 17370.0 | 13840.0 | 15833.3 | 1044.3 |
| 72 | 15430.0 | 14920.0 | 14280.0 | 14876.7 | 332.7 |
| 120 | 11180.0 | 11480.0 | 11440.0 | 11366.7 | 94.0 |
| 168 | 9170.0 | # | # | 9170.0 | N/A |
| 240 | 6800.0 | 7380.0 | 7600.0 | 7260.0 | 238.6 |
| 336 | 2870.0 | 3860.0 | 3480.0 | 3403.3 | 288.3 |
| 432 | — | — | 3030.0 | 3030.0 | N/A |
| 528 | 1150.0 | 1680.0 | 1400.0 | 1410.0 | 153.1 |

— = initial run failed, not enough sample for repeat analysis
N/A = not applicable
# = mislabeled tube, sample excluded from the analysis

TABLE 61

Mean (±SD) pharmacokinetic parameters of FP2 following 1 mg/kg IV and SC administration in cynomolgus monkey.

| Route | | $t_{1/2}$ (day) | CL or CL/F (ml/day/kg) | Vz or Vz/F (ml/kg) | $C_{max}$ (ng/ml) | $T_{max}$* (day) | $AUC_{0\text{-}last}$ (day*ng/ml) | $AUC_{0\text{-}inf}$ (day*ng/ml) |
|---|---|---|---|---|---|---|---|---|
| SC | Mean | 8.51 | 4.6 | 56 | 16178 | 1.67 | 180792 | 221032 |
| | SD | 1.28 | 0.8 | 7 | 3065 | | 29990 | 44931 |
| IV | Mean | 7.05 | 4.9 | 51 | 28208 | 0.042 | 183468 | 202380 |
| | SD | 1.45 | 0.2 | 12 | 4082 | | 18268 | 9617 |

PK parameters are mean values based on NCA of immunoassay PK data.
*Tmax (median)

Human Plasma Stability Assay

The ex vivo stability of FP2 was examined in fresh heparinized plasma at 37° C. for up to 48 hours. Fresh, non-frozen human plasma was generated from heparinized blood from two subjects (one male and one female) by centrifugation. FP2 was incubated in this matrix at 37° C. with gentle mixing or 0. 4. 24 and 48 hours. The concentration of FP2 was determine using an immunoassay method. An independent immunoaffinity capture followed by LCMS method was used to quantitate the concentration of the intact dimer present in this matrix under the assay conditions.

Figure 29:
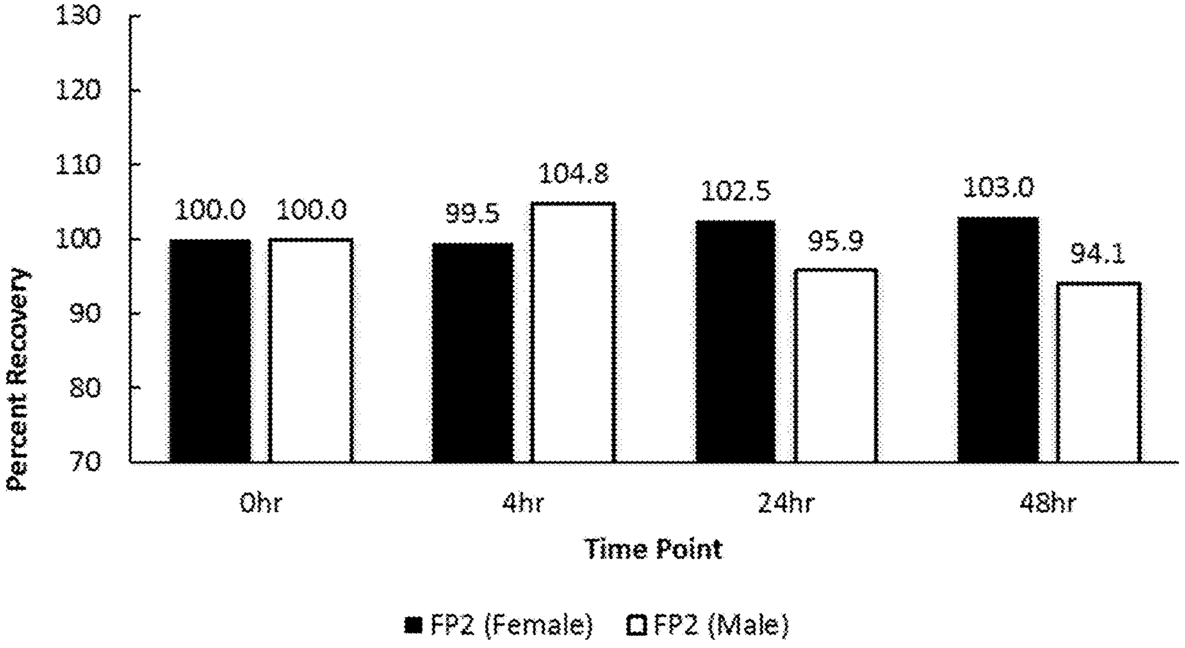
FIG. 29 shows ex vivo stability of FP2 (Normalized Percent Recovery) over 48 hours in human plasma measured by immunoassay.
Figure 30:
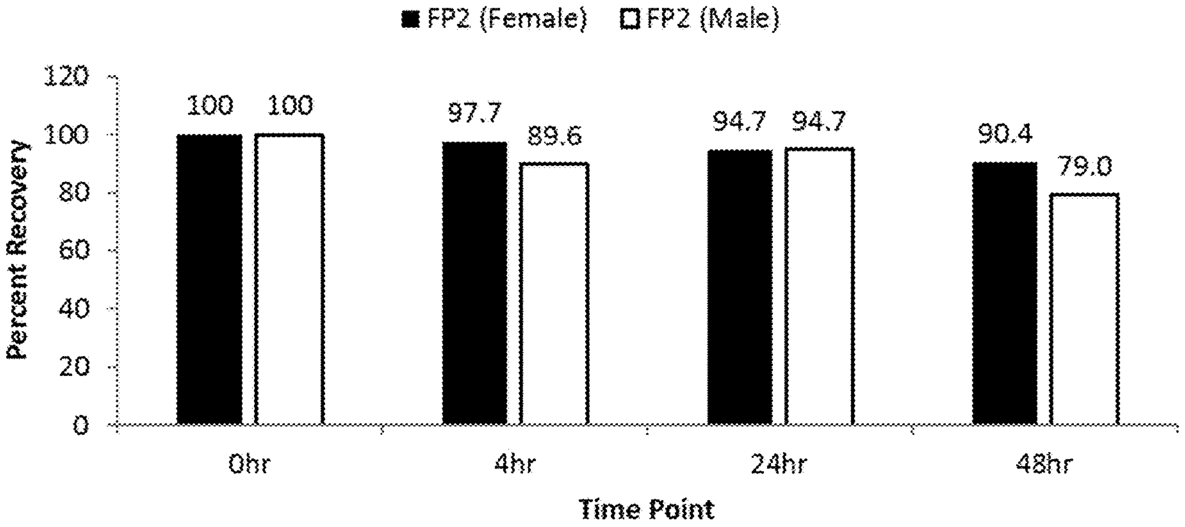
FIG. 30 shows ex vivo stability of FP2 (Normalized Percent Recovery) over 48 hours in human plasma measured by intact LC/MS.
Figure 31:
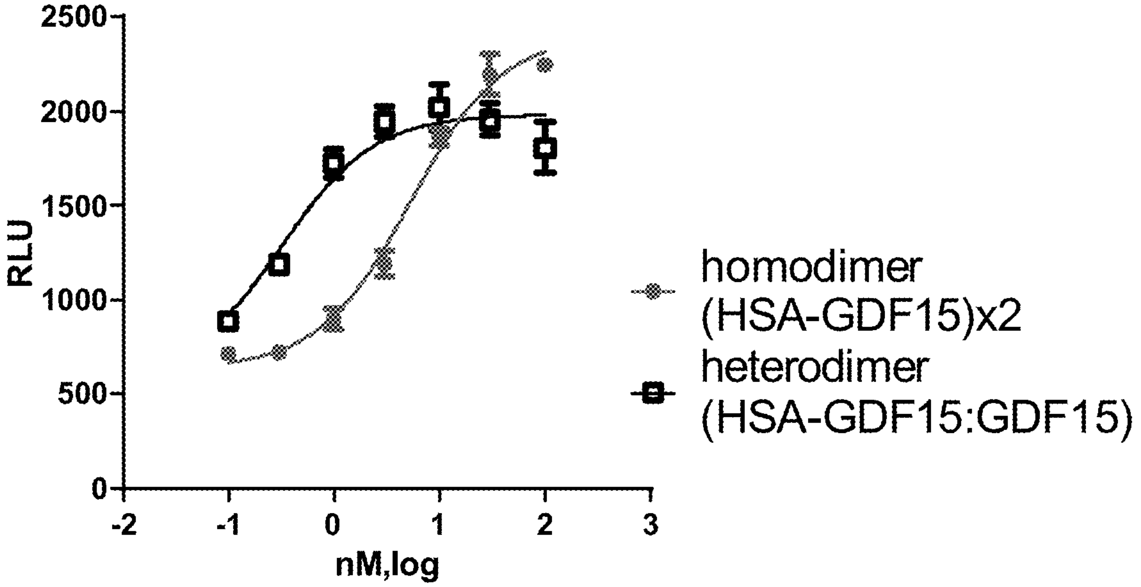
FIG. 31 shows concentration response curves for FP2 and HSA-GDF15:GDF15 heterodimer using pAKT Assays in SK-N-AS cells expressing recombinant human GFRAL receptor (N=3).

In the immunoassay method, the percent recovery from the starting concentration ranged from 104.8 to 94.1 and did not decrease over time, demonstrating that FP2 is stable in human plasma up to 48 hours ex vivo (FIG. 29 and Table 62). The LCMS method showed that concentrations were stable over time demonstrating that JNJ-64739090 remains an intact dimer in human plasma up to 48 hours ex vivo (FIG. 30 and Table 63).

TABLE 62

Ex vivo stability of FP2 (Normalized Percent Recovery) over 48 hours in human plasma (ng/ml) measured by immunoassay.

| Compound | Gender | Time (hr) | Concentration (ng/mL) | Normalized % Recovery |
|---|---|---|---|---|
| FP2 | female | 0 | 9104 | 100.0 |
| | | 4 | 9056 | 99.5 |
| | | 24 | 9332 | 102.5 |
| | | 48 | 9374 | 103.0 |
| | male | 0 | 9473 | 100.0 |
| | | 4 | 9929 | 104.8 |
| | | 24 | 9081 | 95.9 |
| | | 48 | 8912 | 94.1 |

TABLE 63

Ex vivo stability of FP2 (Normalized Percent Recovery) over 48 hours in human plasma (ng/ml) measured by intact LC/MS.

| Compound | Gender | Time (hr) | Concentration (ng/mL) | Normalized % Recovery |
|---|---|---|---|---|
| FP2 | female | 0 | 11090 | 100.0 |
| | | 4 | 10830 | 97.7 |
| | | 24 | 10500 | 94.7 |
| | | 48 | 10030 | 90.4 |
| | male | 0 | 10760 | 100.0 |
| | | 4 | 9640 | 89.6 |
| | | 24 | 10190 | 94.7 |
| | | 48 | 8500 | 79.0 |

Example 19: Efficacy of FP1 and FP2 in Cynomolgus Monkeys

The effects of FP1 and FP2 on food intake and body weight after a single dose in naïve cynomolgus monkeys were evaluated.

FP1 was administered subcutaneously to a cohort of naïve cynomolgus monkeys at three dose levels; 1, 3 and 10 nmol/kg. A vehicle treated group was also included. The animals were treated in a blinded manner. The study lasted a total of 6 weeks: 2 weeks of baseline food intake measurement and data collection, 4 weeks of data collection after single administration of compound. Plasma drug exposures were measured on days 1, 7, 14, 21, and 28 following dosing.

Figure 32:
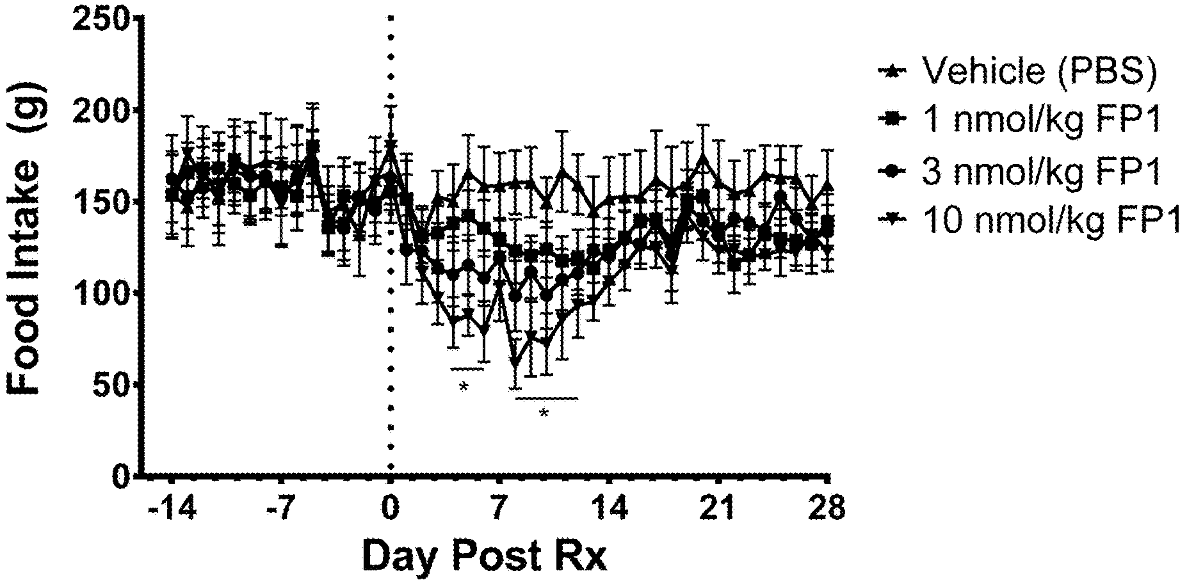
FIG. 32 shows daily food intake (g) prior to and following a single dose of FP1 in cynomolgus monkeys. *–p<0.05 for 10 mg/kg of FP1 as compared to vehicle.
Figure 33:
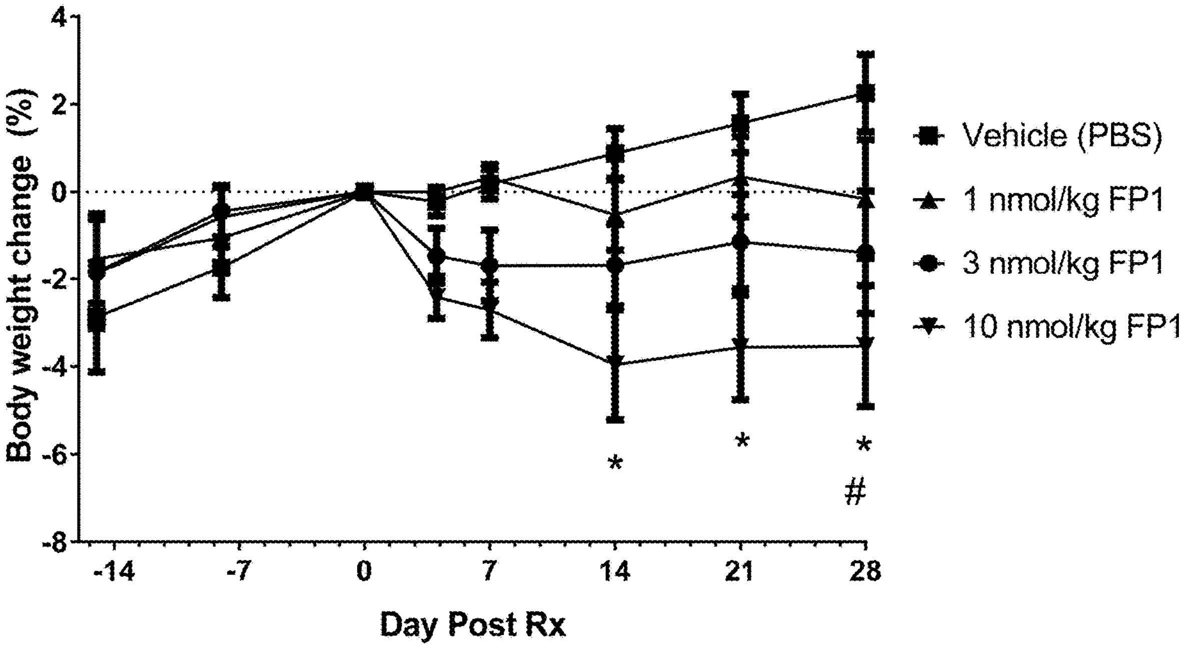
FIG. 33 shows percent body weight change prior to and following a single dose of FP1 in cynomolgus monkeys. *–p<0.05 for 10 mg/kg FP1 as compared to vehicle; #–p<0.05 for 3 mg/kg as compared to vehicle using Two Way RM ANOVA and Tukey's multiple comparisons test, for n=8 animals per group.

Treatment of cynomolgus monkeys with a single dose of FP1 reduced food intake and body weight compared to vehicle treatment (FIGS. 32-33). A significant reduction in daily food intake was seen on days 4, 5, 6, and 8 through 12 for the 10 nmol/kg dose level (FIG. 32). The weekly average of daily food intake was significantly reduced for during week 2 post administration for the 10 nmol/kg dose level. The 3 nmol/kg dose level had a significant percent reduction from the average weekly food intake prior to dosing on week 2 post administration and the 10 nmol/kg dose level had a significant percent reduction from the average weekly food intake prior to dosing in weeks 1 and 2 post administration. A significant reduction in percent body weight change from day 0 was seen at day 28 for the 3 nmol/kg dose level, and on day 14, 21, and 28 for the 10 nmol/kg dose level (FIG. 33).

FP2 was administered subcutaneously to a cohort of naïve cynomolgus monkeys at three dose levels; 1, 3 and 10 nmol/kg. A vehicle treated group was also included. The animals were treated in a blinded manner. The study lasted a total of 11 weeks: 5 weeks of baseline food intake measurement and data collection, 1 week of treatment and 5 weeks of wash-out phase data collection. Plasma drug exposures were measured on days 1, 7, 14, 21, 28, 35, and 42 following dosing.

Figure 34:
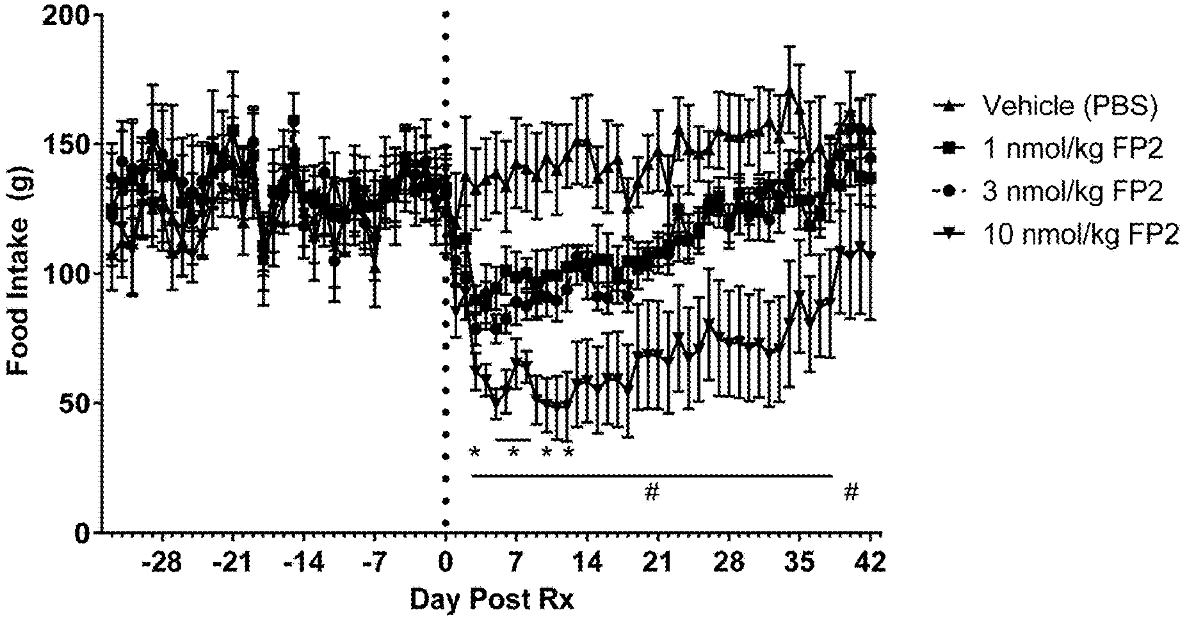
FIG. 34 shows daily food intake (g) prior to and following a single dose of FP2 in cynomolgus monkeys. *–p<0.05, as compared to Vehicle, using Two Way RM ANOVA and Tukey's multiple comparisons test, for n=8 animals per group.
Figure 35:
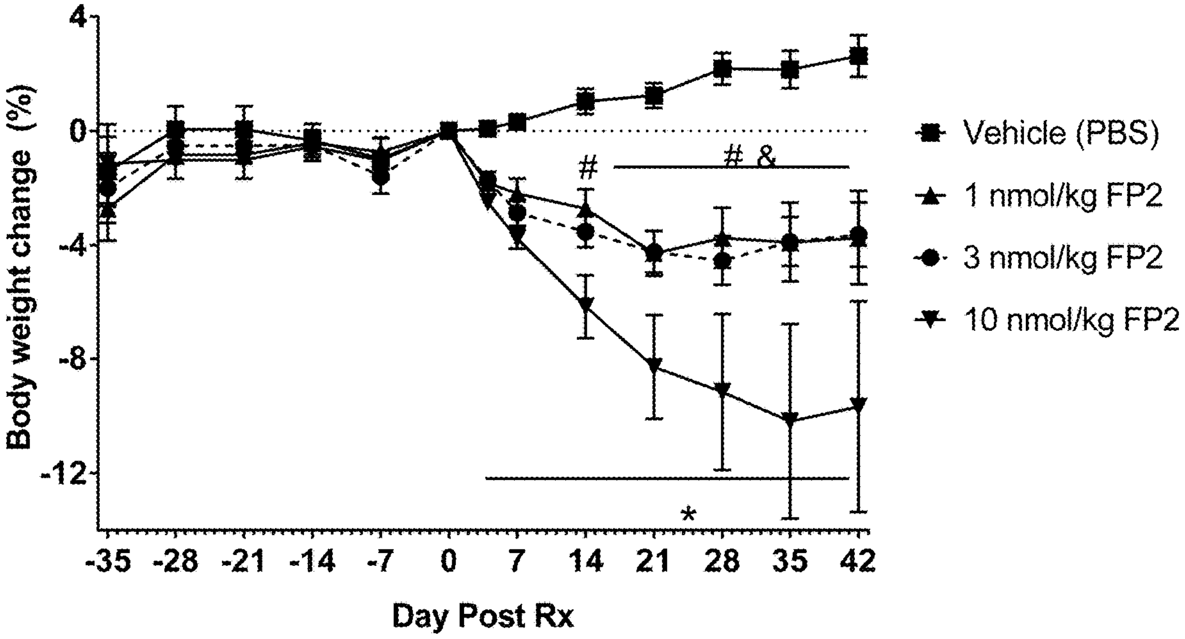
FIG. 35 shows percent body weight change prior to and following a single dose of FP2 in cynomolgus monkeys. *–$p<0.05$, for 10 nmol/kg of FP2 as compared to Vehicle, #–$p<0.05$, for 3 nmol/kg of FP2 as compared to Vehicle, & –$p<0.05$, for 1 nmol/kg of FP2 as compared to Vehicle, using Two Way RM ANOVA and Tukey's multiple comparisons test, for n=8 animals per group.

Treatment of cynomolgus monkeys with a single dose of FP2 reduced food intake and body weight compared to vehicle treatment (FIGS. 34-35). A significant reduction in daily food intake was seen on days 3, 5 through 8, 10 and 12 for the 3 nmol/kg dose level and from days 3 through 38 and day 40 for the 10 nmol/kg dose level (FIG. 34). The weekly average of daily food intake was significantly reduced for week 1 post administration for the 3 nmol/kg dose level and significantly reduced for weeks 1 through 6 for the 10 nmol/kg dose level. The 3 nmol/kg dose level had a significant percent reduction from the week prior to dosing in weekly average daily food intake on week 2 post administration and the 10 nmol/kg dose level had a significant percent reduction from the week prior to dosing in weekly average daily food intake on weeks 1 through 6 post administration. A significant reduction in percent body weight change from day 0 was seen from days 21 through 42 for the 1 nmol/kg dose level, from days 14 through 42 for the 3 nmol/kg dose level and from days 7 through 42 for the 10 nmol/kg dose level (FIG. 34).

Example 20: HSA-GDF15:GDF15 Heterodimer

Bioactivity of HSA-GDF15:GDF15 heterodimer was investigated.

To generate an HSA-GDF15:GDF15 heterodimer two constructs were designed. The first construct contained HSA fused to the N-terminus of mature GDF15 (AA 203-308) via a glycine-serine linker (SEQ ID NO: 93). The second construct contained a 6× histidine tagged HSA fused to the N-terminus of mature GDF15 (AA 197-308) via a glycine-serine linker and an HRV3C protease cleavage site (SEQ ID NO: 94). The plasmids were co-transfected at a 1:1 ratio using the Expi293™ Expression System (Thermo Fisher Scientific) according to the manufacturer's protocol. Peptides were secreted as HSA-GDF15 proteins, including both heterodimer and homodimer forms, wherein monomers were linked by disulfide bonds.

Cell supernatants from transiently transfected Expi293™ cells were harvested 5 days after transfection, clarified by centrifugation and sterile filtered (0.2μ PES membrane, Corning). Clarified supernatants were loaded onto a Histrap HP column (GE Healthcare) equilibrated with 20 mM sodium phosphate, 500 mM NaCl, pH 7.4. After loading, unbound protein was removed by washing the column with equilibration buffer. HSA-GDF15 proteins, including both heterodimer and homodimer forms, bound to the column and were eluted with 20 mM sodium phosphate, 150 mM imidazole, pH 7.4. Eluate fractions were pooled and incubated overnight at 4° C. in the presence of 6× histidine tagged HRV3C enzyme (Janssen) to generate the HSA-GDF15:GDF15 heterodimer. Following incubation, the protein solution was dialyzed into equilibration buffer to remove imidazole before being applied to a HisTrap HP column one more time. The HSA-GDF15:GDF15 heterodimer eluted in the 20 mM sodium phosphate, 50 mM imidazole, pH 7.4 wash step, while histidine tagged proteins were retained. The heterodimer was further polished by size exclusion chromatography (SEC) using a HiLoad 26/60 Superdex 200 pg column (GE Healthcare) equilibrated in 1×DPBS, pH 7.2. Eluate fractions from the SEC with high purity (determined by SDS-PAGE) of the HSA-GDF15:GDF15 heterodimer were pooled and filtered. The protein concentration was determined by absorbance at 280 nm on a BioTek SynergyHT™ spectrophotometer. The quality of the purified protein was assessed by SDS-PAGE and analytical size exclusion HPLC (Ultimate3000 HPLC system). Endotoxin levels were measured using an LAL assay (Pyrotell®-T, Associates of Cape Cod). The purified protein was stored at 4° C.

SK-N-AS cells (ATCC) stably expressing GDF15 receptor (GFRAL) were seeded in growth medium (10% FBS) in a 96-well plate 24 hours prior to the assay. After 24 hrs the cells were starved by replacing the culture medium with 200 μl of DMEM medium supplemented with 1% HI horse serum for 3 hours in a 37° C. incubator. The 1% HI horse serum supplemented medium was then replaced with 200 μl of AB1 and incubated for an additional 2 hours in a 37° C. incubator. To perform the assay, the AB1 was aspirated from all wells and 100 μl of variable concentrations of the testing compound in AB2 was added and the plate was incubated for 15 min in a 37° C. incubator. After 15 minutes, the testing solution was removed and 30 μl of lysis buffer (provided in the detection kit) was added and the plate was shaken on a plate shaker at room temperature for 30 min. For detection, 16 μl of the lysed sample was transferred to a 384-well assay plate and 4 μl of HTRF pAKT detection antibodies were added. The plate was incubated overnight at room temperature and then the HTRF signal read on the Envision (Perkin Elmer).

$EC_{50}$ values were calculated using GraphPad Prism® Nonlinear Regression (Curve fit). Data are expressed as the Mean±Standard Error (SE) from three separate experiments with three replicates per data point. Molecular identity of the HSA-GDF15:GDF15 heterodimer was confirmed by mass spectrometry. The left-shift of the heterodimer curve suggested that the HSA-GDF15:GDF15 heterodimer is more potent in inducing pAKT than the relevant homodimer molecule with an additional albumin.

Example 21: Linker Thermal Stability

Thermal stability was investigated for various linkers that connect HSA and GDF15. To evaluate the potential to fragment and aggregate, HSA-GDF15 fusion proteins with various linkers were diluted to 10 mg/ml. After addition of EDTA and Methionine, the samples were incubated under 40° C. for 14 days. Then samples were diluted to the concentration of 1 mg/ml and evaluated under size-exclusion high-performance liquid chromatography (SE-HPLC). Percent of intact protein as well as aggregate and fragment were quantified for these proteins. Table 64 shows that the HSA-GDF15 proteins with linkers that consist of AP repeats are most stable against fragment under thermal stress.

To evaluate the whether these linker affects GDF15 interaction with its receptor, an immunoassay with GFRAL-Fc fusion protein coated on plate and anti-GDF15 or anti-HSA detection was performed, using monoclonal antibodies for GDF15 (Janssen) and HSA (Kerafast, Inc., Boston, Mass.). The assay showed all these linker variants in Table 66 has similar binding to receptor.

TABLE 64

SE-HPLC results after thermal stress for 14 days.

| SEQ ID NO | Linker | aggregate (%) | intact (%) | fragment (%) |
|---|---|---|---|---|
| 113 | $GS(GGGGS)_8$ | 3.33 | 84.44 | 12.22 |
| 115 | $GA(GGGGA)_8$ | 3.51 | 87.98 | 8.5 |
| 117 | $(AP)_{10}$ | 1.64 | 98.36 | 0 |
| 119 | $(AP)_{12}$ | 2.36 | 97.64 | 0 |
| 121 | $GGS-(EGKSSGSGSESKST)_3-GGS$ | 1.67 | 85.24 | 13.09 |
| 123 | $GS(PGGGS)_8$ | 2.96 | 88.12 | 8.91 |
| 125 | $GS(AGGGS)_8$ | 3.44 | 86.22 | 10.34 |
| 127 | $GGS-(EGKSSGSGSESKST)_2-GGS$ | 1.71 | 91.17 | 7.12 |

While the invention has been described in detail, and with reference to specific embodiments thereof, it will be apparent to one of ordinary skill in the art that various changes and modifications can be made therein without departing from the spirit and scope of the invention.

The sequences referenced in this application are provided in the table below:

WT-wild type

| SEQ ID NO | Description | Sequence |
|---|---|---|
| 1 | Human Serum Albumin, WT (HSA) | DAHKSEVAHRFKDLGEENFKALVLIAFAQYLQQCPFEDHVKLVNE<br>VTEFAKTCVADESAENCDKSLHTLFGDKLCTVATLRETYGEMADC<br>CAKQEPERNECFLQHKDDNPNLPRLVRPEVDVMCTAFHDNEETFL<br>KKYLYEIARRHPYFYAPELLFFAKRYKAAFTECCQAADKAACLLPK<br>LDELRDEGKASSAKQRLKCASLQKFGERAFKAWAVARLSQRFPKA<br>EFAEVSKLVTDLTKVHTECCHGDLLECADDRADLAKYICENQDSIS<br>SKLKECCEKPLLEKSHCIAEVENDEMPADLPSLAADFVESKDVCKN<br>YAEAKDVFLGMFLYEYARRHPDYSVVLLLRLAKTYETTLEKCCAA<br>ADPHECYAKVFDEFKPLVEEPQNLIKQNCELFEQLGEYKFQNALLV<br>RYTKKVPQVSTPTLVEVSRNLGKVGSKCCKHPEAKRMPCAEDYLS<br>VVLNQLCVLHEKTPVSDRVTKCCTESLVNRRPCFSALEVDETYVPK<br>EFNAETFTFHADICTLSEKERQIKKQTALVELVKHKPKATKEQLKA<br>VMDDFAAFVEKCCKADDKETCFAEEGKKLVAASQAALGL |
| 2 | HSA variant, C34S | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGL |
| 3 | HSA variant, C34A | DAHKSEVAHRFKDLGEENFKALVLIAFAQYLQQAPFEDHVKLVNE<br>VTEFAKTCVADESAENCDKSLHTLFGDKLCTVATLRETYGEMADC<br>CAKQEPERNECFLQHKDDNPNLPRLVRPEVDVMCTAFHDNEETFL<br>KKYLYEIARRHPYFYAPELLFFAKRYKAAFTECCQAADKAACLLPK<br>LDELRDEGKASSAKQRLKCASLQKFGERAFKAWAVARLSQRFPKA<br>EFAEVSKLVTDLTKVHTECCHGDLLECADDRADLAKYICENQDSIS<br>SKLKECCEKPLLEKSHCIAEVENDEMPADLPSLAADFVESKDVCKN<br>YAEAKDVFLGMFLYEYARRHPDYSVVLLLRLAKTYETTLEKCCAA<br>ADPHECYAKVFDEFKPLVEEPQNLIKQNCELFEQLGEYKFQNALLV<br>RYTKKVPQVSTPTLVEVSRNLGKVGSKCCKHPEAKRMPCAEDYLS<br>VVLNQLCVLHEKTPVSDRVTKCCTESLVNRRPCFSALEVDETYVPK<br>EFNAETFTFHADICTLSEKERQIKKQTALVELVKHKPKATKEQLKA<br>VMDDFAAFVEKCCKADDKETCFAEEGKKLVAASQAALGL |

-continued

| WT-wild type | | |
|---|---|---|
| SEQ ID NO | Description | Sequence |
| 5 | HSA (C34S)-GS(GGGGS)$_4$-GDF15 (WT) Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSARNGDHCPLGPGRCCRLHTVRASLEDLGW ADWVLSPREVQVTMCIGACPSQFRAANMHAQIKTSLHRLKPDTVP APCCVPASYNPMVLIQKTDTGVSLQTYDDLLAKDCHCI |
| 6 | Mature GDF15 (197-308) | ARNGDHCPLGPGRCCRLHTVRASLEDLGWADWVLSPREVQVTMCI GACPSQFRAANMHAQIKTSLHRLKPDTVPAPCCVPASYNPMVLIQK TDTGVSLQTYDDLLAKDCHCI |
| 7 | Truncated mature GDF15 (200-308) | GDHCPLGPGRCCRLHTVRASLEDLGWADWVLSPREVQVTMCIGAC PSQFRAANMHAQIKTSLHRLKPDTVPAPCCVPASYNPMVLIQKTDT GVSLQTYDDLLAKDCHCI |
| 8 | Truncated mature GDF15 (201-308) | DHCPLGPGRCCRLHTVRASLEDLGWADWVLSPREVQVTMCIGACP SQFRAANMHAQIKTSLHRLKPDTVPAPCCVPASYNPMVLIQKTDTG VSLQTYDDLLAKDCHCI |
| 9 | Truncated mature GDF15 (202-308) | HCPLGPGRCCRLHTVRASLEDLGWADWVLSPREVQVTMCIGACPS QFRAANMHAQIKTSLHRLKPDTVPAPCCVPASYNPMVLIQKTDTGV SLQTYDDLLAKDCHCI |
| 10 | Truncated mature GDF15 (203-308) | CPLGPGRCCRLHTVRASLEDLGWADWVLSPREVQVTMCIGACPSQ FRAANMHAQIKTSLHRLKPDTVPAPCCVPASYNPMVLIQKTDTGVS LQTYDDLLAKDCHCI |
| 11 | Truncated mature GDF15 (211-308) | CRLHTVRASLEDLGWADWVLSPREVQVTMCIGACPSQFRAANMH AQIKTSLHRLKPDTVPAPCCVPASYNPMVLIQKTDTGVSLQTYDDL LAKDCHCI |
| 25 | HSA (C34S)-AS(GGGGS)$_2$GT--GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASGGGG SGGGGSGTARNGDHCPLGPGRCCRLHTVRASLEDLGWADWVLSPR EVQVTMCIGACPSQFRAANMHAQIKTSLHRLKPDTVPAPCCVPASY NPMVLIQKTDTGVSLQTYDDLLAKDCHCI |
| 26 | HSA (C34S)-AS(GGGGS)$_8$GT-GDF15 (WT) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASGGGG SGGGGSGGGGSGGGGSGGGGSGGGGSGGGGSGGGGSGTARNGDH |

-continued

WT-wild type

| SEQ ID NO | Description | Sequence |
|---|---|---|
| | | CPLGPGRCCRLHTVRASLEDLGWADWVLSPREVQVTMCIGACPSQ FRAANMHAQIKTSLHRLKPDTVPAPCCVPASYNPMVLIQKTDTGVS LQTYDDLLAKDCHCI |
| 27 | HSA (C34S)-AS(AP)$_5$GT-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASAPAPA PAPAPGTARNGDHCPLGPGRCCRLHTVRASLEDLGWADWVLSPRE VQVTMCIGACPSQFRAANMHAQIKTSLHRLKPDTVPAPCCVPASYN PMVLIQKTDTGVSLQTYDDLLAKDCHCI |
| 28 | HSA (C34S) AS(AP)$_{10}$GT-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASAPAPA PAPAPAPAPAPAPGTARNGDHCPLGPGRCCRLHTVRASLEDLGW ADWVLSPREVQVTMCIGACPSQFRAANMHAQIKTSLHRLKPDTVP APCCVPASYNPMVLIQKTDTGVSLQTYDDLLAKDCHCI |
| 29 | HSA (C34S)-AS(AP)$_{20}$GT-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASAPAPA PAPAPAPAPAPAPAPAPAPAPAPAPAPAPAPAPGTARNGDHCPLG PGRCCRLHTVRASLEDLGWADWVLSPREVQVTMCIGACPSQFRAA NMHAQIKTSLHRLKPDTVPAPCCVPASYNPMVLIQKTDTGVSLQTY DDLLAKDCHCI |
| 30 | HSA (C34S)-AS(EAAAK)$_4$GT-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASEAAA KEAAAKEAAAKEAAAKGTARNGDHCPLGPGRCCRLHTVRASLEDL GWADWVLSPREVQVTMCIGACPSQFRAANMHAQIKTSLHRLKPDT VPAPCCVPASYNPMVLIQKTDTGVSLQTYDDLLAKDCHCI |

-continued

WT-wild type

| SEQ ID NO | Description | Sequence |
|---|---|---|
| 31 | HSA (C34S)-AS(EAAAK)$_8$GT-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLASEAAA KEAAAKEAAAKEAAAKEAAAKEAAAKEAAAKEAAAKGTARNGD HCPLGPGRCCRLHTVRASLEDLGWADWVLSPREVQVTMCIGACPS QFRAANMHAQIKTSLHRLKPDTVPAPCCVPASYNPMVLIQKTDTGV SLQTYDDLLAKDCHCI |
| 36 | HSA (C34S)-GS(GGGGS)$_4$-GDF15 Fusion (deletion 13 mutant) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSCSRLHTVRASLEDLGWADWVLSPREVQVT MCIGACPSQFRAANMHAQIKTSLHRLKPDTVPAPCCVPASYNPMVL IQKTDTGVSLQTYDDLLAKDCHCI |
| 37 | HSA (C34S)-GS(GGGGS)$_4$-GDF15 Fusion (deletion 14 mutant) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSCRLHTVRASLEDLGWADWVLSPREVQVT MCIGACPSQFRAANMHAQIKTSLHRLKPDTVPAPCCVPASYNPMVL IQKTDTGVSLQTYDDLLAKDCHCI |
| 40 | HSA (C34S)-GS(GGGGS)$_4$-GDF15 Fusion | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSARNGDHCPLGPGRCCRLHTVRASLEDLGW ADWVLSPREVQVTMCIGACPSQFRAANMHAQIKTSLHRLKPDTVP APCCVPASYNPMVLIQKTDTGVSLQTYDDLLAKDCHCI |
| 48 | HSA (C34A)-GS(GGGGS)$_4$-GDF15 Fusion | DAHKSEVAHRFKDLGEENFKALVLIAFAQYLQQAPFEDHVKLVNE VTEFAKTCVADESAENCDKSLHTLFGDKLCTVATLRETYGEMADC CAKQEPERNECFLQHKDDNPNLPRLVRPEVDVMCTAFHDNEETFL KKYLYEIARRHPYFYAPELLFFAKRYKAAFTECCQAADKAACLLPK |

-continued

WT-wild type

| SEQ ID NO | Description | Sequence |
|---|---|---|
| | | LDELRDEGKASSAKQRLKCASLQKFGERAFKAWAVARLSQRFPKA<br>EFAEVSKLVTDLTKVHTECCHGDLLECADDRADLAKYICENQDSIS<br>SKLKECCEKPLLEKSHCIAEVENDEMPADLPSLAADFVESKDVCKN<br>YAEAKDVFLGMFLYEYARRHPDYSVVLLLRLAKTYETTLEKCCAA<br>ADPHECYAKVFDEFKPLVEEPQNLIKQNCELFEQLGEYKFQNALLV<br>RYTKKVPQVSTPTLVEVSRNLGKVGSKCCKHPEAKRMPCAEDYLS<br>VVLNQLCVLHEKTPVSDRVTKCCTESLVNRRPCFSALEVDETYVPK<br>EFNAETFTFHADICTLSEKERQIKKQTALVELVKHKPKATKEQLKA<br>VMDDFAAFVEKCCKADDKETCFAEEGKKLVAASQAALGLGSGGG<br>GSGGGGSGGGGSGGGGSARNGDHCPLGPGRCCRLHTVRASLEDLG<br>WADWVLSPREVQVTMCIGACPSQFRAANMHAQIKTSLHRLKPDTV<br>PAPCCVPASYNPMVLIQKTDTGVSLQTYDDLLAKDCHCI |
| 55 | HSA(C34A)-<br>GS(GGGGS)$_8$-<br>GDF15 | DAHKSEVAHRFKDLGEENFKALVLIAFAQYLQQAPFEDHVKLVNE<br>VTEFAKTCVADESAENCDKSLHTLFGDKLCTVATLRETYGEMADC<br>CAKQEPERNECFLQHKDDNPNLPRLVRPEVDVMCTAFHDNEETFL<br>KKYLYEIARRHPYFYAPELLFFAKRYKAAFTECCQAADKAACLLPK<br>LDELRDEGKASSAKQRLKCASLQKFGERAFKAWAVARLSQRFPKA<br>EFAEVSKLVTDLTKVHTECCHGDLLECADDRADLAKYICENQDSIS<br>SKLKECCEKPLLEKSHCIAEVENDEMPADLPSLAADFVESKDVCKN<br>YAEAKDVFLGMFLYEYARRHPDYSVVLLLRLAKTYETTLEKCCAA<br>ADPHECYAKVFDEFKPLVEEPQNLIKQNCELFEQLGEYKFQNALLV<br>RYTKKVPQVSTPTLVEVSRNLGKVGSKCCKHPEAKRMPCAEDYLS<br>VVLNQLCVLHEKTPVSDRVTKCCTESLVNRRPCFSALEVDETYVPK<br>EFNAETFTFHADICTLSEKERQIKKQTALVELVKHKPKATKEQLKA<br>VMDDFAAFVEKCCKADDKETCFAEEGKKLVAASQAALGLGSGGG<br>GSGGGGSGGGGSGGGGSGGGGSGGGGSGGGGSGGGGSARNGDHC<br>PLGPGRCCRLHTVRASLEDLGWADWVLSPREVQVTMCIGACPSQF<br>RAANMHAQIKTSLHRLKPDTVPAPCCVPASYNPMVLIQKTDTGVSL<br>QTYDDLLAKDCHCI |
| 56 | HSA (C34A)-<br>(AP)$_{10}$-<br>GDF15 | DAHKSEVAHRFKDLGEENFKALVLIAFAQYLQQAPFEDHVKLVNE<br>VTEFAKTCVADESAENCDKSLHTLFGDKLCTVATLRETYGEMADC<br>CAKQEPERNECFLQHKDDNPNLPRLVRPEVDVMCTAFHDNEETFL<br>KKYLYEIARRHPYFYAPELLFFAKRYKAAFTECCQAADKAACLLPK<br>LDELRDEGKASSAKQRLKCASLQKFGERAFKAWAVARLSQRFPKA<br>EFAEVSKLVTDLTKVHTECCHGDLLECADDRADLAKYICENQDSIS<br>SKLKECCEKPLLEKSHCIAEVENDEMPADLPSLAADFVESKDVCKN<br>YAEAKDVFLGMFLYEYARRHPDYSVVLLLRLAKTYETTLEKCCAA<br>ADPHECYAKVFDEFKPLVEEPQNLIKQNCELFEQLGEYKFQNALLV<br>RYTKKVPQVSTPTLVEVSRNLGKVGSKCCKHPEAKRMPCAEDYLS<br>VVLNQLCVLHEKTPVSDRVTKCCTESLVNRRPCFSALEVDETYVPK<br>EFNAETFTFHADICTLSEKERQIKKQTALVELVKHKPKATKEQLKA<br>VMDDFAAFVEKCCKADDKETCFAEEGKKLVAASQAALGLAPAPAP<br>APAPAPAPAPAPAPARNGDHCPLGPGRCCRLHTVRASLEDLGWAD<br>WVLSPREVQVTMCIGACPSQFRAANMHAQIKTSLHRLKPDTVPAPC<br>CVPASYNPMVLIQKTDTGVSLQTYDDLLAKDCHCI |
| 59 | HSA (C34S)-<br>(AP)$_{10}$-<br>GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLAPAPAPA<br>PAPAPAPAPAPAPARNGDHCPLGPGRCCRLHTVRASLEDLGWADW<br>VLSPREVQVTMCIGACPSQFRAANMHAQIKTSLHRLKPDTVPAPCC<br>VPASYNPMVLIQKTDTGVSLQTYDDLLAKDCHCI |
| 60 | HSA (C34S)-<br>GS-(GGGGS)$_8$-<br>GDF15(WT) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA |

-continued

WT-wild type

| SEQ ID NO | Description | Sequence |
|---|---|---|
| | | DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSGGGGSGGGGSGGGGSGGGGSARNGDHCP LGPGRCCRLHTVRASLEDLGWADWVLSPREVQVTMCIGACPSQFR AANMHAQIKTSLHRLKPDTVPAPCCVPASYNPMVLIQKTDTGVSLQ TYDDLLAKDCHCI |
| 64 | HSA (C34S)-GS(GGGGS)$_4$-GDF15 (I89R) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSARNGDHCPLGPGRCCRLHTVRASLEDLGW ADWVLSPREVQVTMCIGACPSQFRAANMHAQIKTSLHRLKPDTVP APCCVPASYNPMVLRQKTDTGVSLQTYDDLLAKDCHCI |
| 65 | HSA (C34S)-GS(GGGGS)$_4$-GDF15 (I89W) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSARNGDHCPLGPGRCCRLHTVRASLEDLGW ADWVLSPREVQVTMCIGACPSQFRAANMHAQIKTSLHRLKPDTVP APCCVPASYNPMVLWQKTDTGVSLQTYDDLLAKDCHCI |
| 66 | HSA (C34S)-GS(GGGGS)$_4$-GDF15 (L34A, S35A, R37A) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSGGGG SGGGGSGGGGSGGGGSARNGDHCPLGPGRCCRLHTVRASLEDLGW ADWVAAPAEVQVTMCIGACPSQFRAANMHAQIKTSLHRLKPDTVP APCCVPASYNPMVLIQKTDTGVSLQTYDDLLAKDCHCI |
| 67 | HSA (C34S)-GS(GGGGS)$_4$-GDF15 (V87A, I89A, L98A) | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV |

-continued

WT-wild type

| SEQ ID NO | Description | Sequence |
|---|---|---|
| | | MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADWVLSPREVQVTMCIGACPSQFRAANMHAQIKTSLHRLKPDTVP<br>APCCVPASYNPMALAQKTDTGVSAQTYDDLLAKDCHCI |
| 68 | HSA (C34S)-GS(GGGGS)$_4$-GDF15 (L34A, S35A, I89A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADWVAAPREVQVTMCIGACPSQFRAANMHAQIKTSLHRLKPDTVP<br>APCCVPASYNPMVLAQKTDTGVSLQTYDDLLAKDCHCI |
| 69 | HSA (C34S)-GS(GGGGS)$_4$-GDF15 (V87A, I89A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADWVLSPREVQVTMCIGACPSQFRAANMHAQIKTSLHRLKPDTVP<br>APCCVPASYNPMALAQKTDTGVSLQTYDDLLAKDCHCI |
| 70 | HSA (C34S)-GS(GGGGS)$_4$-GDF15 (Q60W) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADWVLSPREVQVTMCIGACPSQFRAANMHAWIKTSLHRLKPDTVP<br>APCCVPASYNPMVLIQKTDTGVSLQTYDDLLAKDCHCI |
| 71 | HSA (C34S)-GS(GGGGS)$_4$-GDF15 (W32A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADAVLSPREVQVTMCIGACPSQFRAANMHAQIKTSLHRLKPDTVPA<br>PCCVPASYNPMVLIQKTDTGVSLQTYDDLLAKDCHCI |

-continued

WT-wild type

| SEQ ID NO | Description | Sequence |
|---|---|---|
| 72 | HSA (C34S)-<br>GS(GGGGS)$_4$-<br>GDF15 (W29A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGA<br>ADWVLSPREVQVTMCIGACPSQFRAANMHAQIKTSLHRLKPDTVP<br>APCCVPASYNPMVLIQKTDTGVSLQTYDDLLAKDCHCI |
| 73 | HSA (C34S)-<br>GS(GGGGS)$_4$-<br>GDF15 (Q60A,<br>S64A, R67A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGW<br>ADWVLSPREVQVTMCIGACPSQFRAANMHAAIKTALHALKPDTVP<br>APCCVPASYNPMVLIQKTDTGVSLQTYDDLLAKDCHCI |
| 74 | HSA (C34S)-<br>GS(GGGGS)$_4$-<br>GDF15 (W29A,<br>Q60A, I61A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGA<br>ADWVLSPREVQVTMCIGACPSQFRAANMHAAAKTSLHRLKPDTVP<br>APCCVPASYNPMVLIQKTDTGVSLQTYDDLLAKDCHCI |
| 75 | HSA (C34S)-<br>GS(GGGGS)$_4$-<br>GDF15 (W29A,<br>W32A) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSARNGDHCPLGPGRCCRLHTVRASLEDLGA<br>ADAVLSPREVQVTMCIGACPSQFRAANMHAQIKTSLHRLKPDTVPA<br>PCCVPASYNPMVLIQKTDTGVSLQTYDDLLAKDCHCI |
| 76 | nucleic acid<br>encoding<br>SEQ ID NO: 5 | gacgcccacaagagcgaggtggcccaccggttcaaggacctgggcgaggagaacttcaaggc<br>cctggtgctgatcgccttcgcccagtacctgcagcagtccccatcgaggaccacgtgaagctgg<br>tgaacgaggtgaccgagttcgccaagacctgcgtggccgacgagagcgccgagaactgcgac<br>aagagcctgcacaccctgttcggcgacaagctgtgcaccgtggccaccctgcgggagacctac<br>ggcgagatggccgactgctgcgccaagcaggagcccgagcggaacgagtgatcctgcagca |

-continued

WT-wild type

| SEQ ID NO | Description | Sequence |
|---|---|---|
| | | caaggacgacaaccccaacctgccccggctggtgcggcccgaggtggacgtgatgtgcaccg<br>ccttccacgacaacgaggagaccttcctgaagaagtacctgtacgagatcgcccggcggcaccc<br>ctacttctacgcccccgagctgctgttcttcgccaagcggtacaaggccgccttcaccgagtgctg<br>ccaggccgccgacaaggccgcctgcctgctgcccaagctggacgagctgcgggacgagggc<br>aaggccagcagcgccaagcagcggctgaagtgcgccagcctgcagaagttcggcgagcggg<br>ccttcaaggcctgggccgtggcccggctgagccagcggttccccaaggccgagttcgccgagg<br>tgagcaagctggtgaccgacctgaccaaggtgcacaccgagtgctgccacggcgacctgctgg<br>agtgcgccgacgaccgggccgacctggccaagtacatctgcgagaaccaggacagcatcagc<br>agcaagctgaaggagtgctgcgagaagcccctgctggagaagagccactgcatcgccgaggtg<br>gagaacgacgagatgcccgccgacctgcccagcctggccgccgacttcgtggagagcaagga<br>cgtgtgcaagaactacgccgaggccaaggacgtgttcctgggcatgttcctgtacgagtacgccc<br>ggcggcaccccgactacagcgtggtgctgctgctgcggctggccaagacctacgagaccaccc<br>tggagaagtgctgcgccgccgccgacccccacgagtgctacgccaaggtgttcgacgagttcaa<br>gcccctggtggaggagccccagaacctgatcaagcagaactgcgagctgttcgagcagctggg<br>cgagtacaagttccagaacgccctgctggtgcggtacaccaagaaggtgccccaggtgagcac<br>ccccaccctggtggaggtgagccggaacctgggcaaggtgggcagcaagtgctgcaagcacc<br>ccgaggccaagcggatgccctgcgccgaggactacctgagcgtggtgctgaaccagctgtgcg<br>tgctgcacgagaagacccccgtgagcgaccgggtgaccaagtgctgcaccgagagcctggtga<br>accggcggccctgatcagcgccctggaggtggacgagacctacgtgcccaaggagttcaacg<br>ccgagaccttcaccttccacgccgacatctgcaccctgagcgagaaggagcggcagatcaaga<br>agcagaccgccctggtggagctggtgaagcacaagcccaaggccaccaaggagcagctgaag<br>gccgtgatggacgacttcgccgccttcgtggagaagtgctgcaaggccgacgacaaggagacc<br>tgcttcgccgaggagggcaagaagctggtggccgccagccaggccgccctgggcctgggcag<br>cggcggcggcggcagcggcggcggcggatctggtggaggtggcagtggaggagggggatc<br>cgctcgcaacggtgaccactgccctctgggtcctggtcgctgctgccgcctgcacaccgttcgcg<br>cttctctggaagacctgggttgggctgactgggttctgtctcctcgcgaagttcaggttaccatgtgc<br>atcggtgatgcccttctcagttccgcgctgctaacatgcacgctcagatcaaaacctctctgcacc<br>gcctgaaacctgacaccgttcctgctccttgctgcgttcctgcttcttacaaccctatggttctgatcc<br>agaaaaccgacaccggtgtttctctgcagacctacgacgacctgctggctaaagactgccactgc<br>atc |
| 77 | nucleic acid encoding SEQ ID NO: 25 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc<br>cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa<br>gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac<br>ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgcttcgccgaagaaggaaagaagctcgtggcagcgtcacaggc<br>cgctctgggcctcgctagcggtggagggggcagcggtggtggaggatccggtaccgcgcgca<br>acggggaccactgtccgctcgggcccgggcgttgctgccgtctgcacacggtccgcgcgtcgct<br>ggaagacctgggctgggccgattgggtgctgtcgccacgggaggtgcaagtgaccatgtgcatc<br>ggcgcgtgcccgagccagttccgggcggcaaacatgcacgcgcagatcaagacgagcctgca<br>ccgcctgaagcccgacacggtgccagcgccctgctgcgtgcccgccagctacaatcccatggtg<br>ctcattcaaaagaccgacaccggggtgtcgctccagacctatgatgacttgttagccaaagactgc<br>cactgcata |
| 78 | nucleic acid encoding SEQ ID NO: 26 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc |

-continued

WT-wild type

| SEQ ID NO | Description | Sequence |
|---|---|---|
| | | cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa<br>gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac<br>ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgatcgccgaagaaggaaagaagctcgtggcagcgtcacaggc<br>cgctctgggcctcgctagcggaggtggcggatcaggtggcggaggtagcggtggaggcggct<br>ctggcggaggtggatcaggcggaggaggttccggtggaggaggctcaggaggaggaggaag<br>tggaggaggggatccggtaccgcgcgcaacggggaccactgtccgctcgggcccgggcgtt<br>gctgccgtctgcacacggtccgcgcgtcgctggaagacctgggctgggccgattgggtgctgtc<br>gccacgggaggtgcaagtgaccatgtgcatcggcgcgtgcccgagccagttccgggcggcaa<br>acatgcacgcgcagatcaagacgagcctgcaccgcctgaagcccgacacggtgccagcgccct<br>gctgcgtgcccgccagctacaatcccatggtgctcattcaaaagaccgacaccggggtgtcgctc<br>cagacctatgatgacttgttagccaaagactgccactgcata |
| 79 | nucleic acid encoding SEQ ID NO: 27 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc<br>cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa<br>gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac<br>ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgatcgccgaagaaggaaagaagctcgtggcagcgtcacaggc<br>cgctctgggcctcgctagcgcacctgcccccgctccagctcctgcaccaggtaccgcgcgcaac<br>ggggaccactgtccgctcgggcccgggcgttgctgccgtctgcacacggtccgcgcgtcgctg<br>gaagacctgggctgggccgattgggtgctgtcgccacgggaggtgcaagtgaccatgtgcatcg<br>gcgcgtgcccgagccagttccgggcggcaaacatgcacgcgcagatcaagacgagcctgcac<br>cgcctgaagcccgacacggtgccagcgccctgctgcgtgcccgccagctacaatcccatggtgc<br>tcattcaaaagaccgacaccggggtgtcgctccagacctatgatgacttgttagccaaagactgcc<br>actgcata |
| 80 | nucleic acid encoding SEQ ID NO: 28 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc<br>cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa |

-continued

WT-wild type

| SEQ ID NO | Description | Sequence |
|---|---|---|
| | | gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac<br>ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgatcgccgaagaaggaaagaagctcgtggcagcgtcacaggc<br>cgctctgggcctcgctagcgcacctgcccccgctccagcacccgccccagcccctgctcccgca<br>ccagctcctgcaccaggtaccgctcgcaacggtgaccactgccctctgggtcctggtcgctgctg<br>ccgcctgcacaccgttcgcgcttctctggaagacctgggttgggctgactgggttctgtctcctcgc<br>gaagttcaggttaccatgtgcatcggtgcttgcccttctcagttccgcgctgctaacatgcacgctca<br>gatcaaaacctctctgcaccgcctgaaacctgacaccgttcctgctccttgctgcgttcctgcttctta<br>caaccctatggttctgatccagaaaaccgacaccggtgtttctctgcagacctacgacgacctgct<br>ggctaaagactgccactgcatc |
| 81 | nucleic acid encoding SEQ ID NO: 29 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc<br>cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa<br>gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac<br>ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgatcgccgaagaaggaaagaagctcgtggcagcgtcacaggc<br>cgctctgggcctcgctagcgcacctgcccccgctccagccccagctcctgcacctgctccagca<br>ccagctcctgcaccagctccagcccctgcacctgcacccgctccagccccagctcctgcacctg<br>ctccagcaccaggtaccgcgcgcaacggggaccactgtccgctcgggcccgggcgttgctgcc<br>gtctgcacacggtccgcgcgtcgctggaagacctgggctgggccgattgggtgctgtcgccacg<br>ggaggtgcaagtgaccatgtgcatcggcgcgtgcccgagccagttccgggcggcaaacatgca<br>cgcgcagatcaagacgagcctgcaccgcctgaagcccgacacggtgccagcgccctgctgcgt<br>gcccgccagctacaatcccatggtgctcattcaaaagaccgacaccggggtgtcgctccagacct<br>atgatgacttgttagccaaagactgccactgcata |
| 82 | nucleic acid encoding SEQ ID NO: 30 | gatgctcataagtccgaagtcgcccacagattcaaggacctcggagaagaaaattttaaggccct<br>cgtgcttatcgccttcgcccaatacctccagcagtccccgttcgaggaccacgtgaagctcgtgaa<br>cgaagtgaccgagtttgccaagacttgtgtggcggatgaatccgccgagaactgcgacaagagc<br>ctccacacgctgttcggcgacaagctgtgcaccgtcgccacgctgagagaaacttacggagaga<br>tggccgactgctgcgcaaagcaggagccggaacggaacgaatgcttcctgcaacataaggacg<br>ataaccctaacttgcctcgcctggtccgccctgaggtcgacgtgatgtgcaccgcgttccacgaca<br>acgaggaaacctttcttaagaagtacctgtacgagattgcgcggaggcacccttatttctacgcccc<br>cgaactgttgttcttcgccaagcggtacaaggctgcctttaccgaatgctgccaggccgccgataa<br>ggcggcttgcctgctgccgaagctcgacgagttgcgcgatgaggggaaggcgtcctccgctaa<br>gcagcggctgaaatgtgcgagcctccagaagttcggggagcgcgccttcaaggcctgggccgt<br>ggcgcgcctgtctcaacggttcccgaaggccgagttcgccgaagtgtcgaagctggtcaccgac |

-continued

WT-wild type

| SEQ ID NO | Description | Sequence |
|---|---|---|
| | | ctgacgaaagtgcacaccgaatgttgtcacggcgatctgctggaatgcgccgatgacagagccg<br>atttggccaagtacatctgcgaaaaccaggacagcatttcgtcaaagctgaaggaatgctgcgaa<br>aagcccttgctggaaaagtcccactgcatcgcggaagtggagaacgacgagatgcccgccgac<br>ctcccgtccctggccgccgatttcgtggagtcgaaggatgtgtgcaagaactacgcagaagccaa<br>ggacgtgttcctgggaatgtttctgtatgagtacgcccgccgccacccggactactcggtcgtgct<br>cctgctgcgactggcaaagacctacgaaaccactctggagaagtgctgcgccgccgcggaccc<br>gcacgagtgctacgcaaaggtgttcgacgagttcaagccacttgtcgaggagcctcagaacctga<br>tcaagcagaactgcgaactgttcgagcagctgggagagtacaaattccagaacgcgcttctcgtg<br>cgctacaccaagaaggtcccccaggtgtccactccgaccctggtggaagtgtccaggaacctgg<br>gaaaggtcggctccaagtgttgcaagcatcccgaggctaagcgcatgccctgcgccgaggacta<br>cttgtccgtggtgctgaatcagctgtgcgtgctccatgaaaagaccccagtgtccgacagagtgac<br>caagtgctgtaccgaatcgctcgtgaaccggcggccgtgcttttccgcactggaggtggacgaaa<br>cctacgtgccgaaggagttcaacgcagaaaccttcactttccacgccgacatctgcactctgtccg<br>agaaggagcggcagattaagaagcagactgccctggtggagcttgtgaaacacaagcctaagg<br>ccaccaaagagcagctgaaggccgtcatggatgatttcgcggccttcgtggaaaagtgttgtaaa<br>gcggacgacaaggagacttgatcgccgaagaaggaaagaagctcgtggcagcgtcacaggc<br>cgctctgggcctcgctagcgaagcagcagccaaagaagcagccgcaaaagaagcagccgcta<br>aggaggccgcagcaaagggtaccgcgcgcaacggggaccactgtccgctcgggcccgggcg<br>ttgctgccgtctgcacacggtccgcgcgtcgctggaagacctgggctgggccgattgggtgctgt<br>cgccacgggaggtgcaagtgaccatgtgcatcggcgcgtgcccgagccagttccgggcggca<br>aacatgcacgcgcagatcaagacgagcctgcaccgcctgaagcccgacacggtgccagcgcc<br>ctgctgcgtgcccgccagctacaatcccatggtgctcattcaaaagaccgacaccggggtgtcgc<br>tccagacctatgatgacttgttagccaaagactgccactgcata |
| 83 | nucleic acid encoding SEQ ID NO: 40 | gacgcccacaagagcgaggtggcccaccggttcaaggacctgggcgaggagaacttcaaggc<br>cctggtgctgatcgccttcgcccagtacctgcagcagtccccatcgaggaccacgtgaagctgg<br>tgaacgaggtgaccgagttcgccaagacctgcgtggccgacgagagcgccgagaactgcgac<br>aagagcctgcacaccctgttcggcgacaagctgtgcaccgtggccaccctgcgggagacctac<br>ggcgagatggccgactgctgcgccaagcaggagcccgagcggaacgagtgatcctgcagca<br>caaggacgacaaccccaacctgccccggctggtgcggcccgaggtggacgtgatgtgcaccg<br>ccttccacgacaacgaggagaccttcctgaagaagtacctgtacgagatcgcccggcggcaccc<br>ctacttctacgcccccgagctgctgttcttcgccaagcggtacaaggccgccttcaccgagtgctg<br>ccaggccgccgacaaggccgcctgcctgctgcccaagctggacgagctgcgggacgagggc<br>aaggccagcagcgccaagcagcggctgaagtgcgccagcctgcagaagttcggcgagcggg<br>ccttcaaggcctgggccgtggcccggctgagccagcggttccccaaggccgagttcgccgagg<br>tgagcaagctggtgaccgacctgaccaaggtgcacaccgagtgctgccacggcgacctgctgg<br>agtgcgccgacgaccgggccgacctggccaagtacatctgcgagaaccaggacagcatcagc<br>agcaagctgaaggagtgctgcgagaagcccctgctggagaagagccactgcatcgccgaggtg<br>gagaacgacgagatgcccgccgacctgcccagcctggccgccgacttcgtggagagcaagga<br>cgtgtgcaagaactacgccgaggccaaggacgtgttcctgggcatgttcctgtacgagtacgccc<br>ggcggcaccccgactacagcgtggtgctgctgctgcggctggccaagacctacgagaccaccc<br>tggagaagtgctgcgccgccgccgacccccacgagtgctacgccaaggtgttcgacgagttcaa<br>gcccctggtggaggagccccagaacctgatcaagcagaactgcgagctgttcgagcagctggg<br>cgagtacaagttccagaacgccctgctggtgcggtacaccaagaaggtgccccaggtgagcac<br>ccccaccctggtggaggtgagccggaacctgggcaaggtgggcagcaagtgctgcaagcacc<br>ccgaggccaagcggatgccctgcgccgaggactacctgagcgtggtgctgaaccagctgtgcg<br>tgctgcacgagaagacccccgtgagcgaccgggtgaccaagtgctgcaccgagagcctggtga<br>accggcggccctgatcagcgccctggaggtggacgagacctacgtgcccaaggagttcaacg<br>ccgagaccttcaccttccacgccgacatctgcaccctgagcgagaaggagcggcagatcaaga<br>agcagaccgccctggtggagctggtgaagcacaagcccaaggccaccaaggagcagctgaag<br>gccgtgatggacgacttcgccgccttcgtggagaagtgctgcaaggccgacgacaaggagacc<br>tgcttcgccgaggagggcaagaagctggtggccgccagccaggccgccctgggcctgggcag<br>cggcggcggcggcagcggcggcggcggatctggtggaggtggcagtggaggagggggatc<br>cgcgcgcaacggggaccactgtccgctcgggcccgggcgttgctgccgtctgcacacggtccg<br>cgcgtcgctggaagacctgggctgggccgattgggtgctgtcgccacgggaggtgcaagtgac<br>catgtgcatcggcgcgtgcccgagccagttccgggcggcaaacatgcacgcgcagatcaagac<br>gagcctgcaccgcctgaagcccgacacggtgccagcgccctgctgcgtgcccgccagctacaa<br>tcccatggtgctcattcaaaagaccgacaccggggtgtcgctccagacctatgatgacttgttagc<br>caaagactgccactgcata |
| 84 | nucleic acid encoding SEQ ID NO: 55 | gatgcacacaagagtgaggttgctcatcggtttaaagatttgggagaagaaaatttcaaagccttg<br>gtgttgattgcctttgctcagtatcttcagcaggccccatttgaagatcatgtaaaattagtgaatgaa<br>gtaactgaatttgcaaaaacatgtgttgctgatgagtcagctgaaaattgtgacaaatcacttcatac<br>ccttttggagacaaattatgcacagttgcaactcttcgtgaaacctatggtgaaatggctgactgct<br>gtgcaaaacaagaacctgagagaaatgaatgcttcttgcaacacaaagatgacaacccaaacctc<br>cccgattggtgagaccagaggttgatgtgatgtgcactgcttttcatgacaatgaagagacatttt<br>gaaaaatacttatatgaaattgccagaagacatccttacttttatgccccggaactccttttctttgct<br>aaaaggtataaagctgcttttacagaatgttgccaagctgctgataaagctgcctgcctgttgccaa<br>agctcgatgaacttcgggatgaagggaaggcttcgtctgccaaacagagactcaagtgtgccagt<br>ctccaaaaatttggagaaagagctttcaaagcatgggcagtagctcgcctgagccagagatttccc<br>aaagctgagtttgcagaagtttccaagttagtgacagatcttaccaaagtccacacggaatgctgcc<br>atggagatctgcttgaatgtgctgatgacagggcggaccttgccaagtatatctgtgaaaatcaag<br>attcgatctccagtaaactgaaggaatgctgtgaaaaacctctgttggaaaaatcccactgcattgc |

-continued

WT-wild type

| SEQ ID NO | Description | Sequence |
|---|---|---|
| | | cgaagtggaaaatgatgagatgcctgctgacttgccttcattagctgctgattttgttgaaagtaagg<br>atgtttgcaaaaactatgctgaggcaaaggatgtcttcctgggcatgtttttgtatgaatatgcaagaa<br>ggcatcctgattactctgtcgtgctgctgctgagacttgccaagacatatgaaaccactctagagaa<br>gtgctgtgccgctgcagatcctcatgaatgctatgccaaagtgttcgatgaatttaaacctatgtgg<br>aagagcctcagaatttaatcaaacaaaattgtgagctttttgagcagcttggagagtacaaattcca<br>gaatgcgctattagttcgttacaccaagaaagtaccccaagtgtcaactccaactcttgtagaggtct<br>caagaaacctaggaaaagtgggcagcaaatgttgtaaacatcctgaagcaaaaagaatgccctgt<br>gcagaagactatctatccgtggtcctgaaccagttatgtgtgttgcatgagaaaacgccagtaagtg<br>acagagtcaccaaatgctgcacagaatccttggtgaacaggcgaccatgcttttcagctctggaag<br>tcgatgaaacatacgttcccaaagagtttaatgctgaaacattcaccttccatgcagatatatgcaca<br>ctttctgagaaggagagacaaatcaagaaacaaactgcacttgttgagctcgtgaaacacaagcc<br>caaggcaacaaaagagcaactgaaagctgttatggatgatttcgcagatttgtagagaagtgctg<br>caaggctgacgataaggagacctgattgccgaggagggtaaaaaacttgttgctgcaagtcaag<br>ctgccttaggcttaggcagcggcggcggcggcagcggcggcggcggatctggtggaggtggc<br>agtggaggagggggatccggcggcggcggcagcggcggcggcggatctggtggaggtggc<br>agtggaggagggggatccgcgcgcaacggggaccactgtccgctcgggcccgggcgttgctg<br>ccgtctgcacacggtccgcgcgtcgctggaagacctgggctgggccgattgggtgctgtcgcca<br>cgggaggtgcaagtgaccatgtgcatcggcgcgtgcccgagccagttccgggcggcaaacatg<br>cacgcgcagatcaagacgagcctgcaccgcctgaagcccgacacggtgccagcgccctgctg<br>cgtgcccgccagctacaatcccatggtgctcattcaaaagaccgacaccggggtgtcgctccaga<br>cctatgatgacttgttagccaaagactgccactgcata |
| 85 | nucleic acid encoding SEQ ID NO: 56 | gatgcacacaagagtgaggttgctcatcggtttaaagatttgggagaagaaaatttcaaagccttg<br>gtgttgattgcctttgctcagtatcttcagcaggccccatttgaagatcatgtaaaattagtgaatgaa<br>gtaactgaatttgcaaaaacatgtgttgctgatgagtcagctgaaaattgtgacaaatcacttcatac<br>cctttttggagacaaattatgcacagttgcaactcttcgtgaaacctatggtgaaatggctgactgct<br>gtgcaaaacaagaacctgagagaaatgaatgcttcttgcaacacaaagatgacaacccaaacctc<br>cccgattggtgagaccagaggttgatgtgatgtgcactgcttttcatgacaatgaagagacatttt<br>gaaaaatacttatatgaaattgccagaagacatccttacttttatgccccggaactcctttttctttgct<br>aaaaggtataaagctgcttttacagaatgttgccaagctgctgataaagctgcctgcctgttgccaa<br>agctcgatgaacttcgggatgaagggaaggcttcgtctgccaaacagagactcaagtgtgccagt<br>ctccaaaaatttggagaaagagctttcaaagcatgggcagtagctcgcctgagccagagatttccc<br>aaagctgagtttgcagaagtttccaagttagtgacagatcttaccaaagtccacacggaatgctgcc<br>atggagatctgcttgaatgtgctgatgacagggcggaccttgccaagtatatctgtgaaaatcaag<br>attcgatctccagtaaactgaaggaatgctgtgaaaaacctctgttggaaaaatcccactgcattgc<br>cgaagtggaaaatgatgagatgcctgctgacttgccttcattagctgctgattttgttgaaagtaagg<br>atgtttgcaaaaactatgctgaggcaaaggatgtcttcctgggcatgtttttgtatgaatatgcaagaa<br>ggcatcctgattactctgtcgtgctgctgctgagacttgccaagacatatgaaaccactctagagaa<br>gtgctgtgccgctgcagatcctcatgaatgctatgccaaagtgttcgatgaatttaaacctcttgtgg<br>aagagcctcagaatttaatcaaacaaaattgtgagctttttgagcagcttggagagtacaaattcca<br>gaatgcgctattagttcgttacaccaagaaagtaccccaagtgtcaactccaactcttgtagaggtct<br>caagaaacctaggaaaagtgggcagcaaatgttgtaaacatcctgaagcaaaaagaatgccctgt<br>gcagaagactatctatccgtggtcctgaaccagttatgtgtgttgcatgagaaaacgccagtaagtg<br>acagagtcaccaaatgctgcacagaatccttggtgaacaggcgaccatgcttttcagctctggaag<br>tcgatgaaacatacgttcccaaagagtttaatgctgaaacattcaccttccatgcagatatatgcaca<br>ctttctgagaaggagagacaaatcaagaaacaaactgcacttgttgagctcgtgaaacacaagcc<br>caaggcaacaaaagagcaactgaaagctgttatggatgatttcgcagcttttgtagagaagtgctg<br>caaggctgacgataaggagacctgattgccgaggagggtaaaaaacttgttgctgcaagtcaag<br>ctgccttaggcttagcacctgcccccgctccagcacccgccccagcccctgctcccgcaccagct<br>cctgcaccagcgcgcaacggggaccactgtccgctcgggcccgggcgttgctgccgtctgcac<br>acggtccgcgcgtcgctggaagacctgggctgggccgattgggtgctgtcgccacgggaggtg<br>caagtgaccatgtgcatcggcgcgtgcccgagccagttccgggcggcaaacatgcacgcgcag<br>atcaagacgagcctgcaccgcctgaagcccgacacggtgccagcgccctgctgcgtgcccgcc<br>agctacaatcccatggtgctcattcaaaagaccgacaccggggtgtcgctccagacctatgatga<br>cttgttagccaaagactgccactgcata |
| 86 | nucleic acid encoding SEQ ID NO: 40 (Codon optimization 1) | gatgcacacaagagtgaggttgctcatcggtttaaagatttgggagaagaaaatttcaaagccttg<br>gtgttgattgcctttgctcagtatcttcagcagtccccatttgaagatcatgtaaaattagtgaatgaag<br>taactgaatttgcaaaaacatgtgttgctgatgagtcagctgaaaattgtgacaaatcacttcatacc<br>ctttttggagacaaattatgcacagttgcaactcttcgtgaaacctatggtgaaatggctgactgctgt<br>gcaaaacaagaacctgagagaaatgaatgcttcttgcaacacaaagatgacaacccaaacctccc<br>ccgattggtgagaccagaggttgatgtgatgtgcactgcttttcatgacaatgaagagacatttttga<br>aaaaatacttatatgaaattgccagaagacatccttacttttatgccccggaactcctttttctttgctaa<br>aaggtataaagctgcttttacagaatgttgccaagctgctgataaagctgcctgcctgttgccaaag<br>ctcgatgaacttcgggatgaagggaaggcttcgtctgccaaacagagactcaagtgtgccagtct<br>ccaaaaatttggagaaagagctttcaaagcatgggcagtagctcgcctgagccagagatttccca<br>aagctgagtttgcagaagtttccaagttagtgacagatcttaccaaagtccacacggaatgctgcca<br>tggagatctgcttgaatgtgctgatgacagggcggaccttgccaagtatatctgtgaaaatcaagat<br>tcgatctccagtaaactgaaggaatgctgtgaaaaacctctgttggaaaaatcccactgcattgccg<br>aagtggaaaatgatgagatgcctgctgacttgccttcattagctgctgattttgttgaaagtaaggat<br>gtttgcaaaaactatgctgaggcaaaggatgtcttcctgggcatgtttttgtatgaatatgcaagaag<br>gcatcctgattactctgtcgtgctgctgctgagacttgccaagacatatgaaaccactctagagaag<br>tgctgtgccgctgcagatcctcatgaatgctatgccaaagtgttcgatgaatttaaacctcttgtgga |

-continued

WT-wild type

| SEQ ID NO | Description | Sequence |
|---|---|---|
| | | agagcctcagaatttaatcaaacaaaattgtgagattttgagcagatggagagtacaaattccag<br>aatgcgctattagttcgttacaccaagaaagtaccccaagtgtcaactccaactatgtagaggtctc<br>aagaaacctaggaaaagtgggcagcaaatgttgtaaacatcctgaagcaaaaagaatgccctgtg<br>cagaagactatctatccgtggtcctgaaccagttatgtgtgttgcatgagaaaacgccagtaagtga<br>cagagtcaccaaatgctgcacagaatccttggtgaacaggcgaccatgcttttcagctctggaagt<br>cgatgaaacatacgttcccaaagagtttaatgctgaaacattcaccttccatgcagatatatgcacac<br>tttctgagaaggagagacaaatcaagaaacaaactgcacttgttgagctcgtgaaacacaagccc<br>aaggcaacaaaagagcaactgaaagctgttatggatgatttcgcagcttttgtagagaagtgctgc<br>aaggctgacgataaggagacctgctttgccgaggagggtaaaaaacttgttgctgcaagtcaagc<br>tgccttaggcttaggcagcggcggcggcggcagcggcggcggcggatctggtggaggtggca<br>gtggaggagggggatccgcgcgcaacggggaccactgtccgctcgggcccgggcgttgctgc<br>cgtctgcacacggtccgcgcgtcgctggaagacctgggctgggccgattgggtgctgtcgccac<br>gggaggtgcaagtgaccatgtgcatcggcgcgtgcccgagccagttccgggcggcaaacatgc<br>acgcgcagatcaagacgagcctgcaccgcctgaagcccgacacggtgccagcgccctgctgc<br>gtgcccgccagctacaatcccatggtgctcattcaaaagaccgacaccggggtgtcgctccagac<br>ctatgatgacttgttagccaaagactgccactgcata |
| 87 | nucleic acid encoding SEQ ID NO: 40 (Codon optimization 2) | gacgcccacaagagcgaggtggcccacagattcaaggacctgggcgaggaaaacttcaaggc<br>cctggtgctgatcgccttcgcccagtacctgcagcagagcccatcgaggaccacgtgaagctgg<br>tcaacgaagtgaccgagttcgccaagacctgcgtggccgacgagagcgccgagaactgcgaca<br>agagcctgcacaccctgttcggcgacaagctgtgcaccgtggccaccctgcgggaaacctacg<br>gcgagatggccgactgctgcgccaagcaggaacccgagcggaacgagtgcttcctgcagcac<br>aaggacgacaaccccaacctgcccagactcgtgcggcccgaggtggacgtgatgtgcaccgcc<br>ttccacgacaacgaggaaaccttcctgaagaagtacctgtacgagatcgccagacggcacccct<br>acttctacgcccccgagctgctgttcttcgccaagcggtacaaggccgccttcaccgagtgctgcc<br>aggccgccgataaggccgcctgcctgctgcccaagctggacgagctgagagatgagggcaag<br>gccagctccgccaagcagcggctgaagtgcgccagcctgcagaagttcggcgagcgggccttt<br>aaggcttgggctgtggcccggctgagccagagattccccaaggccgagtttgccgaggtgtcca<br>agctggtcaccgacctgaccaaggtgcacaccgagtgttgtcacggcgacctgctggaatgcgc<br>cgacgacagagccgacctggccaagtacatctgcgagaaccaggacagcatcagcagcaagct<br>gaaagagtgctgcgagaagcccctgctggaaaagagccactgtatcgccgaggtggaaaacga<br>cgagatgcccgctgacctgcccagcctggccgccgacttcgtggaaagcaaggacgtgtgcaa<br>gaactacgccgaggccaaggatgtgttcctgggcatgttcctgtatgagtacgcccgcagacacc<br>ccgactacagcgtggtgctgctgctgcggctggccaagacctacgagacaaccctggaaaagtg<br>ctgcgccgctgccgacccccacgagtgctacgccaaggtgttcgacgagttcaagcctctggtg<br>gaagaaccccagaacctgatcaagcagaactgcgagctgttcgagcagctgggcgagtacaag<br>ttccagaacgccctgctcgtgcggtacaccaagaaagtgccccaggtgtccacccccaccctggt<br>cgaagtgtcccggaacctgggcaaagtgggcagcaagtgctgcaagcaccctgaggccaagc<br>ggatgccctgcgccgaggactacctgtccgtggtgctgaaccagctgtgcgtgctgcacgagaa<br>aacccccgtgtccgacagagtgaccaagtgctgtaccgagagcctggtcaacagacggccctgc<br>ttcagcgccctggaagtggacgagacatacgtgcccaaagagttcaacgccgagacattcacctt<br>ccacgccgacatctgcaccctgagcgagaaagagcggcagatcaagaagcagaccgccctgg<br>tcgagctggtcaagcacaagcccaaggccaccaaagaacagctgaaggccgtgatggacgact<br>tcgccgccttcgtcgagaagtgttgcaaggccgacgacaaagagacatgcttcgccgaagaggg<br>caagaaactggtggccgcctctcaggccgccctgggactgggatctggcggcggaggaagcg<br>gaggcggaggatctgggggaggcggctctggcggagggggatccgccagaaatggcgacca<br>ctgtcccctgggccctggccggtgttgcagactgcacacagtgcgggccagcctggaagatctg<br>ggctgggccgattgggtgctgagccccagagaagtgcaggtcacaatgtgcatcggcgcctgcc<br>ccagccagttcagagccgccaacatgcacgcccagatcaagaccagcctgcaccggctgaagc<br>ccgacaccgtgcctgccccttgttgcgtgcccgccagctacaaccccatggtgctgattcagaaa<br>accgacaccggcgtgtccctgcagacctacgacgatctgctggccaaggactgccactgcatc |
| 88 | nucleic acid encoding SEQ ID NO: 48 | gatgcacacaagagtgaggttgctcatcggtttaaagatttgggagaagaaaatttcaaagccttg<br>gtgttgattgcctttgctcagtatcttcagcaggccccatttgaagatcatgtaaaattagtgaatgaa<br>gtaactgaatttgcaaaaacatgtgttgctgatgagtcagctgaaaattgtgacaaatcacttcatac<br>cctttttggagacaaattatgcacagttgcaactcttcgtgaaacctatggtgaaatggctgactgct<br>gtgcaaaacaagaacctgagagaaatgaatgcttcttgcaacacaaagatgacaacccaaacctc<br>cccgattggtgagaccagaggttgatgtgatgtgcactgcttttcatgacaatgaagagacattttt<br>gaaaaaatacttatatgaaattgccagaagacatccttacttttatgccccggaactcctttttctttgct<br>aaaaggtataaagctgcttttacagaatgttgccaagctgctgataaagctgcctgcctgttgccaa<br>agctcgatgaacttcgggatgaagggaaggcttcgtctgccaaacagagactcaagtgtgccagt<br>ctccaaaaatttggagaaagagctttcaaagcatgggcagtagctcgcctgagccagagatttccc<br>aaagctgagtttgcagaagtttccaagttagtgacagatcttaccaaagtccacacggaatgctgcc<br>atggagatctgcttgaatgtgctgatgacagggcggaccttgccaagtatatctgtgaaaatcaag<br>attcgatctccagtaaactgaaggaatgctgtgaaaaacctctgttggaaaaatcccactgcattgc<br>cgaagtggaaaatgatgagatgcctgctgacttgccttcattagctgctgattttgttgaaagtaagg<br>atgtttgcaaaaactatgctgaggcaaaggatgtcttcctgggcatgtttttgtatgaatatgcaagaa<br>ggcatcctgattactctgtcgtgctgctgctgagacttgccaagacatatgaaaccactctagagaa<br>gtgctgtgccgctgcagatcctcatgaatgctatgccaaagtgttcgatgaatttaaacctcttgtgg<br>aagagcctcagaatttaatcaaacaaaattgtgagcttttgagcagcttggagagtacaaattcca<br>gaatgcgctattagttcgttacaccaagaaagtaccccaagtgtcaactccaactcttgtagaggtct<br>caagaaacctaggaaaagtgggcagcaaatgttgtaaacatcctgaagcaaaaagaatgccctgt<br>gcagaagactatctatccgtggtcctgaaccagttatgtgtgttgcatgagaaaacgccagtaagtg |

-continued

WT-wild type

| SEQ ID NO | Description | Sequence |
|---|---|---|
| | | acagagtcaccaaatgctgcacagaatccttggtgaacaggcgaccatgcttttcagctctggaag<br>tcgatgaaacatacgttcccaaagagtttaatgctgaaacattcaccttccatgcagatatatgcaca<br>ctttctgagaaggagagacaaatcaagaaacaaactgcacttgttgagctcgtgaaacacaagcc<br>caaggcaacaaaagagcaactgaaagctgttatggatgatttcgcagcttttgtagagaagtgctg<br>caaggctgacgataaggagacctgctttgccgaggagggtaaaaacttgttgctgcaagtcaag<br>ctgccttaggcttaggcagcggcggcggcggcagcggcggcggcggatctggtggaggtggc<br>agtggaggagggggatccgcgcgcaacggggaccactgtccgctcgggcccgggcgttgctg<br>ccgtctgcacacggtccgcgcgtcgctggaagacctgggctgggccgattgggtgctgtcgcca<br>cgggaggtgcaagtgaccatgtgcatcggcgcgtgcccgagccagttccgggcggcaaacatg<br>cacgcgcagatcaagacgagcctgcaccgcctgaagcccgacacggtgccagcgccctgctg<br>cgtgcccgccagctacaatcccatggtgctcattcaaaagaccgacaccggggtgtcgctccaga<br>cctatgatgacttgttagccaaagactgccactgcata |
| 89 | nucleic acid encoding SEQ ID NO: 59 | gatgcacacaagagtgaggttgctcatcggtttaaagatttgggagaagaaaatttcaaagccttg<br>gtgttgattgcctttgctcagtatcttcagcagtccccatttgaagatcatgtaaaattagtgaatgaag<br>taactgaatttgcaaaaacatgtgttgctgatgagtcagctgaaaattgtgacaaatcacttcatacc<br>atttggagacaaattatgcacagttgcaactatcgtgaaacctatggtgaaatggctgactgctgt<br>gcaaaacaagaacctgagagaaatgaatgcttcttgcaacacaaagatgacaacccaaacctccc<br>ccgattggtgagaccagaggttgatgtgatgtgcactgcttttcatgacaatgaagagacatttttga<br>aaaaatacttatatgaaattgccagaagacatccttacttttatgccccggaactccttttctttgctaa<br>aaggtataaagctgcttttacagaatgttgccaagctgctgataaagctgcctgcctgttgccaaag<br>ctcgatgaacttcgggatgaagggaaggcttcgtctgccaaacagagactcaagtgtgccagtct<br>ccaaaaatttggagaaagagctttcaaagcatgggcagtagctcgcctgagccagagatttccca<br>aagctgagtttgcagaagtttccaagttagtgacagatcttaccaaagtccacacggaatgctgcca<br>tggagatctgcttgaatgtgctgatgacagggcggaccttgccaagtatatctgtgaaaatcaagat<br>tcgatctccagtaaactgaaggaatgctgtgaaaaacctctgttggaaaaatcccactgcattgccg<br>aagtggaaaatgatgagatgcctgctgacttgccttcattagctgctgattttgttgaaagtaaggat<br>gtttgcaaaaactatgctgaggcaaaggatgtcttcctgggcatgtttttgtatgaatatgcaagaag<br>gcatcctgattactctgtcgtgctgctgctgagacttgccaagacatatgaaaccactctagagaag<br>tgctgtgccgctgcagatcctcatgaatgctatgccaaagtgttcgatgaatttaaacctcttgtgga<br>agagcctcagaatttaatcaaacaaaattgtgagattttgagcagcttggagagtacaaattccag<br>aatgcgctattagttcgttacaccaagaaagtaccccaagtgtcaactccaactcttgtagaggtctc<br>aagaaacctaggaaaagtgggcagcaaatgttgtaaacatcctgaagcaaaaagaatgccctgtg<br>cagaagactatctatccgtggtcctgaaccagttatgtgtgttgcatgagaaaacgccagtaagtga<br>cagagtcaccaaatgctgcacagaatccttggtgaacaggcgaccatgcttttcagctctggaagt<br>cgatgaaacatacgttcccaaagagtttaatgctgaaacattcaccttccatgcagatatatgcacac<br>tttctgagaaggagagacaaatcaagaaacaaactgcacttgttgagctcgtgaaacacaagccc<br>aaggcaacaaaagagcaactgaaagctgttatggatgatttcgcagcttttgtagagaagtgctgc<br>aaggctgacgataaggagacctgctttgccgaggagggtaaaaacttgttgctgcaagtcaagc<br>tgccttaggcttagcacctgcccccgctccagcacccgccccagcccctgctcccgcaccagctc<br>ctgcaccagcgcgcaacggggaccactgtccgctcgggcccgggcgttgctgccgtctgcaca<br>cggtccgcgcgtcgctggaagacctgggctgggccgattgggtgctgtcgccacgggaggtgc<br>aagtgaccatgtgcatcggcgcgtgcccgagccagttccgggcggcaaacatgcacgcgcaga<br>tcaagacgagcctgcaccgcctgaagcccgacacggtgccagcgccctgctgcgtgcccgcca<br>gctacaatcccatggtgctcattcaaaagaccgacaccggggtgtcgctccagacctatgatgact<br>tgttagccaaagactgccactgcata |
| 90 | nucleic acid encoding SEQ ID NO: 60 (Codon optimization 1) | gatgcacacaagagtgaggttgctcatcggtttaaagatttgggagaagaaaatttcaaagccttg<br>gtgttgattgcctttgctcagtatcttcagcagtccccatttgaagatcatgtaaaattagtgaatgaag<br>taactgaatttgcaaaaacatgtgttgctgatgagtcagctgaaaattgtgacaaatcacttcatacc<br>ctttttggagacaaattatgcacagttgcaactatcgtgaaacctatggtgaaatggctgactgctgt<br>gcaaaacaagaacctgagagaaatgaatgcttcttgcaacacaaagatgacaacccaaacctccc<br>ccgattggtgagaccagaggttgatgtgatgtgcactgcttttcatgacaatgaagagacatttttga<br>aaaaatacttatatgaaattgccagaagacatccttacttttatgccccggaactccttttctttgctaa<br>aaggtataaagctgcttttacagaatgttgccaagctgctgataaagctgcctgcctgttgccaaag<br>ctcgatgaacttcgggatgaagggaaggcttcgtctgccaaacagagactcaagtgtgccagtct<br>ccaaaaatttggagaaagagctttcaaagcatgggcagtagctcgcctgagccagagatttccca<br>aagctgagtttgcagaagtttccaagttagtgacagatcttaccaaagtccacacggaatgctgcca<br>tggagatctgcttgaatgtgctgatgacagggcggaccttgccaagtatatctgtgaaaatcaagat<br>tcgatctccagtaaactgaaggaatgctgtgaaaaacctctgttggaaaaatcccactgcattgccg<br>aagtggaaaatgatgagatgcctgctgacttgccttcattagctgctgattttgttgaaagtaaggat<br>gtttgcaaaaactatgctgaggcaaaggatgtcttcctgggcatgtttttgtatgaatatgcaagaag<br>gcatcctgattactctgtcgtgctgctgctgagacttgccaagacatatgaaaccactctagagaag<br>tgctgtgccgctgcagatcctcatgaatgctatgccaaagtgttcgatgaatttaaacctcttgtgga<br>agagcctcagaatttaatcaaacaaaattgtgagattttgagcagatggagagtacaaattccag<br>aatgcgctattagttcgttacaccaagaaagtaccccaagtgtcaactccaactcttgtagaggtctc<br>aagaaacctaggaaaagtgggcagcaaatgttgtaaacatcctgaagcaaaaagaatgccctgtg<br>cagaagactatctatccgtggtcctgaaccagttatgtgtgttgcatgagaaaacgccagtaagtga<br>cagagtcaccaaatgctgcacagaatccttggtgaacaggcgaccatgcttttcagctctggaagt<br>cgatgaaacatacgttcccaaagagtttaatgctgaaacattcaccttccatgcagatatatgcacac<br>tttctgagaaggagagacaaatcaagaaacaaactgcacttgttgagctcgtgaaacacaagccc<br>aaggcaacaaaagagcaactgaaagctgttatggatgatttcgcagcttttgtagagaagtgctgc<br>aaggctgacgataaggagacctgctttgccgaggagggtaaaaacttgttgctgcaagtcaagc |

-continued

WT-wild type

| SEQ ID NO | Description | Sequence |
|---|---|---|
| | | tgccttaggcttaggcagcggcggcggcggcagcggcggcggcggatctggtggaggtggca<br>gtggaggaggggggatccggcggcggcggcagcggcggcggcggatctggtggaggtggca<br>gtggaggagggggatccgcgcgcaacggggaccactgtccgctcgggcccgggcgttgctgc<br>cgtctgcacacggtccgcgcgtcgctggaagacctgggctgggccgattgggtgctgtcgccac<br>gggaggtgcaagtgaccatgtgcatcggcgcgtgcccgagccagttccgggcggcaaacatgc<br>acgcgcagatcaagacgagcctgcaccgcctgaagcccgacacggtgccagcgccctgctgc<br>gtgcccgccagctacaatcccatggtgctcattcaaaagaccgacaccggggtgtcgctccagac<br>ctatgatgacttgttagccaaagactgccactgcata |
| 91 | nucleic acid encoding SEQ ID NO: 70 | gacgcccacaagagcgaggtggcccaccggttcaaggacctgggcgaggagaacttcaaggc<br>cctggtgctgatcgccttcgcccagtacctgcagcagtccccatcgaggaccacgtgaagctgg<br>tgaacgaggtgaccgagttcgccaagacctgcgtggccgacgagagcgccgagaactgcgac<br>aagagcctgcacaccctgttcggcgacaagctgtgcaccgtggccaccctgcgggagacctac<br>ggcgagatggccgactgctgcgccaagcaggagcccgagcggaacgagtgatcctgcagca<br>caaggacgacaaccccaacctgccccggctggtgcggcccgaggtggacgtgatgtgcaccg<br>ccttccacgacaacgaggagaccttcctgaagaagtacctgtacgagatcgcccggcggcaccc<br>ctacttctacgcccccgagctgctgttcttcgccaagcggtacaaggccgccttcaccgagtgctg<br>ccaggccgccgacaaggccgcctgcctgctgcccaagctggacgagctgcgggacgagggc<br>aaggccagcagcgccaagcagcggctgaagtgcgccagcctgcagaagttcggcgagcggg<br>ccttcaaggcctgggccgtggcccggctgagccagcggttccccaaggccgagttcgccgagg<br>tgagcaagctggtgaccgacctgaccaaggtgcacaccgagtgctgccacggcgacctgctgg<br>agtgcgccgacgaccgggccgacctggccaagtacatctgcgagaaccaggacagcatcagc<br>agcaagctgaaggagtgctgcgagaagcccctgctggagaagagccactgcatcgccgaggtg<br>gagaacgacgagatgcccgccgacctgcccagcctggccgccgacttcgtggagagcaagga<br>cgtgtgcaagaactacgccgaggccaaggacgtgttcctgggcatgttcctgtacgagtacgccc<br>ggcggcaccccgactacagcgtggtgctgctgctgcggctggccaagacctacgagaccaccc<br>tggagaagtgctgcgccgccgccgacccccacgagtgctacgccaaggtgttcgacgagttcaa<br>gcccctggtggaggagccccagaacctgatcaagcagaactgcgagctgttcgagcagctggg<br>cgagtacaagttccagaacgccctgctggtgcggtacaccaagaaggtgccccaggtgagcac<br>ccccaccctggtggaggtgagccggaacctgggcaaggtgggcagcaagtgctgcaagcacc<br>ccgaggccaagcggatgccctgcgccgaggactacctgagcgtggtgctgaaccagctgtgcg<br>tgctgcacgagaagacccccgtgagcgaccgggtgaccaagtgctgcaccgagagcctggtga<br>accggcggccctgatcagcgccctggaggtggacgagacctacgtgcccaaggagttcaacg<br>ccgagaccttcaccttccacgccgacatctgcaccctgagcgagaaggagcggcagatcaaga<br>agcagaccgccctggtggagctggtgaagcacaagcccaaggccaccaaggagcagctgaag<br>gccgtgatggacgacttcgccgccttcgtggagaagtgctgcaaggccgacgacaaggagacc<br>tgcttcgccgaggagggcaagaagctggtggccgccagccaggccgccctgggcctgggcag<br>cggcggcggcggcagcggcggcggcggatctggtggaggtggcagtggaggagggggatc<br>cgctcgcaacggtgaccactgccctctgggtcctggtcgctgctgccgcctgcacaccgttcgcg<br>cttctctggaagacctgggttgggctgactgggttctgtctcctcgcgaagttcaggttaccatgtgc<br>atcggtgcttgcccttctcagttccgcgctgctaacatgcacgcttggatcaaaacctctctgcacc<br>gcctgaaacctgacaccgttcctgctccttgctgcgttcctgcttcttacaaccctatggttctgatcc<br>agaaaaccgacaccggtgtttctctgcagacctacgacgacctgctggctaaagactgccactgc<br>atc |
| 92 | HSA (C34S)-GS-$(GGGGS)_8$-GDF15 (deletion 4) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSGGGGSGGGGSGGGGSGGGGSDHCPLGPG<br>RCCRLHTVRASLEDLGWADWVLSPREVQVTMCIGACPSQFRAANM<br>HAQIKTSLHRLKPDTVPAPCCVPASYNPMVLIQKTDTGVSLQTYDD<br>LLAKDCHCI |
| 93 | HSA (C34S)-GS-$(GGGGS)_8$-GDF15 (deletion 5) | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV |

-continued

WT-wild type

| SEQ ID NO | Description | Sequence |
|---|---|---|
| | | VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSGGGGSGGGGSGGGGSGGGGSHCPLGPGR<br>CCRLHTVRASLEDLGWADWVLSPREVQVTMCIGACPSQFRAANM<br>HAQIKTSLHRLKPDTVPAPCCVPASYNPMVLIQKTDTGVSLQTYDD<br>LLAKDCHCI |
| 94 | 6x histidine tag-HSA (C34S)-GS-(GGGGS)$_8$-HRV3C site GDF15 | EFHHHHHHDAHKSEVAHRFKDLGEENFKALVLIAFAQYLQQSPFED<br>HVKLVNEVTEFAKTCVADESAENCDKSLHTLFGDKLCTVATLRET<br>YGEMADCCAKQEPERNECFLQHKDDNPNLPRLVRPEVDVMCTAFH<br>DNEETFLKKYLYEIARRHPYFYAPELLFFAKRYKAAFTECCQAADK<br>AACLLPKLDELRDEGKASSAKQRLKCASLQKFGERAFKAWAVARL<br>SQRFPKAEFAEVSKLVTDLTKVHTECCHGDLLECADDRADLAKYIC<br>ENQDSISSKLKECCEKPLLEKSHCIAEVENDEMPADLPSLAADFVES<br>KDVCKNYAEAKDVFLGMFLYEYARRHPDYSVVLLLRLAKTYETTL<br>EKCCAAADPHECYAKVFDEFKPLVEEPQNLIKQNCELFEQLGEYKF<br>QNALLVRYTKKVPQVSTPTLVEVSRNLGKVGSKCCKHPEAKRMPC<br>AEDYLSVVLNQLCVLHEKTPVSDRVTKCCTESLVNRRPCFSALEVD<br>ETYVPKEFNAETFTFHADICTLSEKERQIKKQTALVELVKHKPKATK<br>EQLKAVMDDFAAFVEKCCKADDKETCFAEEGKKLVAASQAALGL<br>GSGGGGSGGGGSGGGGSGGGGSLEVLFQGPARNGDHCPLGPGRCC<br>RLHTVRASLEDLGWADWVLSPREVQVTMCIGACPSQFRAANMHA<br>QIKTSLHRLKPDTVPAPCCVPASYNPMVLIQKTDTGVSLQTYDDLL<br>AKDCHCI |
| 95 | nucleic acid encoding SEQ ID NO: 92 (Codon optimization 1) | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA<br>AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC<br>AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG<br>TCACCAAATGCTGCACAGAATCCTTGGTGAACAGGCGACCATGC<br>TTTTCAGCTCTGGAAGTCGATGAAACATACGTTCCCAAAGAGTTT<br>AATGCTGAAACATTCACCTTCCATGCAGATATATGCACACTTTCT<br>GAGAAGGAGAGACAAATCAAGAAACAAACTGCACTTGTTGAGC<br>TCGTGAAACACAAGCCCAAGGCAACAAAAGAGCAACTGAAAGC<br>TGTTATGGATGATTTCGCAGCTTTTGTAGAGAAGTGCTGCAAGGC<br>TGACGATAAGGAGACCTGCTTTGCCGAGGAGGGTAAAAAACTTG<br>TTGCTGCAAGTCAAGCTGCCTTAGGGCTTGGAAGCGGCGGAGGG<br>GGGAGTGGCGGCGGTGGCTCCGGGGGGGGCGGATCCGGCGGAG<br>GGGGCAGCGGGGGTGGAGGGAGTGGCGGGGGAGGATCAGGGGG<br>AGGAGGATCAGGAGGGGGCGGAAGTGATCATTGCCCTCTCGGGC<br>CCGGACGGTGTTGCCGCCTCCACACTGTGAGGGCTTCACTTGAA<br>GACCTTGGATGGGCCGACTGGGTGCTGTCCCCAAGAGAGGTACA<br>AGTCACAATGTGTATTGGCGCCTGCCCCAGCCAGTTTCGCGCCGC<br>TAACATGCACGCCCAGATAAAAACCAGCCTGCACCGCCTGAAGC |

-continued

| WT-wild type | | |
|---|---|---|
| SEQ ID NO | Description | Sequence |
| | | CCGACACGGTGCCAGCGCCCTGCTGCGTGCCCGCCAGCTACAAT<br>CCCATGGTGCTCATTCAAAAGACCGACACCGGGGTGTCGCTCCA<br>GACCTATGATGACTTGTTAGCCAAAGACTGCCACTGCATA |
| 96 | nucleic acid encoding SEQ ID NO: 7 | GGGGACCACTGTCCGCTCGGGCCCGGGCGTTGCTGCCGTCTGCA<br>CACGGTCCGCGCGTCGCTGGAAGACCTGGGCTGGGCCGATTGGG<br>TGCTGTCGCCACGGGAGGTGCAAGTGACCATGTGCATCGGCGCG<br>TGCCCGAGCCAGTTCCGGGCGGCAAACATGCACGCGCAGATCAA<br>GACGAGCCTGCACCGCCTGAAGCCCGACACGGTGCCAGCGCCCT<br>GCTGCGTGCCCGCCAGCTACAATCCCATGGTGCTCATTCAAAAG<br>ACCGACACCGGGGTGTCGCTCCAGACCTATGATGACTTGTTAGC<br>CAAAGACTGCCACTGCATA |
| 97 | nucleic acid encoding SEQ ID NO: 8 (Codon optimization 1) | GACCACTGTCCGCTCGGGCCCGGGCGTTGCTGCCGTCTGCACAC<br>GGTCCGCGCGTCGCTGGAAGACCTGGGCTGGGCCGATTGGGTGC<br>TGTCGCCACGGGAGGTGCAAGTGACCATGTGCATCGGCGCGTGC<br>CCGAGCCAGTTCCGGGCGGCAAACATGCACGCGCAGATCAAGAC<br>GAGCCTGCACCGCCTGAAGCCCGACACGGTGCCAGCGCCCTGCT<br>GCGTGCCCGCCAGCTACAATCCCATGGTGCTCATTCAAAAGACC<br>GACACCGGGGTGTCGCTCCAGACCTATGATGACTTGTTAGCCAA<br>AGACTGCCACTGCATA |
| 98 | nucleic acid encoding SEQ ID NO: 8 (Codon optimization 2) | GATCATTGCCCTCTCGGGCCCGGACGGTGTTGCCGCCTCCACACT<br>GTGAGGGCTTCACTTGAAGACCTTGGATGGGCCGACTGGGTGCT<br>GTCCCCAAGAGAGGTACAAGTCACAATGTGTATTGGCGCCTGCC<br>CCAGCCAGTTTCGCGCCGCTAACATGCACGCCCAGATAAAAACC<br>AGCCTGCACCGCCTGAAGCCCGACACGGTGCCAGCGCCCTGCTG<br>CGTGCCCGCCAGCTACAATCCCATGGTGCTCATTCAAAAGACCG<br>ACACCGGGGTGTCGCTCCAGACCTATGATGACTTGTTAGCCAAA<br>GACTGCCACTGCATA |
| 99 | nucleic acid encoding SEQ ID NO: 8 (Codon optimization 3) | GATCATTGTCCCCTTGGACCGGGTAGATGCTGTCGCCTGCACACT<br>GTGCGGGCTTCACTGGAGGACCTCGGCTGGGCTGACTGGGTGCT<br>GTCCCCACGGGAGGTGCAAGTGACCATGTGCATCGGCGCCTGTC<br>CTTCGCAATTCCGGGCCGCGAATATGCACGCCCAGATCAAGACC<br>TCCCTGCATCGCCTCAAGCCCGACACTGTGCCTGCTCCATGCTGT<br>GTGCCGGCCTCCTATAACCCCATGGTGCTGATCCAGAAAACCGA<br>TACCGGCGTCAGCCTGCAGACGTATGATGATCTGCTGGCCAAGG<br>ACTGCCATTGCATC |
| 100 | nucleic acid encoding SEQ ID NO: 9 (Codon optimization 1) | CACTGTCCGCTCGGGCCCGGGCGTTGCTGCCGTCTGCACACGGTC<br>CGCGCGTCGCTGGAAGACCTGGGCTGGGCCGATTGGGTGCTGTC<br>GCCACGGGAGGTGCAAGTGACCATGTGCATCGGCGCGTGCCCGA<br>GCCAGTTCCGGGCGGCAAACATGCACGCGCAGATCAAGACGAG<br>CCTGCACCGCCTGAAGCCCGACACGGTGCCAGCGCCCTGCTGCG<br>TGCCCGCCAGCTACAATCCCATGGTGCTCATTCAAAAGACCGAC<br>ACCGGGGTGTCGCTCCAGACCTATGATGACTTGTTAGCCAAAGA<br>CTGCCACTGCATA |
| 101 | nucleic acid encoding SEQ ID NO: 9 (Codon optimization 2) | CATTGCCCTCTCGGGCCCGGACGGTGTTGCCGCCTCCACACTGTG<br>AGGGCTTCACTTGAAGACCTTGGATGGGCCGACTGGGTGCTGTC<br>CCCAAGAGAGGTACAAGTCACAATGTGTATTGGCGCCTGCCCCA<br>GCCAGTTTCGCGCCGCTAACATGCACGCCCAGATAAAAACCAGC<br>CTGCACCGCCTGAAGCCCGACACGGTGCCAGCGCCCTGCTGCGT<br>GCCCGCCAGCTACAATCCCATGGTGCTCATTCAAAAGACCGACA<br>CCGGGGTGTCGCTCCAGACCTATGATGACTTGTTAGCCAAAGAC<br>TGCCACTGCATA |
| 102 | nucleic acid encoding SEQ ID NO: 9 (Codon optimization 3) | CATTGTCCCCTTGGACCGGGTAGATGCTGTCGCCTGCACACTGTG<br>CGGGCTTCACTGGAGGACCTCGGCTGGGCTGACTGGGTGCTGTC<br>CCCACGGGAGGTGCAAGTGACCATGTGCATCGGCGCCTGTCCTT<br>CGCAATTCCGGGCCGCGAATATGCACGCCCAGATCAAGACCTCC<br>CTGCATCGCCTCAAGCCCGACACTGTGCCTGCTCCATGCTGTGTG<br>CCGGCCTCCTATAACCCCATGGTGCTGATCCAGAAAACCGATAC<br>CGGCGTCAGCCTGCAGACGTATGATGATCTGCTGGCCAAGGACT<br>GCCATTGCATC |
| 103 | nucleic acid encoding SEQ ID NO: 10 (Codon optimization 1) | TGTCCGCTCGGGCCCGGGCGTTGCTGCCGTCTGCACACGGTCCGC<br>GCGTCGCTGGAAGACCTGGGCTGGGCCGATTGGGTGCTGTCGCC<br>ACGGGAGGTGCAAGTGACCATGTGCATCGGCGCGTGCCCGAGCC<br>AGTTCCGGGCGGCAAACATGCACGCGCAGATCAAGACGAGCCTG<br>CACCGCCTGAAGCCCGACACGGTGCCAGCGCCCTGCTGCGTGCC<br>CGCCAGCTACAATCCCATGGTGCTCATTCAAAAGACCGACACCG |

-continued

| WT-wild type | | |
|---|---|---|
| SEQ ID NO | Description | Sequence |
| | | GGGTGTCGCTCCAGACCTATGATGACTTGTTAGCCAAAGACTGC<br>CACTGCATA |
| 104 | nucleic acid encoding SEQ ID NO: 10 (Codon optimization 2) | TGCCCTCTCGGGCCCGGACGGTGTTGCCGCCTCCACACTGTGAG<br>GGCTTCACTTGAAGACCTTGGATGGGCCGACTGGGTGCTGTCCC<br>CAAGAGAGGTACAAGTCACAATGTGTATTGGCGCCTGCCCCAGC<br>CAGTTTCGCGCCGCTAACATGCACGCCCAGATAAAAACCAGCCT<br>GCACCGCCTGAAGCCCGACACGGTGCCAGCGCCCTGCTGCGTGC<br>CCGCCAGCTACAATCCCATGGTGCTCATTCAAAAGACCGACACC<br>GGGGTGTCGCTCCAGACCTATGATGACTTGTTAGCCAAAGACTG<br>CCACTGCATA |
| 105 | nucleic acid encoding SEQ ID NO: 10 (Codon optimization 3) | TGTCCCCTTGGACCGGGTAGATGCTGTCGCCTGCACACTGTGCGG<br>GCTTCACTGGAGGACCTCGGCTGGGCTGACTGGGTGCTGTCCCC<br>ACGGGAGGTGCAAGTGACCATGTGCATCGGCGCCTGTCCTTCGC<br>AATTCCGGGCCGCGAATATGCACGCCCAGATCAAGACCTCCCTG<br>CATCGCCTCAAGCCCGACACTGTGCCTGCTCCATGCTGTGTGCCG<br>GCCTCCTATAACCCCATGGTGCTGATCCAGAAAACCGATACCGG<br>CGTCAGCCTGCAGACGTATGATGATCTGCTGGCCAAGGACTGCC<br>ATTGCATC |
| 106 | nucleic acid encoding SEQ ID NO: 11 (Codon optimization 1) | TGCCGTCTGCACACGGTCCGCGCGTCGCTGGAAGACCTGGGCTG<br>GGCCGATTGGGTGCTGTCGCCACGGGAGGTGCAAGTGACCATGT<br>GCATCGGCGCGTGCCCGAGCCAGTTCCGGGCGGCAAACATGCAC<br>GCGCAGATCAAGACGAGCCTGCACCGCCTGAAGCCCGACACGGT<br>GCCAGCGCCCTGCTGCGTGCCCGCCAGCTACAATCCCATGGTGC<br>TCATTCAAAAGACCGACACCGGGGTGTCGCTCCAGACCTATGAT<br>GACTTGTTAGCCAAAGACTGCCACTGCATA |
| 107 | nucleic acid encoding SEQ ID NO: 11 (Codon optimization 2) | TGCCGCCTCCACACTGTGAGGGCTTCACTTGAAGACCTTGGATG<br>GGCCGACTGGGTGCTGTCCCCAAGAGAGGTACAAGTCACAATGT<br>GTATTGGCGCCTGCCCCAGCCAGTTTCGCGCCGCTAACATGCAC<br>GCCCAGATAAAAACCAGCCTGCACCGCCTGAAGCCCGACACGGT<br>GCCAGCGCCCTGCTGCGTGCCCGCCAGCTACAATCCCATGGTGC<br>TCATTCAAAAGACCGACACCGGGGTGTCGCTCCAGACCTATGAT<br>GACTTGTTAGCCAAAGACTGCCACTGCATA |
| 108 | nucleic acid encoding SEQ ID NO: 11 (Codon optimization 3) | TGTCGCCTGCACACTGTGCGGGCTTCACTGGAGGACCTCGGCTG<br>GGCTGACTGGGTGCTGTCCCCACGGGAGGTGCAAGTGACCATGT<br>GCATCGGCGCCTGTCCTTCGCAATTCCGGGCCGCGAATATGCAC<br>GCCCAGATCAAGACCTCCCTGCATCGCCTCAAGCCCGACACTGT<br>GCCTGCTCCATGCTGTGTGCCGGCCTCCTATAACCCCATGGTGCT<br>GATCCAGAAAACCGATACCGGCGTCAGCCTGCAGACGTATGATG<br>ATCTGCTGGCCAAGGACTGCCATTGCATC |
| 109 | nucleic acid encoding SEQ ID NO: 60 (Codon optimization 2) | GATGCGCACAAGTCGGAAGTGGCCCATCGCTTTAAGGACCTGGG<br>AGAAGAGAACTTCAAGGCCCTGGTCCTGATCGCGTTCGCCCAGT<br>ACCTCCAGCAGTCCCCGTTTGAGGACCACGTCAAGCTTGTGAAC<br>GAAGTGACCGAGTTCGCAAAGACTTGTGTGGCCGATGAGTCCGC<br>CGAAAACTGCGACAAGTCCCTGCACACCTTGTTCGGAGACAAGC<br>TGTGCACCGTCGCGACTTTGCGGGAGACTTACGGCGAAATGGCG<br>GACTGCTGCGCAAAGCAGGAGCCCGAAAGGAACGAGTGCTTCCT<br>GCAACACAAGGACGACAACCCGAACCTTCCGAGACTCGTGCGGC<br>CTGAGGTCGACGTGATGTGCACTGCATTCCATGATAACGAAGAA<br>ACATTCCTGAAGAAGTACCTGTATGAAATTGCCAGACGCCACCC<br>GTACTTCTACGCCCCCGAACTGCTGTTCTTCGCCAAGAGATACAA<br>GGCCGCCTTTACCGAATGTTGTCAAGCCGCCGATAAGGCAGCGT<br>GCCTGCTGCCGAAGTTGGACGAGCTCAGGGACGAAGGAAAGGC<br>CTCGTCCGCCAAGCAGAGGCTGAAGTGCGCGTCGCTCCAGAAGT<br>TTGGAGAGCGGGCTTTTAAGGCCTGGGCAGTGGCTAGGTTGAGC<br>CAGAGGTTCCCCAAGGCGGAGTTTGCCGAAGTGTCCAAGCTCGT<br>GACTGACCTGACTAAAGTCCATACCGAATGCTGCCACGGCGATC<br>TGCTCGAATGCGCAGATGACCGGGCGGATTTGGCCAAGTACATT<br>TGCGAAAACCAAGACTCCATAAGCTCCAAGCTGAAGGAGTGCTG<br>TGAAAAGCCTCTGCTCGAGAAGTCCCACTGTATCGCCGAGGTGG<br>AGAACGACGAAATGCCGGCAGACCTCCCTAGCCTGGCAGCCGAC<br>TTCGTCGAATCCAAGGACGTGTGCAAGAACTACGCCGAAGCGAA<br>GGACGTGTTCCTGGGAATGTTCCTGTACGAGTACGCCAGACGGC<br>ATCCAGACTACTCCGTGGTGCTTCTCTTGCGGCTGGCCAAGACTT<br>ATGAAACGACCCTGGAGAAATGTTGCGCTGCTGCTGACCCACAC<br>GAGTGCTACGCCAAAGTGTTCGACGAGTTTAAGCCTCTCGTGGA<br>GGAACCCCAGAACCTCATCAAGCAGAACTGCGAACTTTTCGAGC<br>AGCTCGGGGAGTACAAGTTCCAAAACGCGCTGCTTGTCCGCTAC |

-continued

WT-wild type

| SEQ ID NO | Description | Sequence |
|---|---|---|
| | | ACCAAGAAAGTGCCGCAAGTGTCCACACCGACCCTCGTGGAAGT<br>GTCCAGGAACCTGGGCAAAGTCGGAAGCAAATGTTGCAAGCACC<br>CCGAAGCCAAGCGCATGCCGTGCGCAGAGGACTACCTTTCGGTG<br>GTGTTGAACCAGCTCTGCGTCCTGCACGAAAAGACCCCGGTGTC<br>AGACCGCGTGACCAAGTGCTGTACCGAAAGCCTCGTGAATCGGC<br>GCCCCTGCTTCTCGGCCCTGGAGGTGGACGAAACTTACGTGCCG<br>AAAGAGTTCAACGCGGAAACCTTCACCTTTCATGCCGATATCTG<br>CACCCTGTCCGAGAAGGAGCGGCAGATCAAGAAGCAGACCGCC<br>CTGGTGGAGCTTGTGAAACACAAGCCGAAGGCCACTAAGGAAC<br>AGCTGAAGGCCGTCATGGACGATTTCGCTGCCTTCGTCGAGAAG<br>TGCTGCAAGGCCGACGACAAGGAGACTTGCTTCGCTGAAGAAGG<br>GAAGAAGCTTGTGGCCGCTAGCCAGGCTGCACTGGGACTGGGTA<br>GCGGTGGAGGGGGATCAGGGGGTGGTGGATCGGGAGGAGGAGG<br>ATCAGGAGGTGGCGGCTCAGGAGGAGGCGGATCAGGCGGTGGA<br>GGATCCGGAGGCGGAGGATCGGGTGGAGGAGGCTCAGCGAGGA<br>ACGGGGATCATTGTCCCCTTGGACCGGGTAGATGCTGTCGCCTG<br>CACACTGTGCGGGCTTCACTGGAGGACCTCGGCTGGGCTGACTG<br>GGTGCTGTCCCCACGGGAGGTGCAAGTGACCATGTGCATCGGCG<br>CCTGTCCTTCGCAATTCCGGGCCGCGAATATGCACGCCCAGATC<br>AAGACCTCCCTGCATCGCCTCAAGCCCGACACTGTGCCTGCTCCA<br>TGCTGTGTGCCGGCCTCCTATAACCCCATGGTGCTGATCCAGAAA<br>ACCGATACCGGCGTCAGCCTGCAGACGTATGATGATCTGCTGGC<br>CAAGGACTGCCATTGCATC |
| 110 | nucleic acid encoding SEQ ID NO: 92 (Codon optimization 2) | GATGCGCACAAGTCGGAAGTGGCCCATCGCTTTAAGGACCTGGG<br>AGAAGAGAACTTCAAGGCCCTGGTCCTGATCGCGTTCGCCCAGT<br>ACCTCCAGCAGTCCCCGTTTGAGGACCACGTCAAGCTTGTGAAC<br>GAAGTGACCGAGTTCGCAAAGACTTGTGTGGCCGATGAGTCCGC<br>CGAAAACTGCGACAAGTCCCTGCACACCTTGTTCGGAGACAAGC<br>TGTGCACCGTCGCGACTTTGCGGGAGACTTACGGCGAAATGGCG<br>GACTGCTGCGCAAAGCAGGAGCCCGAAAGGAACGAGTGCTTCCT<br>GCAACACAAGGACGACAACCCGAACCTTCCGAGACTCGTGCGGC<br>CTGAGGTCGACGTGATGTGCACTGCATTCCATGATAACGAAGAA<br>ACATTCCTGAAGAAGTACCTGTATGAAATTGCCAGACGCCACCC<br>GTACTTCTACGCCCCCGAACTGCTGTTCTTCGCCAAGAGATACAA<br>GGCCGCCTTTACCGAATGTTGTCAAGCCGCCGATAAGGCAGCGT<br>GCCTGCTGCCGAAGTTGGACGAGCTCAGGGACGAAGGAAAGGC<br>CTCGTCCGCCAAGCAGAGGCTGAAGTGCGCGTCGCTCCAGAAGT<br>TTGGAGAGCGGGCTTTTAAGGCCTGGGCAGTGGCTAGGTTGAGC<br>CAGAGGTTCCCCAAGGCGGAGTTTGCCGAAGTGTCCAAGCTCGT<br>GACTGACCTGACTAAAGTCCATACCGAATGCTGCCACGGCGATC<br>TGCTCGAATGCGCAGATGACCGGGCGGATTTGGCCAAGTACATT<br>TGCGAAAACCAAGACTCCATAAGCTCCAAGCTGAAGGAGTGCTG<br>TGAAAAGCCTCTGCTCGAGAAGTCCCACTGTATCGCCGAGGTGG<br>AGAACGACGAAATGCCGGCAGACCTCCCTAGCCTGGCAGCCGAC<br>TTCGTCGAATCCAAGGACGTGTGCAAGAACTACGCCGAAGCGAA<br>GGACGTGTTCCTGGGAATGTTCCTGTACGAGTACGCCAGACGGC<br>ATCCAGACTACTCCGTGGTGCTTCTCTTGCGGCTGGCCAAGACTT<br>ATGAAACGACCCTGGAGAAATGTTGCGCTGCTGCTGACCCACAC<br>GAGTGCTACGCCAAAGTGTTCGACGAGTTTAAGCCTCTCGTGGA<br>GGAACCCCAGAACCTCATCAAGCAGAACTGCGAACTTTTCGAGC<br>AGCTCGGGGAGTACAAGTTCCAAAACGCGCTGCTTGTCCGCTAC<br>ACCAAGAAAGTGCCGCAAGTGTCCACACCGACCCTCGTGGAAGT<br>GTCCAGGAACCTGGGCAAAGTCGGAAGCAAATGTTGCAAGCACC<br>CCGAAGCCAAGCGCATGCCGTGCGCAGAGGACTACCTTTCGGTG<br>GTGTTGAACCAGCTCTGCGTCCTGCACGAAAAGACCCCGGTGTC<br>AGACCGCGTGACCAAGTGCTGTACCGAAAGCCTCGTGAATCGGC<br>GCCCCTGCTTCTCGGCCCTGGAGGTGGACGAAACTTACGTGCCG<br>AAAGAGTTCAACGCGGAAACCTTCACCTTTCATGCCGATATCTG<br>CACCCTGTCCGAGAAGGAGCGGCAGATCAAGAAGCAGACCGCC<br>CTGGTGGAGCTTGTGAAACACAAGCCGAAGGCCACTAAGGAAC<br>AGCTGAAGGCCGTCATGGACGATTTCGCTGCCTTCGTCGAGAAG<br>TGCTGCAAGGCCGACGACAAGGAGACTTGCTTCGCTGAAGAAGG<br>GAAGAAGCTTGTGGCCGCTAGCCAGGCTGCACTGGGACTGGGTA<br>GCGGTGGAGGGGGATCAGGGGGTGGTGGATCGGGAGGAGGAGG<br>ATCAGGAGGTGGCGGCTCAGGAGGAGGCGGATCAGGCGGTGGA<br>GGATCCGGAGGCGGAGGATCGGGTGGAGGAGGCTCAGATCATT<br>GTCCCCTTGGACCGGGTAGATGCTGTCGCCTGCACACTGTGCGG<br>GCTTCACTGGAGGACCTCGGCTGGGCTGACTGGGTGCTGTCCCC<br>ACGGGAGGTGCAAGTGACCATGTGCATCGGCGCCTGTCCTTCGC<br>AATTCCGGGCCGCGAATATGCACGCCCAGATCAAGACCTCCCTG<br>CATCGCCTCAAGCCCGACACTGTGCCTGCTCCATGCTGTGTGCCG<br>GCCTCCTATAACCCCATGGTGCTGATCCAGAAAACCGATACCGG |

-continued

WT-wild type

| SEQ ID NO | Description | Sequence |
|---|---|---|
| | | CGTCAGCCTGCAGACGTATGATGATCTGCTGGCCAAGGACTGCC<br>ATTGCATC |
| 111 | HSA (C34S)-GS-(GGGGS)$_8$-(Deletion 5) GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSGGGGSGGGGSGGGGSGGGGSHCPLGPGR<br>CCRLHTVRASLEDLGWADWVLSPREVQVTMCIGACPSQFRAANM<br>HAQIKTSLHRLKPDTVPAPCCVPASYNPMVLIQKTDTGVSLQTYDD<br>LLAKDCHCI |
| 112 | HSA (C34S)-GS-(GGGGS)$_8$-(deletion 14) GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSGGGG<br>SGGGGSGGGGSGGGGSGGGGSGGGGSGGGGSGGGGSCRLHTVRA<br>SLEDLGWADWVLSPREVQVTMCIGACPSQFRAANMHAQIKTSLHR<br>LKPDTVPAPCCVPASYNPMVLIQKTDTGVSLQTYDDLLAKDCHCI |
| 113 | (Deletion 2) HSA (C34S)-GS-(GGGGS)$_8$-(deletion 4) GDF15 | HKSEVAHRFKDLGEENFKALVLIAFAQYLQQSPFEDHVKLVNEVTE<br>FAKTCVADESAENCDKSLHTLFGDKLCTVATLRETYGEMADCCAK<br>QEPERNECFLQHKDDNPNLPRLVRPEVDVMCTAFHDNEETFLKKYL<br>YEIARRHPYFYAPELLFFAKRYKAAFTECCQAADKAACLLPKLDEL<br>RDEGKASSAKQRLKCASLQKFGERAFKAWAVARLSQRFPKAEFAE<br>VSKLVTDLTKVHTECCHGDLLECADDRADLAKYICENQDSISSKLK<br>ECCEKPLLEKSHCIAEVENDEMPADLPSLAADFVESKDVCKNYAEA<br>KDVFLGMFLYEYARRHPDYSVVLLLRLAKTYETTLEKCCAAADPH<br>ECYAKVFDEFKPLVEEPQNLIKQNCELFEQLGEYKFQNALLVRYTK<br>KVPQVSTPTLVEVSRNLGKVGSKCCKHPEAKRMPCAEDYLSVVLN<br>QLCVLHEKTPVSDRVTKCCTESLVNRRPCFSALEVDETYVPKEFNA<br>ETFTFHADICTLSEKERQIKKQTALVELVKHKPKATKEQLKAVMDD<br>FAAFVEKCCKADDKETCFAEEGKKLVAASQAALGLGSGGGGSGGG<br>GSGGGGSGGGGSGGGGSGGGGSGGGGSGGGGSDHCPLGPGRCCR<br>LHTVRASLEDLGWADWVLSPREVQVTMCIGACPSQFRAANMHAQI<br>KTSLHRLKPDTVPAPCCVPASYNPMVLIQKTDTGVSLQTYDDLLAK<br>DCHCI |
| 114 | DNA for SEQ ID NO: 113 (Deletion 2) HSA (C34S)-GS-(GGGGS)$_8$-(deletion 4) GDF15 | CACAAGAGTGAGGTTGCTCATCGGTTTAAAGATTTGGGAGAAGA<br>AAATTTCAAAGCCTTGGTGTTGATTGCCTTTGCTCAGTATCTTCA<br>GCAGTCCCCATTTGAAGATCATGTAAAATTAGTGAATGAAGTAA<br>CTGAATTTGCAAAAACATGTGTTGCTGATGAGTCAGCTGAAAAT<br>TGTGACAAATCACTTCATACCCTTTTTGGAGACAAATTATGCACA<br>GTTGCAACTCTTCGTGAAACCTATGGTGAAATGGCTGACTGCTGT<br>GCAAAACAAGAACCTGAGAGAAATGAATGCTTCTTGCAACACAA<br>AGATGACAACCCAAACCTCCCCCGATTGGTGAGACCAGAGGTTG<br>ATGTGATGTGCACTGCTTTTCATGACAATGAAGAGACATTTTTGA<br>AAAAATACTTATATGAAATTGCCAGAAGACATCCTTACTTTTATG<br>CCCCGGAACTCCTTTTCTTTGCTAAAAGGTATAAAGCTGCTTTTA<br>CAGAATGTTGCCAAGCTGCTGATAAAGCTGCCTGCCTGTTGCCA<br>AAGCTCGATGAACTTCGGGATGAAGGGAAGGCTTCGTCTGCCAA<br>ACAGAGACTCAAGTGTGCCAGTCTCCAAAAATTTGGAGAAAGAG<br>CTTTCAAAGCATGGGCAGTAGCTCGCCTGAGCCAGAGATTTCCC<br>AAAGCTGAGTTTGCAGAAGTTTCCAAGTTAGTGACAGATCTTAC<br>CAAAGTCCACACGGAATGCTGCCATGGAGATCTGCTTGAATGTG |

-continued

WT-wild type

| SEQ ID NO | Description | Sequence |
|---|---|---|
| | | CTGATGACAGGGCGGACCTTGCCAAGTATATCTGTGAAAATCAA<br>GATTCGATCTCCAGTAAACTGAAGGAATGCTGTGAAAAACCTCT<br>GTTGGAAAAATCCCACTGCATTGCCGAAGTGGAAAATGATGAGA<br>TGCCTGCTGACTTGCCTTCATTAGCTGCTGATTTTGTTGAAAGTA<br>AGGATGTTTGCAAAAACTATGCTGAGGCAAAGGATGTCTTCCTG<br>GGCATGTTTTTGTATGAATATGCAAGAAGGCATCCTGATTACTCT<br>GTCGTGCTGCTGCTGAGACTTGCCAAGACATATGAAACCACTCT<br>AGAGAAGTGCTGTGCCGCTGCAGATCCTCATGAATGCTATGCCA<br>AAGTGTTCGATGAATTTAAACCTCTTGTGGAAGAGCCTCAGAAT<br>TTAATCAAACAAAATTGTGAGCTTTTTGAGCAGCTTGGAGAGTA<br>CAAATTCCAGAATGCGCTATTAGTTCGTTACACCAAGAAAGTAC<br>CCCAAGTGTCAACTCCAACTCTTGTAGAGGTCTCAAGAAACCTA<br>GGAAAAGTGGGCAGCAAATGTTGTAAACATCCTGAAGCAAAAA<br>GAATGCCCTGTGCAGAAGACTATCTATCCGTGGTCCTGAACCAG<br>TTATGTGTGTTGCATGAGAAAACGCCAGTAAGTGACAGAGTCAC<br>CAAATGCTGCACAGAATCCTTGGTGAACAGGCGACCATGCTTTT<br>CAGCTCTGGAAGTCGATGAAACATACGTTCCCAAAGAGTTTAAT<br>GCTGAAACATTCACCTTCCATGCAGATATATGCACACTTTCTGAG<br>AAGGAGAGACAAATCAAGAAACAAACTGCACTTGTTGAGCTCGT<br>GAAACACAAGCCCAAGGCAACAAAAGAGCAACTGAAAGCTGTT<br>ATGGATGATTTCGCAGCTTTTGTAGAGAAGTGCTGCAAGGCTGA<br>CGATAAGGAGACCTGCTTTGCCGAGGAGGGTAAAAAACTTGTTG<br>CTGCAAGTCAAGCTGCCTTAGGGCTTGGAAGCGGCGGAGGGGGG<br>AGTGGCGGCGGTGGCTCCGGGGGGGGCGGATCCGGCGGAGGGG<br>GCAGCGGGGGTGGAGGGAGTGGCGGGGGAGGATCAGGGGGAGG<br>AGGATCAGGAGGGGGCGGAAGTGATCATTGCCCTCTCGGGCCCG<br>GACGGTGTTGCCGCCTCCACACTGTGAGGGCTTCACTTGAAGAC<br>CTTGGATGGGCCGACTGGGTGCTGTCCCCAAGAGAGGTACAAGT<br>CACAATGTGTATTGGCGCCTGCCCCAGCCAGTTTCGCGCCGCTAA<br>CATGCACGCCCAGATAAAAACCAGCCTGCACCGCCTGAAGCCCG<br>ACACGGTGCCAGCGCCCTGCTGCGTGCCCGCCAGCTACAATCCC<br>ATGGTGCTCATTCAAAAGACCGACACCGGGGTGTCGCTCCAGAC<br>CTATGATGACTTGTTAGCCAAAGACTGCCACTGCATA |
| 115 | HSA (C34S)-GA-$(GGGGA)_8$-(deletion 4) GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGAGGGG<br>AGGGGAGGGGAGGGGAGGGGAGGGGAGGGGAGGGGADHCPLG<br>PGRCCRLHTVRASLEDLGWADWVLSPREVQVTMCIGACPSQFRAA<br>NMHAQIKTSLHRLKPDTVPAPCCVPASYNPMVLIQKTDTGVSLQTY<br>DDLLAKDCHCI |
| 116 | DNA for SEQ ID NO: 115 HSA (C34S)-GA-$(GGGGA)_8$-(deletion 4) GDF15 | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA |

-continued

WT-wild type

| SEQ ID NO | Description | Sequence |
|---|---|---|
| | | AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC<br>AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG<br>TCACCAAATGCTGCACAGAATCCTTGGTGAACAGGCGACCATGC<br>TTTTCAGCTCTGGAAGTCGATGAAACATACGTTCCCAAAGAGTTT<br>AATGCTGAAACATTCACCTTCCATGCAGATATATGCACACTTTCT<br>GAGAAGGAGAGACAAATCAAGAAACAAACTGCACTTGTTGAGC<br>TCGTGAAACACAAGCCCAAGGCAACAAAAGAGCAACTGAAAGC<br>TGTTATGGATGATTTCGCAGCTTTTGTAGAGAAGTGCTGCAAGGC<br>TGACGATAAGGAGACCTGCTTTGCCGAGGAGGGTAAAAAACTTG<br>TTGCTGCAAGTCAAGCTGCCTTAGGGCTTGGTGCTGGAGGAGGC<br>GGGGCGGGCGGCGGGGGTGCCGGTGGGGGTGGCGCAGGGGGAG<br>GTGGTGCGGGTGGTGGTGGGGCTGGTGGGGGAGGTGCAGGCGG<br>TGGCGGTGCCGGGGGGGGTGGCGCGGATCATTGCCCTCTCGGGC<br>CCGGACGGTGTTGCCGCCTCCACACTGTGAGGGCTTCACTTGAA<br>GACCTTGGATGGGCCGACTGGGTGCTGTCCCCAAGAGAGGTACA<br>AGTCACAATGTGTATTGGCGCCTGCCCCAGCCAGTTTCGCGCCGC<br>TAACATGCACGCCCAGATAAAAACCAGCCTGCACCGCCTGAAGC<br>CCGACACGGTGCCAGCGCCCTGCTGCGTGCCCGCCAGCTACAAT<br>CCCATGGTGCTCATTCAAAAGACCGACACCGGGGTGTCGCTCCA<br>GACCTATGATGACTTGTTAGCCAAAGACTGCCACTGCATA |
| 117 | HSA (C34S)-<br>$(AP)_{10}$-<br>(deletion 4)<br>GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLAPAPAPA<br>PAPAPAPAPAPAPDHCPLGPGRCCRLHTVRASLEDLGWADWVLSP<br>REVQVTMCIGACPSQFRAANMHAQIKTSLHRLKPDTVPAPCCVPAS<br>YNPMVLIQKTDTGVSLQTYDDLLAKDCHCI |
| 118 | DNA for SEQ<br>ID NO: 117<br>HSA (C34S)-<br>$(AP)_{10}$-<br>(deletion 4)<br>GDF15 | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA<br>AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC |

-continued

| WT-wild type | | |
|---|---|---|
| SEQ ID NO | Description | Sequence |
| | | AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG<br>TCACCAAATGCTGCACAGAATCCTTGGTGAACAGGCGACCATGC<br>TTTTCAGCTCTGGAAGTCGATGAAACATACGTTCCCAAAGAGTTT<br>AATGCTGAAACATTCACCTTCCATGCAGATATATGCACACTTTCT<br>GAGAAGGAGAGACAAATCAAGAAACAAACTGCACTTGTTGAGC<br>TCGTGAAACACAAGCCCAAGGCAACAAAAGAGCAACTGAAAGC<br>TGTTATGGATGATTTCGCAGCTTTTGTAGAGAAGTGCTGCAAGGC<br>TGACGATAAGGAGACCTGCTTTGCCGAGGAGGGTAAAAAACTTG<br>TTGCTGCAAGTCAAGCTGCCTTAGGGCTTGCACCAGCCCCTGCCC<br>CTGCACCTGCACCTGCTCCCGCACCGGCTCCAGCCCCAGCTCCG<br>GATCATTGCCCTCTCGGGCCCGGACGGTGTTGCCGCCTCCACACT<br>GTGAGGGCTTCACTTGAAGACCTTGGATGGGCCGACTGGGTGCT<br>GTCCCCAAGAGAGGTACAAGTCACAATGTGTATTGGCGCCTGCC<br>CCAGCCAGTTTCGCGCCGCTAACATGCACGCCCAGATAAAAACC<br>AGCCTGCACCGCCTGAAGCCCGACACGGTGCCAGCGCCCTGCTG<br>CGTGCCCGCCAGCTACAATCCCATGGTGCTCATTCAAAAGACCG<br>ACACCGGGGTGTCGCTCCAGACCTATGATGACTTGTTAGCCAAA<br>GACTGCCACTGCATA |
| 119 | HSA (C34S)-<br>$(AP)_{12}$-<br>(deletion 4)<br>GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLAPAPAPA<br>PAPAPAPAPAPAPAPAPDHCPLGPGRCCRLHTVRASLEDLGWADW<br>VLSPREVQVTMCIGACPSQFRAANMHAQIKTSLHRLKPDTVPAPCC<br>VPASYNPMVLIQKTDTGVSLQTYDDLLAKDCHCI |
| 120 | DNA for SEQ<br>ID NO: 119<br>HSA (C34S)-<br>$(AP)_{12}$-<br>(deletion 4)<br>GDF15 | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA<br>AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC<br>AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG |

-continued

| WT-wild type | | |
|---|---|---|
| SEQ ID NO | Description | Sequence |
| | | TCACCAAATGCTGCACAGAATCCTTGGTGAACAGGCGACCATGC TTTTCAGCTCTGGAAGTCGATGAAACATACGTTCCCAAAGAGTTT AATGCTGAAACATTCACCTTCCATGCAGATATATGCACACTTTCT GAGAAGGAGAGACAAATCAAGAAACAAACTGCACTTGTTGAGC TCGTGAAACACAAGCCCAAGGCAACAAAAGAGCAACTGAAAGC TGTTATGGATGATTTCGCAGCTTTTGTAGAGAAGTGCTGCAAGGC TGACGATAAGGAGACCTGCTTTGCCGAGGAGGGTAAAAAACTTG TTGCTGCAAGTCAAGCTGCCTTAGGGCTTGCACCAGCCCCTGCCC CTGCACCTGCACCTGCTCCCGCACCGGCTCCAGCCCCAGCTCCG GCTCCAGCTCCTGATCATTGCCCTCTCGGGCCCGGACGGTGTTGC CGCCTCCACACTGTGAGGGCTTCACTTGAAGACCTTGGATGGGC CGACTGGGTGCTGTCCCCAAGAGAGGTACAAGTCACAATGTGTA TTGGCGCCTGCCCCAGCCAGTTTCGCGCCGCTAACATGCACGCCC AGATAAAAACCAGCCTGCACCGCCTGAAGCCCGACACGGTGCCA GCGCCCTGCTGCGTGCCCGCCAGCTACAATCCCATGGTGCTCATT CAAAAGACCGACACCGGGGTGTCGCTCCAGACCTATGATGACTT GTTAGCCAAAGACTGCCACTGCATA |
| 121 | HSA (C34S)-GGS-(EGKSSGSGSESKST)$_3$-GGS-(deletion4) GDF15 | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGGSEGKS SGSGSESKSTEGKSSGSGSESKSTEGKSSGSGSESKSTGGSDHCPLGP GRCCRLHTVRASLEDLGWADWVLSPREVQVTMCIGACPSQFRAAN MHAQIKTSLHRLKPDTVPAPCCVPASYNPMVLIQKTDTGVSLQTYD DLLAKDCHCI |
| 122 | DNA for SEQ ID NO: 121 HSA (C34S)-GGS-(EGKSSGSGSESKST)$_3$-GGS-(deletion4) GDF15 | GATGCACACAAGAGTGAGGTTGCTCATCGGTTTAAAGATTTGGG AGAAGAAAATTTCAAAGCCTTGGTGTTGATTGCCTTTGCTCAGTA TCTTCAGCAGTCCCCATTTGAAGATCATGTAAAATTAGTGAATGA AGTAACTGAATTTGCAAAAACATGTGTTGCTGATGAGTCAGCTG AAAATTGTGACAAATCACTTCATACCCTTTTTGGAGACAAATTAT GCACAGTTGCAACTCTTCGTGAAACCTATGGTGAAATGGCTGAC TGCTGTGCAAAACAAGAACCTGAGAGAAATGAATGCTTCTTGCA ACACAAAGATGACAACCCAAACCTCCCCCGATTGGTGAGACCAG AGGTTGATGTGATGTGCACTGCTTTTCATGACAATGAAGAGACA TTTTTGAAAAAATACTTATATGAAATTGCCAGAAGACATCCTTAC TTTTATGCCCCGGAACTCCTTTTCTTTGCTAAAAGGTATAAAGCT GCTTTTACAGAATGTTGCCAAGCTGCTGATAAAGCTGCCTGCCTG TTGCCAAAGCTCGATGAACTTCGGGATGAAGGGAAGGCTTCGTC TGCCAAACAGAGACTCAAGTGTGCCAGTCTCCAAAAATTTGGAG AAAGAGCTTTCAAAGCATGGGCAGTAGCTCGCCTGAGCCAGAGA TTTCCCAAAGCTGAGTTTGCAGAAGTTTCCAAGTTAGTGACAGAT CTTACCAAAGTCCACACGGAATGCTGCCATGGAGATCTGCTTGA ATGTGCTGATGACAGGGCGGACCTTGCCAAGTATATCTGTGAAA ATCAAGATTCGATCTCCAGTAAACTGAAGGAATGCTGTGAAAAA CCTCTGTTGGAAAAATCCCACTGCATTGCCGAAGTGGAAAATGA TGAGATGCCTGCTGACTTGCCTTCATTAGCTGCTGATTTTGTTGA AAGTAAGGATGTTTGCAAAAACTATGCTGAGGCAAAGGATGTCT TCCTGGGCATGTTTTTGTATGAATATGCAAGAAGGCATCCTGATT ACTCTGTCGTGCTGCTGCTGAGACTTGCCAAGACATATGAAACC ACTCTAGAGAAGTGCTGTGCCGCTGCAGATCCTCATGAATGCTA TGCCAAAGTGTTCGATGAATTTAAACCTCTTGTGGAAGAGCCTC AGAATTTAATCAAACAAAATTGTGAGCTTTTTGAGCAGCTTGGA GAGTACAAATTCCAGAATGCGCTATTAGTTCGTTACACCAAGAA AGTACCCCAAGTGTCAACTCCAACTCTTGTAGAGGTCTCAAGAA ACCTAGGAAAAGTGGGCAGCAAATGTTGTAAACATCCTGAAGCA AAAAGAATGCCCTGTGCAGAAGACTATCTATCCGTGGTCCTGAA CCAGTTATGTGTGTTGCATGAGAAAACGCCAGTAAGTGACAGAG TCACAAAATGCTGTACTGAGAGCTTGGTCAACAGGCGGCCGTGC TTCAGCGCCCTCGAGGTGGATGAGACTTATGTCCCAAAGGAGTT TAATGCGGAAACTTTTACTTTCCACGCAGACATTTGCACCTTGTC TGAAAAGGAAAGACAGATTAAGAAACAGACTGCTCTTGTGGAA CTGGTAAAACATAAACCAAAAGCTACGAAGGAGCAGCTTAAGG |

-continued

| WT-wild type | | |
|---|---|---|
| SEQ ID NO | Description | Sequence |
| | | CTGTTATGGATGATTTCGCCGCGTTTGTCGAGAAGTGCTGCAAAG CGGACGATAAGGAAACTTGCTTTGCAGAGGAAGGTAAGAAACTC GTAGCGGCAAGTCAGGCTGCGCTTGGCCTTGGAGGCAGTGAAGG CAAATCCTCTGGGAGTGGCTCTGAAAGTAAATCCACCGAGGGCA AATCCAGTGGATCTGGGTCTGAATCTAAGTCTACCGAGGGGAAG TCTTCTGGCAGTGGGTCAGAATCTAAATCTACAGGCGGCTCTGA CCATTGCCCGTTGGGACCAGGACGCTGCTGTCGCCTTCATACAGT GCGAGCGAGTTTGGAAGACCTGGGCTGGGCTGACTGGGTGCTTA GCCCTCGGGAGGTCCAGGTCACAATGTGCATTGGCGCGTGTCCC AGTCAATTTAGAGCAGCAAATATGCACGCCCAAATAAAAACCTC CCTGCATAGGCTTAAGCCAGATACTGTCCCCGCACCATGCTGTGT GCCTGCTTCTTACAATCCTATGGTACTCATCCAGAAGACCGACAC GGGAGTTAGCCTCCAGACTTATGACGACCTCTTGGCTAAAGATT GCCATTGTATT |
| 123 | HSA (C34S)-GS-(PGGGS)$_8$-(deletion4) GDF15 | DAHKSEVAHRFKDLGEENFKALVLIAFAQYLQQSPFEDHVKLVNEV TEFAKTCVADESAENCDKSLHTLFGDKLCTVATLRETYGEMADCC AKQEPERNECFLQHKDDNPNLPRLVRPEVDVMCTAFHDNEETFLK KYLYEIARRHPYFYAPELLFFAKRYKAAFTECCQAADKAACLLPKL DELRDEGKASSAKQRLKCASLQKFGERAFKAWAVARLSQRFPKAE FAEVSKLVTDLTKVHTECCHGDLLECADDRADLAKYICENQDSISS KLKECCEKPLLEKSHCIAEVENDEMPADLPSLAADFVESKDVCKNY AEAKDVFLGMFLYEYARRHPDYSVVLLLRLAKTYETTLEKCCAAA DPHECYAKVFDEFKPLVEEPQNLIKQNCELFEQLGEYKFQNALLVR YTKKVPQVSTPTLVEVSRNLGKVGSKCCKHPEAKRMPCAEDYLSV VLNQLCVLHEKTPVSDRVTKCCTESLVNRRPCFSALEVDETYVPKE FNAETFTFHADICTLSEKERQIKKQTALVELVKHKPKATKEQLKAV MDDFAAFVEKCCKADDKETCFAEEGKKLVAASQAALGLGSPGGGS PGGGSPGGGSPGGGSPGGGSPGGGSPGGGSPGGGSDHCPLGPGRCC RLHTVRASLEDLGWADWVLSPREVQVTMCIGACPSQFRAANMHA QIKTSLHRLKPDTVPAPCCVPASYNPMVLIQKTDTGVSLQTYDDLL AKDCHCI |
| 124 | DNA for SEQ ID NO: 123 HSA (C34S)-GS-(PGGGS)$_8$-(deletion4) GDF15 | GATGCACACAAGAGTGAGGTTGCTCATCGGTTTAAAGATTTGGG AGAAGAAAATTTCAAAGCCTTGGTGTTGATTGCCTTTGCTCAGTA TCTTCAGCAGTCCCCATTTGAAGATCATGTAAAATTAGTGAATGA AGTAACTGAATTTGCAAAAACATGTGTTGCTGATGAGTCAGCTG AAAATTGTGACAAATCACTTCATACCCTTTTTGGAGACAAATTAT GCACAGTTGCAACTCTTCGTGAAACCTATGGTGAAATGGCTGAC TGCTGTGCAAAACAAGAACCTGAGAGAAATGAATGCTTCTTGCA ACACAAAGATGACAACCCAAACCTCCCCCGATTGGTGAGACCAG AGGTTGATGTGATGTGCACTGCTTTTCATGACAATGAAGAGACA TTTTTGAAAAAATACTTATATGAAATTGCCAGAAGACATCCTTAC TTTTATGCCCCGGAACTCCTTTTCTTTGCTAAAAGGTATAAAGCT GCTTTTACAGAATGTTGCCAAGCTGCTGATAAAGCTGCCTGCCTG TTGCCAAAGCTCGATGAACTTCGGGATGAAGGGAAGGCTTCGTC TGCCAAACAGAGACTCAAGTGTGCCAGTCTCCAAAAATTTGGAG AAAGAGCTTTCAAAGCATGGGCAGTAGCTCGCCTGAGCCAGAGA TTTCCCAAAGCTGAGTTTGCAGAAGTTTCCAAGTTAGTGACAGAT CTTACCAAAGTCCACACGGAATGCTGCCATGGAGATCTGCTTGA ATGTGCTGATGACAGGGCGGACCTTGCCAAGTATATCTGTGAAA ATCAAGATTCGATCTCCAGTAAACTGAAGGAATGCTGTGAAAAA CCTCTGTTGGAAAAATCCCACTGCATTGCCGAAGTGGAAAATGA TGAGATGCCTGCTGACTTGCCTTCATTAGCTGCTGATTTTGTTGA AAGTAAGGATGTTTGCAAAAACTATGCTGAGGCAAAGGATGTCT TCCTGGGCATGTTTTTGTATGAATATGCAAGAAGGCATCCTGATT ACTCTGTCGTGCTGCTGCTGAGACTTGCCAAGACATATGAAACC ACTCTAGAGAAGTGCTGTGCCGCTGCAGATCCTCATGAATGCTA TGCCAAAGTGTTCGATGAATTTAAACCTCTTGTGGAAGAGCCTC AGAATTTAATCAAACAAAATTGTGAGCTTTTTGAGCAGCTTGGA GAGTACAAATTCCAGAATGCGCTATTAGTTCGTTACACCAAGAA AGTACCCCAAGTGTCAACTCCAACTCTTGTAGAGGTCTCAAGAA ACCTAGGAAAAGTGGGCAGCAAATGTTGTAAACATCCTGAAGCA AAAAGAATGCCCTGTGCAGAAGACTATCTATCCGTGGTCCTGAA CCAGTTATGTGTGTTGCATGAGAAAACGCCAGTAAGTGACAGAG TCACGAAATGTTGCACAGAGTCACTGGTCAACAGGAGACCTTGC TTCTCCGCTCTTGAGGTTGACGAAACGTATGTCCCAAAAGAGTTC AACGCCGAAACGTTTACGTTTCATGCGGACATATGCACTCTCAGT GAGAAGGAGCGACAAATCAAAAAACAGACTGCTCTTGTAGAGTT GGTAAAACACAAACCTAAAGCAACAAAAGAGCAATTGAAAGCT GTGATGGACGATTTTGCAGCTTTCGTAGAAAAGTGCTGCAAGGC CGACGATAAAGAAACCTGTTTCGCTGAAGAAGGCAAAAAACTTG TTGCGGCATCTCAGGCCGCTCTTGGACTTGGGAGCCCGGGTGGC |

-continued

| WT-wild type | | |
|---|---|---|
| SEQ ID NO | Description | Sequence |
| | | GGGTCTCCAGGCGGAGGCTCTCCGGGCGGAGGTAGTCCCGGAGG<br>GGGTAGTCCGGGCGGCGGTTCTCCAGGTGGAGGTTCTCCTGGTG<br>GTGGCAGTCCTGGCGGAGGATCTGATCACTGTCCCCTTGGGCCC<br>GGGAGGTGCTGCCGACTTCATACAGTTCGCGCCAGCCTTGAAGA<br>TTTGGGGTGGGCCGACTGGGTGTTGAGCCCGAGAGAGGTCCAAG<br>TCACGATGTGTATTGGAGCCTGTCCCTCTCAATTCCGAGCCGCAA<br>ATATGCATGCGCAAATAAAGACGAGTCTCCATCGGTTGAAGCCT<br>GATACTGTCCCAGCTCCGTGCTGCGTCCCCGCGAGTTATAATCCC<br>ATGGTCCTTATACAGAAAACAGACACTGGTGTCAGCCTTCAGAC<br>GTATGACGATTTGCTTGCTAAAGACTGTCATTGTATT |
| 125 | HSA (C34S)-GS-(AGGGS)$_8$-(deletion 4) GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGSAGGG<br>SAGGGSAGGGSAGGGSAGGGSAGGGSAGGGSAGGGSDHCPLGPG<br>RCCRLHTVRASLEDLGWADWVLSPREVQVTMCIGACPSQFRAANM<br>HAQIKTSLHRLKPDTVPAPCCVPASYNPMVLIQKTDTGVSLQTYDD<br>LLAKDCHCI |
| 126 | DNA for SEQ ID NO: 125 | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA<br>AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC<br>AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG<br>TCACTAAATGTTGTACCGAGTCTCTTGTTAATAGGCGGCCATGCT<br>TCAGTGCATTGGAAGTCGACGAAACCTATGTACCAAAGGAGTTC<br>AACGCAGAAACATTTACATTCCATGCTGATATCTGCACATTGAG<br>CGAGAAAGAGAGACAGATTAAGAAACAGACAGCGCTTGTTGAA<br>CTGGTTAAACACAAACCAAAAGCTACCAAGGAGCAGCTTAAGGC<br>AGTAATGGATGACTTCGCGGCCTTTGTCGAGAAATGTTGTAAAG<br>CGGATGATAAAGAGACATGCTTCGCCGAAGAGGGCAAAAAACT<br>TGTAGCGGCAAGCCAGGCCGCACTGGGTCTCGGTAGTGCGGGCG<br>GTGGTTCAGCGGGGGGAGGATCTGCAGGTGGTGGCTCAGCGGGT<br>GGCGGTAGCGCTGGGGGGGGCTCCGCAGGTGGGGGATCAGCAG<br>GCGGCGGATCAGCCGGCGGTGGATCCGACCACTGTCCTCTCGGG<br>CCTGGTCGGTGTTGCCGCCTCCATACTGTGCGCGCGTCTCTTGAG |

-continued

WT-wild type

| SEQ ID NO | Description | Sequence |
| --- | --- | --- |
| | | GATCTGGGGTGGGCTGATTGGGTTCTCTCTCCCCGCGAAGTGCA<br>GGTGACCATGTGTATTGGTGCTTGCCCAAGTCAATTCCGAGCAG<br>CTAACATGCACGCCCAGATCAAGACTAGCCTGCATCGGCTTAAG<br>CCCGACACTGTTCCTGCCCCTTGCTGTGTTCCTGCATCTTATAATC<br>CAATGGTCCTGATCCAGAAAACCGATACGGGTGTATCATTGCAA<br>ACATACGACGACTTGCTTGCCAAAGATTGCCATTGCATT |
| 127 | HSA (C34S)-<br>GGS-<br>$(EGKSSGSGSESKST)_2$-<br>GGS-<br>(deletion4)<br>GDF15 | DAHKSEVAHRFKDLGEENFKALVLIAFAQYLQQSPFEDHVKLVNEV<br>TEFAKTCVADESAENCDKSLHTLFGDKLCTVATLRETYGEMADCC<br>AKQEPERNECFLQHKDDNPNLPRLVRPEVDVMCTAFHDNEETFLK<br>KYLYEIARRHPYFYAPELLFFAKRYKAAFTECCQAADKAACLLPKL<br>DELRDEGKASSAKQRLKCASLQKFGERAFKAWAVARLSQRFPKAE<br>FAEVSKLVTDLTKVHTECCHGDLLECADDRADLAKYICENQDSISS<br>KLKECCEKPLLEKSHCIAEVENDEMPADLPSLAADFVESKDVCKNY<br>AEAKDVFLGMFLYEYARRHPDYSVVLLLRLAKTYETTLEKCCAAA<br>DPHECYAKVFDEFKPLVEEPQNLIKQNCELFEQLGEYKFQNALLVR<br>YTKKVPQVSTPTLVEVSRNLGKVGSKCCKHPEAKRMPCAEDYLSV<br>VLNQLCVLHEKTPVSDRVTKCCTESLVNRRPCFSALEVDETYVPKE<br>FNAETFTFHADICTLSEKERQIKKQTALVELVKHKPKATKEQLKAV<br>MDDFAAFVEKCCKADDKETCFAEEGKKLVAASQAALGLGGSEGKS<br>SGSGSESKSTEGKSSGSGSESKSTGGSDHCPLGPGRCCRLHTVRASL<br>EDLGWADWVLSPREVQVTMCIGACPSQFRAANMHAQIKTSLHRLK<br>PDTVPAPCCVPASYNPMVLIQKTDTGVSLQTYDDLLAKDCHCI |
| 128 | DNA for SEQ<br>ID NO: 127 | GATGCACACAAGAGTGAGGTTGCTCATCGGTTTAAAGATTTGGG<br>AGAAGAAAATTTCAAAGCCTTGGTGTTGATTGCCTTTGCTCAGTA<br>TCTTCAGCAGTCCCCATTTGAAGATCATGTAAAATTAGTGAATGA<br>AGTAACTGAATTTGCAAAAACATGTGTTGCTGATGAGTCAGCTG<br>AAAATTGTGACAAATCACTTCATACCCTTTTTGGAGACAAATTAT<br>GCACAGTTGCAACTCTTCGTGAAACCTATGGTGAAATGGCTGAC<br>TGCTGTGCAAAACAAGAACCTGAGAGAAATGAATGCTTCTTGCA<br>ACACAAAGATGACAACCCAAACCTCCCCCGATTGGTGAGACCAG<br>AGGTTGATGTGATGTGCACTGCTTTTCATGACAATGAAGAGACA<br>TTTTTGAAAAAATACTTATATGAAATTGCCAGAAGACATCCTTAC<br>TTTTATGCCCCGGAACTCCTTTTCTTTGCTAAAAGGTATAAAGCT<br>GCTTTTACAGAATGTTGCCAAGCTGCTGATAAAGCTGCCTGCCTG<br>TTGCCAAAGCTCGATGAACTTCGGGATGAAGGGAAGGCTTCGTC<br>TGCCAAACAGAGACTCAAGTGTGCCAGTCTCCAAAAATTTGGAG<br>AAAGAGCTTTCAAAGCATGGGCAGTAGCTCGCCTGAGCCAGAGA<br>TTTCCCAAAGCTGAGTTTGCAGAAGTTTCCAAGTTAGTGACAGAT<br>CTTACCAAAGTCCACACGGAATGCTGCCATGGAGATCTGCTTGA<br>ATGTGCTGATGACAGGGCGGACCTTGCCAAGTATATCTGTGAAA<br>ATCAAGATTCGATCTCCAGTAAACTGAAGGAATGCTGTGAAAAA<br>CCTCTGTTGGAAAAATCCCACTGCATTGCCGAAGTGGAAAATGA<br>TGAGATGCCTGCTGACTTGCCTTCATTAGCTGCTGATTTTGTTGA<br>AAGTAAGGATGTTTGCAAAAACTATGCTGAGGCAAAGGATGTCT<br>TCCTGGGCATGTTTTTGTATGAATATGCAAGAAGGCATCCTGATT<br>ACTCTGTCGTGCTGCTGCTGAGACTTGCCAAGACATATGAAACC<br>ACTCTAGAGAAGTGCTGTGCCGCTGCAGATCCTCATGAATGCTA<br>TGCCAAAGTGTTCGATGAATTTAAACCTCTTGTGGAAGAGCCTC<br>AGAATTTAATCAAACAAAATTGTGAGCTTTTTGAGCAGCTTGGA<br>GAGTACAAATTCCAGAATGCGCTATTAGTTCGTTACACCAAGAA<br>AGTACCCCAAGTGTCAACTCCAACTCTTGTAGAGGTCTCAAGAA<br>ACCTAGGAAAAGTGGGCAGCAAATGTTGTAAACATCCTGAAGCA<br>AAAAGAATGCCCTGTGCAGAAGACTATCTATCCGTGGTCCTGAA<br>CCAGTTATGTGTGTTGCATGAGAAAACGCCAGTAAGTGACAGAG<br>TCACGAAATGCTGTACAGAATCCCTCGTGAATAGAAGGCCCTGC<br>TTCTCTGCCCTTGAGGTGGACGAGACTTACGTCCCTAAGGAGTTT<br>AACGCCGAGACCTTTACTTTTCATGCTGATATTTGCACCCTTTCC<br>GAAAAGGAGCGGCAGATCAAGAAACAAACAGCCTTGGTGGAAC<br>TCGTAAAACATAAACCCAAAGCCACCAAGGAACAACTTAAAGCT<br>GTTATGGATGACTTCGCAGCCTTCGTCGAGAAATGTTGCAAGGC<br>GGATGATAAGGAAACGTGTTTTGCTGAGGAAGGGAAGAAGTTG<br>GTTGCTGCCTCTCAAGCGGCTCTGGGGCTTGGCGGATCAGAGGG<br>GAAGTCCTCCGGGTCCGGTAGCGAGTCCAAATCTACGGAAGGGA<br>AGTCATCCGGTTCTGGGTCAGAGTCCAAATCCACAGGAGGATCA<br>GACCATTGCCCATTGGGACCAGGACGATGTTGTCGCCTGCATAC<br>GGTAAGAGCGTCTCTGGAGGATCTCGGCTGGGCCGATTGGGTTC<br>TCTCACCACGAGAAGTACAGGTCACAATGTGCATAGGAGCTTGT<br>CCGAGCCAATTCCGGGCGGCTAATATGCACGCACAGATCAAGAC<br>CTCTTTGCACCGCTTGAAGCCCGATACCGTGCCAGCACCGTGTTG |

-continued

| WT-wild type | | |
|---|---|---|
| SEQ ID NO | Description | Sequence |
| | | CGTCCCAGCATCTTACAACCCTATGGTTTTGATACAGAAAACTGA CACAGGTGTGAGCCTCCAGACATATGATGATTTGCTGGCTAAGG ATTGCCACTGTATA |

We claim:

1. A method of treating obesity, comprising administering to a subject in need thereof a therapeutically effective amount of a pharmaceutical composition comprising a fusion protein comprising:
   a. the amino acid sequence of SEQ ID NO:2;
   b. a linker having a length of 35-48 amino acids and comprising the amino acid sequence of (GGGGS)n, wherein n is 7 or 8 (SEQ ID NO:42 or SEQ ID NO:43); and
   c. a truncated GDF15 consisting of the amino acid sequence of SEQ ID NO:8; wherein the fusion protein is arranged from N-terminus to C-terminus in the order (a)-(b)-(c), and the C-terminus of the amino acid sequence of SEQ ID NO:2 is fused to the N-terminus of the truncated GDF15 through the linker.

2. The method of claim 1, wherein the linker comprises the sequence (GGGGS)n, wherein n is 8 (SEQ ID NO:43).

3. The method of claim 2, wherein the linker consists of the amino acid sequence of SEQ ID NO:12.

4. The method of claim 3, wherein the pharmaceutical composition comprises the fusion protein comprising the amino acid sequence of SEQ ID NO:92.

5. A method of treating type 2 diabetes, comprising administering to a subject in need thereof a therapeutically effective amount of a pharmaceutical composition comprising a fusion protein comprising:
   a. the amino acid sequence of SEQ ID NO:2;
   b. a linker having a length of 35-48 amino acids and comprising the amino acid sequence of (GGGGS)n, wherein n is 7 or 8 (SEQ ID NO:42 or SEQ ID NO:43); and
   c. a truncated GDF15 consisting of the amino acid sequence of SEQ ID NO:8;

wherein the fusion protein is arranged from N-terminus to C-terminus in the order (a)-(b)-(c), and the C-terminus of the amino acid sequence of SEQ ID NO:2 is fused to the N-terminus of the truncated GDF15 through the linker.

6. The method of claim 5, wherein the linker comprises the sequence (GGGGS)n, wherein n is 8 (SEQ ID NO:43).

7. The method of claim 6, wherein the linker consists of the amino acid sequence of SEQ ID NO:12.

8. The method of claim 7, wherein the pharmaceutical composition comprises the fusion protein comprising the amino acid sequence of SEQ ID NO:92.

9. A method of reducing food intake, comprising administering to a subject in need thereof a therapeutically effective amount of a pharmaceutical composition comprising a fusion protein and a pharmaceutically acceptable, wherein the fusion protein comprises:

a. the amino acid sequence of SEQ ID NO:2;

b. a linker having a length of 35-48 amino acids and comprising the amino acid sequence of (GGGGS)n, wherein n is 7 or 8 (SEQ ID NO:42 or SEQ ID NO: 43); and c. a truncated GDF15 consisting of the amino acid sequence of SEQ ID NO:8;

wherein the fusion protein is arranged from N-terminus to C-terminus in the order (a)-(b)-(c), and the C-terminus of the amino acid sequence of SEQ ID NO:2 is fused to the N-terminus of the truncated GDF15 through the linker.

10. The method of claim 9, wherein the linker comprises the sequence (GGGGS)n, wherein n is 8 (SEQ ID NO:43).

11. The method of claim 10, wherein the linker consists of the amino acid sequence of SEQ ID NO:12.

12. The method of claim 11, wherein the pharmaceutical composition comprises the fusion protein comprising the amino acid sequence of SEQ ID NO:92.

13. A method of reducing body weight, comprising administering to a subject in need thereof a therapeutically effective amount of a pharmaceutical composition comprising a fusion protein and a pharmaceutically acceptable, wherein the fusion protein comprises:

a. the amino acid sequence of SEQ ID NO:2;

b. a linker having a length of 35-48 amino acids and comprising the amino acid sequence of (GGGGS)n, wherein n is 7 or 8 (SEQ ID NO:42 or SEQ ID NO:43); and c. a truncated GDF15 consisting of the amino acid sequence of SEQ ID NO:8;

wherein the fusion protein is arranged from N-terminus to C-terminus in the order (a)-(b)-(c), and the C-terminus of the amino acid sequence of SEQ ID NO:2 is fused to the N-terminus of the truncated GDF15 through the linker.

14. The method of claim 13, wherein the linker comprises the sequence (GGGGS)n, wherein n is 8 (SEQ ID NO: 43).

15. The method of claim 14, wherein the linker consists of the amino acid sequence of SEQ ID NO: 12.

16. The method of claim 15, wherein the pharmaceutical composition comprises the fusion protein comprising the amino acid sequence of SEQ ID NO:92.

17. A method of reducing blood glucose level, comprising administering to a subject in need thereof a therapeutically effective amount of a pharmaceutical composition comprising a fusion protein and a pharmaceutically acceptable, wherein the fusion protein comprises:

a. the amino acid sequence of SEQ ID NO:2;

b. a linker having a length of 35-48 amino acids and comprising the amino acid sequence of (GGGGS)n, wherein n is 7 or 8 (SEQ ID NO:42 or SEQ ID NO:43); and c. a truncated GDF15 consisting of the amino acid sequence of SEQ ID NO:8;

wherein the fusion protein is arranged from N-terminus to C-terminus in the order (a)-(b)-(c), and the C-terminus of the amino acid sequence of SEQ ID NO:2 is fused to the N-terminus of the truncated GDF15 through the linker.

18. The method of claim 17, wherein the linker comprises the sequence (GGGGS)n, wherein n is 8 (SEQ ID NO:43).

19. The method of claim 18, wherein the linker consists of the amino acid sequence of SEQ ID NO:12.

20. The method of claim 19, wherein the pharmaceutical composition comprises the fusion protein comprising the amino acid sequence of SEQ ID NO:92.

* * * * *

SEQUENCE LISTING

<160> NUMBER OF SEQ ID NOS: 145

<210> SEQ ID NO 1
<211> LENGTH: 585
<212> TYPE: PRT
<213> ORGANISM: Artificial Sequence
<220> FEATURE:
<223> OTHER INFORMATION: HSA variant

<400> SEQUENCE: 1

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
```

-continued

```
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585


<210> SEQ ID NO 2
<211> LENGTH: 585
<212> TYPE: PRT
<213> ORGANISM: Artificial Sequence
<220> FEATURE:
<223> OTHER INFORMATION: HSA variant

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
```

-continued

```
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480
```

Leu Val Asn Arg Arg Pro Cys Phe Ser Ala Leu Glu Val Asp Glu Thr
485 490 495

Tyr Val Pro Lys Glu Phe Asn Ala Glu Thr Phe Thr Phe His Ala Asp
500 505 510

Ile Cys Thr Leu Ser Glu Lys Glu Arg Gln Ile Lys Lys Gln Thr Ala
515 520 525

Leu Val Glu Leu Val Lys His Lys Pro Lys Ala Thr Lys Glu Gln Leu
530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu
580 585

<210> SEQ ID NO 3
<211> LENGTH: 585
<212> TYPE: PRT
<213> ORGANISM: Artificial Sequence
<220> FEATURE:
<223> OTHER INFORMATION: HSA variant

<400> SEQUENCE: 3

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ala Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

-continued

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 4
<211> LENGTH: 20
<212> TYPE: PRT
<213> ORGANISM: Artificial sequence
<220> FEATURE:
<223> OTHER INFORMATION: Linker

<400> SEQUENCE: 4

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 5
<211> LENGTH: 719
<212> TYPE: PRT
<213> ORGANISM: Artificial Sequence
<220> FEATURE:
<223> OTHER INFORMATION: fusion protein

<400> SEQUENCE: 5

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

```
Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 6
<211> LENGTH: 112
<212> TYPE: PRT
<213> ORGANISM: Artificial Sequence
<220> FEATURE:
<223> OTHER INFORMATION: GDF15 variant

<400> SEQUENCE: 6

Ala Arg Asn Gly Asp His Cys Pro Leu Gly Pro Gly Arg Cys Cys Arg
1               5                   10                  15
```

```
Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 7
<211> LENGTH: 109
<212> TYPE: PRT
<213> ORGANISM: Artificial Sequence
<220> FEATURE:
<223> OTHER INFORMATION: GDF15 variant

<400> SEQUENCE: 7

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105


<210> SEQ ID NO 8
<211> LENGTH: 108
<212> TYPE: PRT
<213> ORGANISM: Artificial Sequence
<220> FEATURE:
<223> OTHER INFORMATION: GDF15 variant

<400> SEQUENCE: 8

Asp His Cys Pro Leu Gly Pro Gly Arg Cys Cys Arg Leu His Thr Val
1               5                   10                  15

Arg Ala Ser Leu Glu Asp Leu Gly Trp Ala Asp Trp Val Leu Ser Pro
            20                  25                  30

Arg Glu Val Gln Val Thr Met Cys Ile Gly Ala Cys Pro Ser Gln Phe
        35                  40                  45

Arg Ala Ala Asn Met His Ala Gln Ile Lys Thr Ser Leu His Arg Leu
    50                  55                  60

Lys Pro Asp Thr Val Pro Ala Pro Cys Cys Val Pro Ala Ser Tyr Asn
65                  70                  75                  80

Pro Met Val Leu Ile Gln Lys Thr Asp Thr Gly Val Ser Leu Gln Thr
                85                  90                  95

Tyr Asp Asp Leu Leu Ala Lys Asp Cys His Cys Ile
```

```
            100                 105


<210> SEQ ID NO 9
<211> LENGTH: 107
<212> TYPE: PRT
<213> ORGANISM: Artificial Sequence
<220> FEATURE:
<223> OTHER INFORMATION: GDF15 variant

<400> SEQUENCE: 9

His Cys Pro Leu Gly Pro Gly Arg Cys Cys Arg Leu His Thr Val Arg
1               5                   10                  15

Ala Ser Leu Glu Asp Leu Gly Trp Ala Asp Trp Val Leu Ser Pro Arg
            20                  25                  30

Glu Val Gln Val Thr Met Cys Ile Gly Ala Cys Pro Ser Gln Phe Arg
        35                  40                  45

Ala Ala Asn Met His Ala Gln Ile Lys Thr Ser Leu His Arg Leu Lys
    50                  55                  60

Pro Asp Thr Val Pro Ala Pro Cys Cys Val Pro Ala Ser Tyr Asn Pro
65                  70                  75                  80

Met Val Leu Ile Gln Lys Thr Asp Thr Gly Val Ser Leu Gln Thr Tyr
                85                  90                  95

Asp Asp Leu Leu Ala Lys Asp Cys His Cys Ile
            100                 105


<210> SEQ ID NO 10
<211> LENGTH: 106
<212> TYPE: PRT
<213> ORGANISM: Artificial Sequence
<220> FEATURE:
<223> OTHER INFORMATION: GDF15 variant

<400> SEQUENCE: 10

Cys Pro Leu Gly Pro Gly Arg Cys Cys Arg Leu His Thr Val Arg Ala
1               5                   10                  15

Ser Leu Glu Asp Leu Gly Trp Ala Asp Trp Val Leu Ser Pro Arg Glu
            20                  25                  30

Val Gln Val Thr Met Cys Ile Gly Ala Cys Pro Ser Gln Phe Arg Ala
        35                  40                  45

Ala Asn Met His Ala Gln Ile Lys Thr Ser Leu His Arg Leu Lys Pro
    50                  55                  60

Asp Thr Val Pro Ala Pro Cys Cys Val Pro Ala Ser Tyr Asn Pro Met
65                  70                  75                  80

Val Leu Ile Gln Lys Thr Asp Thr Gly Val Ser Leu Gln Thr Tyr Asp
                85                  90                  95

Asp Leu Leu Ala Lys Asp Cys His Cys Ile
            100                 105


<210> SEQ ID NO 11
<211> LENGTH: 98
<212> TYPE: PRT
<213> ORGANISM: Artificial Sequence
<220> FEATURE:
<223> OTHER INFORMATION: GDF15 variant

<400> SEQUENCE: 11

Cys Arg Leu His Thr Val Arg Ala Ser Leu Glu Asp Leu Gly Trp Ala
1               5                   10                  15

Asp Trp Val Leu Ser Pro Arg Glu Val Gln Val Thr Met Cys Ile Gly
            20                  25                  30
```

```
Ala Cys Pro Ser Gln Phe Arg Ala Ala Asn Met His Ala Gln Ile Lys
        35                  40                  45

Thr Ser Leu His Arg Leu Lys Pro Asp Thr Val Pro Ala Pro Cys Cys
    50                  55                  60

Val Pro Ala Ser Tyr Asn Pro Met Val Leu Ile Gln Lys Thr Asp Thr
65                  70                  75                  80

Gly Val Ser Leu Gln Thr Tyr Asp Asp Leu Leu Ala Lys Asp Cys His
                85                  90                  95

Cys Ile


<210> SEQ ID NO 12
<211> LENGTH: 42
<212> TYPE: PRT
<213> ORGANISM: Artificial sequence
<220> FEATURE:
<223> OTHER INFORMATION: Linker

<400> SEQUENCE: 12

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40


<210> SEQ ID NO 13
<211> LENGTH: 42
<212> TYPE: PRT
<213> ORGANISM: Artificial sequence
<220> FEATURE:
<223> OTHER INFORMATION: Linker

<400> SEQUENCE: 13

Gly Ala Gly Gly Gly Gly Ala Gly Gly Gly Gly Ala Gly Gly Gly Gly
1               5                   10                  15

Ala Gly Gly Gly Gly Ala Gly Gly Gly Gly Ala Gly Gly Gly Gly Ala
            20                  25                  30

Gly Gly Gly Gly Ala Gly Gly Gly Gly Ala
        35                  40


<210> SEQ ID NO 14
<211> LENGTH: 20
<212> TYPE: PRT
<213> ORGANISM: Artificial sequence
<220> FEATURE:
<223> OTHER INFORMATION: linker

<400> SEQUENCE: 14

Ala Pro Ala Pro Ala Pro Ala Pro Ala Pro Ala Pro Ala Pro Ala Pro
1               5                   10                  15

Ala Pro Ala Pro
            20


<210> SEQ ID NO 15
<211> LENGTH: 24
<212> TYPE: PRT
<213> ORGANISM: Artificial sequence
<220> FEATURE:
<223> OTHER INFORMATION: linker

<400> SEQUENCE: 15
```

```
Ala Pro Ala Pro Ala Pro Ala Pro Ala Pro Ala Pro Ala Pro Ala Pro
1               5                   10                  15

Ala Pro Ala Pro Ala Pro Ala Pro
            20


<210> SEQ ID NO 16
<211> LENGTH: 48
<212> TYPE: PRT
<213> ORGANISM: Artificial sequence
<220> FEATURE:
<223> OTHER INFORMATION: linker

<400> SEQUENCE: 16

Gly Gly Ser Glu Gly Lys Ser Ser Gly Ser Gly Ser Glu Ser Lys Ser
1               5                   10                  15

Thr Glu Gly Lys Ser Ser Gly Ser Gly Ser Glu Ser Lys Ser Thr Glu
            20                  25                  30

Gly Lys Ser Ser Gly Ser Gly Ser Glu Ser Lys Ser Thr Gly Gly Ser
        35                  40                  45


<210> SEQ ID NO 17
<211> LENGTH: 42
<212> TYPE: PRT
<213> ORGANISM: Artificial sequence
<220> FEATURE:
<223> OTHER INFORMATION: linker

<400> SEQUENCE: 17

Gly Ser Pro Gly Gly Gly Ser Pro Gly Gly Gly Ser Pro Gly Gly Gly
1               5                   10                  15

Ser Pro Gly Gly Gly Ser Pro Gly Gly Gly Ser Pro Gly Gly Gly Ser
            20                  25                  30

Pro Gly Gly Gly Ser Pro Gly Gly Gly Ser
        35                  40


<210> SEQ ID NO 18
<211> LENGTH: 42
<212> TYPE: PRT
<213> ORGANISM: Artificial sequence
<220> FEATURE:
<223> OTHER INFORMATION: linker

<400> SEQUENCE: 18

Gly Ser Ala Gly Gly Gly Ser Ala Gly Gly Gly Ser Ala Gly Gly Gly
1               5                   10                  15

Ser Ala Gly Gly Gly Ser Ala Gly Gly Gly Ser Ala Gly Gly Gly Ser
            20                  25                  30

Ala Gly Gly Gly Ser Ala Gly Gly Gly Ser
        35                  40


<210> SEQ ID NO 19
<211> LENGTH: 34
<212> TYPE: PRT
<213> ORGANISM: Artificial sequence
<220> FEATURE:
<223> OTHER INFORMATION: linker

<400> SEQUENCE: 19

Gly Gly Ser Glu Gly Lys Ser Ser Gly Ser Gly Ser Glu Ser Lys Ser
1               5                   10                  15

Thr Glu Gly Lys Ser Ser Gly Ser Gly Ser Glu Ser Lys Ser Thr Gly
            20                  25                  30
```

-continued

Gly Ser

<210> SEQ ID NO 20
<211> LENGTH: 14
<212> TYPE: PRT
<213> ORGANISM: Artificial sequence
<220> FEATURE:
<223> OTHER INFORMATION: linker

<400> SEQUENCE: 20

Ala Ser Gly Gly Gly Gly Ser Gly Gly Gly Gly Ser Gly Thr
1 5 10

<210> SEQ ID NO 21
<211> LENGTH: 44
<212> TYPE: PRT
<213> ORGANISM: Artificial sequence
<220> FEATURE:
<223> OTHER INFORMATION: linker

<400> SEQUENCE: 21

Ala Ser Gly Gly Gly Gly Ser Gly Gly Gly Gly Ser Gly Gly Gly Gly
1 5 10 15

Ser Gly Gly Gly Gly Ser Gly Gly Gly Gly Ser Gly Gly Gly Gly Ser
20 25 30

Gly Gly Gly Gly Ser Gly Gly Gly Gly Ser Gly Thr
35 40

<210> SEQ ID NO 22
<211> LENGTH: 14
<212> TYPE: PRT
<213> ORGANISM: Artificial sequence
<220> FEATURE:
<223> OTHER INFORMATION: linker

<400> SEQUENCE: 22

Ala Ser Ala Pro Ala Pro Ala Pro Ala Pro Ala Pro Gly Thr
1 5 10

<210> SEQ ID NO 23
<211> LENGTH: 24
<212> TYPE: PRT
<213> ORGANISM: Artificial sequence
<220> FEATURE:
<223> OTHER INFORMATION: linker

<400> SEQUENCE: 23

Ala Ser Ala Pro Ala Pro Ala Pro Ala Pro Ala Pro Ala Pro Ala Pro
1 5 10 15

Ala Pro Ala Pro Ala Pro Gly Thr
20

<210> SEQ ID NO 24
<211> LENGTH: 44
<212> TYPE: PRT
<213> ORGANISM: Artificial sequence
<220> FEATURE:
<223> OTHER INFORMATION: linker

<400> SEQUENCE: 24

Ala Ser Ala Pro Ala Pro Ala Pro Ala Pro Ala Pro Ala Pro Ala Pro
1 5 10 15

Ala Pro Ala Pro Ala Pro Ala Pro Ala Pro Ala Pro Ala Pro Ala Pro
20 25 30

```
Ala Pro Ala Pro Ala Pro Ala Pro Ala Pro Gly Thr
        35                  40


<210> SEQ ID NO 25
<211> LENGTH: 711
<212> TYPE: PRT
<213> ORGANISM: Artificial Sequence
<220> FEATURE:
<223> OTHER INFORMATION: fusion protein

<400> SEQUENCE: 25

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

```
Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Gly Gly Gly Gly Ser
            580                 585                 590

Gly Gly Gly Gly Ser Gly Thr Ala Arg Asn Gly Asp His Cys Pro Leu
        595                 600                 605

Gly Pro Gly Arg Cys Cys Arg Leu His Thr Val Arg Ala Ser Leu Glu
    610                 615                 620

Asp Leu Gly Trp Ala Asp Trp Val Leu Ser Pro Arg Glu Val Gln Val
625                 630                 635                 640

Thr Met Cys Ile Gly Ala Cys Pro Ser Gln Phe Arg Ala Ala Asn Met
                645                 650                 655

His Ala Gln Ile Lys Thr Ser Leu His Arg Leu Lys Pro Asp Thr Val
            660                 665                 670

Pro Ala Pro Cys Cys Val Pro Ala Ser Tyr Asn Pro Met Val Leu Ile
        675                 680                 685

Gln Lys Thr Asp Thr Gly Val Ser Leu Gln Thr Tyr Asp Asp Leu Leu
    690                 695                 700

Ala Lys Asp Cys His Cys Ile
705                 710
```

<210> SEQ ID NO 26
<211> LENGTH: 741
<212> TYPE: PRT
<213> ORGANISM: Artificial Sequence
<220> FEATURE:
<223> OTHER INFORMATION: fusion protein

<400> SEQUENCE: 26

-continued

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
```

```
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
    610                 615                 620

Gly Gly Ser Gly Thr Ala Arg Asn Gly Asp His Cys Pro Leu Gly Pro
625                 630                 635                 640

Gly Arg Cys Cys Arg Leu His Thr Val Arg Ala Ser Leu Glu Asp Leu
                645                 650                 655

Gly Trp Ala Asp Trp Val Leu Ser Pro Arg Glu Val Gln Val Thr Met
            660                 665                 670

Cys Ile Gly Ala Cys Pro Ser Gln Phe Arg Ala Ala Asn Met His Ala
        675                 680                 685

Gln Ile Lys Thr Ser Leu His Arg Leu Lys Pro Asp Thr Val Pro Ala
    690                 695                 700

Pro Cys Cys Val Pro Ala Ser Tyr Asn Pro Met Val Leu Ile Gln Lys
705                 710                 715                 720

Thr Asp Thr Gly Val Ser Leu Gln Thr Tyr Asp Asp Leu Leu Ala Lys
                725                 730                 735

Asp Cys His Cys Ile
            740


<210> SEQ ID NO 27
<211> LENGTH: 711
<212> TYPE: PRT
<213> ORGANISM: Artificial Sequence
<220> FEATURE:
<223> OTHER INFORMATION: fusion protein

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
```

-continued

```
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Ala Pro Ala Pro Ala
            580                 585                 590

Pro Ala Pro Ala Pro Gly Thr Ala Arg Asn Gly Asp His Cys Pro Leu
        595                 600                 605

Gly Pro Gly Arg Cys Cys Arg Leu His Thr Val Arg Ala Ser Leu Glu
    610                 615                 620

Asp Leu Gly Trp Ala Asp Trp Val Leu Ser Pro Arg Glu Val Gln Val
625                 630                 635                 640

Thr Met Cys Ile Gly Ala Cys Pro Ser Gln Phe Arg Ala Ala Asn Met
                645                 650                 655

His Ala Gln Ile Lys Thr Ser Leu His Arg Leu Lys Pro Asp Thr Val
            660                 665                 670

Pro Ala Pro Cys Cys Val Pro Ala Ser Tyr Asn Pro Met Val Leu Ile
        675                 680                 685

Gln Lys Thr Asp Thr Gly Val Ser Leu Gln Thr Tyr Asp Asp Leu Leu
    690                 695                 700

Ala Lys Asp Cys His Cys Ile
705                 710


<210> SEQ ID NO 28
<211> LENGTH: 721
<212> TYPE: PRT
<213> ORGANISM: Artificial Sequence
<220> FEATURE:
<223> OTHER INFORMATION: fusion protein

<400> SEQUENCE: 28

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

-continued

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525
```

```
Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Ala Pro Ala Pro Ala
            580                 585                 590

Pro Ala Pro Ala Pro Ala Pro Ala Pro Ala Pro Ala Pro Ala Pro Gly
        595                 600                 605

Thr Ala Arg Asn Gly Asp His Cys Pro Leu Gly Pro Gly Arg Cys Cys
    610                 615                 620

Arg Leu His Thr Val Arg Ala Ser Leu Glu Asp Leu Gly Trp Ala Asp
625                 630                 635                 640

Trp Val Leu Ser Pro Arg Glu Val Gln Val Thr Met Cys Ile Gly Ala
                645                 650                 655

Cys Pro Ser Gln Phe Arg Ala Ala Asn Met His Ala Gln Ile Lys Thr
            660                 665                 670

Ser Leu His Arg Leu Lys Pro Asp Thr Val Pro Ala Pro Cys Cys Val
        675                 680                 685

Pro Ala Ser Tyr Asn Pro Met Val Leu Ile Gln Lys Thr Asp Thr Gly
    690                 695                 700

Val Ser Leu Gln Thr Tyr Asp Asp Leu Leu Ala Lys Asp Cys His Cys
705                 710                 715                 720

Ile


<210> SEQ ID NO 29
<211> LENGTH: 741
<212> TYPE: PRT
<213> ORGANISM: Artificial Sequence
<220> FEATURE:
<223> OTHER INFORMATION: fusion protein

<400> SEQUENCE: 29

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

-continued

```
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Ala Pro Ala Pro Ala
            580                 585                 590
```

Pro Ala Pro Ala Pro Ala Pro Ala Pro Ala Pro Ala Pro Ala Pro Ala
595 600 605

Pro Ala Pro Ala Pro Ala Pro Ala Pro Ala Pro Ala Pro Ala Pro Ala
610 615 620

Pro Ala Pro Gly Thr Ala Arg Asn Gly Asp His Cys Pro Leu Gly Pro
625 630 635 640

Gly Arg Cys Cys Arg Leu His Thr Val Arg Ala Ser Leu Glu Asp Leu
645 650 655

Gly Trp Ala Asp Trp Val Leu Ser Pro Arg Glu Val Gln Val Thr Met
660 665 670

Cys Ile Gly Ala Cys Pro Ser Gln Phe Arg Ala Ala Asn Met His Ala
675 680 685

Gln Ile Lys Thr Ser Leu His Arg Leu Lys Pro Asp Thr Val Pro Ala
690 695 700

Pro Cys Cys Val Pro Ala Ser Tyr Asn Pro Met Val Leu Ile Gln Lys
705 710 715 720

Thr Asp Thr Gly Val Ser Leu Gln Thr Tyr Asp Asp Leu Leu Ala Lys
725 730 735

Asp Cys His Cys Ile
740

<210> SEQ ID NO 30
<211> LENGTH: 721
<212> TYPE: PRT
<213> ORGANISM: Artificial Sequence
<220> FEATURE:
<223> OTHER INFORMATION: fusion protein

<400> SEQUENCE: 30

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

-continued

```
Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Glu Ala Ala Ala Lys
            580                 585                 590

Glu Ala Ala Ala Lys Glu Ala Ala Ala Lys Glu Ala Ala Ala Lys Gly
        595                 600                 605

Thr Ala Arg Asn Gly Asp His Cys Pro Leu Gly Pro Gly Arg Cys Cys
    610                 615                 620
```

```
Arg Leu His Thr Val Arg Ala Ser Leu Glu Asp Leu Gly Trp Ala Asp
625                 630                 635                 640

Trp Val Leu Ser Pro Arg Glu Val Gln Val Thr Met Cys Ile Gly Ala
                645                 650                 655

Cys Pro Ser Gln Phe Arg Ala Ala Asn Met His Ala Gln Ile Lys Thr
            660                 665                 670

Ser Leu His Arg Leu Lys Pro Asp Thr Val Pro Ala Pro Cys Cys Val
        675                 680                 685

Pro Ala Ser Tyr Asn Pro Met Val Leu Ile Gln Lys Thr Asp Thr Gly
    690                 695                 700

Val Ser Leu Gln Thr Tyr Asp Asp Leu Leu Ala Lys Asp Cys His Cys
705                 710                 715                 720

Ile


<210> SEQ ID NO 31
<211> LENGTH: 741
<212> TYPE: PRT
<213> ORGANISM: Artificial Sequence
<220> FEATURE:
<223> OTHER INFORMATION: fusion protein

<400> SEQUENCE: 31

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
```

-continued

```
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ser Glu Ala Ala Ala Lys
            580                 585                 590

Glu Ala Ala Ala Lys Glu Ala Ala Ala Lys Glu Ala Ala Ala Lys Glu
        595                 600                 605

Ala Ala Ala Lys Glu Ala Ala Ala Lys Glu Ala Ala Ala Lys Glu Ala
    610                 615                 620

Ala Ala Lys Gly Thr Ala Arg Asn Gly Asp His Cys Pro Leu Gly Pro
625                 630                 635                 640

Gly Arg Cys Cys Arg Leu His Thr Val Arg Ala Ser Leu Glu Asp Leu
                645                 650                 655

Gly Trp Ala Asp Trp Val Leu Ser Pro Arg Glu Val Gln Val Thr Met
            660                 665                 670

Cys Ile Gly Ala Cys Pro Ser Gln Phe Arg Ala Ala Asn Met His Ala
        675                 680                 685
```

Gln Ile Lys Thr Ser Leu His Arg Leu Lys Pro Asp Thr Val Pro Ala
    690                 695                 700

Pro Cys Cys Val Pro Ala Ser Tyr Asn Pro Met Val Leu Ile Gln Lys
705                 710                 715                 720

Thr Asp Thr Gly Val Ser Leu Gln Thr Tyr Asp Asp Leu Leu Ala Lys
                725                 730                 735

Asp Cys His Cys Ile
            740

<210> SEQ ID NO 32
<211> LENGTH: 24
<212> TYPE: PRT
<213> ORGANISM: Artificial sequence
<220> FEATURE:
<223> OTHER INFORMATION: linker

<400> SEQUENCE: 32

Ala Ser Glu Ala Ala Ala Lys Glu Ala Ala Ala Lys Glu Ala Ala Ala
1               5                   10                  15

Lys Glu Ala Ala Ala Lys Gly Thr
            20

<210> SEQ ID NO 33
<211> LENGTH: 44
<212> TYPE: PRT
<213> ORGANISM: Artificial sequence
<220> FEATURE:
<223> OTHER INFORMATION: linker

<400> SEQUENCE: 33

Ala Ser Glu Ala Ala Ala Lys Glu Ala Ala Ala Lys Glu Ala Ala Ala
1               5                   10                  15

Lys Glu Ala Ala Ala Lys Glu Ala Ala Ala Lys Glu Ala Ala Ala Lys
            20                  25                  30

Glu Ala Ala Ala Lys Glu Ala Ala Ala Lys Gly Thr
        35                  40

<210> SEQ ID NO 34
<211> LENGTH: 10
<212> TYPE: PRT
<213> ORGANISM: Artificial sequence
<220> FEATURE:
<223> OTHER INFORMATION: linker

<400> SEQUENCE: 34

Gly Gly Gly Gly Ser Gly Gly Gly Gly Ser
1               5                   10

<210> SEQ ID NO 35
<211> LENGTH: 15
<212> TYPE: PRT
<213> ORGANISM: Artificial sequence
<220> FEATURE:
<223> OTHER INFORMATION: linker

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 706
<212> TYPE: PRT
<213> ORGANISM: Artificial Sequence -continued

```
<220> FEATURE:
<223> OTHER INFORMATION: fusion protein

<400> SEQUENCE: 36

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Cys
        595                 600                 605

Ser Arg Leu His Thr Val Arg Ala Ser Leu Glu Asp Leu Gly Trp Ala
    610                 615                 620

Asp Trp Val Leu Ser Pro Arg Glu Val Gln Val Thr Met Cys Ile Gly
625                 630                 635                 640

Ala Cys Pro Ser Gln Phe Arg Ala Ala Asn Met His Ala Gln Ile Lys
                645                 650                 655

Thr Ser Leu His Arg Leu Lys Pro Asp Thr Val Pro Ala Pro Cys Cys
            660                 665                 670

Val Pro Ala Ser Tyr Asn Pro Met Val Leu Ile Gln Lys Thr Asp Thr
        675                 680                 685

Gly Val Ser Leu Gln Thr Tyr Asp Asp Leu Leu Ala Lys Asp Cys His
    690                 695                 700

Cys Ile
705


<210> SEQ ID NO 37
<211> LENGTH: 705
<212> TYPE: PRT
<213> ORGANISM: Artificial Sequence
<220> FEATURE:
<223> OTHER INFORMATION: fusion protein

<400> SEQUENCE: 37

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45
```

-continued

```
Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Cys
        595                 600                 605

Arg Leu His Thr Val Arg Ala Ser Leu Glu Asp Leu Gly Trp Ala Asp
    610                 615                 620

Trp Val Leu Ser Pro Arg Glu Val Gln Val Thr Met Cys Ile Gly Ala
625                 630                 635                 640

Cys Pro Ser Gln Phe Arg Ala Ala Asn Met His Ala Gln Ile Lys Thr
                645                 650                 655

Ser Leu His Arg Leu Lys Pro Asp Thr Val Pro Ala Pro Cys Cys Val
            660                 665                 670

Pro Ala Ser Tyr Asn Pro Met Val Leu Ile Gln Lys Thr Asp Thr Gly
        675                 680                 685

Val Ser Leu Gln Thr Tyr Asp Asp Leu Leu Ala Lys Asp Cys His Cys
    690                 695                 700

Ile
705


<210> SEQ ID NO 38
<211> LENGTH: 20
<212> TYPE: PRT
<213> ORGANISM: Artificial sequence
<220> FEATURE:
<223> OTHER INFORMATION: linker

<400> SEQUENCE: 38

Gly Gly Gly Gly Ser Gly Gly Gly Gly Ser Gly Gly Gly Gly Ser Gly
1               5                   10                  15

Gly Gly Gly Ser
            20


<210> SEQ ID NO 39
<211> LENGTH: 25
<212> TYPE: PRT
<213> ORGANISM: Artificial sequence
<220> FEATURE:
<223> OTHER INFORMATION: linker

<400> SEQUENCE: 39

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 40
<211> LENGTH: 719
<212> TYPE: PRT
<213> ORGANISM: Artificial Sequence
<220> FEATURE:
<223> OTHER INFORMATION: fusion protein

<400> SEQUENCE: 40

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365
```

```
Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 41
<211> LENGTH: 30
<212> TYPE: PRT
<213> ORGANISM: Artificial sequence
<220> FEATURE:
<223> OTHER INFORMATION: linker

<400> SEQUENCE: 41

Gly Gly Gly Gly Ser Gly Gly Gly Gly Ser Gly Gly Gly Gly Ser Gly
1               5                   10                  15
```

-continued

```
Gly Gly Gly Ser Gly Gly Gly Gly Ser Gly Gly Gly Gly Ser
            20                  25                  30


<210> SEQ ID NO 42
<211> LENGTH: 35
<212> TYPE: PRT
<213> ORGANISM: Artificial sequence
<220> FEATURE:
<223> OTHER INFORMATION: linker

<400> SEQUENCE: 42

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35


<210> SEQ ID NO 43
<211> LENGTH: 40
<212> TYPE: PRT
<213> ORGANISM: Artificial sequence
<220> FEATURE:
<223> OTHER INFORMATION: linker

<400> SEQUENCE: 43

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 44
<211> LENGTH: 45
<212> TYPE: PRT
<213> ORGANISM: Artificial sequence
<220> FEATURE:
<223> OTHER INFORMATION: linker

<400> SEQUENCE: 44

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45


<210> SEQ ID NO 45
<211> LENGTH: 50
<212> TYPE: PRT
<213> ORGANISM: Artificial sequence
<220> FEATURE:
<223> OTHER INFORMATION: linker

<400> SEQUENCE: 45

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45
```

```
Gly Ser
    50


<210> SEQ ID NO 46
<211> LENGTH: 55
<212> TYPE: PRT
<213> ORGANISM: Artificial sequence
<220> FEATURE:
<223> OTHER INFORMATION: linker

<400> SEQUENCE: 46

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55


<210> SEQ ID NO 47
<211> LENGTH: 60
<212> TYPE: PRT
<213> ORGANISM: Artificial sequence
<220> FEATURE:
<223> OTHER INFORMATION: linker

<400> SEQUENCE: 47

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60


<210> SEQ ID NO 48
<211> LENGTH: 719
<212> TYPE: PRT
<213> ORGANISM: Artificial Sequence
<220> FEATURE:
<223> OTHER INFORMATION: fusion protein

<400> SEQUENCE: 48

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

-continued

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
```

-continued 530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu Gly Ser Gly Gly Gly Gly Ser
580 585 590

Gly Gly Gly Gly Ser Gly Gly Gly Gly Ser Gly Gly Gly Gly Ser Ala
595 600 605

Arg Asn Gly Asp His Cys Pro Leu Gly Pro Gly Arg Cys Cys Arg Leu
610 615 620

His Thr Val Arg Ala Ser Leu Glu Asp Leu Gly Trp Ala Asp Trp Val
625 630 635 640

Leu Ser Pro Arg Glu Val Gln Val Thr Met Cys Ile Gly Ala Cys Pro
645 650 655

Ser Gln Phe Arg Ala Ala Asn Met His Ala Gln Ile Lys Thr Ser Leu
660 665 670

His Arg Leu Lys Pro Asp Thr Val Pro Ala Pro Cys Cys Val Pro Ala
675 680 685

Ser Tyr Asn Pro Met Val Leu Ile Gln Lys Thr Asp Thr Gly Val Ser
690 695 700

Leu Gln Thr Tyr Asp Asp Leu Leu Ala Lys Asp Cys His Cys Ile
705 710 715

<210> SEQ ID NO 49
<211> LENGTH: 65
<212> TYPE: PRT
<213> ORGANISM: Artificial sequence
<220> FEATURE:
<223> OTHER INFORMATION: linker

<400> SEQUENCE: 49

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

Ser
65

<210> SEQ ID NO 50
<211> LENGTH: 70
<212> TYPE: PRT
<213> ORGANISM: Artificial sequence
<220> FEATURE:
<223> OTHER INFORMATION: linker

<400> SEQUENCE: 50

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

```
Gly Ser Gly Gly Gly Gly Ser Gly Gly Gly Gly Ser Gly Gly Gly Gly
    50                  55                  60

Ser Gly Gly Gly Gly Ser
65                  70
```

<210> SEQ ID NO 51
<211> LENGTH: 75
<212> TYPE: PRT
<213> ORGANISM: Artificial sequence
<220> FEATURE:
<223> OTHER INFORMATION: linker

<400> SEQUENCE: 51

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser
65                  70                  75
```

<210> SEQ ID NO 52
<211> LENGTH: 80
<212> TYPE: PRT
<213> ORGANISM: Artificial sequence
<220> FEATURE:
<223> OTHER INFORMATION: linker

<400> SEQUENCE: 52

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80
```

<210> SEQ ID NO 53
<211> LENGTH: 85
<212> TYPE: PRT
<213> ORGANISM: Artificial sequence
<220> FEATURE:
<223> OTHER INFORMATION: linker

<400> SEQUENCE: 53

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
```

```
65                  70                  75                  80

Gly Gly Gly Gly Ser
                85


<210> SEQ ID NO 54
<211> LENGTH: 90
<212> TYPE: PRT
<213> ORGANISM: Artificial sequence
<220> FEATURE:
<223> OTHER INFORMATION: linker

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90


<210> SEQ ID NO 55
<211> LENGTH: 739
<212> TYPE: PRT
<213> ORGANISM: Artificial Sequence
<220> FEATURE:
<223> OTHER INFORMATION: fusion protein

<400> SEQUENCE: 55

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

-continued

```
Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
```

```
    610                 615                 620

Gly Gly Ser Ala Arg Asn Gly Asp His Cys Pro Leu Gly Pro Gly Arg
625                 630                 635                 640

Cys Cys Arg Leu His Thr Val Arg Ala Ser Leu Glu Asp Leu Gly Trp
                645                 650                 655

Ala Asp Trp Val Leu Ser Pro Arg Glu Val Gln Val Thr Met Cys Ile
            660                 665                 670

Gly Ala Cys Pro Ser Gln Phe Arg Ala Ala Asn Met His Ala Gln Ile
        675                 680                 685

Lys Thr Ser Leu His Arg Leu Lys Pro Asp Thr Val Pro Ala Pro Cys
    690                 695                 700

Cys Val Pro Ala Ser Tyr Asn Pro Met Val Leu Ile Gln Lys Thr Asp
705                 710                 715                 720

Thr Gly Val Ser Leu Gln Thr Tyr Asp Asp Leu Leu Ala Lys Asp Cys
                725                 730                 735

His Cys Ile
```

<210> SEQ ID NO 56
<211> LENGTH: 717
<212> TYPE: PRT
<213> ORGANISM: Artificial Sequence
<220> FEATURE:
<223> OTHER INFORMATION: fusion protein

<400> SEQUENCE: 56

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Ala Arg Asn
        595                 600                 605

Gly Asp His Cys Pro Leu Gly Pro Gly Arg Cys Cys Arg Leu His Thr
    610                 615                 620

Val Arg Ala Ser Leu Glu Asp Leu Gly Trp Ala Asp Trp Val Leu Ser
625                 630                 635                 640

Pro Arg Glu Val Gln Val Thr Met Cys Ile Gly Ala Cys Pro Ser Gln
                645                 650                 655
```

```
Phe Arg Ala Ala Asn Met His Ala Gln Ile Lys Thr Ser Leu His Arg
            660                 665                 670

Leu Lys Pro Asp Thr Val Pro Ala Pro Cys Cys Val Pro Ala Ser Tyr
        675                 680                 685

Asn Pro Met Val Leu Ile Gln Lys Thr Asp Thr Gly Val Ser Leu Gln
    690                 695                 700

Thr Tyr Asp Asp Leu Leu Ala Lys Asp Cys His Cys Ile
705                 710                 715


<210> SEQ ID NO 57
<211> LENGTH: 719
<212> TYPE: PRT
<213> ORGANISM: Artificial Sequence
<220> FEATURE:
<223> OTHER INFORMATION: fusion protein

<400> SEQUENCE: 57

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

-continued

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715
```

<210> SEQ ID NO 58
<211> LENGTH: 719
<212> TYPE: PRT
<213> ORGANISM: Artificial Sequence
<220> FEATURE:
<223> OTHER INFORMATION: fusion protein

<400> SEQUENCE: 58

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
```

370 375 380

Gln Asn Leu Ile Lys Gln Asn Cys Glu Leu Phe Glu Gln Leu Gly Glu
385 390 395 400

Tyr Lys Phe Gln Asn Ala Leu Leu Val Arg Tyr Thr Lys Lys Val Pro
405 410 415

Gln Val Ser Thr Pro Thr Leu Val Glu Val Ser Arg Asn Leu Gly Lys
420 425 430

Val Gly Ser Lys Cys Cys Lys His Pro Glu Ala Lys Arg Met Pro Cys
435 440 445

Ala Glu Asp Tyr Leu Ser Val Val Leu Asn Gln Leu Cys Val Leu His
450 455 460

Glu Lys Thr Pro Val Ser Asp Arg Val Thr Lys Cys Cys Thr Glu Ser
465 470 475 480

Leu Val Asn Arg Arg Pro Cys Phe Ser Ala Leu Glu Val Asp Glu Thr
485 490 495

Tyr Val Pro Lys Glu Phe Asn Ala Glu Thr Phe Thr Phe His Ala Asp
500 505 510

Ile Cys Thr Leu Ser Glu Lys Glu Arg Gln Ile Lys Lys Gln Thr Ala
515 520 525

Leu Val Glu Leu Val Lys His Lys Pro Lys Ala Thr Lys Glu Gln Leu
530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu Gly Ser Gly Gly Gly Gly Ser
580 585 590

Gly Gly Gly Gly Ser Gly Gly Gly Gly Ser Gly Gly Gly Gly Ser Ala
595 600 605

Arg Asn Gly Asp His Cys Pro Leu Gly Pro Gly Arg Cys Cys Arg Leu
610 615 620

His Thr Val Arg Ala Ser Leu Glu Asp Leu Gly Trp Ala Asp Trp Val
625 630 635 640

Leu Ser Pro Arg Glu Val Gln Val Thr Met Cys Ile Gly Ala Cys Pro
645 650 655

Ser Gln Phe Arg Ala Ala Asn Met His Ala Gln Ile Lys Thr Ser Leu
660 665 670

His Arg Leu Lys Pro Asp Thr Val Pro Ala Pro Cys Cys Val Pro Ala
675 680 685

Ser Tyr Asn Pro Met Val Leu Ile Gln Lys Thr Asp Thr Gly Val Ser
690 695 700

Leu Gln Thr Tyr Asp Asp Leu Leu Ala Lys Asp Cys His Cys Ile
705 710 715

<210> SEQ ID NO 59
<211> LENGTH: 717
<212> TYPE: PRT
<213> ORGANISM: Artificial Sequence
<220> FEATURE:
<223> OTHER INFORMATION: fusion protein

<400> SEQUENCE: 59

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln

-continued

```
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
```

```
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Ala Arg Asn
        595                 600                 605

Gly Asp His Cys Pro Leu Gly Pro Gly Arg Cys Cys Arg Leu His Thr
    610                 615                 620

Val Arg Ala Ser Leu Glu Asp Leu Gly Trp Ala Asp Trp Val Leu Ser
625                 630                 635                 640

Pro Arg Glu Val Gln Val Thr Met Cys Ile Gly Ala Cys Pro Ser Gln
                645                 650                 655

Phe Arg Ala Ala Asn Met His Ala Gln Ile Lys Thr Ser Leu His Arg
            660                 665                 670

Leu Lys Pro Asp Thr Val Pro Ala Pro Cys Cys Val Pro Ala Ser Tyr
        675                 680                 685

Asn Pro Met Val Leu Ile Gln Lys Thr Asp Thr Gly Val Ser Leu Gln
    690                 695                 700

Thr Tyr Asp Asp Leu Leu Ala Lys Asp Cys His Cys Ile
705                 710                 715


<210> SEQ ID NO 60
<211> LENGTH: 739
<212> TYPE: PRT
<213> ORGANISM: Artificial Sequence
<220> FEATURE:
<223> OTHER INFORMATION: fusion protein

<400> SEQUENCE: 60

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

Ile Cys Thr Leu Ser Glu Lys Glu Arg Gln Ile Lys Lys Gln Thr Ala
515 520 525

Leu Val Glu Leu Val Lys His Lys Pro Lys Ala Thr Lys Glu Gln Leu
530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu Gly Ser Gly Gly Gly Gly Ser
580 585 590

Gly Gly Gly Gly Ser Gly Gly Gly Gly Ser Gly Gly Gly Gly Ser Gly
595 600 605

Gly Gly Gly Ser Gly Gly Gly Gly Ser Gly Gly Gly Gly Ser Gly Gly
610 615 620

Gly Gly Ser Ala Arg Asn Gly Asp His Cys Pro Leu Gly Pro Gly Arg
625 630 635 640

Cys Cys Arg Leu His Thr Val Arg Ala Ser Leu Glu Asp Leu Gly Trp
645 650 655

Ala Asp Trp Val Leu Ser Pro Arg Glu Val Gln Val Thr Met Cys Ile
660 665 670

Gly Ala Cys Pro Ser Gln Phe Arg Ala Ala Asn Met His Ala Gln Ile
675 680 685

Lys Thr Ser Leu His Arg Leu Lys Pro Asp Thr Val Pro Ala Pro Cys
690 695 700

Cys Val Pro Ala Ser Tyr Asn Pro Met Val Leu Ile Gln Lys Thr Asp
705 710 715 720

Thr Gly Val Ser Leu Gln Thr Tyr Asp Asp Leu Leu Ala Lys Asp Cys
725 730 735

His Cys Ile

<210> SEQ ID NO 61
<211> LENGTH: 95
<212> TYPE: PRT
<213> ORGANISM: Artificial sequence
<220> FEATURE:
<223> OTHER INFORMATION: linker

<400> SEQUENCE: 61

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

Ser Gly Gly Gly Gly Ser Gly Gly Gly Gly Ser Gly Gly Gly Gly Ser
65 70 75 80

Gly Gly Gly Gly Ser Gly Gly Gly Gly Ser Gly Gly Gly Gly Ser
85 90 95

<210> SEQ ID NO 62
<211> LENGTH: 100
<212> TYPE: PRT
<213> ORGANISM: Artificial sequence
<220> FEATURE:
<223> OTHER INFORMATION: linker

<400> SEQUENCE: 62

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100
```

<210> SEQ ID NO 63
<211> LENGTH: 10
<212> TYPE: PRT
<213> ORGANISM: Artificial sequence
<220> FEATURE:
<223> OTHER INFORMATION: linker

<400> SEQUENCE: 63

```
Glu Ala Ala Ala Lys Glu Ala Ala Ala Lys
1               5                   10
```

<210> SEQ ID NO 64
<211> LENGTH: 719
<212> TYPE: PRT
<213> ORGANISM: Artificial Sequence
<220> FEATURE:
<223> OTHER INFORMATION: fusion protein

<400> SEQUENCE: 64

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590
```

```
Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Arg Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 65
<211> LENGTH: 719
<212> TYPE: PRT
<213> ORGANISM: Artificial Sequence
<220> FEATURE:
<223> OTHER INFORMATION: fusion protein

<400> SEQUENCE: 65

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
```

```
            660                 665                 670

His Arg Leu Lys Pro Asp Thr Val Pro Ala Pro Cys Cys Val Pro Ala
        675                 680                 685

Ser Tyr Asn Pro Met Val Leu Trp Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 66
<211> LENGTH: 719
<212> TYPE: PRT
<213> ORGANISM: Artificial Sequence
<220> FEATURE:
<223> OTHER INFORMATION: fusion protein

<400> SEQUENCE: 66

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
```

-continued

```
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Ala Ala Pro Ala Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715
```

<210> SEQ ID NO 67

<211> LENGTH: 719
<212> TYPE: PRT
<213> ORGANISM: Artificial Sequence
<220> FEATURE:
<223> OTHER INFORMATION: fusion protein

<400> SEQUENCE: 67

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380
```

Gln Asn Leu Ile Lys Gln Asn Cys Glu Leu Phe Glu Gln Leu Gly Glu
385 390 395 400

Tyr Lys Phe Gln Asn Ala Leu Leu Val Arg Tyr Thr Lys Lys Val Pro
405 410 415

Gln Val Ser Thr Pro Thr Leu Val Glu Val Ser Arg Asn Leu Gly Lys
420 425 430

Val Gly Ser Lys Cys Cys Lys His Pro Glu Ala Lys Arg Met Pro Cys
435 440 445

Ala Glu Asp Tyr Leu Ser Val Val Leu Asn Gln Leu Cys Val Leu His
450 455 460

Glu Lys Thr Pro Val Ser Asp Arg Val Thr Lys Cys Cys Thr Glu Ser
465 470 475 480

Leu Val Asn Arg Arg Pro Cys Phe Ser Ala Leu Glu Val Asp Glu Thr
485 490 495

Tyr Val Pro Lys Glu Phe Asn Ala Glu Thr Phe Thr Phe His Ala Asp
500 505 510

Ile Cys Thr Leu Ser Glu Lys Glu Arg Gln Ile Lys Lys Gln Thr Ala
515 520 525

Leu Val Glu Leu Val Lys His Lys Pro Lys Ala Thr Lys Glu Gln Leu
530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu Gly Ser Gly Gly Gly Gly Ser
580 585 590

Gly Gly Gly Gly Ser Gly Gly Gly Gly Ser Gly Gly Gly Gly Ser Ala
595 600 605

Arg Asn Gly Asp His Cys Pro Leu Gly Pro Gly Arg Cys Cys Arg Leu
610 615 620

His Thr Val Arg Ala Ser Leu Glu Asp Leu Gly Trp Ala Asp Trp Val
625 630 635 640

Leu Ser Pro Arg Glu Val Gln Val Thr Met Cys Ile Gly Ala Cys Pro
645 650 655

Ser Gln Phe Arg Ala Ala Asn Met His Ala Gln Ile Lys Thr Ser Leu
660 665 670

His Arg Leu Lys Pro Asp Thr Val Pro Ala Pro Cys Cys Val Pro Ala
675 680 685

Ser Tyr Asn Pro Met Ala Leu Ala Gln Lys Thr Asp Thr Gly Val Ser
690 695 700

Ala Gln Thr Tyr Asp Asp Leu Leu Ala Lys Asp Cys His Cys Ile
705 710 715

<210> SEQ ID NO 68
<211> LENGTH: 719
<212> TYPE: PRT
<213> ORGANISM: Artificial Sequence
<220> FEATURE:
<223> OTHER INFORMATION: fusion protein

<400> SEQUENCE: 68

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

```
Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
```

```
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Ala Ala Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ala Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 69
<211> LENGTH: 719
<212> TYPE: PRT
<213> ORGANISM: Artificial Sequence
<220> FEATURE:
<223> OTHER INFORMATION: fusion protein

<400> SEQUENCE: 69

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
```

```
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Ala Leu Ala Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 70
<211> LENGTH: 719
<212> TYPE: PRT
<213> ORGANISM: Artificial Sequence
<220> FEATURE:
<223> OTHER INFORMATION: fusion protein

<400> SEQUENCE: 70

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

-continued

```
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590
```

```
Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Trp Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 71
<211> LENGTH: 719
<212> TYPE: PRT
<213> ORGANISM: Artificial Sequence
<220> FEATURE:
<223> OTHER INFORMATION: fusion protein

<400> SEQUENCE: 71

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Ala Val
625                 630                 635                 640

Leu Ser Pro Arg Glu Val Gln Val Thr Met Cys Ile Gly Ala Cys Pro
                645                 650                 655
```

```
Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 72
<211> LENGTH: 719
<212> TYPE: PRT
<213> ORGANISM: Artificial Sequence
<220> FEATURE:
<223> OTHER INFORMATION: fusion protein

<400> SEQUENCE: 72

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

-continued

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Ala Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715
```

<210> SEQ ID NO 73
<211> LENGTH: 719
<212> TYPE: PRT
<213> ORGANISM: Artificial Sequence
<220> FEATURE:
<223> OTHER INFORMATION: fusion protein

<400> SEQUENCE: 73

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
```

```
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Trp Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Ala Ile Lys Thr Ala Leu
            660                 665                 670

His Ala Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 74
<211> LENGTH: 719
<212> TYPE: PRT
<213> ORGANISM: Artificial Sequence
<220> FEATURE:
<223> OTHER INFORMATION: fusion protein

<400> SEQUENCE: 74

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
```

```
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Ala Ala Asp Trp Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Ala Ala Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 75
<211> LENGTH: 719
<212> TYPE: PRT
<213> ORGANISM: Artificial Sequence
<220> FEATURE:
<223> OTHER INFORMATION: fusion protein

<400> SEQUENCE: 75

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Ala
        595                 600                 605

Arg Asn Gly Asp His Cys Pro Leu Gly Pro Gly Arg Cys Cys Arg Leu
    610                 615                 620

His Thr Val Arg Ala Ser Leu Glu Asp Leu Gly Ala Ala Asp Ala Val
625                 630                 635                 640

Leu Ser Pro Arg Glu Val Gln Val Thr Met Cys Ile Gly Ala Cys Pro
                645                 650                 655

Ser Gln Phe Arg Ala Ala Asn Met His Ala Gln Ile Lys Thr Ser Leu
            660                 665                 670

His Arg Leu Lys Pro Asp Thr Val Pro Ala Pro Cys Cys Val Pro Ala
        675                 680                 685

Ser Tyr Asn Pro Met Val Leu Ile Gln Lys Thr Asp Thr Gly Val Ser
    690                 695                 700

Leu Gln Thr Tyr Asp Asp Leu Leu Ala Lys Asp Cys His Cys Ile
705                 710                 715


<210> SEQ ID NO 76
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 76

gacgcccaca agagcgaggt ggcccaccgg ttcaaggacc tgggcgagga gaacttcaag      60

gccctggtgc tgatcgcctt cgcccagtac ctgcagcagt cccccttcga ggaccacgtg     120

aagctggtga acgaggtgac cgagttcgcc aagacctgcg tggccgacga gagcgccgag     180

aactgcgaca agagcctgca caccctgttc ggcgacaagc tgtgcaccgt ggccaccctg     240

cgggagacct acggcgagat ggccgactgc tgcgccaagc aggagcccga gcggaacgag     300

tgcttcctgc agcacaagga cgacaacccc aacctgcccc ggctggtgcg gcccgaggtg     360

gacgtgatgt gcaccgcctt ccacgacaac gaggagacct tcctgaagaa gtacctgtac     420

gagatcgccc ggcggcaccc ctacttctac gccccccgagc tgctgttctt cgccaagcgg     480

tacaaggccg ccttcaccga gtgctgccag gccgccgaca aggccgcctg cctgctgccc     540

aagctggacg agctgcggga cgagggcaag gccagcagcg ccaagcagcg gctgaagtgc     600

gccagcctgc agaagttcgg cgagcgggcc ttcaaggcct gggccgtggc ccggctgagc     660

cagcggttcc ccaaggccga gttcgccgag gtgagcaagc tggtgaccga cctgaccaag     720

gtgcacaccg agtgctgcca cggcgacctg ctggagtgcg ccgacgaccg ggccgacctg     780

gccaagtaca tctgcgagaa ccaggacagc atcagcagca agctgaagga gtgctgcgag     840

aagcccctgc tggagaagag ccactgcatc gccgaggtgg agaacgacga gatgcccgcc     900
```

```
gacctgccca gcctggccgc cgacttcgtg gagagcaagg acgtgtgcaa gaactacgcc    960
gaggccaagg acgtgttcct gggcatgttc ctgtacgagt acgcccggcg gcaccccgac   1020
tacagcgtgg tgctgctgct gcggctggcc aagacctacg agaccaccct ggagaagtgc   1080
tgcgccgccg ccgaccccca cgagtgctac gccaaggtgt tcgacgagtt caagcccctg   1140
gtggaggagc cccagaacct gatcaagcag aactgcgagc tgttcgagca gctgggcgag   1200
tacaagttcc agaacgccct gctggtgcgg tacaccaaga aggtgcccca ggtgagcacc   1260
cccaccctgg tggaggtgag ccggaacctg ggcaaggtgg gcagcaagtg ctgcaagcac   1320
cccgaggcca agcggatgcc ctgcgccgag gactacctga gcgtggtgct gaaccagctg   1380
tgcgtgctgc acgagaagac ccccgtgagc gaccgggtga ccaagtgctg caccgagagc   1440
ctggtgaacc ggcggccctg cttcagcgcc ctggaggtgg acgagaccta cgtgcccaag   1500
gagttcaacg ccgagacctt caccttccac gccgacatct gcaccctgag cgagaaggag   1560
cggcagatca agaagcagac cgccctggtg gagctggtga agcacaagcc caaggccacc   1620
aaggagcagc tgaaggccgt gatggacgac ttcgccgcct tcgtggagaa gtgctgcaag   1680
gccgacgaca aggagacctg cttcgccgag gagggcaaga agctggtggc cgccagccag   1740
gccgccctgg gcctgggcag cggcggcggc ggcagcggcg gcggcggatc tggtggaggt   1800
ggcagtggag gaggggggatc cgctcgcaac ggtgaccact gccctctggg tcctggtcgc   1860
tgctgccgcc tgcacaccgt tcgcgcttct ctggaagacc tgggttgggc tgactgggtt   1920
ctgtctcctc gcgaagttca ggttaccatg tgcatcggtg cttgcccttc tcagttccgc   1980
gctgctaaca tgcacgctca gatcaaaacc tctctgcacc gcctgaaacc tgacaccgtt   2040
cctgctcctt gctgcgttcc tgcttcttac aaccctatgg ttctgatcca gaaaaccgac   2100
accggtgttt ctctgcagac ctacgacgac ctgctggcta aagactgcca ctgcatc      2157
```

```
<210> SEQ ID NO 77
<211> LENGTH: 2133
<212> TYPE: DNA
<213> ORGANISM: Artificial Sequence
<220> FEATURE:
<223> OTHER INFORMATION: fusion protein coding sequence

<400> SEQUENCE: 77

gatgctcata agtccgaagt cgcccacaga ttcaaggacc tcggagaaga aaattttaag     60
gccctcgtgc ttatcgcctt cgcccaatac ctccagcagt ccccgttcga ggaccacgtg    120
aagctcgtga acgaagtgac cgagtttgcc aagacttgtg tggcggatga atccgccgag    180
aactgcgaca agagcctcca cacgctgttc ggcgacaagc tgtgcaccgt cgccacgctg    240
agagaaactt acggagagat ggccgactgc tgcgcaaagc aggagccgga acggaacgaa    300
tgcttcctgc aacataagga cgataaccct aacttgcctc gcctggtccg ccctgaggtc    360
gacgtgatgt gcaccgcgtt ccacgacaac gaggaaacct ttcttaagaa gtacctgtac    420
gagattgcgc ggaggcaccc ttatttctac gcccccgaac tgttgttctt cgccaagcgg    480
tacaaggctg cctttaccga atgctgccag gccgccgata aggcggcttg cctgctgccg    540
aagctcgacg agttgcgcga tgaggggaag gcgtcctccg ctaagcagcg gctgaaatgt    600
gcgagcctcc agaagttcgg ggagcgcgcc ttcaaggcct gggccgtggc gcgcctgtct    660
caacggttcc cgaaggccga gttcgccgaa gtgtcgaagc tggtcaccga cctgacgaaa    720
gtgcacaccg aatgttgtca cggcgatctg ctggaatgcg ccgatgacag agccgatttg    780
gccaagtaca tctgcgaaaa ccaggacagc atttcgtcaa agctgaagga atgctgcgaa    840
```

aagcccttgc tggaaaagtc ccactgcatc gcggaagtgg agaacgacga gatgcccgcc 900
gacctcccgt ccctggccgc cgatttcgtg gagtcgaagg atgtgtgcaa gaactacgca 960
gaagccaagg acgtgttcct gggaatgttt ctgtatgagt acgcccgccg ccacccggac 1020
tactcggtcg tgctcctgct gcgactggca aagacctacg aaaccactct ggagaagtgc 1080
tgcgccgccg cggacccgca cgagtgctac gcaaaggtgt tcgacgagtt caagccactt 1140
gtcgaggagc ctcagaacct gatcaagcag aactgcgaac tgttcgagca gctgggagag 1200
tacaaattcc agaacgcgct tctcgtgcgc tacaccaaga aggtccccca ggtgtccact 1260
ccgaccctgg tggaagtgtc caggaacctg ggaaaggtcg gctccaagtg ttgcaagcat 1320
cccgaggcta agcgcatgcc ctgcgccgag gactacttgt ccgtggtgct gaatcagctg 1380
tgcgtgctcc atgaaaagac cccagtgtcc gacagagtga ccaagtgctg taccgaatcg 1440
ctcgtgaacc ggcggccgtg cttttccgca ctggaggtgg acgaaaccta cgtgccgaag 1500
gagttcaacg cagaaacctt cactttccac gccgacatct gcactctgtc cgagaaggag 1560
cggcagatta agaagcagac tgccctggtg gagcttgtga aacacaagcc taaggccacc 1620
aaagagcagc tgaaggccgt catggatgat ttcgcggcct tcgtggaaaa gtgttgtaaa 1680
gcggacgaca aggagacttg cttcgccgaa gaaggaaaga agctcgtggc agcgtcacag 1740
gccgctctgg gcctcgctag cggtggaggg ggcagcggtg gtggaggatc cggtaccgcg 1800
cgcaacgggg accactgtcc gctcgggccc gggcgttgct gccgtctgca cacggtccgc 1860
gcgtcgctgg aagacctggg ctgggccgat tgggtgctgt cgccacggga ggtgcaagtg 1920
accatgtgca tcggcgcgtg cccgagccag ttccgggcgg caaacatgca cgcgcagatc 1980
aagacgagcc tgcaccgcct gaagcccgac acggtgccag cgccctgctg cgtgcccgcc 2040
agctacaatc ccatggtgct cattcaaaag accgacaccg ggtgtcgct ccagacctat 2100 gatgacttgt tagccaaaga ctgccactgc ata 2133

<210> SEQ ID NO 78
<211> LENGTH: 2223
<212> TYPE: DNA
<213> ORGANISM: Artificial Sequence
<220> FEATURE:
<223> OTHER INFORMATION: fusion protein coding sequence

<400> SEQUENCE: 78
gatgctcata agtccgaagt cgcccacaga ttcaaggacc tcggagaaga aaattttaag 60
gccctcgtgc ttatcgcctt cgcccaatac ctccagcagt ccccgttcga ggaccacgtg 120
aagctcgtga acgaagtgac cgagtttgcc aagacttgtg tggcggatga atccgccgag 180
aactgcgaca agagcctcca cacgctgttc ggcgacaagc tgtgcaccgt cgccacgctg 240
agagaaactt acggagagat ggccgactgc tgcgcaaagc aggagccgga acggaacgaa 300
tgcttcctgc aacataagga cgataaccct aacttgcctc gcctggtccg ccctgaggtc 360
gacgtgatgt gcaccgcgtt ccacgacaac gaggaaacct ttcttaagaa gtacctgtac 420
gagattgcgc ggaggcaccc ttatttctac gcccccgaac tgttgttctt cgccaagcgg 480
tacaaggctg cctttaccga atgctgccag gccgccgata aggcggcttg cctgctgccg 540
aagctcgacg agttgcgcga tgaggggaag gcgtcctccg ctaagcagcg gctgaaatgt 600
gcgagcctcc agaagttcgg ggagcgcgcc ttcaaggcct gggccgtggc gcgcctgtct 660
caacggttcc cgaaggccga gttcgccgaa gtgtcgaagc tggtcaccga cctgacgaaa 720

-continued

```
gtgcacaccg aatgttgtca cggcgatctg ctggaatgcg ccgatgacag agccgatttg    780

gccaagtaca tctgcgaaaa ccaggacagc atttcgtcaa agctgaagga atgctgcgaa    840

aagcccttgc tggaaaagtc ccactgcatc gcggaagtgg agaacgacga gatgcccgcc    900

gacctcccgt ccctggccgc cgatttcgtg gagtcgaagg atgtgtgcaa gaactacgca    960

gaagccaagg acgtgttcct gggaatgttt ctgtatgagt acgcccgccg ccacccggac   1020

tactcggtcg tgctcctgct gcgactggca aagacctacg aaaccactct ggagaagtgc   1080

tgcgccgccg cggacccgca cgagtgctac gcaaaggtgt tcgacgagtt caagccactt   1140

gtcgaggagc ctcagaacct gatcaagcag aactgcgaac tgttcgagca gctgggagag   1200

tacaaattcc agaacgcgct tctcgtgcgc tacaccaaga aggtccccca ggtgtccact   1260

ccgaccctgg tggaagtgtc caggaacctg ggaaaggtcg gctccaagtg ttgcaagcat   1320

cccgaggcta agcgcatgcc ctgcgccgag gactacttgt ccgtggtgct gaatcagctg   1380

tgcgtgctcc atgaaaagac cccagtgtcc gacagagtga ccaagtgctg taccgaatcg   1440

ctcgtgaacc ggcggccgtg cttttccgca ctggaggtgg acgaaaccta cgtgccgaag   1500

gagttcaacg cagaaacctt cactttccac gccgacatct gcactctgtc cgagaaggag   1560

cggcagatta agaagcagac tgccctggtg gagcttgtga aacacaagcc taaggccacc   1620

aaagagcagc tgaaggccgt catggatgat ttcgcggcct tcgtggaaaa gtgttgtaaa   1680

gcggacgaca aggagacttg cttcgccgaa gaaggaaaga agctcgtggc agcgtcacag   1740

gccgctctgg gcctcgctag cggaggtggc ggatcaggtg gcggaggtag cggtggaggc   1800

ggctctggcg gaggtggatc aggcggagga ggttccggtg gaggaggctc aggaggagga   1860

ggaagtggag gagggggatc cggtaccgcg cgcaacgggg accactgtcc gctcgggccc   1920

gggcgttgct gccgtctgca cacggtccgc gcgtcgctgg aagacctggg ctgggccgat   1980

tgggtgctgt cgccacggga ggtgcaagtg accatgtgca tcggcgcgtg cccgagccag   2040

ttccgggcgg caaacatgca cgcgcagatc aagacgagcc tgcaccgcct gaagcccgac   2100

acggtgccag cgccctgctg cgtgcccgcc agctacaatc ccatggtgct cattcaaaag   2160

accgacaccg ggtgtcgct ccagacctat gatgacttgt tagccaaaga ctgccactgc   2220

ata                                                                 2223
```

<210> SEQ ID NO 79
<211> LENGTH: 2133
<212> TYPE: DNA
<213> ORGANISM: Artificial Sequence
<220> FEATURE:
<223> OTHER INFORMATION: fusion protein coding sequence

<400> SEQUENCE: 79

```
gatgctcata agtccgaagt cgcccacaga ttcaaggacc tcggagaaga aaattttaag     60

gccctcgtgc ttatcgcctt cgcccaatac ctccagcagt ccccgttcga ggaccacgtg    120

aagctcgtga acgaagtgac cgagtttgcc aagacttgtg tggcggatga atccgccgag    180

aactgcgaca agagcctcca cacgctgttc ggcgacaagc tgtgcaccgt cgccacgctg    240

agagaaactt acggagagat ggccgactgc tgcgcaaagc aggagccgga acggaacgaa    300

tgcttcctgc aacataagga cgataaccct aacttgcctc gcctggtccg ccctgaggtc    360

gacgtgatgt gcaccgcgtt ccacgacaac gaggaaacct ttcttaagaa gtacctgtac    420

gagattgcgc ggaggcaccc ttatttctac gcccccgaac tgttgttctt cgccaagcgg    480

tacaaggctg cctttaccga atgctgccag gccgccgata aggcggcttg cctgctgccg    540
```

-continued aagctcgacg agttgcgcga tgaggggaag gcgtcctccg ctaagcagcg gctgaaatgt 600
gcgagcctcc agaagttcgg ggagcgcgcc ttcaaggcct gggccgtggc gcgcctgtct 660
caacggttcc cgaaggccga gttcgccgaa gtgtcgaagc tggtcaccga cctgacgaaa 720
gtgcacaccg aatgttgtca cggcgatctg ctggaatgcg ccgatgacag agccgatttg 780
gccaagtaca tctgcgaaaa ccaggacagc atttcgtcaa agctgaagga atgctgcgaa 840
aagcccttgc tggaaaagtc ccactgcatc gcggaagtgg agaacgacga gatgcccgcc 900
gacctcccgt ccctggccgc cgatttcgtg gagtcgaagg atgtgtgcaa gaactacgca 960
gaagccaagg acgtgttcct gggaatgttt ctgtatgagt acgcccgccg ccacccggac 1020
tactcggtcg tgctcctgct gcgactggca aagacctacg aaaccactct ggagaagtgc 1080
tgcgccgccg cggacccgca cgagtgctac gcaaaggtgt tcgacgagtt caagccactt 1140
gtcgaggagc ctcagaacct gatcaagcag aactgcgaac tgttcgagca gctgggagag 1200
tacaaattcc agaacgcgct tctcgtgcgc tacaccaaga aggtccccca ggtgtccact 1260
ccgaccctgg tggaagtgtc caggaacctg ggaaaggtcg gctccaagtg ttgcaagcat 1320
cccgaggcta agcgcatgcc ctgcgccgag gactacttgt ccgtggtgct gaatcagctg 1380
tgcgtgctcc atgaaaagac cccagtgtcc gacagagtga ccaagtgctg taccgaatcg 1440
ctcgtgaacc ggcggccgtg cttttccgca ctggaggtgg acgaaaccta cgtgccgaag 1500
gagttcaacg cagaaacctt cactttccac gccgacatct gcactctgtc cgagaaggag 1560
cggcagatta agaagcagac tgccctggtg gagcttgtga aacacaagcc taaggccacc 1620
aaagagcagc tgaaggccgt catggatgat ttcgcggcct tcgtggaaaa gtgttgtaaa 1680
gcggacgaca aggagacttg cttcgccgaa gaaggaaaga agctcgtggc agcgtcacag 1740
gccgctctgg gcctcgctag cgcacctgcc cccgctccag ctcctgcacc aggtaccgcg 1800
cgcaacgggg accactgtcc gctcgggccc gggcgttgct gccgtctgca cacggtccgc 1860
gcgtcgctgg aagacctggg ctgggccgat tgggtgctgt cgccacggga ggtgcaagtg 1920
accatgtgca tcggcgcgtg cccgagccag ttccgggcgg caaacatgca cgcgcagatc 1980
aagacgagcc tgcaccgcct gaagcccgac acggtgccag cgccctgctg cgtgcccgcc 2040
agctacaatc ccatggtgct cattcaaaag accgacaccg ggtgtcgct ccagacctat 2100 gatgacttgt tagccaaaga ctgccactgc ata 2133

<210> SEQ ID NO 80
<211> LENGTH: 2163
<212> TYPE: DNA
<213> ORGANISM: Artificial Sequence
<220> FEATURE:
<223> OTHER INFORMATION: fusion protein coding sequence

<400> SEQUENCE: 80
gatgctcata agtccgaagt cgcccacaga ttcaaggacc tcggagaaga aaattttaag 60
gccctcgtgc ttatcgcctt cgcccaatac ctccagcagt ccccgttcga ggaccacgtg 120
aagctcgtga acgaagtgac cgagtttgcc aagacttgtg tggcggatga atccgccgag 180
aactgcgaca agagcctcca cacgctgttc ggcgacaagc tgtgcaccgt cgccacgctg 240
agagaaactt acggagagat ggccgactgc tgcgcaaagc aggagccgga acggaacgaa 300
tgcttcctgc aacataagga cgataaccct aacttgcctc gcctggtccg ccctgaggtc 360
gacgtgatgt gcaccgcgtt ccacgacaac gaggaaacct ttcttaagaa gtacctgtac 420

```
gagattgcgc ggaggcaccc ttatttctac gcccccgaac tgttgttctt cgccaagcgg    480

tacaaggctg cctttaccga atgctgccag gccgccgata aggcggcttg cctgctgccg    540

aagctcgacg agttgcgcga tgaggggaag gcgtcctccg ctaagcagcg gctgaaatgt    600

gcgagcctcc agaagttcgg ggagcgcgcc ttcaaggcct gggccgtggc gcgcctgtct    660

caacggttcc cgaaggccga gttcgccgaa gtgtcgaagc tggtcaccga cctgacgaaa    720

gtgcacaccg aatgttgtca cggcgatctg ctggaatgcg ccgatgacag agccgatttg    780

gccaagtaca tctgcgaaaa ccaggacagc atttcgtcaa agctgaagga atgctgcgaa    840

aagcccttgc tggaaaagtc ccactgcatc gcggaagtgg agaacgacga gatgcccgcc    900

gacctcccgt ccctggccgc cgatttcgtg gagtcgaagg atgtgtgcaa gaactacgca    960

gaagccaagg acgtgttcct gggaatgttt ctgtatgagt acgcccgccg ccacccggac   1020

tactcggtcg tgctcctgct gcgactggca aagacctacg aaaccactct ggagaagtgc   1080

tgcgccgccg cggacccgca cgagtgctac gcaaaggtgt tcgacgagtt caagccactt   1140

gtcgaggagc ctcagaacct gatcaagcag aactgcgaac tgttcgagca gctgggagag   1200

tacaaattcc agaacgcgct tctcgtgcgc tacaccaaga aggtccccca ggtgtccact   1260

ccgaccctgg tggaagtgtc caggaacctg ggaaaggtcg gctccaagtg ttgcaagcat   1320

cccgaggcta agcgcatgcc ctgcgccgag gactacttgt ccgtggtgct gaatcagctg   1380

tgcgtgctcc atgaaaagac cccagtgtcc gacagagtga ccaagtgctg taccgaatcg   1440

ctcgtgaacc ggcggccgtg cttttccgca ctggaggtgg acgaaaccta cgtgccgaag   1500

gagttcaacg cagaaacctt cactttccac gccgacatct gcactctgtc cgagaaggag   1560

cggcagatta agaagcagac tgccctggtg gagcttgtga aacacaagcc taaggccacc   1620

aaagagcagc tgaaggccgt catggatgat ttcgcggcct tcgtggaaaa gtgttgtaaa   1680

gcggacgaca aggagacttg cttcgccgaa gaaggaaaga agctcgtggc agcgtcacag   1740

gccgctctgg gcctcgctag cgcacctgcc cccgctccag cacccgcccc agcccctgct   1800

cccgcaccag ctcctgcacc aggtaccgct cgcaacggtg accactgccc tctgggtcct   1860

ggtcgctgct gccgcctgca caccgttcgc gcttctctgg aagacctggg ttgggctgac   1920

tgggttctgt ctcctcgcga agttcaggtt accatgtgca tcggtgcttg cccttctcag   1980

ttccgcgctg ctaacatgca cgctcagatc aaaacctctc tgcaccgcct gaaacctgac   2040

accgttcctg ctccttgctg cgttcctgct tcttacaacc ctatggttct gatccagaaa   2100

accgacaccg gtgtttctct gcagacctac gacgacctgc tggctaaaga ctgccactgc   2160

atc                                                                 2163
```

<210> SEQ ID NO 81
<211> LENGTH: 2223
<212> TYPE: DNA
<213> ORGANISM: Artificial Sequence
<220> FEATURE:
<223> OTHER INFORMATION: fusion protein coding sequence

<400> SEQUENCE: 81

```
gatgctcata agtccgaagt cgcccacaga ttcaaggacc tcggagaaga aaattttaag     60

gccctcgtgc ttatcgcctt cgcccaatac ctccagcagt ccccgttcga ggaccacgtg    120

aagctcgtga acgaagtgac cgagtttgcc aagacttgtg tggcggatga atccgccgag    180

aactgcgaca agagcctcca cacgctgttc ggcgacaagc tgtgcaccgt cgccacgctg    240

agagaaactt acggagagat ggccgactgc tgcgcaaagc aggagccgga acggaacgaa    300
```

```
tgcttcctgc aacataagga cgataaccct aacttgcctc gcctggtccg ccctgaggtc    360
gacgtgatgt gcaccgcgtt ccacgacaac gaggaaacct ttcttaagaa gtacctgtac    420
gagattgcgc ggaggcaccc ttatttctac gcccccgaac tgttgttctt cgccaagcgg    480
tacaaggctg cctttaccga atgctgccag gccgccgata aggcggcttg cctgctgccg    540
aagctcgacg agttgcgcga tgaggggaag gcgtcctccg ctaagcagcg gctgaaatgt    600
gcgagcctcc agaagttcgg ggagcgcgcc ttcaaggcct gggccgtggc gcgcctgtct    660
caacggttcc cgaaggccga gttcgccgaa gtgtcgaagc tggtcaccga cctgacgaaa    720
gtgcacaccg aatgttgtca cggcgatctg ctggaatgcg ccgatgacag agccgatttg    780
gccaagtaca tctgcgaaaa ccaggacagc atttcgtcaa agctgaagga atgctgcgaa    840
aagcccttgc tggaaaagtc ccactgcatc gcggaagtgg agaacgacga gatgcccgcc    900
gacctcccgt ccctggccgc cgatttcgtg gagtcgaagg atgtgtgcaa gaactacgca    960
gaagccaagg acgtgttcct gggaatgttt ctgtatgagt acgcccgccg ccacccggac   1020
tactcggtcg tgctcctgct gcgactggca aagacctacg aaaccactct ggagaagtgc   1080
tgcgccgccg cggacccgca cgagtgctac gcaaaggtgt tcgacgagtt caagccactt   1140
gtcgaggagc ctcagaacct gatcaagcag aactgcgaac tgttcgagca gctgggagag   1200
tacaaattcc agaacgcgct tctcgtgcgc tacaccaaga aggtccccca ggtgtccact   1260
ccgaccctgg tggaagtgtc caggaacctg ggaaaggtcg gctccaagtg ttgcaagcat   1320
cccgaggcta agcgcatgcc ctgcgccgag gactacttgt ccgtggtgct gaatcagctg   1380
tgcgtgctcc atgaaaagac cccagtgtcc gacagagtga ccaagtgctg taccgaatcg   1440
ctcgtgaacc ggcggccgtg cttttccgca ctggaggtgg acgaaaccta cgtgccgaag   1500
gagttcaacg cagaaacctt cactttccac gccgacatct gcactctgtc cgagaaggag   1560
cggcagatta agaagcagac tgccctggtg gagcttgtga aacacaagcc taaggccacc   1620
aaagagcagc tgaaggccgt catggatgat ttcgcggcct tcgtggaaaa gtgttgtaaa   1680
gcggacgaca aggagacttg cttcgccgaa gaaggaaaga agctcgtggc agcgtcacag   1740
gccgctctgg gcctcgctag cgcacctgcc cccgctccag ccccagctcc tgcacctgct   1800
ccagcaccag ctcctgcacc agctccagcc cctgcacctg cacccgctcc agccccagct   1860
cctgcacctg ctccagcacc aggtaccgcg cgcaacgggg accactgtcc gctcgggccc   1920
gggcgttgct gccgtctgca cacggtccgc gcgtcgctgg aagacctggg ctgggccgat   1980
tgggtgctgt cgccacggga ggtgcaagtg accatgtgca tcggcgcgtg cccgagccag   2040
ttccgggcgg caaacatgca cgcgcagatc aagacgagcc tgcaccgcct gaagcccgac   2100
acggtgccag cgccctgctg cgtgcccgcc agctacaatc ccatggtgct cattcaaaag   2160
accgacaccg ggtgtcgct ccagacctat gatgacttgt tagccaaaga ctgccactgc    2220
ata                                                                 2223
```

<210> SEQ ID NO 82
<211> LENGTH: 2163
<212> TYPE: DNA
<213> ORGANISM: Artificial Sequence
<220> FEATURE:
<223> OTHER INFORMATION: fusion protein coding sequence

<400> SEQUENCE: 82

```
gatgctcata agtccgaagt cgcccacaga ttcaaggacc tcggagaaga aaattttaag     60
```

-continued

```
gccctcgtgc ttatcgcctt cgcccaatac ctccagcagt ccccgttcga ggaccacgtg    120
aagctcgtga acgaagtgac cgagtttgcc aagacttgtg tggcggatga atccgccgag    180
aactgcgaca agagcctcca cacgctgttc ggcgacaagc tgtgcaccgt cgccacgctg    240
agagaaactt acggagagat ggccgactgc tgcgcaaagc aggagccgga acggaacgaa    300
tgcttcctgc aacataagga cgataaccct aacttgcctc gcctggtccg ccctgaggtc    360
gacgtgatgt gcaccgcgtt ccacgacaac gaggaaacct ttcttaagaa gtacctgtac    420
gagattgcgc ggaggcaccc ttatttctac gcccccgaac tgttgttctt cgccaagcgg    480
tacaaggctg cctttaccga atgctgccag gccgccgata aggcggcttg cctgctgccg    540
aagctcgacg agttgcgcga tgaggggaag gcgtcctccg ctaagcagcg gctgaaatgt    600
gcgagcctcc agaagttcgg ggagcgcgcc ttcaaggcct gggccgtggc gcgcctgtct    660
caacggttcc cgaaggccga gttcgccgaa gtgtcgaagc tggtcaccga cctgacgaaa    720
gtgcacaccg aatgttgtca cggcgatctg ctggaatgcg ccgatgacag agccgatttg    780
gccaagtaca tctgcgaaaa ccaggacagc atttcgtcaa agctgaagga atgctgcgaa    840
aagcccttgc tggaaaagtc ccactgcatc gcggaagtgg agaacgacga gatgcccgcc    900
gacctcccgt ccctggccgc cgatttcgtg gagtcgaagg atgtgtgcaa gaactacgca    960
gaagccaagg acgtgttcct gggaatgttt ctgtatgagt acgcccgccg ccacccggac   1020
tactcggtcg tgctcctgct gcgactggca aagacctacg aaaccactct ggagaagtgc   1080
tgcgccgccg cggacccgca cgagtgctac gcaaaggtgt tcgacgagtt caagccactt   1140
gtcgaggagc ctcagaacct gatcaagcag aactgcgaac tgttcgagca gctgggagag   1200
tacaaattcc agaacgcgct tctcgtgcgc tacaccaaga aggtccccca ggtgtccact   1260
ccgaccctgg tggaagtgtc caggaacctg ggaaaggtcg gctccaagtg ttgcaagcat   1320
cccgaggcta agcgcatgcc ctgcgccgag gactacttgt ccgtggtgct gaatcagctg   1380
tgcgtgctcc atgaaaagac cccagtgtcc gacagagtga ccaagtgctg taccgaatcg   1440
ctcgtgaacc ggcggccgtg cttttccgca ctggaggtgg acgaaaccta cgtgccgaag   1500
gagttcaacg cagaaacctt cactttccac gccgacatct gcactctgtc cgagaaggag   1560
cggcagatta agaagcagac tgccctggtg gagcttgtga aacacaagcc taaggccacc   1620
aaagagcagc tgaaggccgt catggatgat ttcgcggcct tcgtggaaaa gtgttgtaaa   1680
gcggacgaca aggagacttg cttcgccgaa gaaggaaaga agctcgtggc agcgtcacag   1740
gccgctctgg gcctcgctag cgaagcagca gccaaagaag cagccgcaaa agaagcagcc   1800
gctaaggagg ccgcagcaaa gggtaccgcg cgcaacgggg accactgtcc gctcgggccc   1860
gggcgttgct gccgtctgca cacggtccgc gcgtcgctgg aagacctggg ctgggccgat   1920
tgggtgctgt cgccacggga ggtgcaagtg accatgtgca tcggcgcgtg cccgagccag   1980
ttccgggcgg caaacatgca cgcgcagatc aagacgagcc tgcaccgcct gaagcccgac   2040
acggtgccag cgccctgctg cgtgcccgcc agctacaatc ccatggtgct cattcaaaag   2100
accgacaccg ggtgtcgct ccagacctat gatgacttgt tagccaaaga ctgccactgc   2160
ata                                                                 2163
```

<210> SEQ ID NO 83
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 83
gacgcccaca agagcgaggt ggcccaccgg ttcaaggacc tgggcgagga gaacttcaag 60
gccctggtgc tgatcgcctt cgcccagtac ctgcagcagt ccccctcga ggaccacgtg 120
aagctggtga acgaggtgac cgagttcgcc aagacctgcg tggccgacga gagcgccgag 180
aactgcgaca agagcctgca caccctgttc ggcgacaagc tgtgcaccgt ggccaccctg 240
cgggagacct acggcgagat ggccgactgc tgcgccaagc aggagcccga gcggaacgag 300
tgcttcctgc agcacaagga cgacaacccc aacctgcccc ggctggtgcg gcccgaggtg 360
gacgtgatgt gcaccgcctt ccacgacaac gaggagacct tcctgaagaa gtacctgtac 420
gagatcgccc ggcggcaccc ctacttctac gcccccgagc tgctgttctt cgccaagcgg 480
tacaaggccg ccttcaccga gtgctgccag gccgccgaca aggccgcctg cctgctgccc 540
aagctggacg agctgcggga cgagggcaag gccagcagcg ccaagcagcg gctgaagtgc 600
gccagcctgc agaagttcgg cgagcgggcc ttcaaggcct gggccgtggc ccggctgagc 660
cagcggttcc ccaaggccga gttcgccgag gtgagcaagc tggtgaccga cctgaccaag 720
gtgcacaccg agtgctgcca cggcgacctg ctggagtgcg ccgacgaccg ggccgacctg 780
gccaagtaca tctgcgagaa ccaggacagc atcagcagca agctgaagga gtgctgcgag 840
aagcccctgc tggagaagag ccactgcatc gccgaggtgg agaacgacga gatgcccgcc 900
gacctgccca gcctggccgc cgacttcgtg gagagcaagg acgtgtgcaa gaactacgcc 960
gaggccaagg acgtgttcct gggcatgttc ctgtacgagt acgcccggcg gcacccccgac 1020
tacagcgtgg tgctgctgct gcggctggcc aagacctacg agaccaccct ggagaagtgc 1080
tgcgccgccg ccgaccccca cgagtgctac gccaaggtgt tcgacgagtt caagcccctg 1140
gtggaggagc cccagaacct gatcaagcag aactgcgagc tgttcgagca gctgggcgag 1200
tacaagttcc agaacgccct gctggtgcgg tacaccaaga aggtgcccca ggtgagcacc 1260
cccaccctgg tggaggtgag ccggaacctg ggcaaggtgg gcagcaagtg ctgcaagcac 1320
cccgaggcca agcggatgcc ctgcgccgag gactacctga gcgtggtgct gaaccagctg 1380
tgcgtgctgc acgagaagac ccccgtgagc gaccgggtga ccaagtgctg caccgagagc 1440
ctggtgaacc ggcggccctg cttcagcgcc ctggaggtgg acgagaccta cgtgcccaag 1500
gagttcaacg ccgagacctt caccttccac gccgacatct gcaccctgag cgagaaggag 1560
cggcagatca agaagcagac cgccctggtg gagctggtga agcacaagcc caaggccacc 1620
aaggagcagc tgaaggccgt gatggacgac ttcgccgcct tcgtggagaa gtgctgcaag 1680
gccgacgaca aggagacctg cttcgccgag gagggcaaga agctggtggc cgccagccag 1740
gccgccctgg gcctgggcag cggcggcggc ggcagcggcg gcggcggatc tggtggaggt 1800
ggcagtggag gagggggatc cgcgcgcaac ggggaccact gtccgctcgg gcccgggcgt 1860
tgctgccgtc tgcacacggt ccgcgcgtcg ctggaagacc tgggctgggc cgattgggtg 1920
ctgtcgccac gggaggtgca agtgaccatg tgcatcggcg cgtgcccgag ccagttccgg 1980
gcggcaaaca tgcacgcgca gatcaagacg agcctgcacc gcctgaagcc cgacacggtg 2040
ccagcgccct gctgcgtgcc cgccagctac aatcccatgg tgctcattca aaagaccgac 2100
accggggtgt cgctccagac ctatgatgac ttgttagcca aagactgcca ctgcata 2157

<210> SEQ ID NO 84
<211> LENGTH: 2217
<212> TYPE: DNA

-continued

<213> ORGANISM: Artificial Sequence
<220> FEATURE:
<223> OTHER INFORMATION: fusion protein coding sequence

<400> SEQUENCE: 84
gatgcacaca agagtgaggt tgctcatcgg tttaaagatt tgggagaaga aaatttcaaa 60
gccttggtgt tgattgcctt tgctcagtat cttcagcagg ccccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300
tgcttcttgc aacacaaaga tgacaaccca aacctccccc gattggtgag accagaggtt 360
gatgtgatgt gcactgcttt tcatgacaat gaagagacat tttgaaaaa atacttatat 420 gaaattgcca gaagacatcc ttacttttat gccccggaac tccttttctt tgctaaaagg 480
tataaagctg cttttacaga atgttgccaa gctgctgata aagctgcctg cctgttgcca 540
aagctcgatg aacttcggga tgaagggaag gcttcgtctg ccaaacagag actcaagtgt 600
gccagtctcc aaaaatttgg agaaagagct ttcaaagcat gggcagtagc tcgcctgagc 660
cagagatttc ccaaagctga gtttgcagaa gtttccaagt tagtgacaga tcttaccaaa 720
gtccacacgg aatgctgcca tggagatctg cttgaatgtg ctgatgacag ggcggacctt 780
gccaagtata tctgtgaaaa tcaagattcg atctccagta aactgaagga atgctgtgaa 840
aaacctctgt tggaaaaatc ccactgcatt gccgaagtgg aaaatgatga gatgcctgct 900
gacttgcctt cattagctgc tgattttgtt gaaagtaagg atgtttgcaa aaactatgct 960
gaggcaaagg atgtcttcct gggcatgttt ttgtatgaat atgcaagaag gcatcctgat 1020
tactctgtcg tgctgctgct gagacttgcc aagacatatg aaaccactct agagaagtgc 1080
tgtgccgctg cagatcctca tgaatgctat gccaaagtgt tcgatgaatt taaacctctt 1140
gtggaagagc ctcagaattt aatcaaacaa aattgtgagc tttttgagca gcttggagag 1200
tacaaattcc agaatgcgct attagttcgt tacaccaaga aagtacccca agtgtcaact 1260
ccaactcttg tagaggtctc aagaaaccta ggaaaagtgg gcagcaaatg ttgtaaacat 1320
cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc 1440
ttggtgaaca ggcgaccatg cttttcagct ctggaagtcg atgaaacata cgttcccaaa 1500
gagtttaatg ctgaaacatt caccttccat gcagatatat gcacactttc tgagaaggag 1560
agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag gcttaggcag cggcggcggc ggcagcggcg gcggcggatc tggtggaggt 1800
ggcagtggag gagggggatc cggcggcggc ggcagcggcg gcggcggatc tggtggaggt 1860
ggcagtggag gagggggatc cgcgcgcaac ggggaccact gtccgctcgg gcccgggcgt 1920
tgctgccgtc tgcacacggt ccgcgcgtcg ctggaagacc tgggctgggc cgattgggtg 1980
ctgtcgccac gggaggtgca agtgaccatg tgcatcggcg cgtgcccgag ccagttccgg 2040
gcggcaaaca tgcacgcgca gatcaagacg agcctgcacc gcctgaagcc cgacacggtg 2100
ccagcgccct gctgcgtgcc cgccagctac aatcccatgg tgctcattca aaagaccgac 2160
accggggtgt cgctccagac ctatgatgac ttgttagcca aagactgcca ctgcata 2217

<210> SEQ ID NO 85
<211> LENGTH: 2151
<212> TYPE: DNA
<213> ORGANISM: Artificial Sequence
<220> FEATURE:
<223> OTHER INFORMATION: fusion protein coding sequence

<400> SEQUENCE: 85
gatgcacaca agagtgaggt tgctcatcgg tttaaagatt tgggagaaga aaatttcaaa 60
gccttggtgt tgattgcctt tgctcagtat cttcagcagg ccccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300
tgcttcttgc aacacaaaga tgacaaccca aacctccccc gattggtgag accagaggtt 360
gatgtgatgt gcactgcttt tcatgacaat gaagagacat tttgaaaaa atacttatat 420 gaaattgcca gaagacatcc ttacttttat gccccggaac tccttttctt tgctaaaagg 480
tataaagctg cttttacaga atgttgccaa gctgctgata aagctgcctg cctgttgcca 540
aagctcgatg aacttcggga tgaagggaag gcttcgtctg ccaaacagag actcaagtgt 600
gccagtctcc aaaaatttgg agaaagagct ttcaaagcat gggcagtagc tcgcctgagc 660
cagagatttc ccaaagctga gtttgcagaa gtttccaagt tagtgacaga tcttaccaaa 720
gtccacacgg aatgctgcca tggagatctg cttgaatgtg ctgatgacag ggcggacctt 780
gccaagtata tctgtgaaaa tcaagattcg atctccagta aactgaagga atgctgtgaa 840
aaacctctgt tggaaaaatc ccactgcatt gccgaagtgg aaaatgatga gatgcctgct 900
gacttgcctt cattagctgc tgattttgtt gaaagtaagg atgtttgcaa aaactatgct 960
gaggcaaagg atgtcttcct gggcatgttt ttgtatgaat atgcaagaag gcatcctgat 1020
tactctgtcg tgctgctgct gagacttgcc aagacatatg aaaccactct agagaagtgc 1080
tgtgccgctg cagatcctca tgaatgctat gccaaagtgt tcgatgaatt taaacctctt 1140
gtggaagagc ctcagaattt aatcaaacaa aattgtgagc tttttgagca gcttggagag 1200
tacaaattcc agaatgcgct attagttcgt tacaccaaga aagtacccca agtgtcaact 1260
ccaactcttg tagaggtctc aagaaaccta ggaaaagtgg gcagcaaatg ttgtaaacat 1320
cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc 1440
ttggtgaaca ggcgaccatg cttttcagct ctggaagtcg atgaaacata cgttcccaaa 1500
gagtttaatg ctgaaacatt caccttccat gcagatatat gcacactttc tgagaaggag 1560
agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag gcttagcacc tgccccgct ccagcacccg ccccagcccc tgctcccgca 1800
ccagctcctg caccagcgcg caacggggac cactgtccgc tcgggcccgg gcgttgctgc 1860
cgtctgcaca cggtccgcgc gtcgctggaa gacctgggct gggccgattg ggtgctgtcg 1920
ccacgggagg tgcaagtgac catgtgcatc ggcgcgtgcc cgagccagtt ccgggcggca 1980
aacatgcacg cgcagatcaa gacgagcctg caccgcctga agcccgacac ggtgccagcg 2040

-continued

```
ccctgctgcg tgcccgccag ctacaatccc atggtgctca ttcaaaagac cgacaccggg   2100

gtgtcgctcc agacctatga tgacttgtta gccaaagact gccactgcat a            2151
```

<210> SEQ ID NO 86
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 86

```
gatgcacaca agagtgaggt tgctcatcgg tttaaagatt tgggagaaga aaatttcaaa     60
gccttggtgt tgattgcctt tgctcagtat cttcagcagt ccccatttga agatcatgta    120
aaattagtga atgaagtaac tgaatttgca aaaacatgtg ttgctgatga gtcagctgaa    180
aattgtgaca aatcacttca taccctttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat tttgaaaaa atacttatat    420
gaaattgcca gaagacatcc ttacttttat gccccggaac tcctttctt tgctaaaagg    480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca agaaacaaac tgcacttgtt gagctcgtga aacacaagcc caaggcaaca   1620
aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttaggcag cggcggcggc ggcagcggcg gcggcggatc tggtggaggt   1800
ggcagtggag gagggggatc cgcgcgcaac ggggaccact gtccgctcgg gcccgggcgt   1860
tgctgccgtc tgcacacggt ccgcgcgtcg ctggaagacc tgggctgggc cgattgggtg   1920
ctgtcgccac gggaggtgca agtgaccatg tgcatcggcg cgtgcccgag ccagttccgg   1980
```

gcggcaaaca tgcacgcgca gatcaagacg agcctgcacc gcctgaagcc cgacacggtg 2040
ccagcgccct gctgcgtgcc cgccagctac aatcccatgg tgctcattca aaagaccgac 2100
accggggtgt cgctccagac ctatgatgac ttgttagcca aagactgcca ctgcata 2157

<210> SEQ ID NO 87
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 87
gacgcccaca agagcgaggt ggcccacaga ttcaaggacc tgggcgagga aaacttcaag 60
gccctggtgc tgatcgcctt cgcccagtac ctgcagcaga gccccttcga ggaccacgtg 120
aagctggtca acgaagtgac cgagttcgcc aagacctgcg tggccgacga gagcgccgag 180
aactgcgaca agagcctgca caccctgttc ggcgacaagc tgtgcaccgt ggccaccctg 240
cgggaaacct acggcgagat ggccgactgc tgcgccaagc aggaacccga gcggaacgag 300
tgcttcctgc agcacaagga cgacaacccc aacctgccca gactcgtgcg gcccgaggtg 360
gacgtgatgt gcaccgcctt ccacgacaac gaggaaacct tcctgaagaa gtacctgtac 420
gagatcgcca gacggcaccc ctacttctac gcccccgagc tgctgttctt cgccaagcgg 480
tacaaggccg ccttcaccga gtgctgccag gccgccgata aggccgcctg cctgctgccc 540
aagctggacg agctgagaga tgagggcaag gccagctccg ccaagcagcg gctgaagtgc 600
gccagcctgc agaagttcgg cgagcgggcc tttaaggctt gggctgtggc ccggctgagc 660
cagagattcc ccaaggccga gtttgccgag gtgtccaagc tggtcaccga cctgaccaag 720
gtgcacaccg agtgttgtca cggcgacctg ctggaatgcg ccgacgacag agccgacctg 780
gccaagtaca tctgcgagaa ccaggacagc atcagcagca agctgaaaga gtgctgcgag 840
aagcccctgc tggaaaagag ccactgtatc gccgaggtgg aaaacgacga gatgcccgct 900
gacctgccca gcctggccgc cgacttcgtg gaaagcaagg acgtgtgcaa gaactacgcc 960
gaggccaagg atgtgttcct gggcatgttc ctgtatgagt acgcccgcag acaccccgac 1020
tacagcgtgg tgctgctgct gcggctggcc aagacctacg agacaaccct ggaaaagtgc 1080
tgcgccgctg ccgaccccca cgagtgctac gccaaggtgt tcgacgagtt caagcctctg 1140
gtggaagaac cccagaacct gatcaagcag aactgcgagc tgttcgagca gctgggcgag 1200
tacaagttcc agaacgccct gctcgtgcgg tacaccaaga aagtgcccca ggtgtccacc 1260
cccaccctgg tcgaagtgtc ccggaacctg ggcaaagtgg gcagcaagtg ctgcaagcac 1320
cctgaggcca agcggatgcc ctgcgccgag gactacctgt ccgtggtgct gaaccagctg 1380
tgcgtgctgc acgagaaaac ccccgtgtcc gacagagtga ccaagtgctg taccgagagc 1440
ctggtcaaca gacggccctg cttcagcgcc ctggaagtgg acgagacata cgtgcccaaa 1500
gagttcaacg ccgagacatt caccttccac gccgacatct gcaccctgag cgagaaagag 1560
cggcagatca agaagcagac cgccctggtc gagctggtca agcacaagcc caaggccacc 1620
aaagaacagc tgaaggccgt gatggacgac ttcgccgcct tcgtcgagaa gtgttgcaag 1680
gccgacgaca aagagacatg cttcgccgaa gagggcaaga aactggtggc cgcctctcag 1740
gccgccctgg gactgggatc tggcggcgga ggaagcggag gcggaggatc tgggggaggc 1800
ggctctggcg gagggggatc cgccagaaat ggcgaccact gtcccctggg ccctggccgg 1860
tgttgcagac tgcacacagt gcgggccagc ctggaagatc tgggctgggc cgattgggtg 1920
ctgagcccca gagaagtgca ggtcacaatg tgcatcggcg cctgccccag ccagttcaga 1980
gccgccaaca tgcacgccca gatcaagacc agcctgcacc ggctgaagcc cgacaccgtg 2040
cctgcccctt gttgcgtgcc cgccagctac aaccccatgg tgctgattca gaaaaccgac 2100
accggcgtgt ccctgcagac ctacgacgat ctgctggcca aggactgcca ctgcatc 2157

<210> SEQ ID NO 88
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 88
gatgcacaca agagtgaggt tgctcatcgg tttaaagatt tgggagaaga aaatttcaaa 60
gccttggtgt tgattgcctt tgctcagtat cttcagcagg ccccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300
tgcttcttgc aacacaaaga tgacaaccca aacctccccc gattggtgag accagaggtt 360
gatgtgatgt gcactgcttt tcatgacaat gaagagacat tttgaaaaa atacttatat 420 gaaattgcca gaagacatcc ttacttttat gccccggaac tccttttctt tgctaaaagg 480
tataaagctg cttttacaga atgttgccaa gctgctgata aagctgcctg cctgttgcca 540
aagctcgatg aacttcggga tgaagggaag gcttcgtctg ccaaacagag actcaagtgt 600
gccagtctcc aaaaatttgg agaaagagct ttcaaagcat gggcagtagc tcgcctgagc 660
cagagatttc ccaaagctga gtttgcagaa gtttccaagt tagtgacaga tcttaccaaa 720
gtccacacgg aatgctgcca tggagatctg cttgaatgtg ctgatgacag ggcggacctt 780
gccaagtata tctgtgaaaa tcaagattcg atctccagta aactgaagga atgctgtgaa 840
aaacctctgt tggaaaaatc ccactgcatt gccgaagtgg aaaatgatga gatgcctgct 900
gacttgcctt cattagctgc tgattttgtt gaaagtaagg atgtttgcaa aaactatgct 960
gaggcaaagg atgtcttcct gggcatgttt ttgtatgaat atgcaagaag gcatcctgat 1020
tactctgtcg tgctgctgct gagacttgcc aagacatatg aaaccactct agagaagtgc 1080
tgtgccgctg cagatcctca tgaatgctat gccaaagtgt tcgatgaatt taaacctctt 1140
gtggaagagc ctcagaattt aatcaaacaa aattgtgagc tttttgagca gcttggagag 1200
tacaaattcc agaatgcgct attagttcgt tacaccaaga aagtacccca agtgtcaact 1260
ccaactcttg tagaggtctc aagaaaccta ggaaaagtgg gcagcaaatg ttgtaaacat 1320
cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc 1440
ttggtgaaca ggcgaccatg cttttcagct ctggaagtcg atgaaacata cgttcccaaa 1500
gagtttaatg ctgaaacatt caccttccat gcagatatat gcacactttc tgagaaggag 1560
agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag gcttaggcag cggcggcggc ggcagcggcg gcggcggatc tggtggaggt 1800

```
ggcagtggag gagggggatc cgcgcgcaac ggggaccact gtccgctcgg gcccgggcgt   1860

tgctgccgtc tgcacacggt ccgcgcgtcg ctggaagacc tgggctgggc cgattgggtg   1920

ctgtcgccac gggaggtgca agtgaccatg tgcatcggcg cgtgcccgag ccagttccgg   1980

gcggcaaaca tgcacgcgca gatcaagacg agcctgcacc gcctgaagcc cgacacggtg   2040

ccagcgccct gctgcgtgcc cgccagctac aatcccatgg tgctcattca aaagaccgac   2100

accggggtgt cgctccagac ctatgatgac ttgttagcca aagactgcca ctgcata      2157
```

<210> SEQ ID NO 89
<211> LENGTH: 2151
<212> TYPE: DNA
<213> ORGANISM: Artificial Sequence
<220> FEATURE:
<223> OTHER INFORMATION: fusion protein coding sequence

<400> SEQUENCE: 89

```
gatgcacaca agagtgaggt tgctcatcgg tttaaagatt tgggagaaga aaatttcaaa     60

gccttggtgt tgattgcctt tgctcagtat cttcagcagt ccccatttga agatcatgta    120

aaattagtga atgaagtaac tgaatttgca aaaacatgtg ttgctgatga gtcagctgaa    180

aattgtgaca aatcacttca taccctttttt ggagacaaat tatgcacagt tgcaactctt    240

cgtgaaacct atggtgaaat ggctgactgc tgtgcaaaac aagaacctga gagaaatgaa    300

tgcttcttgc aacacaaaga tgacaaccca aacctccccc gattggtgag accagaggtt    360

gatgtgatgt gcactgcttt tcatgacaat gaagagacat tttgaaaaa atacttatat     420

gaaattgcca gaagacatcc ttacttttat gccccggaac tcctttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagaag gcatcctgat   1020

tactctgtcg tgctgctgct gagacttgcc aagacatatg aaaccactct agagaagtgc   1080

tgtgccgctg cagatcctca tgaatgctat gccaaagtgt tcgatgaatt taaacctctt   1140

gtggaagagc ctcagaattt aatcaaacaa aattgtgagc tttttgagca gcttggagag   1200

tacaaattcc agaatgcgct attagttcgt tacaccaaga aagtacccca agtgtcaact   1260

ccaactcttg tagaggtctc aagaaaccta ggaaaagtgg gcagcaaatg ttgtaaacat   1320

cctgaagcaa aaagaatgcc ctgtgcagaa gactatctat ccgtggtcct gaaccagtta   1380

tgtgtgttgc atgagaaaac gccagtaagt gacagagtca ccaaatgctg cacagaatcc   1440

ttggtgaaca ggcgaccatg cttttcagct ctggaagtcg atgaaacata cgttcccaaa   1500

gagtttaatg ctgaaacatt caccttccat gcagatatat gcacactttc tgagaaggag   1560

agacaaatca agaaacaaac tgcacttgtt gagctcgtga aacacaagcc caaggcaaca   1620

aaagagcaac tgaaagctgt tatggatgat ttcgcagctt ttgtagagaa gtgctgcaag   1680
```

-continued

```
gctgacgata aggagacctg ctttgccgag gagggtaaaa aacttgttgc tgcaagtcaa   1740

gctgccttag gcttagcacc tgccccgct ccagcacccg ccccagcccc tgctcccgca   1800

ccagctcctg caccagcgcg caacggggac cactgtccgc tcgggcccgg gcgttgctgc   1860

cgtctgcaca cggtccgcgc gtcgctggaa gacctgggct gggccgattg ggtgctgtcg   1920

ccacgggagg tgcaagtgac catgtgcatc ggcgcgtgcc cgagccagtt ccgggcggca   1980

aacatgcacg cgcagatcaa gacgagcctg caccgcctga agcccgacac ggtgccagcg   2040

ccctgctgcg tgcccgccag ctacaatccc atggtgctca ttcaaaagac cgacaccggg   2100

gtgtcgctcc agacctatga tgacttgtta gccaaagact gccactgcat a            2151
```

<210> SEQ ID NO 90
<211> LENGTH: 2217
<212> TYPE: DNA
<213> ORGANISM: Artificial Sequence
<220> FEATURE:
<223> OTHER INFORMATION: fusion protein coding sequence

<400> SEQUENCE: 90

```
gatgcacaca agagtgaggt tgctcatcgg tttaaagatt tgggagaaga aaatttcaaa     60

gccttggtgt tgattgcctt tgctcagtat cttcagcagt ccccatttga agatcatgta    120

aaattagtga atgaagtaac tgaatttgca aaaacatgtg ttgctgatga gtcagctgaa    180

aattgtgaca aatcacttca taccctttttt ggagacaaat tatgcacagt tgcaactctt    240

cgtgaaacct atggtgaaat ggctgactgc tgtgcaaaac aagaacctga gagaaatgaa    300

tgcttcttgc aacacaaaga tgacaaccca aacctccccc gattggtgag accagaggtt    360

gatgtgatgt gcactgcttt tcatgacaat gaagagacat tttgaaaaa atacttatat     420

gaaattgcca gaagacatcc ttacttttat gccccggaac tccttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagaag gcatcctgat   1020

tactctgtcg tgctgctgct gagacttgcc aagacatatg aaaccactct agagaagtgc   1080

tgtgccgctg cagatcctca tgaatgctat gccaaagtgt tcgatgaatt taaacctctt   1140

gtggaagagc ctcagaattt aatcaaacaa aattgtgagc tttttgagca gcttggagag   1200

tacaaattcc agaatgcgct attagttcgt tacaccaaga aagtacccca agtgtcaact   1260

ccaactcttg tagaggtctc aagaaaccta ggaaaagtgg gcagcaaatg ttgtaaacat   1320

cctgaagcaa aaagaatgcc ctgtgcagaa gactatctat ccgtggtcct gaaccagtta   1380

tgtgtgttgc atgagaaaac gccagtaagt gacagagtca ccaaatgctg cacagaatcc   1440

ttggtgaaca ggcgaccatg cttttcagct ctggaagtcg atgaaacata cgttcccaaa   1500

gagtttaatg ctgaaacatt caccttccat gcagatatat gcacactttc tgagaaggag   1560

agacaaatca agaaacaaac tgcacttgtt gagctcgtga aacacaagcc caaggcaaca   1620
```

aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag gcttaggcag cggcggcggc ggcagcggcg gcggcggatc tggtggaggt 1800
ggcagtggag gagggggatc cggcggcggc ggcagcggcg gcggcggatc tggtggaggt 1860
ggcagtggag gagggggatc cgcgcgcaac ggggaccact gtccgctcgg gcccgggcgt 1920
tgctgccgtc tgcacacggt ccgcgcgtcg ctggaagacc tgggctgggc cgattgggtg 1980
ctgtcgccac gggaggtgca agtgaccatg tgcatcggcg cgtgcccgag ccagttccgg 2040
gcggcaaaca tgcacgcgca gatcaagacg agcctgcacc gcctgaagcc cgacacggtg 2100
ccagcgccct gctgcgtgcc cgccagctac aatcccatgg tgctcattca aaagaccgac 2160
accggggtgt cgctccagac ctatgatgac ttgttagcca aagactgcca ctgcata 2217

<210> SEQ ID NO 91
<211> LENGTH: 2157
<212> TYPE: DNA
<213> ORGANISM: Artificial Sequence
<220> FEATURE:
<223> OTHER INFORMATION: fusion protein coding sequence

<400> SEQUENCE: 91
gacgcccaca agagcgaggt ggcccaccgg ttcaaggacc tgggcgagga gaacttcaag 60
gccctggtgc tgatcgcctt cgcccagtac ctgcagcagt ccccccttcga ggaccacgtg 120 aagctggtga acgaggtgac cgagttcgcc aagacctgcg tggccgacga gagcgccgag 180
aactgcgaca agagcctgca caccctgttc ggcgacaagc tgtgcaccgt ggccaccctg 240
cgggagacct acggcgagat ggccgactgc tgcgccaagc aggagcccga gcggaacgag 300
tgcttcctgc agcacaagga cgacaacccc aacctgcccc ggctggtgcg gcccgaggtg 360
gacgtgatgt gcaccgcctt ccacgacaac gaggagacct tcctgaagaa gtacctgtac 420
gagatcgccc ggcggcaccc ctacttctac gccccgagc tgctgttctt cgccaagcgg 480
tacaaggccg ccttcaccga gtgctgccag gccgccgaca aggccgcctg cctgctgccc 540
aagctggacg agctgcggga cgagggcaag gccagcagcg ccaagcagcg gctgaagtgc 600
gccagcctgc agaagttcgg cgagcgggcc ttcaaggcct gggccgtggc ccggctgagc 660
cagcggttcc ccaaggccga gttcgccgag gtgagcaagc tggtgaccga cctgaccaag 720
gtgcacaccg agtgctgcca cggcgacctg ctggagtgcg ccgacgaccg ggccgacctg 780
gccaagtaca tctgcgagaa ccaggacagc atcagcagca agctgaagga gtgctgcgag 840
aagcccctgc tggagaagag ccactgcatc gccgaggtgg agaacgacga gatgcccgcc 900
gacctgccca gcctggccgc cgacttcgtg gagagcaagg acgtgtgcaa gaactacgcc 960
gaggccaagg acgtgttcct gggcatgttc ctgtacgagt acgcccggcg gcaccccgac 1020
tacagcgtgg tgctgctgct gcggctggcc aagacctacg agaccaccct ggagaagtgc 1080
tgcgccgccg ccgaccccca cgagtgctac gccaaggtgt tcgacgagtt caagcccctg 1140
gtggaggagc cccagaacct gatcaagcag aactgcgagc tgttcgagca gctgggcgag 1200
tacaagttcc agaacgccct gctggtgcgg tacaccaaga aggtgcccca ggtgagcacc 1260
cccaccctgg tggaggtgag ccggaacctg ggcaaggtgg gcagcaagtg ctgcaagcac 1320
cccgaggcca agcggatgcc ctgcgccgag gactacctga gcgtggtgct gaaccagctg 1380
tgcgtgctgc acgagaagac ccccgtgagc gaccgggtga ccaagtgctg caccgagagc 1440

```
ctggtgaacc ggcggccctg cttcagcgcc ctggaggtgg acgagaccta cgtgcccaag   1500

gagttcaacg ccgagacctt caccttccac gccgacatct gcaccctgag cgagaaggag   1560

cggcagatca agaagcagac cgccctggtg gagctggtga agcacaagcc caaggccacc   1620

aaggagcagc tgaaggccgt gatggacgac ttcgccgcct tcgtggagaa gtgctgcaag   1680

gccgacgaca aggagacctg cttcgccgag gagggcaaga agctggtggc cgccagccag   1740

gccgccctgg gcctgggcag cggcggcggc ggcagcggcg gcggcggatc tggtggaggt   1800

ggcagtggag gagggggatc cgctcgcaac ggtgaccact gccctctggg tcctggtcgc   1860

tgctgccgcc tgcacaccgt tcgcgcttct ctggaagacc tgggttgggc tgactgggtt   1920

ctgtctcctc gcgaagttca ggttaccatg tgcatcggtg cttgcccttc tcagttccgc   1980

gctgctaaca tgcacgcttg gatcaaaacc tctctgcacc gcctgaaacc tgacaccgtt   2040

cctgctcctt gctgcgttcc tgcttcttac aaccctatgg ttctgatcca gaaaaccgac   2100

accggtgttt ctctgcagac ctacgacgac ctgctggcta aagactgcca ctgcatc      2157
```

<210> SEQ ID NO 92
<211> LENGTH: 735
<212> TYPE: PRT
<213> ORGANISM: Artificial Sequence
<220> FEATURE:
<223> OTHER INFORMATION: fusion protein coding sequence

<400> SEQUENCE: 92

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
    610                 615                 620

Gly Gly Ser Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
                645                 650                 655

Leu Ser Pro Arg Glu Val Gln Val Thr Met Cys Ile Gly Ala Cys Pro
```

```
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735


<210> SEQ ID NO 93
<211> LENGTH: 734
<212> TYPE: PRT
<213> ORGANISM: Artificial Sequence
<220> FEATURE:
<223> OTHER INFORMATION: fusion protein coding sequence

<400> SEQUENCE: 93

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
```

-continued

```
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
    610                 615                 620

Gly Gly Ser His Cys Pro Leu Gly Pro Gly Arg Cys Cys Arg Leu His
625                 630                 635                 640

Thr Val Arg Ala Ser Leu Glu Asp Leu Gly Trp Ala Asp Trp Val Leu
            645                 650                 655

Ser Pro Arg Glu Val Gln Val Thr Met Cys Ile Gly Ala Cys Pro Ser
            660                 665                 670

Gln Phe Arg Ala Ala Asn Met His Ala Gln Ile Lys Thr Ser Leu His
        675                 680                 685

Arg Leu Lys Pro Asp Thr Val Pro Ala Pro Cys Cys Val Pro Ala Ser
    690                 695                 700

Tyr Asn Pro Met Val Leu Ile Gln Lys Thr Asp Thr Gly Val Ser Leu
705                 710                 715                 720
```

```
Gln Thr Tyr Asp Asp Leu Leu Ala Lys Asp Cys His Cys Ile
                725                 730
```

<210> SEQ ID NO 94
<211> LENGTH: 735
<212> TYPE: PRT
<213> ORGANISM: Artificial Sequence
<220> FEATURE:
<223> OTHER INFORMATION: fusion protein coding sequence

<400> SEQUENCE: 94

```
Glu Phe His His His His His His Asp Ala His Lys Ser Glu Val Ala
1               5                   10                  15

His Arg Phe Lys Asp Leu Gly Glu Glu Asn Phe Lys Ala Leu Val Leu
            20                  25                  30

Ile Ala Phe Ala Gln Tyr Leu Gln Gln Ser Pro Phe Glu Asp His Val
        35                  40                  45

Lys Leu Val Asn Glu Val Thr Glu Phe Ala Lys Thr Cys Val Ala Asp
    50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
                85                  90                  95

Asp Cys Cys Ala Lys Gln Glu Pro Glu Arg Asn Glu Cys Phe Leu Gln
            100                 105                 110

His Lys Asp Asp Asn Pro Asn Leu Pro Arg Leu Val Arg Pro Glu Val
        115                 120                 125

Asp Val Met Cys Thr Ala Phe His Asp Asn Glu Glu Thr Phe Leu Lys
    130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
    210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
        275                 280                 285

Lys Pro Leu Leu Glu Lys Ser His Cys Ile Ala Glu Val Glu Asn Asp
    290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350
```

```
Leu Leu Leu Arg Leu Ala Lys Thr Tyr Glu Thr Thr Leu Glu Lys Cys
        355                 360                 365

Cys Ala Ala Ala Asp Pro His Glu Cys Tyr Ala Lys Val Phe Asp Glu
    370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430

Glu Val Ser Arg Asn Leu Gly Lys Val Gly Ser Lys Cys Cys Lys His
        435                 440                 445

Pro Glu Ala Lys Arg Met Pro Cys Ala Glu Asp Tyr Leu Ser Val Val
    450                 455                 460

Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
        515                 520                 525

Arg Gln Ile Lys Lys Gln Thr Ala Leu Val Glu Leu Val Lys His Lys
    530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
            580                 585                 590

Leu Gly Ser Gly Gly Gly Gly Ser Gly Gly Gly Gly Ser Gly Gly Gly
        595                 600                 605

Gly Ser Gly Gly Gly Gly Ser Leu Glu Val Leu Phe Gln Gly Pro Ala
    610                 615                 620

Arg Asn Gly Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
                645                 650                 655

Leu Ser Pro Arg Glu Val Gln Val Thr Met Cys Ile Gly Ala Cys Pro
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735
```

<210> SEQ ID NO 95
<211> LENGTH: 2205
<212> TYPE: DNA
<213> ORGANISM: Artificial Sequence
<220> FEATURE:

<223> OTHER INFORMATION: fusion protein coding sequence

<400> SEQUENCE: 95

```
gatgcacaca agagtgaggt tgctcatcgg tttaaagatt tgggagaaga aaatttcaaa      60
gccttggtgt tgattgcctt tgctcagtat cttcagcagt ccccatttga agatcatgta     120
aaattagtga atgaagtaac tgaatttgca aaaacatgtg ttgctgatga gtcagctgaa     180
aattgtgaca aatcacttca taccctttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat tttgaaaaa atacttatat     420
gaaattgcca gaagacatcc ttacttttat gccccggaac tccttttctt tgctaaaagg     480
tataaagctg cttttacaga atgttgccaa gctgctgata aagctgcctg cctgttgcca     540
aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc ctcagaattt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca agaaacaaac tgcacttgtt gagctcgtga aacacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttggaag cggcggaggg gggagtggcg gcggtggctc cgggggggc     1800
ggatccggcg gagggggcag cgggggtgga gggagtggcg ggggaggatc agggggagga    1860
ggatcaggag ggggcggaag tgatcattgc cctctcgggc ccggacggtg ttgccgcctc    1920
cacactgtga gggcttcact tgaagacctt ggatgggccg actgggtgct gtccccaaga    1980
gaggtacaag tcacaatgtg tattggcgcc tgccccagcc agtttcgcgc cgctaacatg    2040
cacgcccaga taaaaaccag cctgcaccgc ctgaagcccg acacggtgcc agcgccctgc    2100
tgcgtgcccg ccagctacaa tcccatggtg ctcattcaaa agaccgacac cggggtgtcg    2160
ctccagacct atgatgactt gttagccaaa gactgccact gcata                    2205
```

<210> SEQ ID NO 96
<211> LENGTH: 327
<212> TYPE: DNA
<213> ORGANISM: Artificial Sequence
<220> FEATURE:
<223> OTHER INFORMATION: GDF15 variant

<400> SEQUENCE: 96
ggggaccact gtccgctcgg gcccgggcgt tgctgccgtc tgcacacggt ccgcgcgtcg 60
ctggaagacc tgggctgggc cgattgggtg ctgtcgccac gggaggtgca agtgaccatg 120
tgcatcggcg cgtgcccgag ccagttccgg gcggcaaaca tgcacgcgca gatcaagacg 180
agcctgcacc gcctgaagcc cgacacggtg ccagcgccct gctgcgtgcc cgccagctac 240
aatcccatgg tgctcattca aaagaccgac accggggtgt cgctccagac ctatgatgac 300
ttgttagcca aagactgcca ctgcata 327

<210> SEQ ID NO 97
<211> LENGTH: 324
<212> TYPE: DNA
<213> ORGANISM: Artificial Sequence
<220> FEATURE:
<223> OTHER INFORMATION: GDF15 variant

<400> SEQUENCE: 97
gaccactgtc cgctcgggcc cgggcgttgc tgccgtctgc acacggtccg cgcgtcgctg 60
gaagacctgg gctgggccga ttgggtgctg tcgccacggg aggtgcaagt gaccatgtgc 120
atcggcgcgt gcccgagcca gttccgggcg gcaaacatgc acgcgcagat caagacgagc 180
ctgcaccgcc tgaagcccga cacggtgcca gcgccctgct gcgtgcccgc cagctacaat 240
cccatggtgc tcattcaaaa gaccgacacc ggggtgtcgc tccagaccta tgatgacttg 300
ttagccaaag actgccactg cata 324

<210> SEQ ID NO 98
<211> LENGTH: 324
<212> TYPE: DNA
<213> ORGANISM: Artificial Sequence
<220> FEATURE:
<223> OTHER INFORMATION: GDF15 variant

<400> SEQUENCE: 98
gatcattgcc ctctcgggcc cggacggtgt tgccgcctcc acactgtgag ggcttcactt 60
gaagaccttg gatgggccga ctgggtgctg tccccaagag aggtacaagt cacaatgtgt 120
attggcgcct gccccagcca gtttcgcgcc gctaacatgc acgcccagat aaaaaccagc 180
ctgcaccgcc tgaagcccga cacggtgcca gcgccctgct gcgtgcccgc cagctacaat 240
cccatggtgc tcattcaaaa gaccgacacc ggggtgtcgc tccagaccta tgatgacttg 300
ttagccaaag actgccactg cata 324

<210> SEQ ID NO 99
<211> LENGTH: 324
<212> TYPE: DNA
<213> ORGANISM: Artificial Sequence
<220> FEATURE:
<223> OTHER INFORMATION: GDF15 variant

<400> SEQUENCE: 99
gatcattgtc cccttggacc gggtagatgc tgtcgcctgc acactgtgcg ggcttcactg 60
gaggacctcg gctgggctga ctgggtgctg tccccacggg aggtgcaagt gaccatgtgc 120
atcggcgcct gtccttcgca attccgggcc gcgaatatgc acgcccagat caagacctcc 180
ctgcatcgcc tcaagcccga cactgtgcct gctccatgct gtgtgccggc ctcctataac 240
cccatggtgc tgatccagaa aaccgatacc ggcgtcagcc tgcagacgta tgatgatctg 300
ctggccaagg actgccattg catc 324

<210> SEQ ID NO 100
<211> LENGTH: 321
<212> TYPE: DNA
<213> ORGANISM: Artificial Sequence
<220> FEATURE:
<223> OTHER INFORMATION: GDF15 variant

<400> SEQUENCE: 100
cactgtccgc tcgggcccgg gcgttgctgc cgtctgcaca cggtccgcgc gtcgctggaa 60
gacctgggct gggccgattg ggtgctgtcg ccacgggagg tgcaagtgac catgtgcatc 120
ggcgcgtgcc cgagccagtt ccgggcggca aacatgcacg cgcagatcaa gacgagcctg 180
caccgcctga agcccgacac ggtgccagcg ccctgctgcg tgcccgccag ctacaatccc 240
atggtgctca ttcaaaagac cgacaccggg gtgtcgctcc agacctatga tgacttgtta 300
gccaaagact gccactgcat a 321

<210> SEQ ID NO 101
<211> LENGTH: 321
<212> TYPE: DNA
<213> ORGANISM: Artificial Sequence
<220> FEATURE:
<223> OTHER INFORMATION: GDF15 variant

<400> SEQUENCE: 101
cattgccctc tcgggcccgg acggtgttgc cgcctccaca ctgtgagggc ttcacttgaa 60
gaccttggat gggccgactg ggtgctgtcc ccaagagagg tacaagtcac aatgtgtatt 120
ggcgcctgcc ccagccagtt tcgcgccgct aacatgcacg cccagataaa aaccagcctg 180
caccgcctga agcccgacac ggtgccagcg ccctgctgcg tgcccgccag ctacaatccc 240
atggtgctca ttcaaaagac cgacaccggg gtgtcgctcc agacctatga tgacttgtta 300
gccaaagact gccactgcat a 321

<210> SEQ ID NO 102
<211> LENGTH: 321
<212> TYPE: DNA
<213> ORGANISM: Artificial Sequence
<220> FEATURE:
<223> OTHER INFORMATION: GDF15 variant

<400> SEQUENCE: 102
cattgtcccc ttggaccggg tagatgctgt cgcctgcaca ctgtgcgggc ttcactggag 60
gacctcggct gggctgactg ggtgctgtcc ccacgggagg tgcaagtgac catgtgcatc 120
ggcgcctgtc cttcgcaatt ccgggccgcg aatatgcacg cccagatcaa gacctccctg 180
catcgcctca agcccgacac tgtgcctgct ccatgctgtg tgccggcctc ctataacccc 240
atggtgctga tccagaaaac cgataccggc gtcagcctgc agacgtatga tgatctgctg 300
gccaaggact gccattgcat c 321

<210> SEQ ID NO 103
<211> LENGTH: 318
<212> TYPE: DNA
<213> ORGANISM: Artificial Sequence
<220> FEATURE:
<223> OTHER INFORMATION: GDF15 variant

<400> SEQUENCE: 103
tgtccgctcg ggcccgggcg ttgctgccgt ctgcacacgg tccgcgcgtc gctggaagac 60
ctgggctggg ccgattgggt gctgtcgcca cgggaggtgc aagtgaccat gtgcatcggc 120
gcgtgcccga gccagttccg ggcggcaaac atgcacgcgc agatcaagac gagcctgcac 180
cgcctgaagc ccgacacggt gccagcgccc tgctgcgtgc ccgccagcta caatcccatg 240
gtgctcattc aaaagaccga caccggggtg tcgctccaga cctatgatga cttgttagcc 300
aaagactgcc actgcata 318

<210> SEQ ID NO 104
<211> LENGTH: 318
<212> TYPE: DNA
<213> ORGANISM: Artificial Sequence
<220> FEATURE:
<223> OTHER INFORMATION: GDF15 variant

<400> SEQUENCE: 104
tgccctctcg ggcccggacg gtgttgccgc ctccacactg tgagggcttc acttgaagac 60
cttggatggg ccgactgggt gctgtcccca agagaggtac aagtcacaat gtgtattggc 120
gcctgcccca gccagtttcg cgccgctaac atgcacgccc agataaaaac cagcctgcac 180
cgcctgaagc ccgacacggt gccagcgccc tgctgcgtgc ccgccagcta caatcccatg 240
gtgctcattc aaaagaccga caccggggtg tcgctccaga cctatgatga cttgttagcc 300
aaagactgcc actgcata 318

<210> SEQ ID NO 105
<211> LENGTH: 318
<212> TYPE: DNA
<213> ORGANISM: Artificial Sequence
<220> FEATURE:
<223> OTHER INFORMATION: GDF15 variant

<400> SEQUENCE: 105
tgtccccttg gaccgggtag atgctgtcgc ctgcacactg tgcgggcttc actggaggac 60
ctcggctggg ctgactgggt gctgtcccca cgggaggtgc aagtgaccat gtgcatcggc 120
gcctgtcctt cgcaattccg ggccgcgaat atgcacgccc agatcaagac ctccctgcat 180
cgcctcaagc ccgacactgt gcctgctcca tgctgtgtgc cggcctccta taaccccatg 240
gtgctgatcc agaaaaccga taccggcgtc agcctgcaga cgtatgatga tctgctggcc 300
aaggactgcc attgcatc 318

<210> SEQ ID NO 106
<211> LENGTH: 294
<212> TYPE: DNA
<213> ORGANISM: Artificial Sequence
<220> FEATURE:
<223> OTHER INFORMATION: GDF15 variant

<400> SEQUENCE: 106
tgccgtctgc acacggtccg cgcgtcgctg gaagacctgg gctgggccga ttgggtgctg 60
tcgccacggg aggtgcaagt gaccatgtgc atcggcgcgt gcccgagcca gttccgggcg 120
gcaaacatgc acgcgcagat caagacgagc ctgcaccgcc tgaagcccga cacggtgcca 180
gcgccctgct gcgtgcccgc cagctacaat cccatggtgc tcattcaaaa gaccgacacc 240
ggggtgtcgc tccagaccta tgatgacttg ttagccaaag actgccactg cata 294

<210> SEQ ID NO 107
<211> LENGTH: 294
<212> TYPE: DNA
<213> ORGANISM: Artificial Sequence
<220> FEATURE:
<223> OTHER INFORMATION: GDF15 variant

<400> SEQUENCE: 107
tgccgcctcc acactgtgag ggcttcactt gaagaccttg gatgggccga ctgggtgctg 60
tccccaagag aggtacaagt cacaatgtgt attggcgcct gccccagcca gtttcgcgcc 120
gctaacatgc acgcccagat aaaaaccagc ctgcaccgcc tgaagcccga cacggtgcca 180
gcgccctgct gcgtgcccgc cagctacaat cccatggtgc tcattcaaaa gaccgacacc 240
ggggtgtcgc tccagaccta tgatgacttg ttagccaaag actgccactg cata 294

<210> SEQ ID NO 108
<211> LENGTH: 294
<212> TYPE: DNA
<213> ORGANISM: Artificial Sequence
<220> FEATURE:
<223> OTHER INFORMATION: GDF15 variant

<400> SEQUENCE: 108
tgtcgcctgc acactgtgcg ggcttcactg gaggacctcg gctgggctga ctgggtgctg 60
tccccacggg aggtgcaagt gaccatgtgc atcggcgcct gtccttcgca attccgggcc 120
gcgaatatgc acgcccagat caagacctcc ctgcatcgcc tcaagcccga cactgtgcct 180
gctccatgct gtgtgccggc ctcctataac cccatggtgc tgatccagaa aaccgatacc 240
ggcgtcagcc tgcagacgta tgatgatctg ctggccaagg actgccattg catc 294

<210> SEQ ID NO 109
<211> LENGTH: 2217
<212> TYPE: DNA
<213> ORGANISM: Artificial Sequence
<220> FEATURE:
<223> OTHER INFORMATION: fusion protein coding sequence

<400> SEQUENCE: 109
gatgcgcaca agtcggaagt ggcccatcgc tttaaggacc tgggagaaga gaacttcaag 60
gccctggtcc tgatcgcgtt cgcccagtac ctccagcagt ccccgtttga ggaccacgtc 120
aagcttgtga acgaagtgac cgagttcgca aagacttgtg tggccgatga gtccgccgaa 180
aactgcgaca agtccctgca caccttgttc ggagacaagc tgtgcaccgt cgcgactttg 240
cgggagactt acggcgaaat ggcggactgc tgcgcaaagc aggagcccga aaggaacgag 300
tgcttcctgc aacacaagga cgacaacccg aaccttccga gactcgtgcg gcctgaggtc 360
gacgtgatgt gcactgcatt ccatgataac gaagaaacat tcctgaagaa gtacctgtat 420
gaaattgcca gacgccaccc gtacttctac gcccccgaac tgctgttctt cgccaagaga 480
tacaaggccg cctttaccga atgttgtcaa gccgccgata aggcagcgtg cctgctgccg 540
aagttggacg agctcaggga cgaaggaaag gcctcgtccg ccaagcagag gctgaagtgc 600
gcgtcgctcc agaagtttgg agagcgggct tttaaggcct gggcagtggc taggttgagc 660
cagaggttcc ccaaggcgga gtttgccgaa gtgtccaagc tcgtgactga cctgactaaa 720
gtccataccg aatgctgcca cggcgatctg ctcgaatgcg cagatgaccg ggcggatttg 780
gccaagtaca tttgcgaaaa ccaagactcc ataagctcca agctgaagga gtgctgtgaa 840
aagcctctgc tcgagaagtc ccactgtatc gccgaggtgg agaacgacga aatgccggca 900
gacctcccta gcctggcagc cgacttcgtc gaatccaagg acgtgtgcaa gaactacgcc 960
gaagcgaagg acgtgttcct gggaatgttc ctgtacgagt acgccagacg gcatccagac 1020
tactccgtgg tgcttctctt gcggctggcc aagacttatg aaacgaccct ggagaaatgt 1080
tgcgctgctg ctgacccaca cgagtgctac gccaaagtgt tcgacgagtt taagcctctc 1140
gtggaggaac cccagaacct catcaagcag aactgcgaac ttttcgagca gctcggggag 1200
tacaagttcc aaaacgcgct gcttgtccgc tacaccaaga aagtgccgca agtgtccaca 1260
ccgaccctcg tggaagtgtc caggaacctg ggcaaagtcg gaagcaaatg ttgcaagcac 1320
cccgaagcca agcgcatgcc gtgcgcagag gactaccttt cggtggtgtt gaaccagctc 1380
tgcgtcctgc acgaaaagac cccggtgtca gaccgcgtga ccaagtgctg taccgaaagc 1440
ctcgtgaatc ggcgcccctg cttctcggcc ctggaggtgg acgaaactta cgtgccgaaa 1500
gagttcaacg cggaaacctt caccttcat gccgatatct gcaccctgtc cgagaaggag 1560
cggcagatca agaagcagac cgccctggtg gagcttgtga aacacaagcc gaaggccact 1620
aaggaacagc tgaaggccgt catggacgat ttcgctgcct tcgtcgagaa gtgctgcaag 1680
gccgacgaca aggagacttg cttcgctgaa gaagggaaga agcttgtggc cgctagccag 1740
gctgcactgg gactgggtag cggtggaggg ggatcagggg gtggtggatc gggaggagga 1800
ggatcaggag gtggcggctc aggaggaggc ggatcaggcg gtggaggatc cggaggcgga 1860
ggatcgggtg gaggaggctc agcgaggaac ggggatcatt gtccccttgg accgggtaga 1920
tgctgtcgcc tgcacactgt gcgggcttca ctggaggacc tcggctgggc tgactgggtg 1980
ctgtccccac gggaggtgca agtgaccatg tgcatcggcg cctgtccttc gcaattccgg 2040
gccgcgaata tgcacgccca gatcaagacc tccctgcatc gcctcaagcc cgacactgtg 2100
cctgctccat gctgtgtgcc ggcctcctat aaccccatgg tgctgatcca gaaaaccgat 2160
accggcgtca gcctgcagac gtatgatgat ctgctggcca aggactgcca ttgcatc 2217

<210> SEQ ID NO 110
<211> LENGTH: 2205
<212> TYPE: DNA
<213> ORGANISM: Artificial Sequence
<220> FEATURE:
<223> OTHER INFORMATION: fusion protein coding sequence

<400> SEQUENCE: 110
gatgcgcaca agtcggaagt ggcccatcgc tttaaggacc tgggagaaga gaacttcaag 60
gccctggtcc tgatcgcgtt cgcccagtac ctccagcagt ccccgtttga ggaccacgtc 120
aagcttgtga acgaagtgac cgagttcgca aagacttgtg tggccgatga gtccgccgaa 180
aactgcgaca agtccctgca caccttgttc ggagacaagc tgtgcaccgt cgcgactttg 240
cgggagactt acggcgaaat ggcggactgc tgcgcaaagc aggagcccga aaggaacgag 300
tgcttcctgc aacacaagga cgacaacccg aaccttccga gactcgtgcg gcctgaggtc 360
gacgtgatgt gcactgcatt ccatgataac gaagaaacat tcctgaagaa gtacctgtat 420
gaaattgcca gacgccaccc gtacttctac gcccccgaac tgctgttctt cgccaagaga 480
tacaaggccg cctttaccga atgttgtcaa gccgccgata aggcagcgtg cctgctgccg 540
aagttggacg agctcaggga cgaaggaaag gcctcgtccg ccaagcagag gctgaagtgc 600
gcgtcgctcc agaagtttgg agagcgggct tttaaggcct gggcagtggc taggttgagc 660

-continued

```
cagaggttcc ccaaggcgga gtttgccgaa gtgtccaagc tcgtgactga cctgactaaa     720
gtccataccg aatgctgcca cggcgatctg ctcgaatgcg cagatgaccg ggcggatttg     780
gccaagtaca tttgcgaaaa ccaagactcc ataagctcca agctgaagga gtgctgtgaa     840
aagcctctgc tcgagaagtc ccactgtatc gccgaggtgg agaacgacga aatgccggca     900
gacctcccta gcctggcagc cgacttcgtc gaatccaagg acgtgtgcaa gaactacgcc     960
gaagcgaagg acgtgttcct gggaatgttc ctgtacgagt acgccagacg gcatccagac    1020
tactccgtgg tgcttctctt gcggctggcc aagacttatg aaacgaccct ggagaaatgt    1080
tgcgctgctg ctgacccaca cgagtgctac gccaaagtgt tcgacgagtt taagcctctc    1140
gtggaggaac cccagaacct catcaagcag aactgcgaac ttttcgagca gctcggggag    1200
tacaagttcc aaaacgcgct gcttgtccgc tacaccaaga aagtgccgca agtgtccaca    1260
ccgaccctcg tggaagtgtc caggaacctg ggcaaagtcg gaagcaaatg ttgcaagcac    1320
cccgaagcca agcgcatgcc gtgcgcagag gactaccttt cggtggtgtt gaaccagctc    1380
tgcgtcctgc acgaaaagac cccggtgtca gaccgcgtga ccaagtgctg taccgaaagc    1440
ctcgtgaatc ggcgcccctg cttctcggcc ctggaggtgg acgaaactta cgtgccgaaa    1500
gagttcaacg cggaaacctt caccttcat gccgatatct gcaccctgtc cgagaaggag    1560
cggcagatca agaagcagac cgccctggtg gagcttgtga aacacaagcc gaaggccact    1620
aaggaacagc tgaaggccgt catggacgat ttcgctgcct tcgtcgagaa gtgctgcaag    1680
gccgacgaca aggagacttg cttcgctgaa gaagggaaga agcttgtggc cgctagccag    1740
gctgcactgg gactgggtag cggtggaggg ggatcagggg gtggtggatc gggaggagga    1800
ggatcaggag gtggcggctc aggaggaggc ggatcaggcg gtggaggatc cggaggcgga    1860
ggatcgggtg gaggaggctc agatcattgt ccccttggac cgggtagatg ctgtcgcctg    1920
cacactgtgc gggcttcact ggaggacctc ggctgggctg actgggtgct gtccccacgg    1980
gaggtgcaag tgaccatgtg catcggcgcc tgtccttcgc aattccgggc cgcgaatatg    2040
cacgcccaga tcaagacctc cctgcatcgc ctcaagcccg acactgtgcc tgctccatgc    2100
tgtgtgccgg cctcctataa ccccatggtg ctgatccaga aaaccgatac cggcgtcagc    2160
ctgcagacgt atgatgatct gctggccaag gactgccatt gcatc                    2205
```

<210> SEQ ID NO 111
<211> LENGTH: 734
<212> TYPE: PRT
<213> ORGANISM: Artificial Sequence
<220> FEATURE:
<223> OTHER INFORMATION: fusion protein

<400> SEQUENCE: 111

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
    610                 615                 620

Gly Gly Ser His Cys Pro Leu Gly Pro Gly Arg Cys Cys Arg Leu His
625                 630                 635                 640

Thr Val Arg Ala Ser Leu Glu Asp Leu Gly Trp Ala Asp Trp Val Leu
                645                 650                 655

Ser Pro Arg Glu Val Gln Val Thr Met Cys Ile Gly Ala Cys Pro Ser
            660                 665                 670

Gln Phe Arg Ala Ala Asn Met His Ala Gln Ile Lys Thr Ser Leu His
        675                 680                 685

Arg Leu Lys Pro Asp Thr Val Pro Ala Pro Cys Cys Val Pro Ala Ser
    690                 695                 700

Tyr Asn Pro Met Val Leu Ile Gln Lys Thr Asp Thr Gly Val Ser Leu
705                 710                 715                 720

Gln Thr Tyr Asp Asp Leu Leu Ala Lys Asp Cys His Cys Ile
                725                 730
```

<210> SEQ ID NO 112
<211> LENGTH: 725
<212> TYPE: PRT
<213> ORGANISM: Artificial Sequence
<220> FEATURE:
<223> OTHER INFORMATION: fusion protein

<400> SEQUENCE: 112

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
```

```
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Gly Ser Gly Gly Gly Gly Ser Gly
        595                 600                 605

Gly Gly Gly Ser Gly Gly Gly Gly Ser Gly Gly Gly Gly Ser Gly Gly
    610                 615                 620

Gly Gly Ser Cys Arg Leu His Thr Val Arg Ala Ser Leu Glu Asp Leu
625                 630                 635                 640

Gly Trp Ala Asp Trp Val Leu Ser Pro Arg Glu Val Gln Val Thr Met
                645                 650                 655

Cys Ile Gly Ala Cys Pro Ser Gln Phe Arg Ala Ala Asn Met His Ala
            660                 665                 670

Gln Ile Lys Thr Ser Leu His Arg Leu Lys Pro Asp Thr Val Pro Ala
        675                 680                 685

Pro Cys Cys Val Pro Ala Ser Tyr Asn Pro Met Val Leu Ile Gln Lys
    690                 695                 700

Thr Asp Thr Gly Val Ser Leu Gln Thr Tyr Asp Asp Leu Leu Ala Lys
705                 710                 715                 720

Asp Cys His Cys Ile
                725


<210> SEQ ID NO 113
<211> LENGTH: 733
<212> TYPE: PRT
<213> ORGANISM: Artificial Sequence
<220> FEATURE:
<223> OTHER INFORMATION: fusion protein

<400> SEQUENCE: 113

His Lys Ser Glu Val Ala His Arg Phe Lys Asp Leu Gly Glu Glu Asn
1               5                   10                  15

Phe Lys Ala Leu Val Leu Ile Ala Phe Ala Gln Tyr Leu Gln Gln Ser
            20                  25                  30

Pro Phe Glu Asp His Val Lys Leu Val Asn Glu Val Thr Glu Phe Ala
        35                  40                  45

Lys Thr Cys Val Ala Asp Glu Ser Ala Glu Asn Cys Asp Lys Ser Leu
    50                  55                  60

His Thr Leu Phe Gly Asp Lys Leu Cys Thr Val Ala Thr Leu Arg Glu
65                  70                  75                  80

Thr Tyr Gly Glu Met Ala Asp Cys Cys Ala Lys Gln Glu Pro Glu Arg
                85                  90                  95

Asn Glu Cys Phe Leu Gln His Lys Asp Asp Asn Pro Asn Leu Pro Arg
            100                 105                 110

Leu Val Arg Pro Glu Val Asp Val Met Cys Thr Ala Phe His Asp Asn
        115                 120                 125

Glu Glu Thr Phe Leu Lys Lys Tyr Leu Tyr Glu Ile Ala Arg Arg His
    130                 135                 140

Pro Tyr Phe Tyr Ala Pro Glu Leu Leu Phe Phe Ala Lys Arg Tyr Lys
145                 150                 155                 160

Ala Ala Phe Thr Glu Cys Cys Gln Ala Ala Asp Lys Ala Ala Cys Leu
                165                 170                 175

Leu Pro Lys Leu Asp Glu Leu Arg Asp Glu Gly Lys Ala Ser Ser Ala
            180                 185                 190

Lys Gln Arg Leu Lys Cys Ala Ser Leu Gln Lys Phe Gly Glu Arg Ala
```

-continued

```
        195                 200                 205

Phe Lys Ala Trp Ala Val Ala Arg Leu Ser Gln Arg Phe Pro Lys Ala
    210                 215                 220

Glu Phe Ala Glu Val Ser Lys Leu Val Thr Asp Leu Thr Lys Val His
225                 230                 235                 240

Thr Glu Cys Cys His Gly Asp Leu Leu Glu Cys Ala Asp Asp Arg Ala
                245                 250                 255

Asp Leu Ala Lys Tyr Ile Cys Glu Asn Gln Asp Ser Ile Ser Ser Lys
            260                 265                 270

Leu Lys Glu Cys Cys Glu Lys Pro Leu Leu Glu Lys Ser His Cys Ile
        275                 280                 285

Ala Glu Val Glu Asn Asp Glu Met Pro Ala Asp Leu Pro Ser Leu Ala
    290                 295                 300

Ala Asp Phe Val Glu Ser Lys Asp Val Cys Lys Asn Tyr Ala Glu Ala
305                 310                 315                 320

Lys Asp Val Phe Leu Gly Met Phe Leu Tyr Glu Tyr Ala Arg Arg His
                325                 330                 335

Pro Asp Tyr Ser Val Val Leu Leu Leu Arg Leu Ala Lys Thr Tyr Glu
            340                 345                 350

Thr Thr Leu Glu Lys Cys Cys Ala Ala Ala Asp Pro His Glu Cys Tyr
        355                 360                 365

Ala Lys Val Phe Asp Glu Phe Lys Pro Leu Val Glu Glu Pro Gln Asn
    370                 375                 380

Leu Ile Lys Gln Asn Cys Glu Leu Phe Glu Gln Leu Gly Glu Tyr Lys
385                 390                 395                 400

Phe Gln Asn Ala Leu Leu Val Arg Tyr Thr Lys Lys Val Pro Gln Val
                405                 410                 415

Ser Thr Pro Thr Leu Val Glu Val Ser Arg Asn Leu Gly Lys Val Gly
            420                 425                 430

Ser Lys Cys Cys Lys His Pro Glu Ala Lys Arg Met Pro Cys Ala Glu
        435                 440                 445

Asp Tyr Leu Ser Val Val Leu Asn Gln Leu Cys Val Leu His Glu Lys
    450                 455                 460

Thr Pro Val Ser Asp Arg Val Thr Lys Cys Cys Thr Glu Ser Leu Val
465                 470                 475                 480

Asn Arg Arg Pro Cys Phe Ser Ala Leu Glu Val Asp Glu Thr Tyr Val
                485                 490                 495

Pro Lys Glu Phe Asn Ala Glu Thr Phe Thr Phe His Ala Asp Ile Cys
            500                 505                 510

Thr Leu Ser Glu Lys Glu Arg Gln Ile Lys Lys Gln Thr Ala Leu Val
        515                 520                 525

Glu Leu Val Lys His Lys Pro Lys Ala Thr Lys Glu Gln Leu Lys Ala
    530                 535                 540

Val Met Asp Asp Phe Ala Ala Phe Val Glu Lys Cys Cys Lys Ala Asp
545                 550                 555                 560

Asp Lys Glu Thr Cys Phe Ala Glu Glu Gly Lys Lys Leu Val Ala Ala
                565                 570                 575

Ser Gln Ala Ala Leu Gly Leu Gly Ser Gly Gly Gly Gly Ser Gly Gly
            580                 585                 590

Gly Gly Ser Gly Gly Gly Gly Ser Gly Gly Gly Gly Ser Gly Gly Gly
        595                 600                 605

Gly Ser Gly Gly Gly Gly Ser Gly Gly Gly Gly Ser Gly Gly Gly Gly
    610                 615                 620
```

```
Ser Asp His Cys Pro Leu Gly Pro Gly Arg Cys Cys Arg Leu His Thr
625                 630                 635                 640

Val Arg Ala Ser Leu Glu Asp Leu Gly Trp Ala Asp Trp Val Leu Ser
                645                 650                 655

Pro Arg Glu Val Gln Val Thr Met Cys Ile Gly Ala Cys Pro Ser Gln
            660                 665                 670

Phe Arg Ala Ala Asn Met His Ala Gln Ile Lys Thr Ser Leu His Arg
        675                 680                 685

Leu Lys Pro Asp Thr Val Pro Ala Pro Cys Cys Val Pro Ala Ser Tyr
    690                 695                 700

Asn Pro Met Val Leu Ile Gln Lys Thr Asp Thr Gly Val Ser Leu Gln
705                 710                 715                 720

Thr Tyr Asp Asp Leu Leu Ala Lys Asp Cys His Cys Ile
                725                 730
```

<210> SEQ ID NO 114
<211> LENGTH: 2199
<212> TYPE: DNA
<213> ORGANISM: Artificial Sequence
<220> FEATURE:
<223> OTHER INFORMATION: fusion protein coding sequence

<400> SEQUENCE: 114

```
cacaagagtg aggttgctca tcggtttaaa gatttgggag aagaaaattt caaagccttg     60

gtgttgattg cctttgctca gtatcttcag cagtccccat ttgaagatca tgtaaaatta    120

gtgaatgaag taactgaatt tgcaaaaaca tgtgttgctg atgagtcagc tgaaaattgt    180

gacaaatcac ttcataccct ttttggagac aaattatgca cagttgcaac tcttcgtgaa    240

acctatggtg aaatggctga ctgctgtgca aaacaagaac ctgagagaaa tgaatgcttc    300

ttgcaacaca aagatgacaa cccaaacctc cccgattgg tgagaccaga ggttgatgtg    360

atgtgcactg cttttcatga caatgaagag acatttttga aaaaatactt atatgaaatt    420

gccagaagac atccttactt ttatgccccg gaactccttt tctttgctaa aaggtataaa    480

gctgctttta cagaatgttg ccaagctgct gataaagctg cctgcctgtt gccaaagctc    540

gatgaacttc gggatgaagg gaaggcttcg tctgccaaac agagactcaa gtgtgccagt    600

ctccaaaaat ttggagaaag agctttcaaa gcatgggcag tagctcgcct gagccagaga    660

tttcccaaag ctgagtttgc agaagtttcc aagttagtga cagatcttac caaagtccac    720

acggaatgct gccatggaga tctgcttgaa tgtgctgatg acagggcgga ccttgccaag    780

tatatctgtg aaaatcaaga ttcgatctcc agtaaactga aggaatgctg tgaaaaacct    840

ctgttggaaa aatcccactg cattgccgaa gtggaaaatg atgagatgcc tgctgacttg    900

ccttcattag ctgctgattt tgttgaaagt aaggatgttt gcaaaaacta tgctgaggca    960

aaggatgtct tcctgggcat gtttttgtat gaatatgcaa gaaggcatcc tgattactct   1020

gtcgtgctgc tgctgagact tgccaagaca tatgaaacca ctctagagaa gtgctgtgcc   1080

gctgcagatc ctcatgaatg ctatgccaaa gtgttcgatg aatttaaacc tcttgtggaa   1140

gagcctcaga atttaatcaa acaaaattgt gagctttttg agcagcttgg agagtacaaa   1200

ttccagaatg cgctattagt tcgttacacc aagaaagtac cccaagtgtc aactccaact   1260

cttgtagagg tctcaagaaa cctaggaaaa gtgggcagca aatgttgtaa acatcctgaa   1320

gcaaaaagaa tgccctgtgc agaagactat ctatccgtgg tcctgaacca gttatgtgtg   1380

ttgcatgaga aaacgccagt aagtgacaga gtcaccaaat gctgcacaga atccttggtg   1440
```

aacaggcgac catgcttttc agctctggaa gtcgatgaaa catacgttcc caaagagttt 1500
aatgctgaaa cattcacctt ccatgcagat atatgcacac tttctgagaa ggagagacaa 1560
atcaagaaac aaactgcact tgttgagctc gtgaaacaca agcccaaggc aacaaaagag 1620
caactgaaag ctgttatgga tgatttcgca gcttttgtag agaagtgctg caaggctgac 1680
gataaggaga cctgctttgc cgaggagggt aaaaaacttg ttgctgcaag tcaagctgcc 1740
ttagggcttg gaagcggcgg aggggggagt ggcggcggtg gctccggggg gggcggatcc 1800
ggcggagggg gcagcggggg tggagggagt ggcgggggag gatcaggggg aggaggatca 1860
ggagggggcg gaagtgatca ttgccctctc gggcccggac ggtgttgccg cctccacact 1920
gtgagggctt cacttgaaga ccttggatgg gccgactggg tgctgtcccc aagagaggta 1980
caagtcacaa tgtgtattgg cgcctgcccc agccagtttc gcgccgctaa catgcacgcc 2040
cagataaaaa ccagcctgca ccgcctgaag cccgacacgg tgccagcgcc ctgctgcgtg 2100
cccgccagct acaatcccat ggtgctcatt caaaagaccg acaccggggt gtcgctccag 2160
acctatgatg acttgttagc caaagactgc cactgcata 2199

<210> SEQ ID NO 115
<211> LENGTH: 735
<212> TYPE: PRT
<213> ORGANISM: Artificial Sequence
<220> FEATURE:
<223> OTHER INFORMATION: fusion protein

<400> SEQUENCE: 115

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ala Gly Gly Gly Gly Ala
            580                 585                 590

Gly Gly Gly Gly Ala Gly Gly Gly Gly Ala Gly Gly Gly Gly Ala Gly
        595                 600                 605

Gly Gly Gly Ala Gly Gly Gly Gly Ala Gly Gly Gly Gly Ala Gly Gly
    610                 615                 620

Gly Gly Ala Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
```

```
                645                 650                 655

Leu Ser Pro Arg Glu Val Gln Val Thr Met Cys Ile Gly Ala Cys Pro
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735


<210> SEQ ID NO 116
<211> LENGTH: 2205
<212> TYPE: DNA
<213> ORGANISM: Artificial Sequence
<220> FEATURE:
<223> OTHER INFORMATION: fusion protein coding sequence

<400> SEQUENCE: 116

gatgcacaca agagtgaggt tgctcatcgg tttaaagatt tgggagaaga aaatttcaaa     60

gccttggtgt tgattgcctt tgctcagtat cttcagcagt ccccatttga agatcatgta    120

aaattagtga atgaagtaac tgaatttgca aaaacatgtg ttgctgatga gtcagctgaa    180

aattgtgaca aatcacttca taccctttttt ggagacaaat tatgcacagt tgcaactctt    240

cgtgaaacct atggtgaaat ggctgactgc tgtgcaaaac aagaacctga gagaaatgaa    300

tgcttcttgc aacacaaaga tgacaaccca aacctccccc gattggtgag accagaggtt    360

gatgtgatgt gcactgcttt tcatgacaat gaagagacat tttgaaaaa atacttatat    420

gaaattgcca gaagacatcc ttacttttat gccccggaac tccttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagaag gcatcctgat   1020

tactctgtcg tgctgctgct gagacttgcc aagacatatg aaaccactct agagaagtgc   1080

tgtgccgctg cagatcctca tgaatgctat gccaaagtgt tcgatgaatt taaacctctt   1140

gtggaagagc ctcagaattt aatcaaacaa aattgtgagc tttttgagca gcttggagag   1200

tacaaattcc agaatgcgct attagttcgt tacaccaaga aagtacccca agtgtcaact   1260

ccaactcttg tagaggtctc aagaaaccta ggaaaagtgg gcagcaaatg ttgtaaacat   1320

cctgaagcaa aaagaatgcc ctgtgcagaa gactatctat ccgtggtcct gaaccagtta   1380

tgtgtgttgc atgagaaaac gccagtaagt gacagagtca ccaaatgctg cacagaatcc   1440

ttggtgaaca ggcgaccatg cttttcagct ctggaagtcg atgaaacata cgttcccaaa   1500

gagtttaatg ctgaaacatt caccttccat gcagatatat gcacactttc tgagaaggag   1560
```

agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag ggcttggtgc tggaggaggc ggggcgggcg gcgggggtgc cggtgggggt 1800
ggcgcagggg gaggtggtgc gggtggtggt ggggctggtg ggggaggtgc aggcggtggc 1860
ggtgccgggg ggggtggcgc ggatcattgc cctctcgggc ccggacggtg ttgccgcctc 1920
cacactgtga gggcttcact tgaagacctt ggatgggccg actgggtgct gtccccaaga 1980
gaggtacaag tcacaatgtg tattggcgcc tgccccagcc agtttcgcgc cgctaacatg 2040
cacgcccaga taaaaaccag cctgcaccgc ctgaagcccg acacggtgcc agcgccctgc 2100
tgcgtgcccg ccagctacaa tcccatggtg ctcattcaaa agaccgacac cggggtgtcg 2160
ctccagacct atgatgactt gttagccaaa gactgccact gcata 2205

<210> SEQ ID NO 117
<211> LENGTH: 713
<212> TYPE: PRT
<213> ORGANISM: Artificial Sequence
<220> FEATURE:
<223> OTHER INFORMATION: fusion protein

<400> SEQUENCE: 117

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

-continued

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Asp His Cys
        595                 600                 605

Pro Leu Gly Pro Gly Arg Cys Cys Arg Leu His Thr Val Arg Ala Ser
    610                 615                 620

Leu Glu Asp Leu Gly Trp Ala Asp Trp Val Leu Ser Pro Arg Glu Val
625                 630                 635                 640

Gln Val Thr Met Cys Ile Gly Ala Cys Pro Ser Gln Phe Arg Ala Ala
                645                 650                 655

Asn Met His Ala Gln Ile Lys Thr Ser Leu His Arg Leu Lys Pro Asp
            660                 665                 670
```

-continued

Thr Val Pro Ala Pro Cys Cys Val Pro Ala Ser Tyr Asn Pro Met Val
        675                 680                 685

Leu Ile Gln Lys Thr Asp Thr Gly Val Ser Leu Gln Thr Tyr Asp Asp
    690                 695                 700

Leu Leu Ala Lys Asp Cys His Cys Ile
705                 710

<210> SEQ ID NO 118
<211> LENGTH: 2139
<212> TYPE: DNA
<213> ORGANISM: Artificial Sequence
<220> FEATURE:
<223> OTHER INFORMATION: fusion protein coding sequence

<400> SEQUENCE: 118
gatgcacaca agagtgaggt tgctcatcgg tttaaagatt tgggagaaga aaatttcaaa 60
gccttggtgt tgattgcctt tgctcagtat cttcagcagt ccccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300
tgcttcttgc aacacaaaga tgacaaccca aacctccccc gattggtgag accagaggtt 360
gatgtgatgt gcactgcttt tcatgacaat gaagagacat tttgaaaaa atacttatat 420 gaaattgcca gaagacatcc ttacttttat gccccggaac tcctttctt tgctaaaagg 480 tataaagctg cttttacaga atgttgccaa gctgctgata aagctgcctg cctgttgcca 540
aagctcgatg aacttcggga tgaagggaag gcttcgtctg ccaaacagag actcaagtgt 600
gccagtctcc aaaaatttgg agaaagagct ttcaaagcat gggcagtagc tcgcctgagc 660
cagagatttc ccaaagctga gtttgcagaa gtttccaagt tagtgacaga tcttaccaaa 720
gtccacacgg aatgctgcca tggagatctg cttgaatgtg ctgatgacag ggcggacctt 780
gccaagtata tctgtgaaaa tcaagattcg atctccagta aactgaagga atgctgtgaa 840
aaacctctgt tggaaaaatc ccactgcatt gccgaagtgg aaaatgatga gatgcctgct 900
gacttgcctt cattagctgc tgattttgtt gaaagtaagg atgtttgcaa aaactatgct 960
gaggcaaagg atgtcttcct gggcatgttt ttgtatgaat atgcaagaag gcatcctgat 1020
tactctgtcg tgctgctgct gagacttgcc aagacatatg aaaccactct agagaagtgc 1080
tgtgccgctg cagatcctca tgaatgctat gccaaagtgt tcgatgaatt taaacctctt 1140
gtggaagagc ctcagaattt aatcaaacaa aattgtgagc tttttgagca gcttggagag 1200
tacaaattcc agaatgcgct attagttcgt tacaccaaga aagtacccca agtgtcaact 1260
ccaactcttg tagaggtctc aagaaaccta ggaaaagtgg gcagcaaatg ttgtaaacat 1320
cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc 1440
ttggtgaaca ggcgaccatg cttttcagct ctggaagtcg atgaaacata cgttcccaaa 1500
gagtttaatg ctgaaacatt caccttccat gcagatatat gcacactttc tgagaaggag 1560
agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag ggcttgcacc agcccctgcc cctgcacctg cacctgctcc cgcaccggct 1800

-continued

```
ccagccccag ctccggatca ttgccctctc gggcccggac ggtgttgccg cctccacact   1860

gtgagggctt cacttgaaga ccttggatgg gccgactggg tgctgtcccc aagagaggta   1920

caagtcacaa tgtgtattgg cgcctgcccc agccagtttc gcgccgctaa catgcacgcc   1980

cagataaaaa ccagcctgca ccgcctgaag cccgacacgg tgccagcgcc ctgctgcgtg   2040

cccgccagct acaatcccat ggtgctcatt caaaagaccg acaccggggt gtcgctccag   2100

acctatgatg acttgttagc caaagactgc cactgcata                          2139
```

```
<210> SEQ ID NO 119
<211> LENGTH: 717
<212> TYPE: PRT
<213> ORGANISM: Artificial Sequence
<220> FEATURE:
<223> OTHER INFORMATION: fusion protein

<400> SEQUENCE: 119

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

-continued

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Ala Pro Ala
        595                 600                 605

Pro Asp His Cys Pro Leu Gly Pro Gly Arg Cys Cys Arg Leu His Thr
    610                 615                 620

Val Arg Ala Ser Leu Glu Asp Leu Gly Trp Ala Asp Trp Val Leu Ser
625                 630                 635                 640

Pro Arg Glu Val Gln Val Thr Met Cys Ile Gly Ala Cys Pro Ser Gln
                645                 650                 655

Phe Arg Ala Ala Asn Met His Ala Gln Ile Lys Thr Ser Leu His Arg
            660                 665                 670

Leu Lys Pro Asp Thr Val Pro Ala Pro Cys Cys Val Pro Ala Ser Tyr
        675                 680                 685

Asn Pro Met Val Leu Ile Gln Lys Thr Asp Thr Gly Val Ser Leu Gln
    690                 695                 700

Thr Tyr Asp Asp Leu Leu Ala Lys Asp Cys His Cys Ile
705                 710                 715
```

<210> SEQ ID NO 120
<211> LENGTH: 2151
<212> TYPE: DNA
<213> ORGANISM: Artificial Sequence
<220> FEATURE:
<223> OTHER INFORMATION: fusion protein coding sequence

<400> SEQUENCE: 120
gatgcacaca agagtgaggt tgctcatcgg tttaaagatt tgggagaaga aaatttcaaa 60
gccttggtgt tgattgcctt tgctcagtat cttcagcagt ccccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300
tgcttcttgc aacacaaaga tgacaaccca aacctccccc gattggtgag accagaggtt 360
gatgtgatgt gcactgcttt tcatgacaat gaagagacat tttgaaaaa atacttatat 420 gaaattgcca gaagacatcc ttacttttat gccccggaac tcctttctt tgctaaaagg 480 tataaagctg cttttacaga atgttgccaa gctgctgata aagctgcctg cctgttgcca 540
aagctcgatg aacttcggga tgaagggaag gcttcgtctg ccaaacagag actcaagtgt 600
gccagtctcc aaaaatttgg agaaagagct ttcaaagcat gggcagtagc tcgcctgagc 660
cagagatttc ccaaagctga gtttgcagaa gtttccaagt tagtgacaga tcttaccaaa 720
gtccacacgg aatgctgcca tggagatctg cttgaatgtg ctgatgacag ggcggacctt 780
gccaagtata tctgtgaaaa tcaagattcg atctccagta aactgaagga atgctgtgaa 840
aaacctctgt tggaaaaatc ccactgcatt gccgaagtgg aaaatgatga gatgcctgct 900
gacttgcctt cattagctgc tgattttgtt gaaagtaagg atgtttgcaa aaactatgct 960
gaggcaaagg atgtcttcct gggcatgttt ttgtatgaat atgcaagaag gcatcctgat 1020
tactctgtcg tgctgctgct gagacttgcc aagacatatg aaaccactct agagaagtgc 1080
tgtgccgctg cagatcctca tgaatgctat gccaaagtgt tcgatgaatt taaacctctt 1140
gtggaagagc ctcagaattt aatcaaacaa aattgtgagc tttttgagca gcttggagag 1200
tacaaattcc agaatgcgct attagttcgt tacaccaaga aagtacccca agtgtcaact 1260
ccaactcttg tagaggtctc aagaaaccta ggaaaagtgg gcagcaaatg ttgtaaacat 1320
cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc 1440
ttggtgaaca ggcgaccatg cttttcagct ctggaagtcg atgaaacata cgttcccaaa 1500
gagtttaatg ctgaaacatt caccttccat gcagatatat gcacactttc tgagaaggag 1560
agacaaatca agaaacaaac tgcacttgtt gagctcgtga aacacaagcc caaggcaaca 1620
aaagagcaac tgaaagctgt tatggatgat ttcgcagctt ttgtagagaa gtgctgcaag 1680
gctgacgata aggagacctg ctttgccgag gagggtaaaa aacttgttgc tgcaagtcaa 1740
gctgccttag ggcttgcacc agcccctgcc cctgcacctg cacctgctcc cgcaccggct 1800
ccagccccag ctccggctcc agctcctgat cattgccctc tcgggcccgg acggtgttgc 1860
cgcctccaca ctgtgagggc ttcacttgaa gaccttggat gggccgactg ggtgctgtcc 1920
ccaagagagg tacaagtcac aatgtgtatt ggcgcctgcc ccagccagtt tcgcgccgct 1980
aacatgcacg cccagataaa aaccagcctg caccgcctga agcccgacac ggtgccagcg 2040
ccctgctgcg tgcccgccag ctacaatccc atggtgctca ttcaaaagac cgacaccggg 2100

```
gtgtcgctcc agacctatga tgacttgtta gccaaagact gccactgcat a          2151


<210> SEQ ID NO 121
<211> LENGTH: 741
<212> TYPE: PRT
<213> ORGANISM: Artificial Sequence
<220> FEATURE:
<223> OTHER INFORMATION: fusion protein

<400> SEQUENCE: 121

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
```

```
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Glu Gly Lys Ser
            580                 585                 590

Ser Gly Ser Gly Ser Glu Ser Lys Ser Thr Glu Gly Lys Ser Ser Gly
        595                 600                 605

Ser Gly Ser Glu Ser Lys Ser Thr Glu Gly Lys Ser Ser Gly Ser Gly
    610                 615                 620

Ser Glu Ser Lys Ser Thr Gly Gly Ser Asp His Cys Pro Leu Gly Pro
625                 630                 635                 640

Gly Arg Cys Cys Arg Leu His Thr Val Arg Ala Ser Leu Glu Asp Leu
                645                 650                 655

Gly Trp Ala Asp Trp Val Leu Ser Pro Arg Glu Val Gln Val Thr Met
            660                 665                 670

Cys Ile Gly Ala Cys Pro Ser Gln Phe Arg Ala Ala Asn Met His Ala
        675                 680                 685

Gln Ile Lys Thr Ser Leu His Arg Leu Lys Pro Asp Thr Val Pro Ala
    690                 695                 700

Pro Cys Cys Val Pro Ala Ser Tyr Asn Pro Met Val Leu Ile Gln Lys
705                 710                 715                 720

Thr Asp Thr Gly Val Ser Leu Gln Thr Tyr Asp Asp Leu Leu Ala Lys
                725                 730                 735

Asp Cys His Cys Ile
            740
```

<210> SEQ ID NO 122
<211> LENGTH: 2223
<212> TYPE: DNA
<213> ORGANISM: Artificial Sequence
<220> FEATURE:
<223> OTHER INFORMATION: fusion protein coding sequence

<400> SEQUENCE: 122

```
gatgcacaca agagtgaggt tgctcatcgg tttaaagatt tgggagaaga aaatttcaaa     60
gccttggtgt tgattgcctt tgctcagtat cttcagcagt ccccatttga agatcatgta    120
aaattagtga atgaagtaac tgaatttgca aaaacatgtg ttgctgatga gtcagctgaa    180
aattgtgaca aatcacttca taccctttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat tttgaaaaa atacttatat    420
gaaattgcca gaagacatcc ttacttttat gccccggaac tccttttctt tgctaaaagg    480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca caaaatgctg tactgagagc   1440
ttggtcaaca ggcggccgtg cttcagcgcc ctcgaggtgg atgagactta tgtcccaaag   1500
gagtttaatg cggaaacttt tactttccac gcagacattt gcaccttgtc tgaaaaggaa   1560
agacagatta agaaacagac tgctcttgtg gaactggtaa aacataaacc aaaagctacg   1620
aaggagcagc ttaaggctgt tatggatgat ttcgccgcgt ttgtcgagaa gtgctgcaaa   1680
gcggacgata aggaaacttg ctttgcagag gaaggtaaga aactcgtagc ggcaagtcag   1740
gctgcgcttg gccttggagg cagtgaaggc aaatcctctg ggagtggctc tgaaagtaaa   1800
tccaccgagg gcaaatccag tggatctggg tctgaatcta agtctaccga ggggaagtct   1860
tctggcagtg ggtcagaatc taaatctaca ggcggctctg accattgccc gttgggacca   1920
ggacgctgct gtcgccttca tacagtgcga gcgagtttgg aagacctggg ctgggctgac   1980
tgggtgctta gccctcggga ggtccaggtc acaatgtgca ttggcgcgtg tcccagtcaa   2040
tttagagcag caaatatgca cgcccaaata aaaacctccc tgcataggct taagccagat   2100
actgtccccg caccatgctg tgtgcctgct tcttacaatc ctatggtact catccagaag   2160
accgacacgg gagttagcct ccagacttat gacgacctct tggctaaaga ttgccattgt   2220
```

-continued att 2223

<210> SEQ ID NO 123
<211> LENGTH: 735
<212> TYPE: PRT
<213> ORGANISM: Artificial Sequence
<220> FEATURE:
<223> OTHER INFORMATION: fusion protein

<400> SEQUENCE: 123

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
```

```
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Pro Gly Gly Gly Ser
            580                 585                 590

Pro Gly Gly Gly Ser Pro Gly Gly Gly Ser Pro Gly Gly Gly Ser Pro
        595                 600                 605

Gly Gly Gly Ser Pro Gly Gly Gly Ser Pro Gly Gly Gly Ser Pro Gly
    610                 615                 620

Gly Gly Ser Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
                645                 650                 655

Leu Ser Pro Arg Glu Val Gln Val Thr Met Cys Ile Gly Ala Cys Pro
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735
```

<210> SEQ ID NO 124
<211> LENGTH: 2205
<212> TYPE: DNA
<213> ORGANISM: Artificial Sequence
<220> FEATURE:
<223> OTHER INFORMATION: fusion protein coding sequence

<400> SEQUENCE: 124

```
gatgcacaca agagtgaggt tgctcatcgg tttaaagatt tgggagaaga aaatttcaaa     60
gccttggtgt tgattgcctt tgctcagtat cttcagcagt ccccatttga agatcatgta    120
aaattagtga atgaagtaac tgaatttgca aaaacatgtg ttgctgatga gtcagctgaa    180
aattgtgaca aatcacttca taccctttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat tttgaaaaa atacttatat     420
gaaattgcca gaagacatcc ttacttttat gccccggaac tccttttctt tgctaaaagg    480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca cgaaatgttg cacagagtca   1440
ctggtcaaca ggagaccttg cttctccgct cttgaggttg acgaaacgta tgtcccaaaa   1500
gagttcaacg ccgaaacgtt tacgtttcat gcggacatat gcactctcag tgagaaggag   1560
cgacaaatca aaaaacagac tgctcttgta gagttggtaa aacacaaacc taaagcaaca   1620
aaagagcaat tgaaagctgt gatggacgat tttgcagctt tcgtagaaaa gtgctgcaag   1680
gccgacgata aagaaacctg tttcgctgaa gaaggcaaaa aacttgttgc ggcatctcag   1740
gccgctcttg gacttgggag cccgggtggc gggtctccag gcggaggctc tccgggcgga   1800
ggtagtcccg gagggggtag tccgggcggc ggttctccag gtggaggttc tcctggtggt   1860
ggcagtcctg gcggaggatc tgatcactgt ccccttgggc ccgggaggtg ctgccgactt   1920
catacagttc gcgccagcct tgaagatttg ggtgggccg actgggtgtt gagcccgaga    1980
gaggtccaag tcacgatgtg tattggagcc tgtccctctc aattccgagc cgcaaatatg   2040
catgcgcaaa taaagacgag tctccatcgg ttgaagcctg atactgtccc agctccgtgc   2100
tgcgtccccg cgagttataa tcccatggtc cttatacaga aacagacac tggtgtcagc    2160
cttcagacgt atgacgattt gcttgctaaa gactgtcatt gtatt                   2205
```

<210> SEQ ID NO 125
<211> LENGTH: 735

```
<212> TYPE: PRT
<213> ORGANISM: Artificial Sequence
<220> FEATURE:
<223> OTHER INFORMATION: fusion protein

<400> SEQUENCE: 125

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380
```

```
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Ala Gly Gly Gly Ser
            580                 585                 590

Ala Gly Gly Gly Ser Ala Gly Gly Gly Ser Ala Gly Gly Gly Ser Ala
        595                 600                 605

Gly Gly Gly Ser Ala Gly Gly Gly Ser Ala Gly Gly Gly Ser Ala Gly
    610                 615                 620

Gly Gly Ser Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
                645                 650                 655

Leu Ser Pro Arg Glu Val Gln Val Thr Met Cys Ile Gly Ala Cys Pro
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735


<210> SEQ ID NO 126
<211> LENGTH: 2205
<212> TYPE: DNA
<213> ORGANISM: Artificial Sequence
<220> FEATURE:
<223> OTHER INFORMATION: fusion protein coding sequence

<400> SEQUENCE: 126

gatgcacaca agagtgaggt tgctcatcgg tttaaagatt tgggagaaga aaatttcaaa      60

gccttggtgt tgattgcctt tgctcagtat cttcagcagt ccccatttga agatcatgta     120
```

```
aaattagtga atgaagtaac tgaatttgca aaaacatgtg ttgctgatga gtcagctgaa    180
aattgtgaca aatcacttca taccctttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat tttgaaaaa atacttatat    420
gaaattgcca gaagacatcc ttacttttat gccccggaac tccttttctt tgctaaaagg    480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ctaaatgttg taccgagtct   1440
cttgttaata ggcggccatg cttcagtgca ttggaagtcg acgaaaccta tgtaccaaag   1500
gagttcaacg cagaaacatt tacattccat gctgatatct gcacattgag cgagaaagag   1560
agacagatta agaaacagac agcgcttgtt gaactggtta aacacaaacc aaaagctacc   1620
aaggagcagc ttaaggcagt aatggatgac ttcgcggcct ttgtcgagaa atgttgtaaa   1680
gcggatgata aagagacatg cttcgccgaa gagggcaaaa aacttgtagc ggcaagccag   1740
gccgcactgg gtctcggtag tgcgggcggt ggttcagcgg ggggaggatc tgcaggtggt   1800
ggctcagcgg gtggcggtag cgctgggggg ggctccgcag gtgggggatc agcaggcggc   1860
ggatcagccg gcggtggatc cgaccactgt cctctcgggc ctggtcggtg ttgccgcctc   1920
catactgtgc gcgcgtctct tgaggatctg ggtgggctg attgggttct ctctccccgc   1980
gaagtgcagg tgaccatgtg tattggtgct tgcccaagtc aattccgagc agctaacatg   2040
cacgcccaga tcaagactag cctgcatcgg cttaagcccg acactgttcc tgccccttgc   2100
tgtgttcctg catcttataa tccaatggtc ctgatccaga aaaccgatac gggtgtatca   2160
ttgcaaacat acgacgactt gcttgccaaa gattgccatt gcatt                   2205
```

<210> SEQ ID NO 127
<211> LENGTH: 727
<212> TYPE: PRT
<213> ORGANISM: Artificial Sequence
<220> FEATURE:
<223> OTHER INFORMATION: fusion protein

<400> SEQUENCE: 127

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Glu Gly Lys Ser
            580                 585                 590

Ser Gly Ser Gly Ser Glu Ser Lys Ser Thr Glu Gly Lys Ser Ser Gly
        595                 600                 605

Ser Gly Ser Glu Ser Lys Ser Thr Gly Gly Ser Asp His Cys Pro Leu
    610                 615                 620

Gly Pro Gly Arg Cys Cys Arg Leu His Thr Val Arg Ala Ser Leu Glu
625                 630                 635                 640

Asp Leu Gly Trp Ala Asp Trp Val Leu Ser Pro Arg Glu Val Gln Val
                645                 650                 655

Thr Met Cys Ile Gly Ala Cys Pro Ser Gln Phe Arg Ala Ala Asn Met
            660                 665                 670

His Ala Gln Ile Lys Thr Ser Leu His Arg Leu Lys Pro Asp Thr Val
        675                 680                 685

Pro Ala Pro Cys Cys Val Pro Ala Ser Tyr Asn Pro Met Val Leu Ile
    690                 695                 700

Gln Lys Thr Asp Thr Gly Val Ser Leu Gln Thr Tyr Asp Asp Leu Leu
705                 710                 715                 720

Ala Lys Asp Cys His Cys Ile
                725
```

<210> SEQ ID NO 128
<211> LENGTH: 2181
<212> TYPE: DNA
<213> ORGANISM: Artificial Sequence
<220> FEATURE:
<223> OTHER INFORMATION: fusion protein coding sequence

<400> SEQUENCE: 128

```
gatgcacaca agagtgaggt tgctcatcgg tttaaagatt tgggagaaga aaatttcaaa      60

gccttggtgt tgattgcctt tgctcagtat cttcagcagt ccccatttga agatcatgta     120

aaattagtga atgaagtaac tgaatttgca aaaacatgtg ttgctgatga gtcagctgaa     180

aattgtgaca aatcacttca taccctttt ggagacaaat tatgcacagt tgcaactctt      240
```

-continued

```
cgtgaaacct atggtgaaat ggctgactgc tgtgcaaaac aagaacctga gagaaatgaa    300

tgcttcttgc aacacaaaga tgacaaccca aacctccccc gattggtgag accagaggtt    360

gatgtgatgt gcactgcttt tcatgacaat gaagagacat ttttgaaaaa atacttatat    420

gaaattgcca gaagacatcc ttacttttat gccccggaac tccttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagaag gcatcctgat   1020

tactctgtcg tgctgctgct gagacttgcc aagacatatg aaaccactct agagaagtgc   1080

tgtgccgctg cagatcctca tgaatgctat gccaaagtgt tcgatgaatt taaacctctt   1140

gtggaagagc ctcagaattt aatcaaacaa aattgtgagc tttttgagca gcttggagag   1200

tacaaattcc agaatgcgct attagttcgt tacaccaaga aagtacccca agtgtcaact   1260

ccaactcttg tagaggtctc aagaaaccta ggaaaagtgg gcagcaaatg ttgtaaacat   1320

cctgaagcaa aaagaatgcc ctgtgcagaa gactatctat ccgtggtcct gaaccagtta   1380

tgtgtgttgc atgagaaaac gccagtaagt gacagagtca cgaaatgctg tacagaatcc   1440

ctcgtgaata gaaggccctg cttctctgcc cttgaggtgg acgagactta cgtccctaag   1500

gagtttaacg ccgagacctt tacttttcat gctgatattt gcaccctttc cgaaaaggag   1560

cggcagatca agaaacaaac agccttggtg gaactcgtaa aacataaacc caaagccacc   1620

aaggaacaac ttaaagctgt tatggatgac ttcgcagcct tcgtcgagaa atgttgcaag   1680

gcggatgata aggaaacgtg ttttgctgag gaagggaaga agttggttgc tgcctctcaa   1740

gcggctctgg ggcttggcgg atcagagggg aagtcctccg ggtccggtag cgagtccaaa   1800

tctacggaag ggaagtcatc cggttctggg tcagagtcca aatccacagg aggatcagac   1860

cattgcccat tgggaccagg acgatgttgt cgcctgcata cggtaagagc gtctctggag   1920

gatctcggct gggccgattg ggttctctca ccacgagaag tacaggtcac aatgtgcata   1980

ggagcttgtc cgagccaatt ccgggcggct aatatgcacg cacagatcaa gacctctttg   2040

caccgcttga agcccgatac cgtgccagca ccgtgttgcg tcccagcatc ttacaaccct   2100

atggttttga tacagaaaac tgacacaggt gtgagcctcc agacatatga tgatttgctg   2160

gctaaggatt gccactgtat a                                             2181
```

<210> SEQ ID NO 129
<211> LENGTH: 100
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(100)
<223> OTHER INFORMATION: synthetic linker, wherein the amino acid
sequence GGGGS is a repeating unit that can be repeated 2-20
times, thus any or all of the GGGGS repeating units from amino acids 11 to 100 can either be present or absent

<400> SEQUENCE: 129

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100
```

<210> SEQ ID NO 130
<211> LENGTH: 100
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(100)
<223> OTHER INFORMATION: synthetic linker, wherein the amino acid sequence EAAAK is a repeating unit that can be repeated 2-20 times, thus any or all of the EAAAK repeating units from amino acids 11 to 100 can either be present or absent

<400> SEQUENCE: 130

```
Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Glu
                85                  90                  95

Ala Ala Ala Lys
            100
```

<210> SEQ ID NO 131
<211> LENGTH: 100
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(100)
<223> OTHER INFORMATION: synthetic linker, wherein the amino acid sequence GGGGA is a repeating unit that can be repeated 2-20 times, thus any or all of the GGGGA repeating units from amino acids 11 to 100 can either be present or absent

<400> SEQUENCE: 131

```
Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Gly Ala Gly Gly
            20                  25                  30

Gly Gly Ala Gly Gly Gly Gly Ala Gly Gly Gly Gly Ala Gly Gly Gly
        35                  40                  45

Gly Ala Gly Gly Gly Gly Ala Gly Gly Gly Gly Ala Gly Gly Gly Gly
    50                  55                  60

Ala Gly Gly Gly Gly Ala Gly Gly Gly Gly Ala Gly Gly Gly Gly Ala
65                  70                  75                  80

Gly Gly Gly Gly Ala Gly Gly Gly Gly Ala Gly Gly Gly Gly Ala Gly
                85                  90                  95

Gly Gly Gly Ala
            100


<210> SEQ ID NO 132
<211> LENGTH: 100
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(100)
<223> OTHER INFORMATION: synthetic linker, wherein the amino acid
      sequence PGGGS is a repeating unit that can be repeated 2-20
      times, thus any or all of the PGGGS repeating units from amino
      acids 11 to 100 can either be present or absent

<400> SEQUENCE: 132

Pro Gly Gly Gly Ser Pro Gly Gly Gly Ser Pro Gly Gly Gly Ser Pro
1               5                   10                  15

Gly Gly Gly Ser Pro Gly Gly Gly Ser Pro Gly Gly Gly Ser Pro Gly
            20                  25                  30

Gly Gly Ser Pro Gly Gly Gly Ser Pro Gly Gly Gly Ser Pro Gly Gly
        35                  40                  45

Gly Ser Pro Gly Gly Gly Ser Pro Gly Gly Gly Ser Pro Gly Gly Gly
    50                  55                  60

Ser Pro Gly Gly Gly Ser Pro Gly Gly Gly Ser Pro Gly Gly Gly Ser
65                  70                  75                  80

Pro Gly Gly Gly Ser Pro Gly Gly Gly Ser Pro Gly Gly Gly Ser Pro
                85                  90                  95

Gly Gly Gly Ser
            100


<210> SEQ ID NO 133
<211> LENGTH: 100
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (11)..(100)
<223> OTHER INFORMATION: synthetic linker, wherein the amino acid
      sequence AGGGS is a repeating unit that can be repeated 2-20
      times, thus any or all of the AGGGS repeating units from amino
      acids 11 to 100 can either be present or absent

<400> SEQUENCE: 133

Ala Gly Gly Gly Ser Ala Gly Gly Gly Ser Ala Gly Gly Gly Ser Ala
1               5                   10                  15
```

```
Gly Gly Gly Ser Ala Gly Gly Gly Ser Ala Gly Gly Gly Ser Ala Gly
            20                  25                  30

Gly Gly Ser Ala Gly Gly Gly Ser Ala Gly Gly Gly Ser Ala Gly Gly
        35                  40                  45

Gly Ser Ala Gly Gly Gly Ser Ala Gly Gly Gly Ser Ala Gly Gly Gly
    50                  55                  60

Ser Ala Gly Gly Gly Ser Ala Gly Gly Gly Ser Ala Gly Gly Gly Ser
65                  70                  75                  80

Ala Gly Gly Gly Ser Ala Gly Gly Gly Ser Ala Gly Gly Gly Ser Ala
                85                  90                  95

Gly Gly Gly Ser
            100


<210> SEQ ID NO 134
<211> LENGTH: 286
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (32)..(283)
<223> OTHER INFORMATION: synthetic linker, wherein the amino acid
      sequence EGKSSGSGSESKST is a repeating unit that can be repeated
      2-20 times, thus any or all of the EGKSSGSGSESKST repeating units
      from amino acids 32 to 283 can either be present or absent

<400> SEQUENCE: 134

Gly Gly Ser Glu Gly Lys Ser Ser Gly Ser Gly Ser Glu Ser Lys Ser
1               5                   10                  15

Thr Glu Gly Lys Ser Ser Gly Ser Gly Ser Glu Ser Lys Ser Thr Glu
            20                  25                  30

Gly Lys Ser Ser Gly Ser Gly Ser Glu Ser Lys Ser Thr Glu Gly Lys
        35                  40                  45

Ser Ser Gly Ser Gly Ser Glu Ser Lys Ser Thr Glu Gly Lys Ser Ser
    50                  55                  60

Gly Ser Gly Ser Glu Ser Lys Ser Thr Glu Gly Lys Ser Ser Gly Ser
65                  70                  75                  80

Gly Ser Glu Ser Lys Ser Thr Glu Gly Lys Ser Ser Gly Ser Gly Ser
                85                  90                  95

Glu Ser Lys Ser Thr Glu Gly Lys Ser Ser Gly Ser Gly Ser Glu Ser
            100                 105                 110

Lys Ser Thr Glu Gly Lys Ser Ser Gly Ser Gly Ser Glu Ser Lys Ser
        115                 120                 125

Thr Glu Gly Lys Ser Ser Gly Ser Gly Ser Glu Ser Lys Ser Thr Glu
    130                 135                 140

Gly Lys Ser Ser Gly Ser Gly Ser Glu Ser Lys Ser Thr Glu Gly Lys
145                 150                 155                 160

Ser Ser Gly Ser Gly Ser Glu Ser Lys Ser Thr Glu Gly Lys Ser Ser
                165                 170                 175

Gly Ser Gly Ser Glu Ser Lys Ser Thr Glu Gly Lys Ser Ser Gly Ser
            180                 185                 190

Gly Ser Glu Ser Lys Ser Thr Glu Gly Lys Ser Ser Gly Ser Gly Ser
        195                 200                 205

Glu Ser Lys Ser Thr Glu Gly Lys Ser Ser Gly Ser Gly Ser Glu Ser
    210                 215                 220

Lys Ser Thr Glu Gly Lys Ser Ser Gly Ser Gly Ser Glu Ser Lys Ser
```

```
225                 230                 235                 240

Thr Glu Gly Lys Ser Ser Gly Ser Gly Ser Glu Ser Lys Ser Thr Glu
                245                 250                 255

Gly Lys Ser Ser Gly Ser Gly Ser Glu Ser Lys Ser Thr Glu Gly Lys
            260                 265                 270

Ser Ser Gly Ser Gly Ser Glu Ser Lys Ser Thr Gly Gly Ser
        275                 280                 285


<210> SEQ ID NO 135
<211> LENGTH: 21
<212> TYPE: PRT
<213> ORGANISM: artificial
<220> FEATURE:
<223> OTHER INFORMATION: peptide

<400> SEQUENCE: 135

Ala Leu Val Leu Ile Ala Phe Ala Gln Tyr Leu Gln Gln Ser Pro Phe
1               5                   10                  15

Glu Asp His Val Lys
            20


<210> SEQ ID NO 136
<211> LENGTH: 16
<212> TYPE: PRT
<213> ORGANISM: artificial
<220> FEATURE:
<223> OTHER INFORMATION: peptide

<400> SEQUENCE: 136

Ala Ser Leu Glu Asp Leu Gly Trp Ala Asp Trp Val Leu Ser Pro Arg
1               5                   10                  15


<210> SEQ ID NO 137
<211> LENGTH: 16
<212> TYPE: PRT
<213> ORGANISM: artificial
<220> FEATURE:
<223> OTHER INFORMATION: peptide

<400> SEQUENCE: 137

Thr Asp Thr Gly Val Ser Leu Gln Thr Tyr Asp Asp Leu Leu Ala Lys
1               5                   10                  15


<210> SEQ ID NO 138
<211> LENGTH: 40
<212> TYPE: PRT
<213> ORGANISM: artificial
<220> FEATURE:
<223> OTHER INFORMATION: peptide linker

<400> SEQUENCE: 138

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys
        35                  40


<210> SEQ ID NO 139
<211> LENGTH: 112
<212> TYPE: PRT
<213> ORGANISM: human

<400> SEQUENCE: 139
```

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 140
<211> LENGTH: 104
<212> TYPE: PRT
<213> ORGANISM: artificial
<220> FEATURE:
<223> OTHER INFORMATION: synthetic linker
<220> FEATURE:
<221> NAME/KEY: MISC_FEATURE
<222> LOCATION: (13)..(102)
<223> OTHER INFORMATION: synthetic linker, wherein the amino acid sequence EAAAK is a repeating unit that can be repeated 2-20 times, thus any or all of the EAAAK repeating units from amino acids 13 to 102 can either be present or absent

<400> SEQUENCE: 140

```
Ala Ser Glu Ala Ala Ala Lys Glu Ala Ala Ala Lys Glu Ala Ala Ala
1               5                   10                  15

Lys Glu Ala Ala Ala Lys Glu Ala Ala Ala Lys Glu Ala Ala Ala Lys
            20                  25                  30

Glu Ala Ala Ala Lys Glu Ala Ala Ala Lys Glu Ala Ala Ala Lys Glu
        35                  40                  45

Ala Ala Ala Lys Glu Ala Ala Ala Lys Glu Ala Ala Ala Lys Glu Ala
    50                  55                  60

Ala Ala Lys Glu Ala Ala Ala Lys Glu Ala Ala Ala Lys Glu Ala Ala
65                  70                  75                  80

Ala Lys Glu Ala Ala Ala Lys Glu Ala Ala Ala Lys Glu Ala Ala Ala
                85                  90                  95

Lys Glu Ala Ala Ala Lys Gly Thr
            100
```

<210> SEQ ID NO 141
<211> LENGTH: 44
<212> TYPE: PRT
<213> ORGANISM: artificial
<220> FEATURE:
<223> OTHER INFORMATION: synthetic linker

<400> SEQUENCE: 141

```
Ala Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Thr
        35                  40
```

<210> SEQ ID NO 142
<211> LENGTH: 102
<212> TYPE: PRT
<213> ORGANISM: artificial
<220> FEATURE:
<223> OTHER INFORMATION: synthetic linker
<220> FEATURE:
<221> NAME/KEY: MISC_FEATURE
<222> LOCATION: (13)..(102)
<223> OTHER INFORMATION: synthetic linker, wherein the amino acid sequence GGGGS is a repeating unit that can be repeated 2-20 times, thus any or all of the GGGGS repeating units from amino acids 13 to 102 can either be present or absent

<400> SEQUENCE: 142

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Gly Gly Gly Gly Ser Gly Gly
    50                  55                  60

Gly Gly Ser Gly Gly Gly Gly Ser Gly Gly Gly Gly Ser Gly Gly Gly
65                  70                  75                  80

Gly Ser Gly Gly Gly Gly Ser Gly Gly Gly Gly Ser Gly Gly Gly Gly
                85                  90                  95

Ser Gly Gly Gly Gly Ser
            100
```

<210> SEQ ID NO 143
<211> LENGTH: 104
<212> TYPE: PRT
<213> ORGANISM: artificial
<220> FEATURE:
<223> OTHER INFORMATION: synthetic linker
<220> FEATURE:
<221> NAME/KEY: MISC_FEATURE
<222> LOCATION: (13)..(102)
<223> OTHER INFORMATION: synthetic linker, wherein the amino acid sequence GGGGS is a repeating unit that can be repeated 2-20 times, thus any or all of the GGGGS repeating units from amino acids 13 to 102 can either be present or absent

<400> SEQUENCE: 143

```
Ala Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Gly Gly Gly Gly Ser Gly Gly
    50                  55                  60

Gly Gly Ser Gly Gly Gly Gly Ser Gly Gly Gly Gly Ser Gly Gly Gly
65                  70                  75                  80

Gly Ser Gly Gly Gly Gly Ser Gly Gly Gly Gly Ser Gly Gly Gly Gly
                85                  90                  95

Ser Gly Gly Gly Gly Ser Gly Thr
            100
```

<210> SEQ ID NO 144
<211> LENGTH: 40

-continued

```
<212> TYPE: PRT
<213> ORGANISM: artificial
<220> FEATURE:
<223> OTHER INFORMATION: synthetic linker
<220> FEATURE:
<221> NAME/KEY: MISC_FEATURE
<222> LOCATION: (5)..(40)
<223> OTHER INFORMATION: synthetic linker, wherein the amino acid
      sequence AP is a repeating unit that can be repeated 2-20 times,
      thus any or all of the AP repeating units from amino acids 5 to 40
      can either be present or absent

<400> SEQUENCE: 144

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40


<210> SEQ ID NO 145
<211> LENGTH: 44
<212> TYPE: PRT
<213> ORGANISM: artificial
<220> FEATURE:
<223> OTHER INFORMATION: synthetic linker
<220> FEATURE:
<221> NAME/KEY: MISC_FEATURE
<222> LOCATION: (7)..(42)
<223> OTHER INFORMATION: synthetic linker, wherein the amino acid
      sequence AP is a repeating unit that can be repeated 2-20 times,
      thus any or all of the AP repeating units from amino acids 7 to 42
      can either be present or absent

<400> SEQUENCE: 145

Ala Ser Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Gly Thr
        35                  40
```